(12) United States Patent
Ryan et al.

(10) Patent No.: US 10,369,346 B2
(45) Date of Patent: Aug. 6, 2019

(54) SYSTEMS AND METHODS FOR TREATING A CAROTID ARTERY

(71) Applicant: Silk Road Medical, Inc., Sunnyvale, CA (US)

(72) Inventors: Ari Ryan, Sunnyvale, CA (US); Alan K. Schaer, Sunnyvale, CA (US); Gregory M. Hyde, Sunnyvale, CA (US); Richard J. Renati, Sunnyvale, CA (US); Michi E. Garrison, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 277 days.

(21) Appl. No.: 15/489,055

(22) Filed: Apr. 17, 2017

(65) Prior Publication Data

US 2017/0312491 A1   Nov. 2, 2017

Related U.S. Application Data

(63) Continuation of application No. 13/816,670, filed as application No. PCT/US2011/046775 on Aug. 5, 2011, now Pat. No. 9,623,228.

(Continued)

(51) Int. Cl.
*A61M 29/00* (2006.01)
*A61M 39/06* (2006.01)
(Continued)

(52) U.S. Cl.
CPC ......... *A61M 39/06* (2013.01); *A61B 17/0057* (2013.01); *A61B 17/0469* (2013.01);
(Continued)

(58) Field of Classification Search
CPC .. A61M 39/06; A61M 39/228; A61M 39/227; A61M 39/0606; A61M 25/0662;
(Continued)

(56) References Cited

U.S. PATENT DOCUMENTS

| 3,861,416 A | 1/1975 | Wichterle |
| 4,218,313 A | 8/1980 | Aid et al. |

(Continued)

FOREIGN PATENT DOCUMENTS

| JP | S59-161808 U | 10/1984 |
| JP | H07-265412 A | 10/1995 |

(Continued)

OTHER PUBLICATIONS

International Search Report dated Mar. 19, 2012 for PCT application No. PCT/US2011/046775.

(Continued)

*Primary Examiner* — Amy R Weisberg
(74) *Attorney, Agent, or Firm* — Mintz Levin Cohn Ferris Glovsky and Popeo, P.C.

(57) ABSTRACT

Systems and methods are adapted for treating the carotid artery. The systems include interventional catheters and blood vessel access devices that are adapted for transcervical insertion into the carotid artery. Embodiments of the systems and methods can be used in combination with embolic protection systems including blood flow reversal mechanisms, arterial filters, and arterial occlusion devices.

10 Claims, 130 Drawing Sheets

Related U.S. Application Data

(60) Provisional application No. 61/373,240, filed on Aug. 12, 2010.

(51) Int. Cl.
| | | |
|---|---|---|
| *A61B 17/00* | (2006.01) | |
| *A61B 17/04* | (2006.01) | |
| *A61B 17/062* | (2006.01) | |
| *A61B 17/34* | (2006.01) | |
| *A61M 39/22* | (2006.01) | |
| *A61B 17/06* | (2006.01) | |
| *A61B 17/064* | (2006.01) | |
| *A61B 90/00* | (2016.01) | |

(52) U.S. Cl.
CPC ...... *A61B 17/0483* (2013.01); *A61B 17/0625* (2013.01); *A61B 17/3415* (2013.01); *A61M 39/0606* (2013.01); *A61M 39/227* (2013.01); *A61M 39/228* (2013.01); *A61B 17/0482* (2013.01); *A61B 2017/00238* (2013.01); *A61B 2017/00646* (2013.01); *A61B 2017/00654* (2013.01); *A61B 2017/00663* (2013.01); *A61B 2017/00668* (2013.01); *A61B 2017/0472* (2013.01); *A61B 2017/0477* (2013.01); *A61B 2017/0641* (2013.01); *A61B 2017/06042* (2013.01); *A61B 2090/0811* (2016.02)

(58) Field of Classification Search
CPC .. A61M 25/10; A61M 25/01; A61M 25/0668; A61M 2025/0675; A61M 2025/0681; A61M 25/0097; A61M 2025/0188; A61M 2039/0258; A61M 2039/0279; A61M 2039/062; A61M 2039/0626; A61M 2039/0673; A61B 17/3415; A61B 17/0625; A61B 17/0483; A61B 17/0057; A61B 17/0469; A61B 2090/0811; A61B 2017/06042; A61B 17/0482; A61B 2017/00238; A61B 2017/00668; A61B 2017/00646; A61B 2017/00663; A61B 2017/0477; A61B 2017/0641; A61B 2017/0472; A61B 2017/00654; A61B 2017/00469; A61B 17/2833; A61B 18/1445; A61B 17/29; A61B 2017/2929; A61B 2017/2927; A61B 2017/2946; Y10T 137/3003; Y10T 137/4643; Y10T 137/4456; Y10T 137/4621
See application file for complete search history.

(56) References Cited

U.S. PATENT DOCUMENTS

| | | |
|---|---|---|
| 4,253,201 A | 3/1981 | Ross et al. |
| 4,493,707 A | 1/1985 | Ishihara |
| 4,865,581 A | 9/1989 | Lundquist et al. |
| 4,895,346 A | 1/1990 | Steigerwald |
| 5,176,652 A | 1/1993 | Littrell |
| 5,207,656 A | 5/1993 | Kranys |
| 5,429,609 A | 7/1995 | Yoon |
| 5,460,616 A * | 10/1995 | Weinstein .......... A61M 39/0606 604/167.03 |
| 5,584,803 A | 12/1996 | Stevens et al. |
| 5,599,305 A | 2/1997 | Hermann et al. |
| 5,769,830 A | 6/1998 | Parker |
| 5,860,990 A | 1/1999 | Nobles et al. |
| 5,916,193 A | 6/1999 | Stevens et al. |
| 6,152,912 A | 11/2000 | Jansen et al. |
| 6,206,868 B1 | 3/2001 | Parodi |
| 6,383,172 B1 | 5/2002 | Barbut |
| 6,413,235 B1 | 7/2002 | Parodi |
| 6,423,032 B2 | 7/2002 | Parodi |
| 6,458,103 B1 | 10/2002 | Albert et al. |
| 6,540,712 B1 | 4/2003 | Parodi et al. |
| 6,595,953 B1 | 7/2003 | Coppi et al. |
| 6,623,510 B2 | 9/2003 | Carley et al. |
| 6,673,040 B1 | 1/2004 | Samson et al. |
| 6,682,505 B2 | 1/2004 | Bates et al. |
| 6,837,881 B1 | 1/2005 | Barbut |
| 6,855,136 B2 | 2/2005 | Dorros et al. |
| 6,878,140 B2 | 4/2005 | Barbut |
| 6,936,060 B2 | 8/2005 | Hogendijk et al. |
| 7,001,400 B1 | 2/2006 | Modesitt et al. |
| 7,004,931 B2 | 2/2006 | Hogendijk |
| 7,004,952 B2 | 2/2006 | Nobles et al. |
| 7,083,594 B2 | 8/2006 | Coppi |
| 7,223,253 B2 | 5/2007 | Hogendijk |
| 7,335,182 B1 | 2/2008 | Hilaire |
| 7,604,612 B2 | 10/2009 | Ressemann et al. |
| 8,157,760 B2 | 4/2012 | Criado et al. |
| 8,262,622 B2 | 9/2012 | Gonzales et al. |
| 2001/0044591 A1 | 11/2001 | Stevens et al. |
| 2002/0058910 A1 | 5/2002 | Hermann et al. |
| 2003/0069468 A1 | 4/2003 | Bolling et al. |
| 2003/0163086 A1 | 8/2003 | Denyer et al. |
| 2003/0212304 A1 | 11/2003 | Lattouf |
| 2004/0064179 A1 | 4/2004 | Linder et al. |
| 2004/0153122 A1 | 8/2004 | Palermo |
| 2004/0153123 A1 | 8/2004 | Palermo et al. |
| 2005/0010238 A1 | 1/2005 | Potter et al. |
| 2005/0131453 A1 | 6/2005 | Parodi |
| 2005/0154344 A1 | 7/2005 | Chang |
| 2005/0154349 A1 | 7/2005 | Renz et al. |
| 2006/0020270 A1 | 1/2006 | Jabba et al. |
| 2006/0041232 A1 | 2/2006 | Stearns et al. |
| 2007/0010787 A1 | 1/2007 | Hackett et al. |
| 2008/0004636 A1 | 1/2008 | Walberg et al. |
| 2008/0312666 A1 | 12/2008 | Ellingwood et al. |
| 2009/0005738 A1 * | 1/2009 | Franer ............... A61B 17/3462 604/164.01 |
| 2009/0076456 A1 | 3/2009 | Armstrong et al. |
| 2009/0163864 A1 | 6/2009 | Breznock et al. |
| 2011/0152625 A1 | 6/2011 | Smith |
| 2011/0270182 A1 | 11/2011 | Breznock et al. |
| 2012/0083661 A1 | 4/2012 | Rockrohr |
| 2013/0035628 A1 | 2/2013 | Garrison et al. |
| 2013/0172661 A1 | 7/2013 | Farnan et al. |
| 2013/0331655 A1 | 12/2013 | Kasprzak et al. |

FOREIGN PATENT DOCUMENTS

| | | |
|---|---|---|
| JP | H08-071161 A | 3/1996 |
| JP | 10-052490 A | 2/1998 |
| JP | H10-033666 A | 2/1998 |
| JP | 2001-523492 A | 11/2001 |
| JP | 2002-522149 A | 7/2002 |
| JP | 2002-543914 A | 12/2002 |
| JP | 2003-521286 A | 7/2003 |
| JP | 2003-521299 A | 7/2003 |
| JP | 2005-523123 A | 8/2005 |
| JP | 2007-301326 A | 11/2007 |
| WO | WO-99/25419 A | 5/1999 |
| WO | WO-00/76390 A2 | 12/2000 |
| WO | WO-03/090831 A2 | 11/2003 |

OTHER PUBLICATIONS

Henry et al. (1999) "Carotid stenting with cerebral protection: First clinical experience using the PercuSurge GuardWire System" *J. Endovasc. Surg.* 6:321-331.

Reimers et al. (2005). "Proximal endovascular flow blockage for cerebral protection during carotid artery stenting: Results froma prospective multicenter registry" J. Endovasc. Ther. 12:156-165.

Ribo et al. (2006). "Transcranial doppler monitoring of transcervical carotid stenting with flow reversal protection: a novel carotid revascularization technique" 37:2846-2849 (originally published online Sep. 28, 2006).

(56) References Cited

OTHER PUBLICATIONS

Stejskal, et al., "Experience of 500 Cases of Neurophysiological Monitoring in Carotid Endarterectomy", Acta Neurochir, 2007, 149:681-689.

* cited by examiner

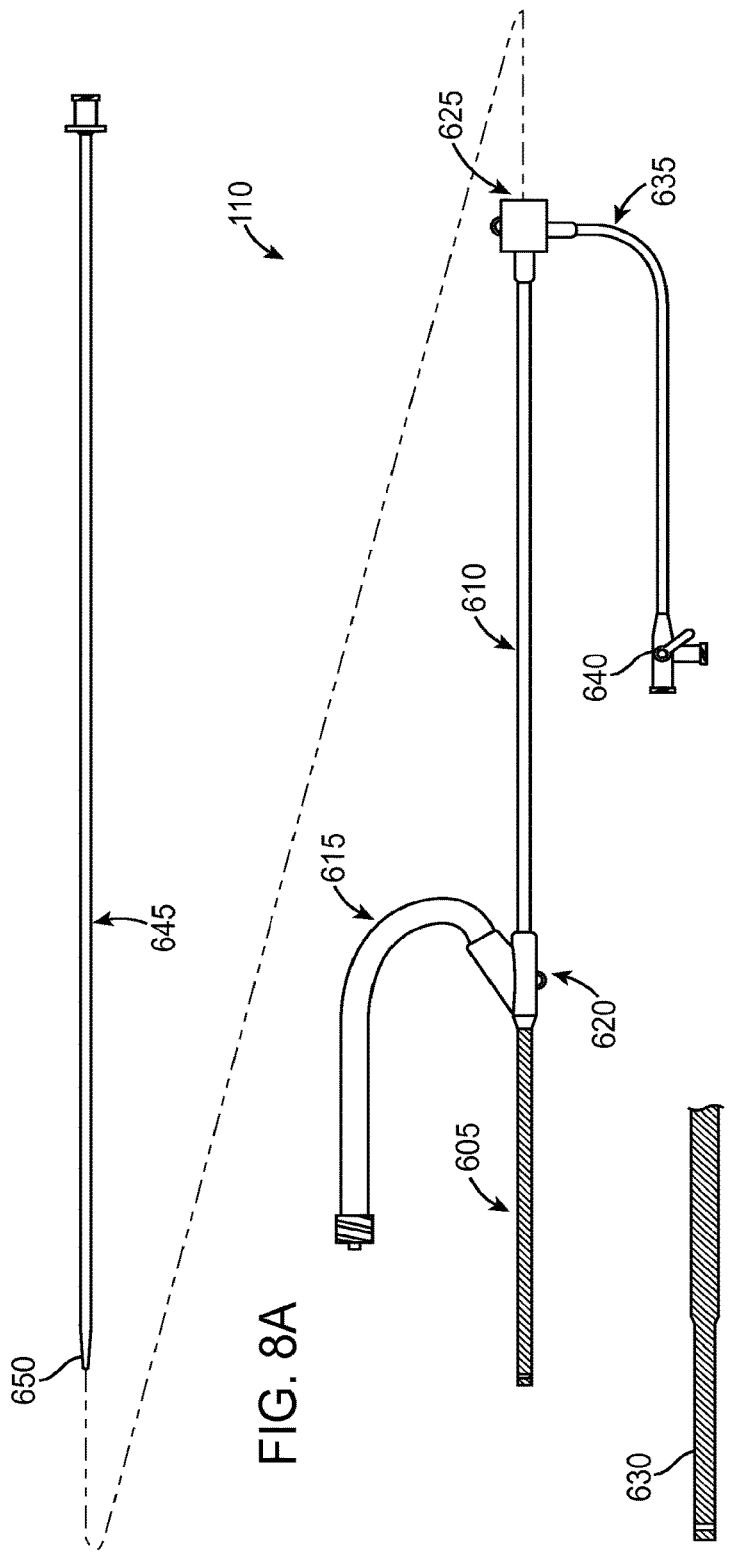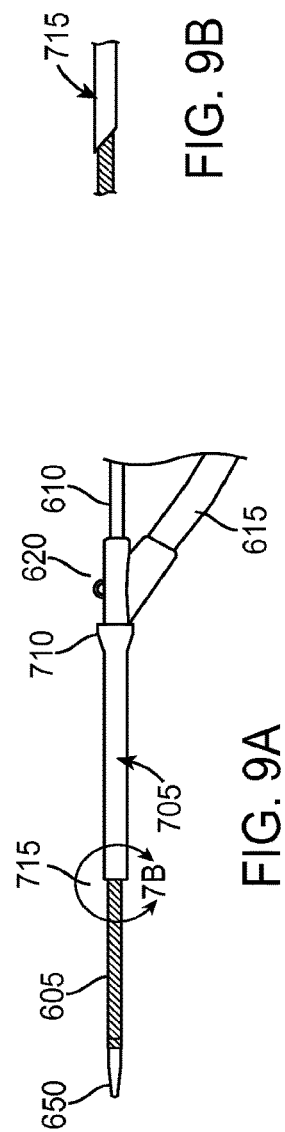

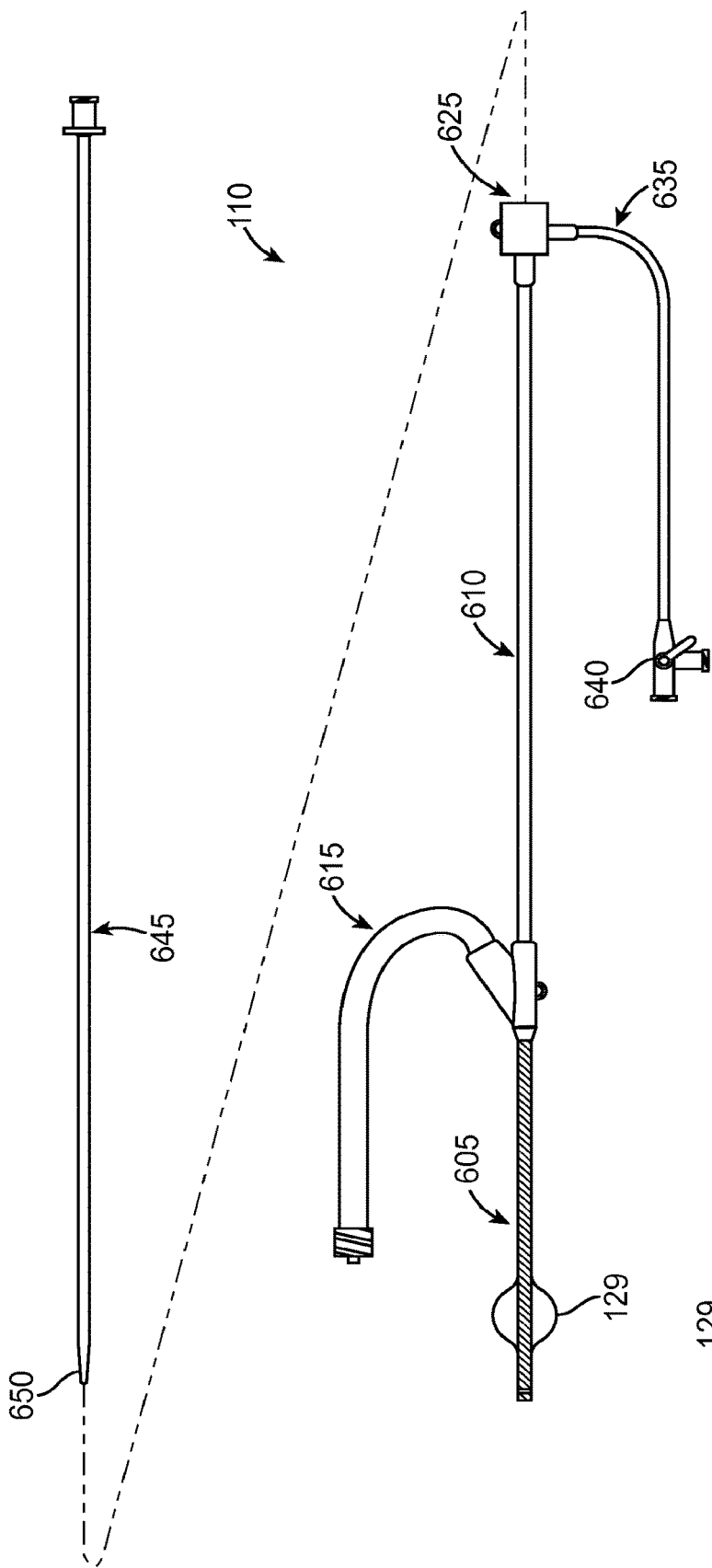
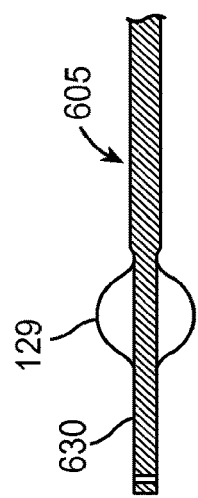
FIG. 15A
FIG. 15B

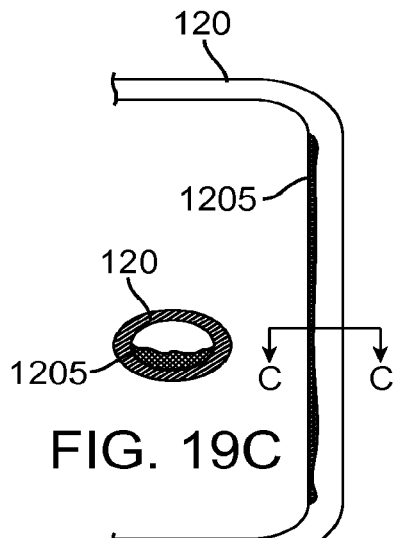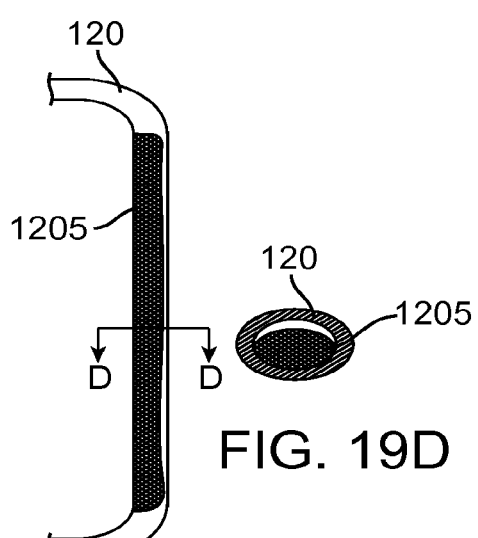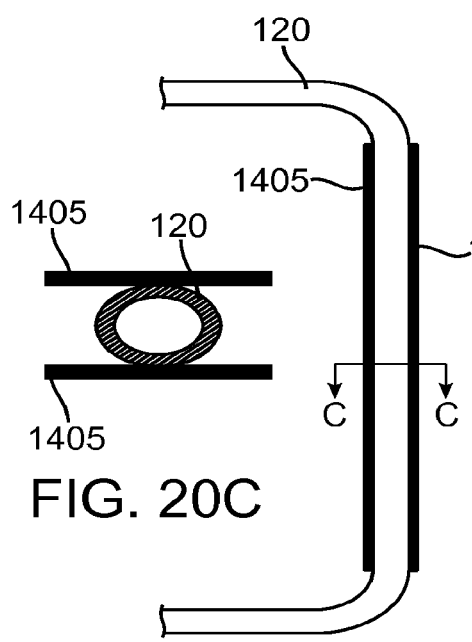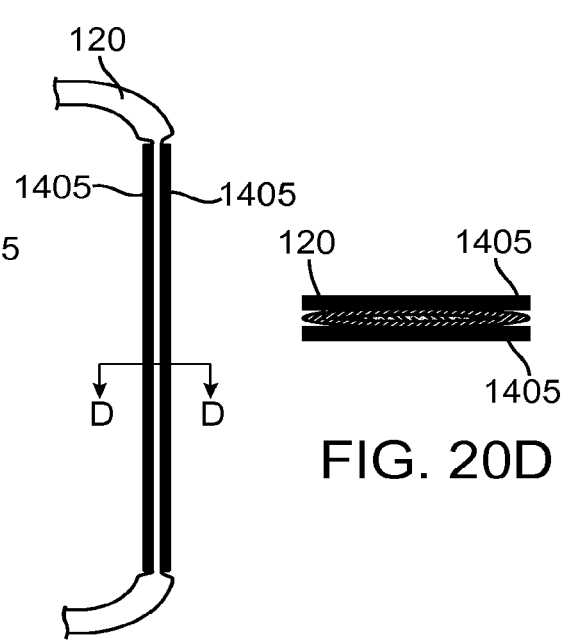

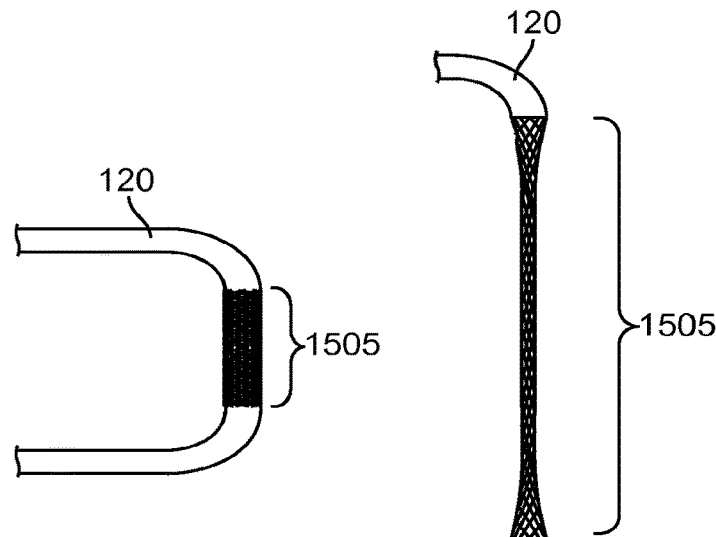
FIG. 21A
FIG. 21B
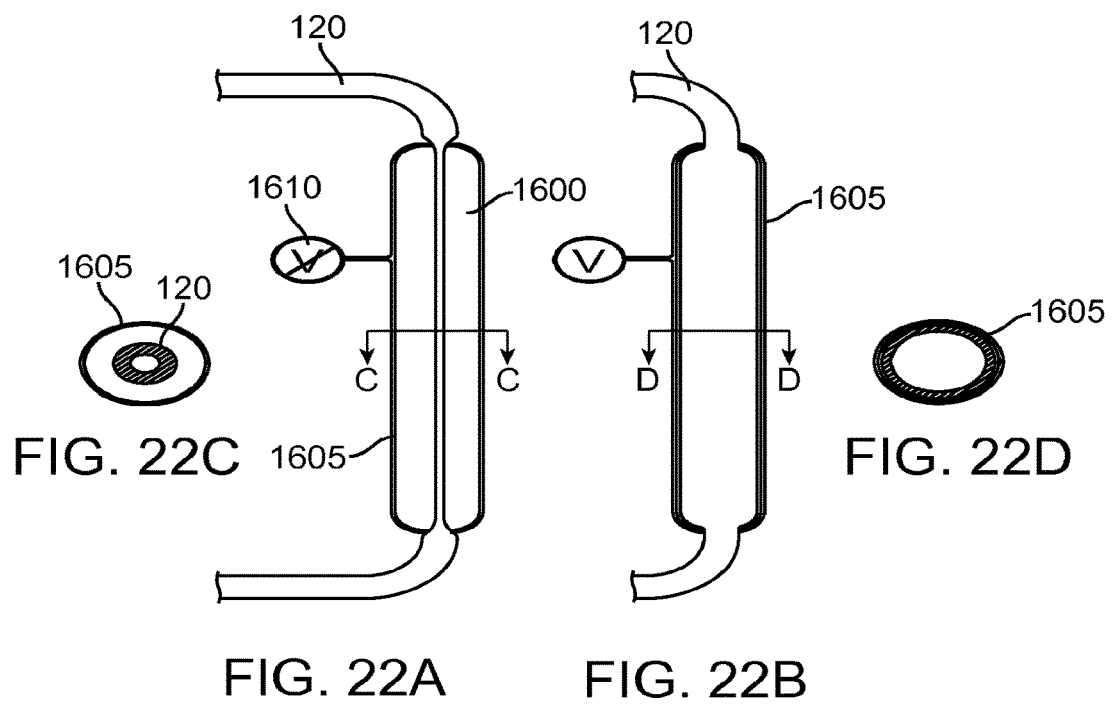
FIG. 22C
FIG. 22A
FIG. 22B
FIG. 22D

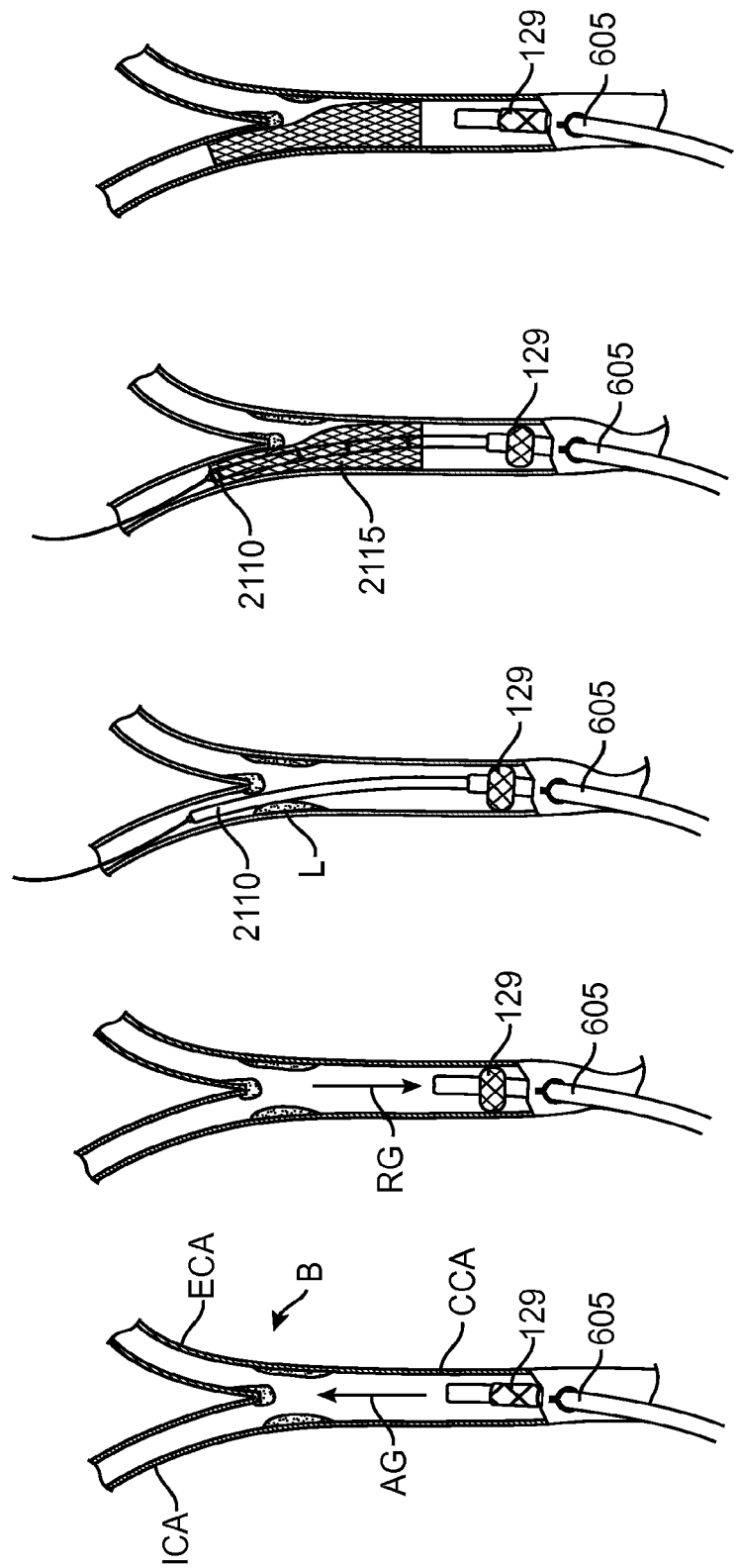

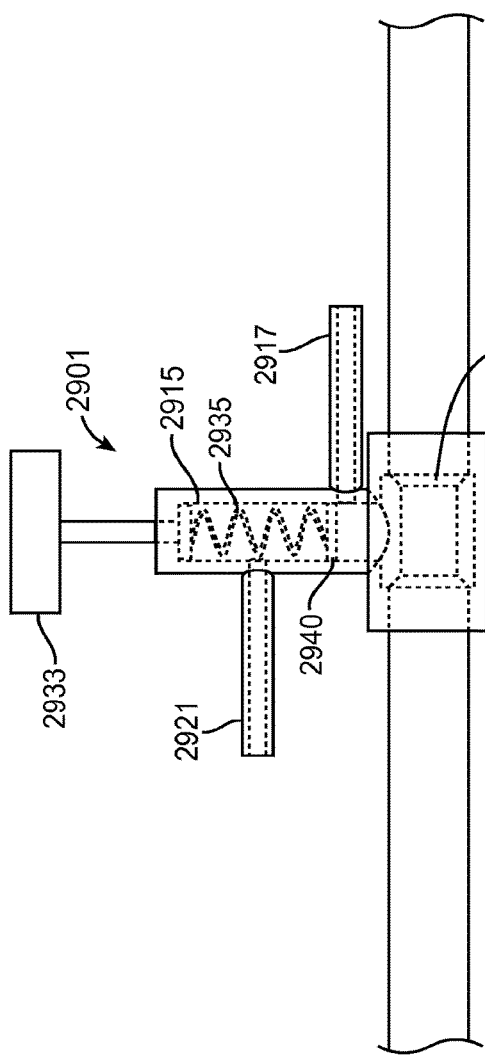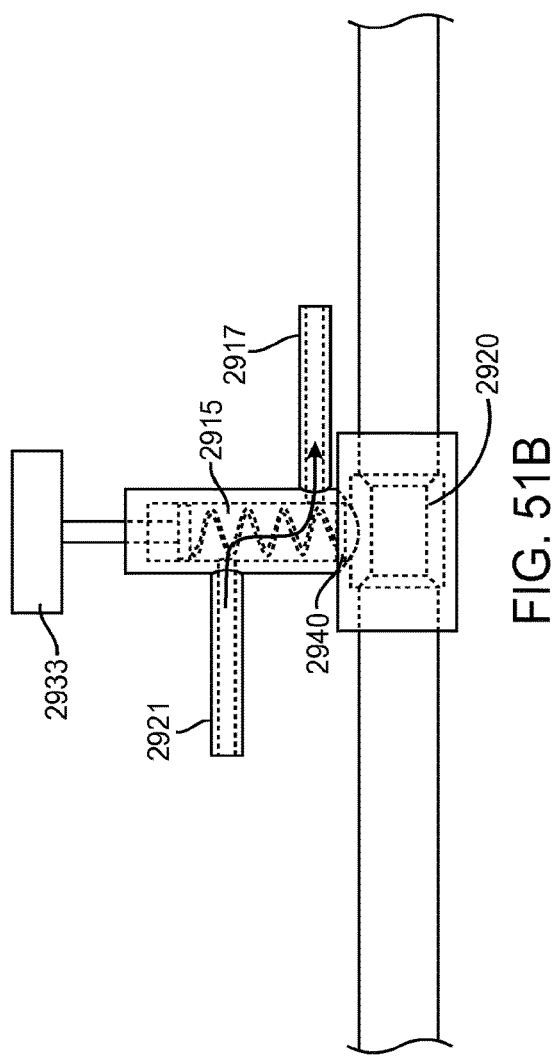

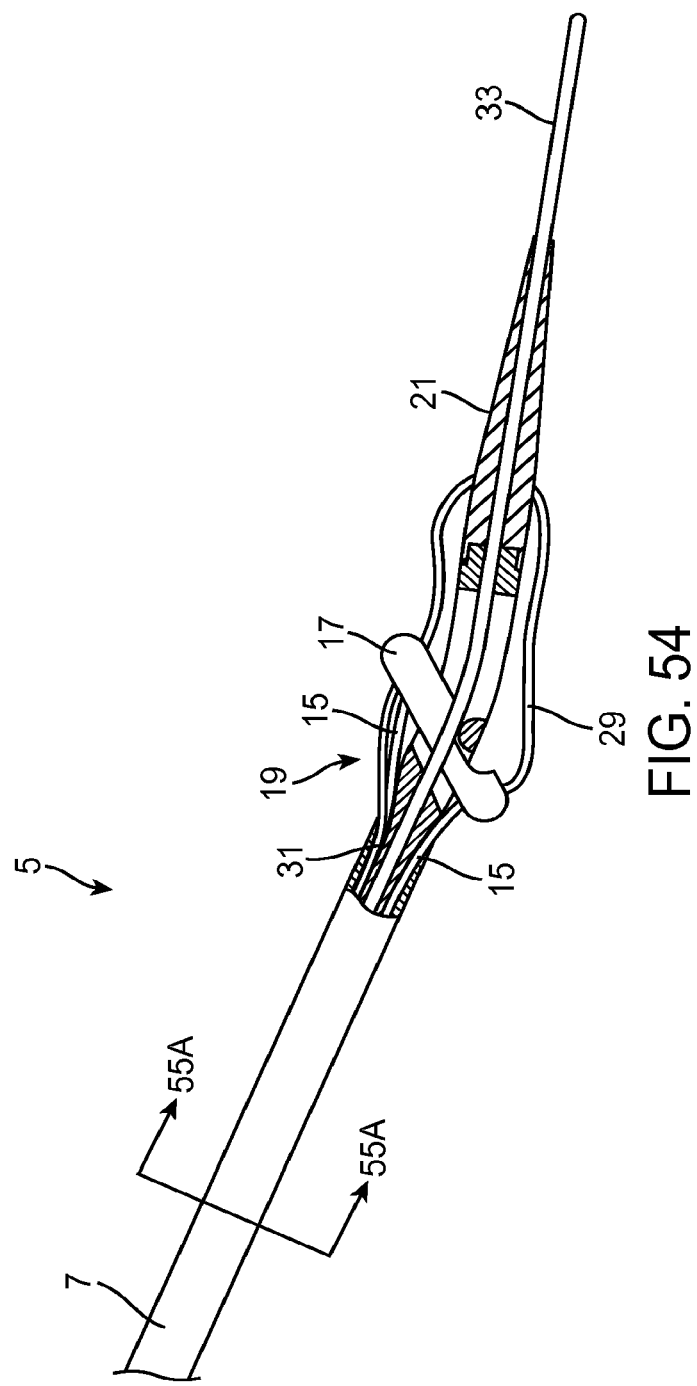

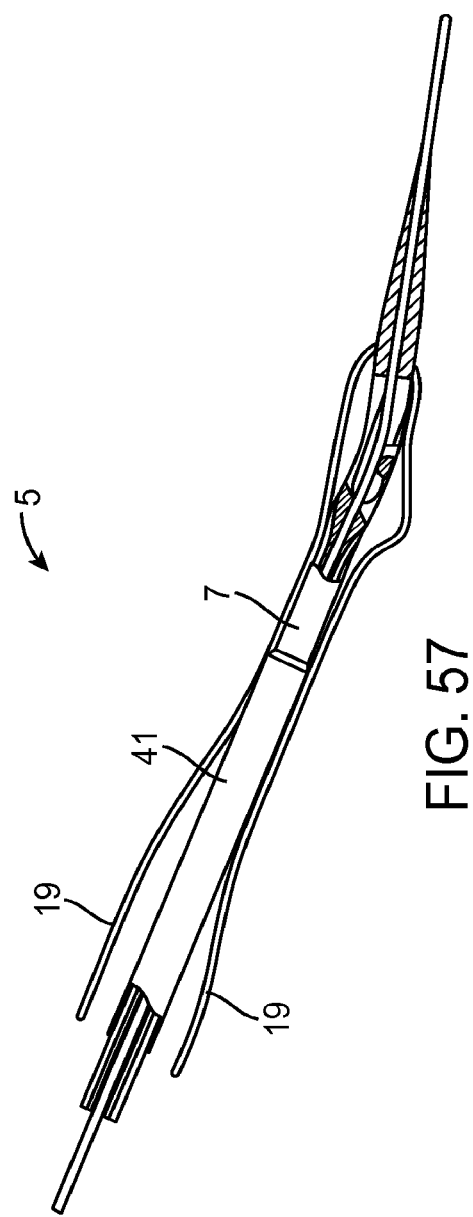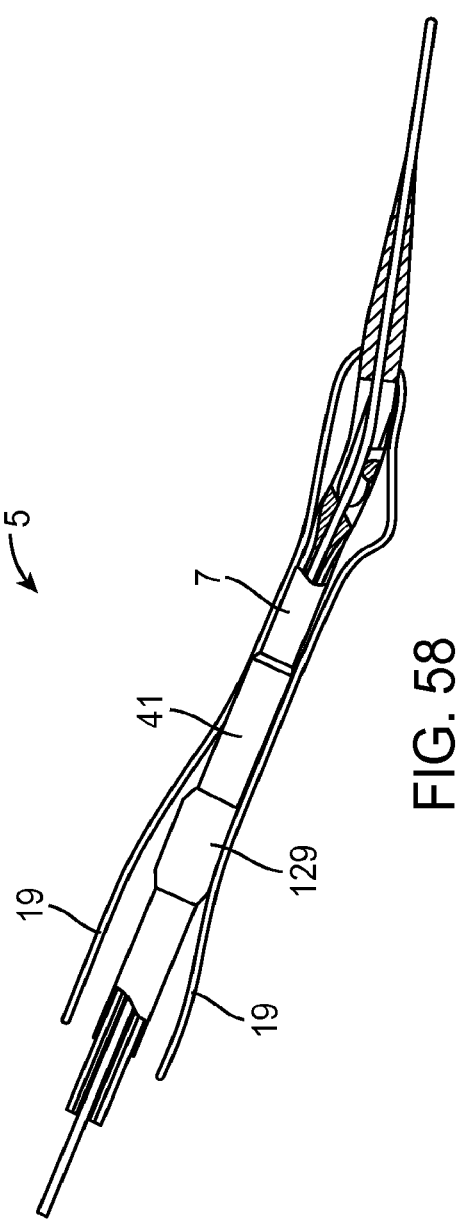

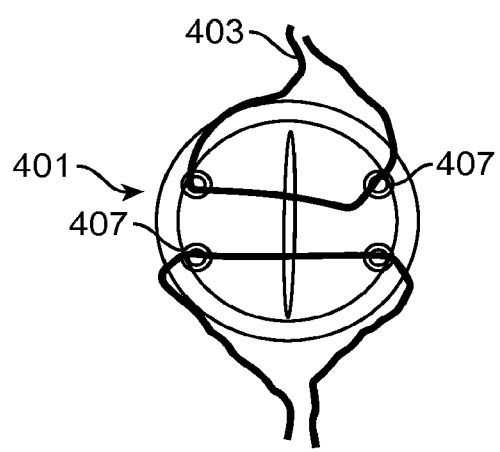
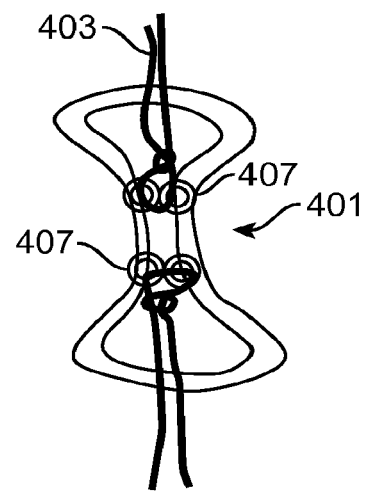
FIG. 86A      FIG. 86B
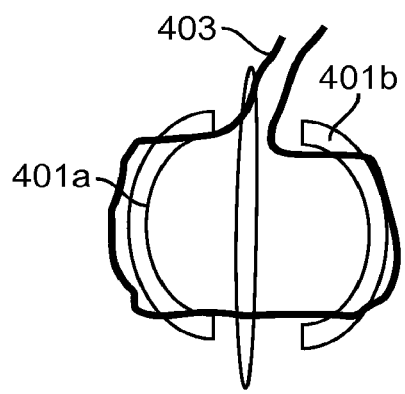
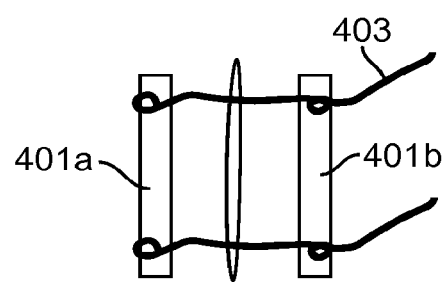
FIG. 87      FIG. 88

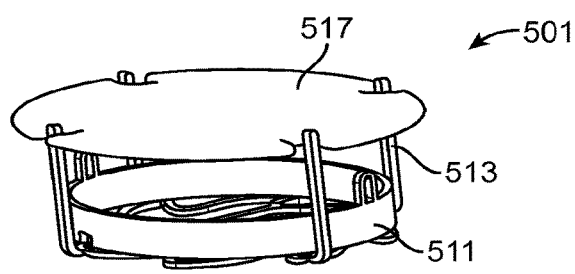
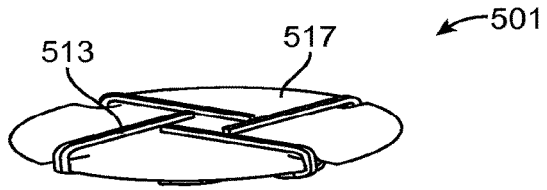
FIG. 91C    FIG. 91D
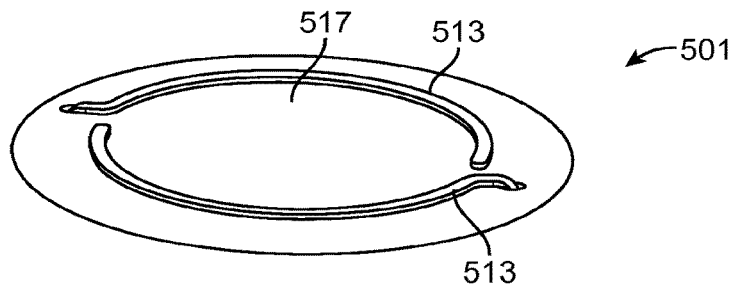
FIG. 92

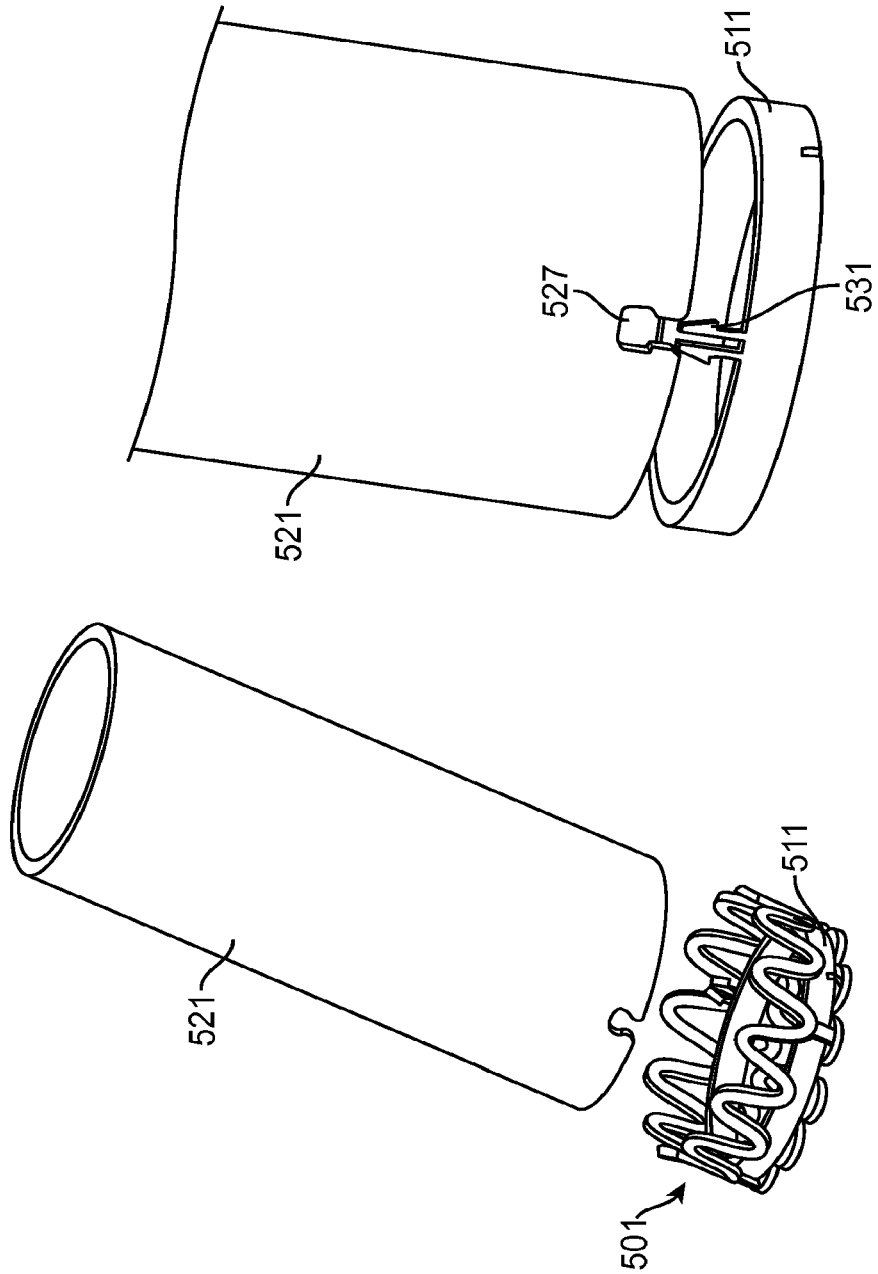

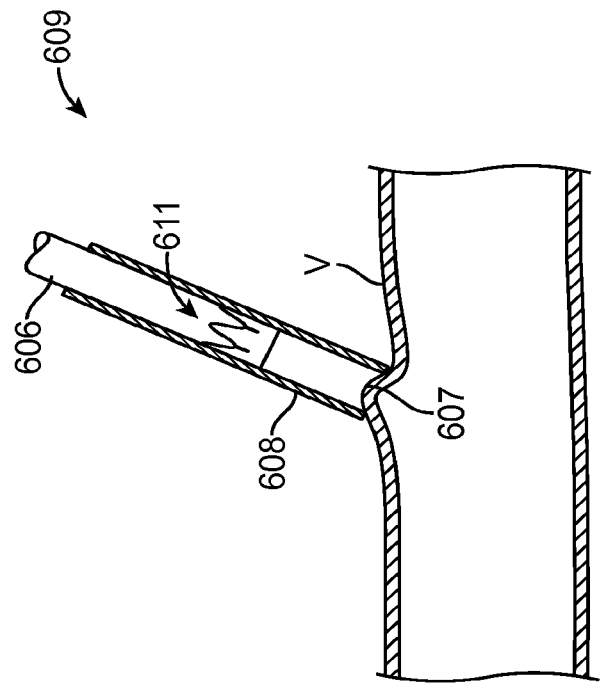
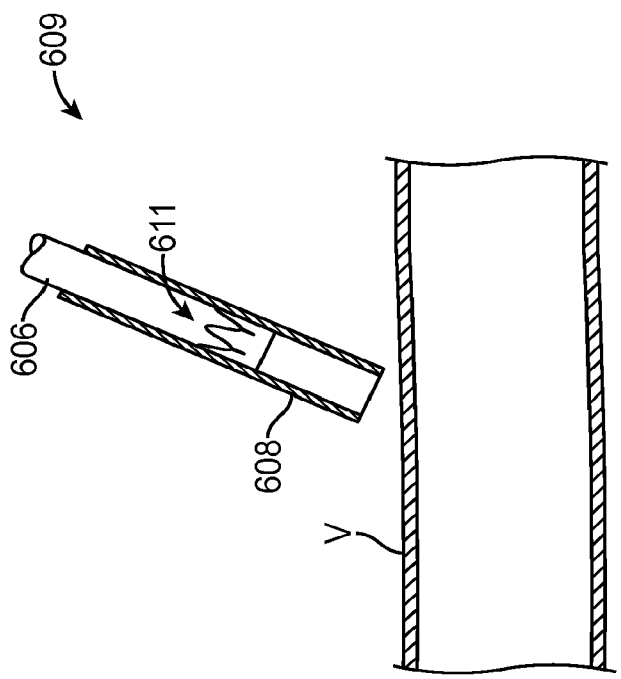

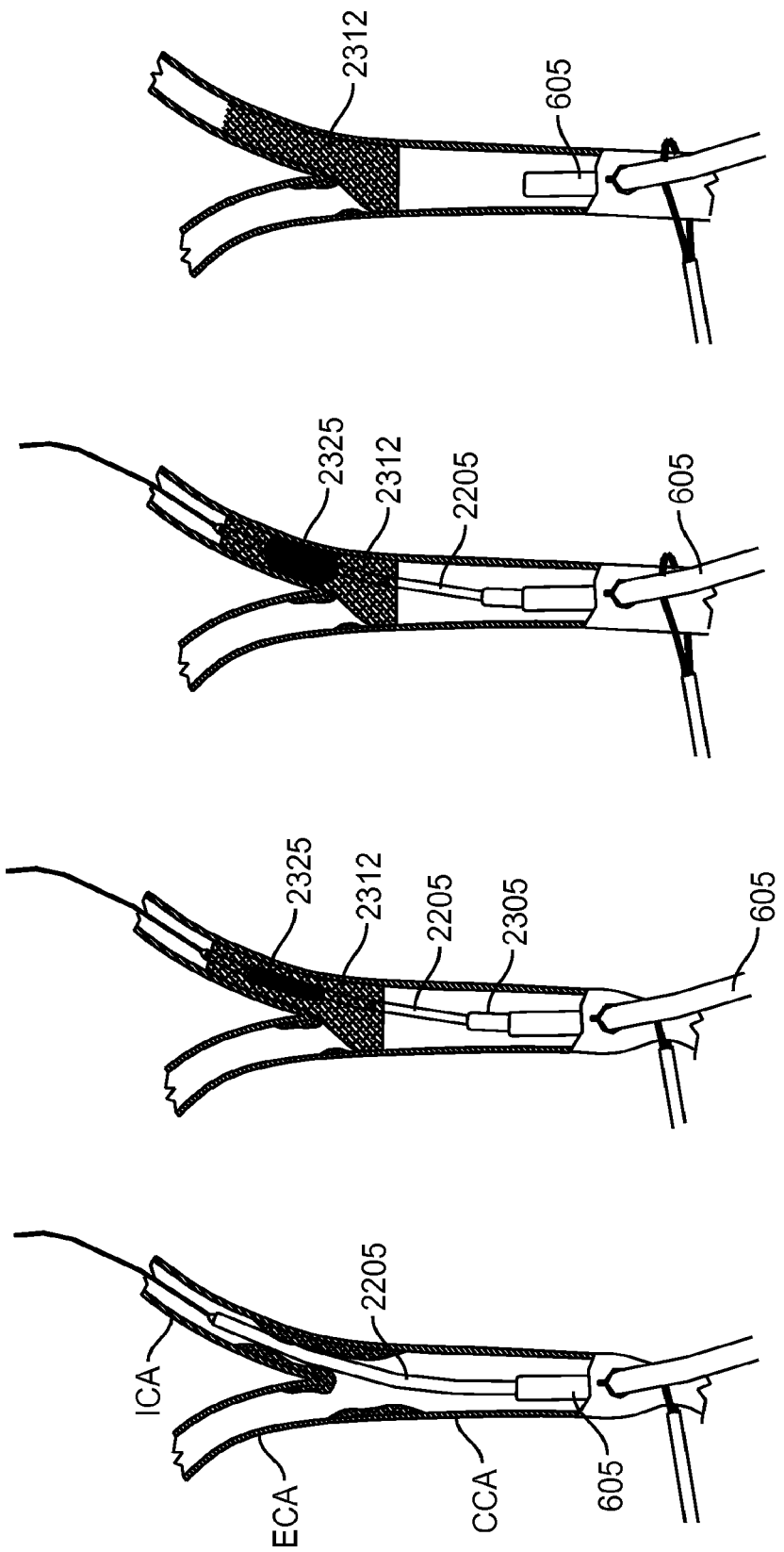

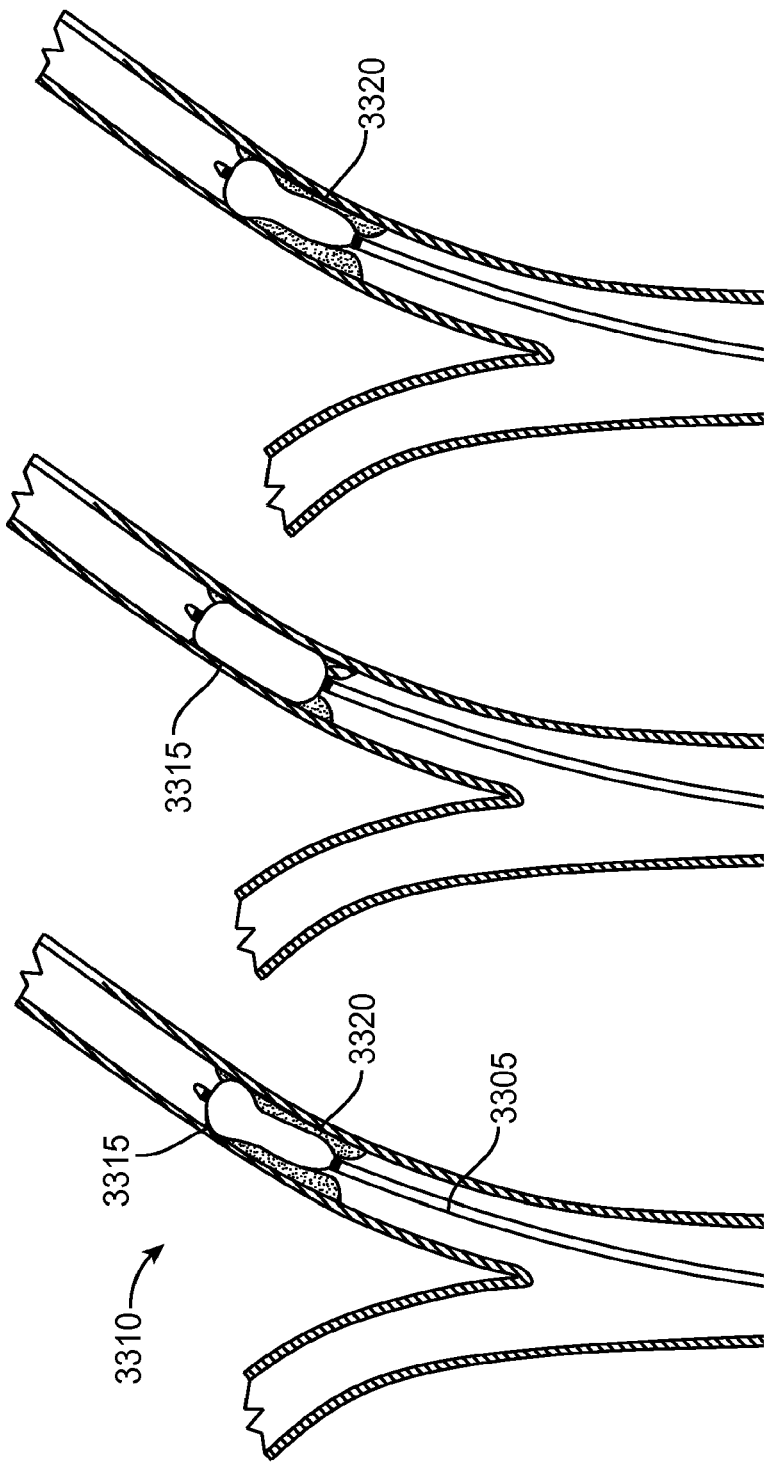

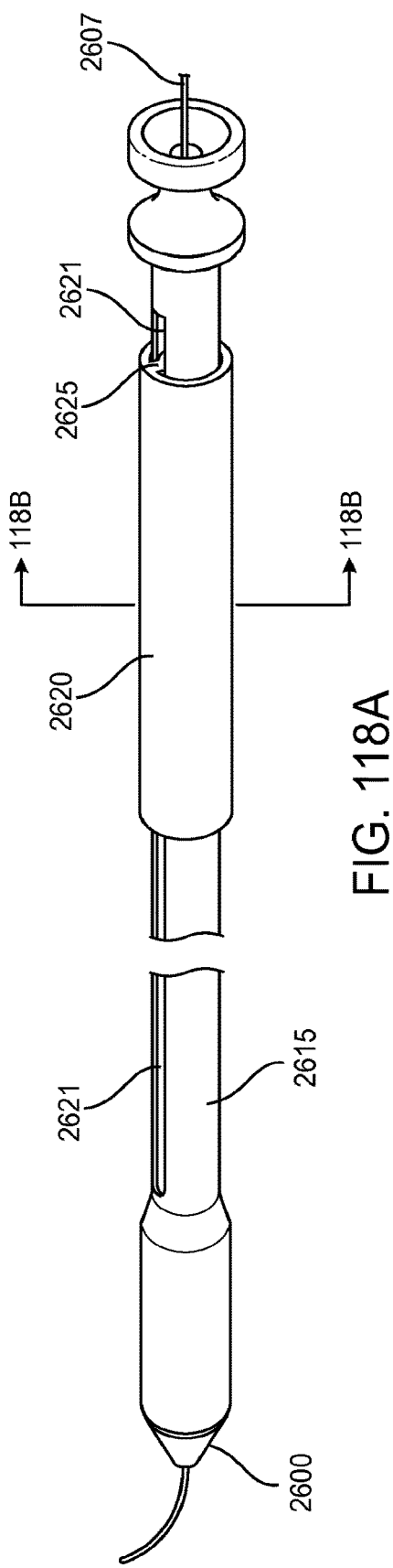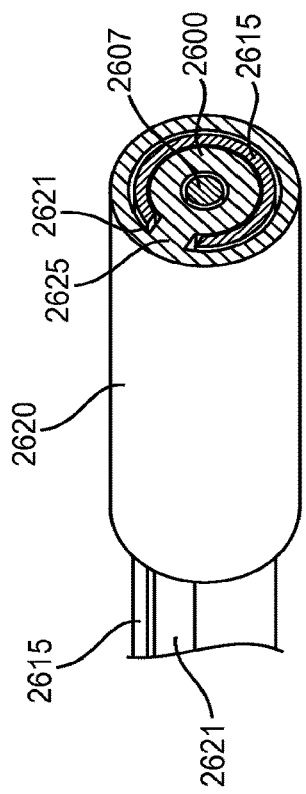
FIG. 118A
FIG. 118B

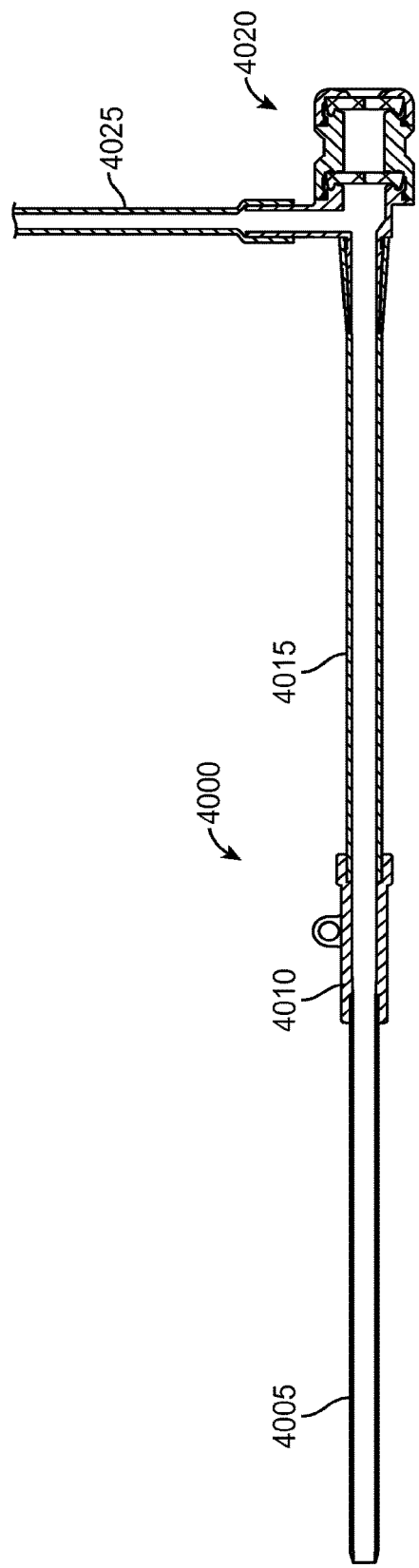
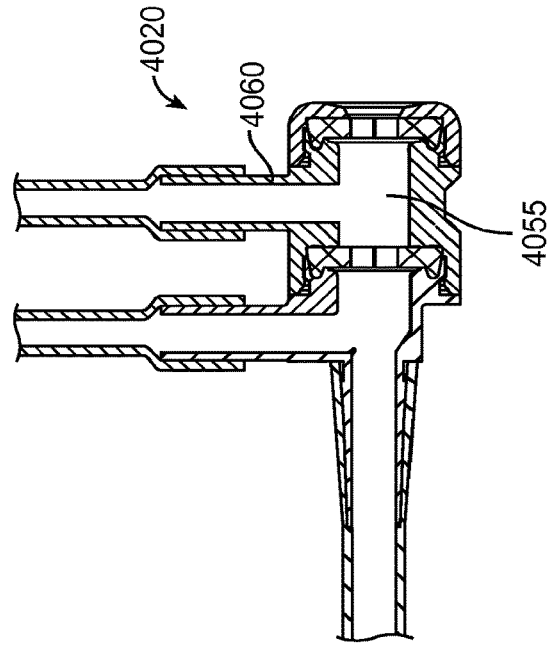
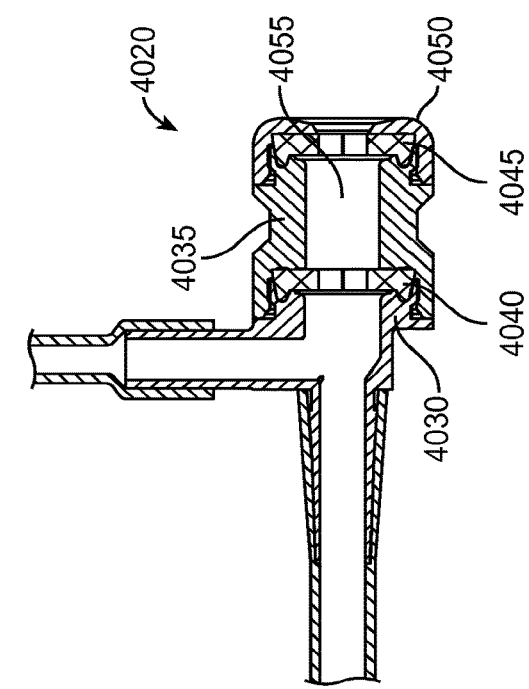
FIG. 122A
FIG. 122B
FIG. 122C

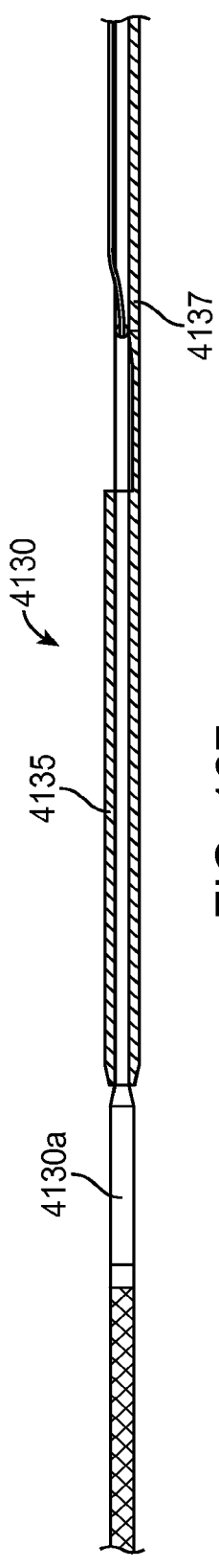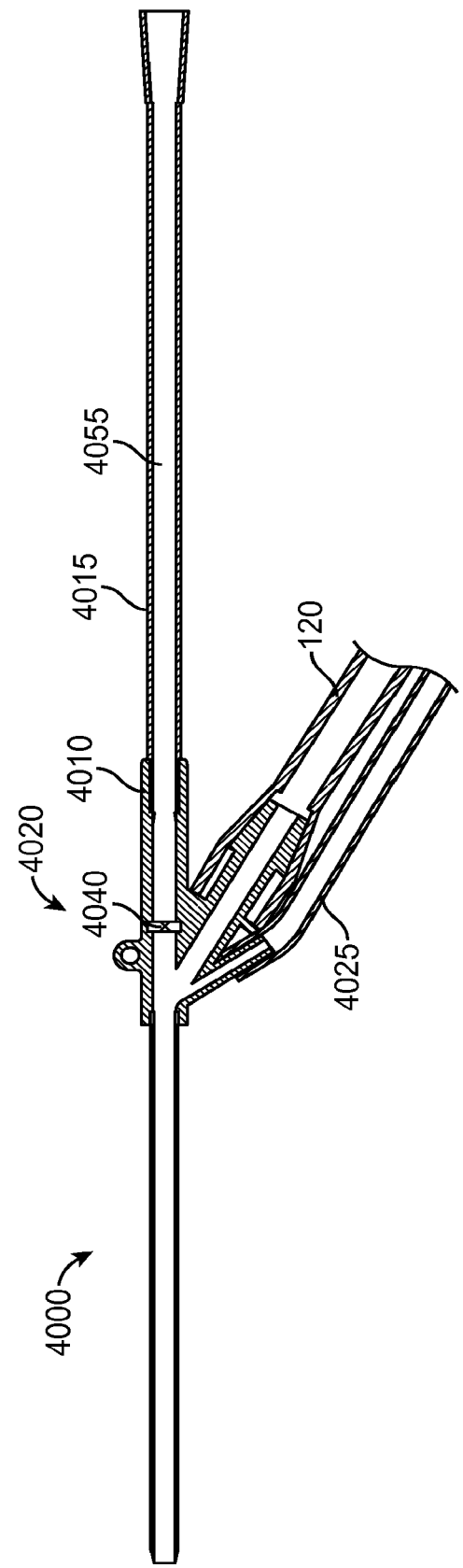

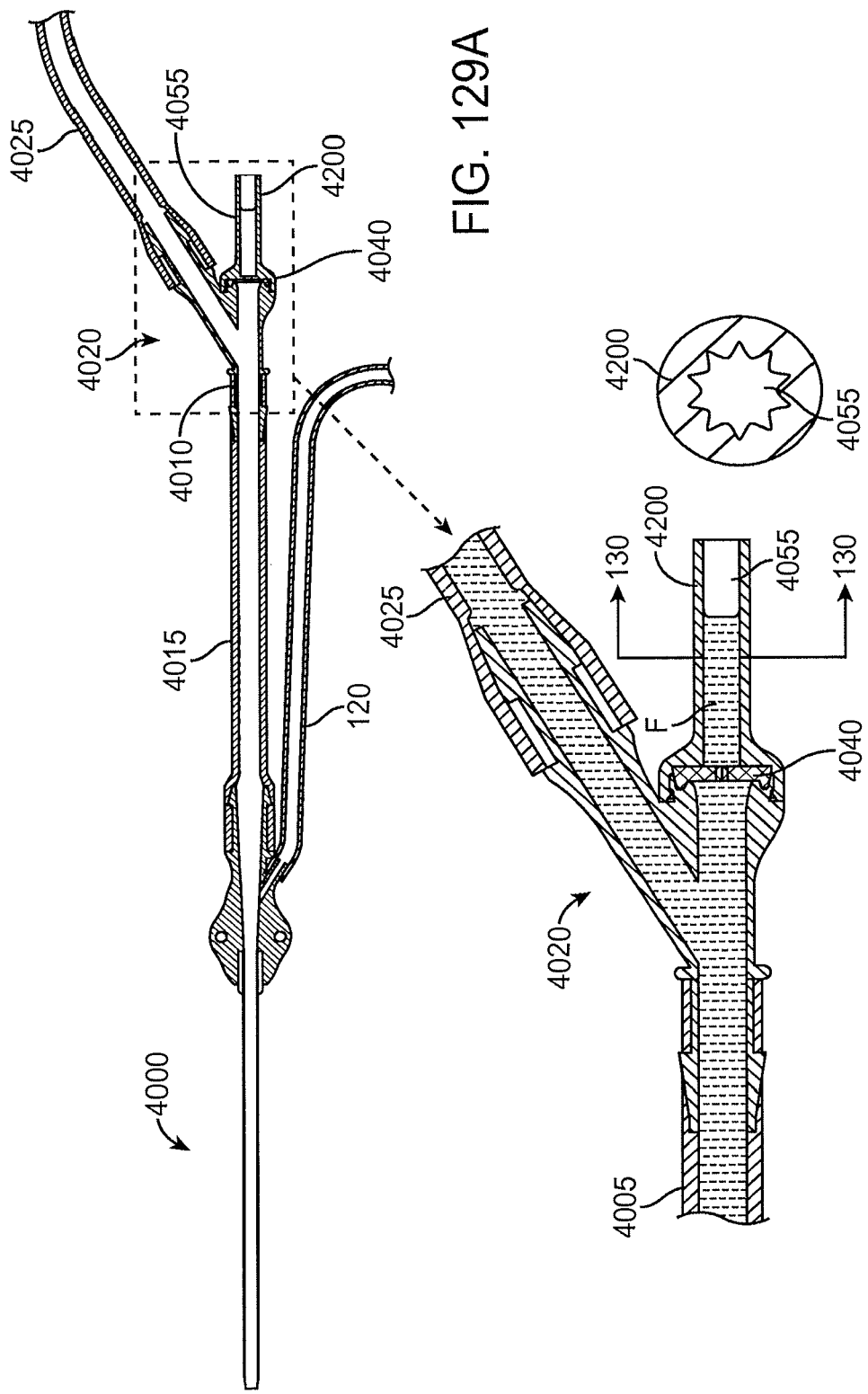

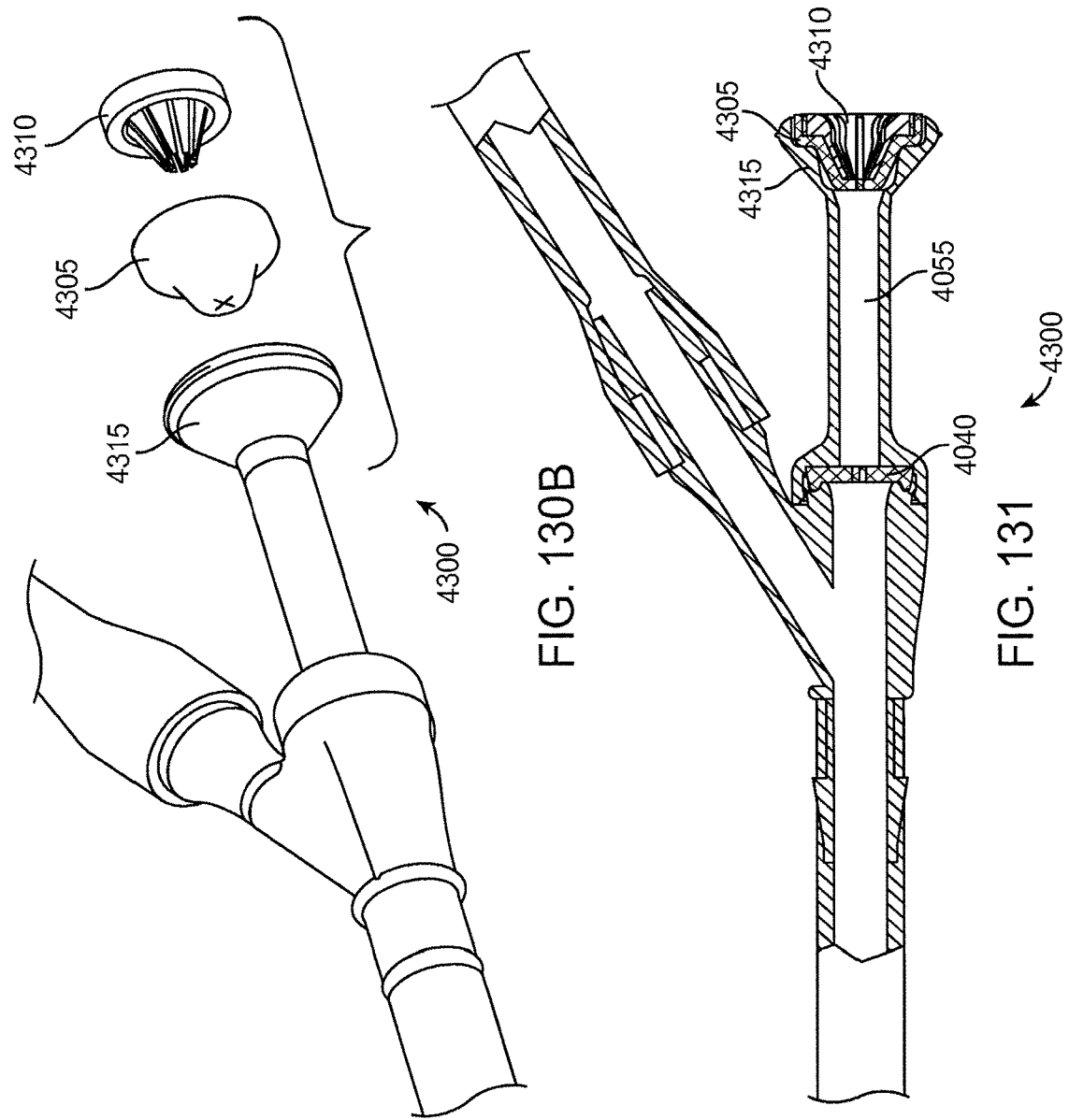

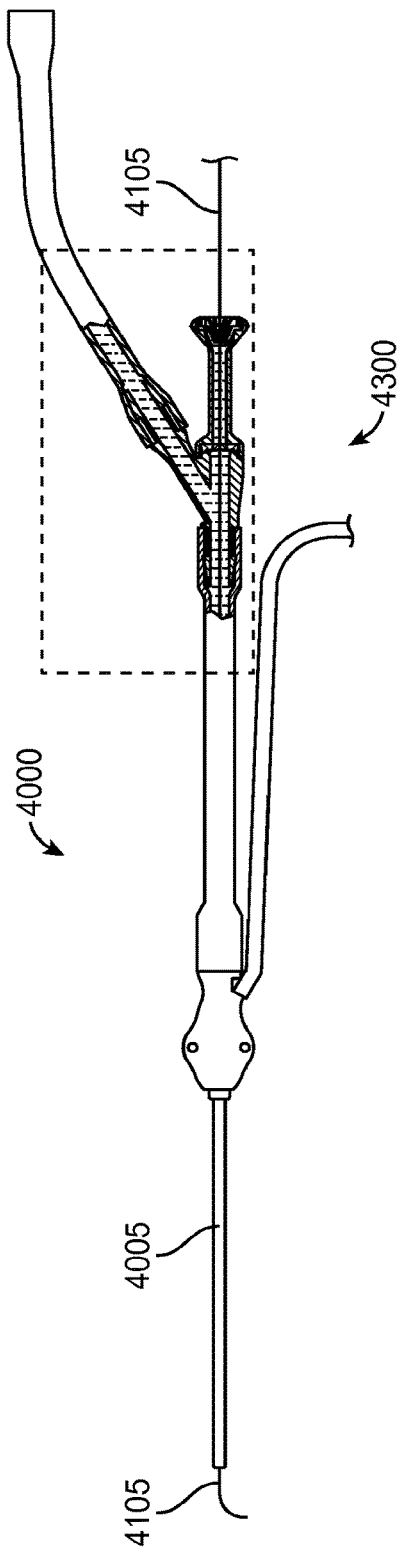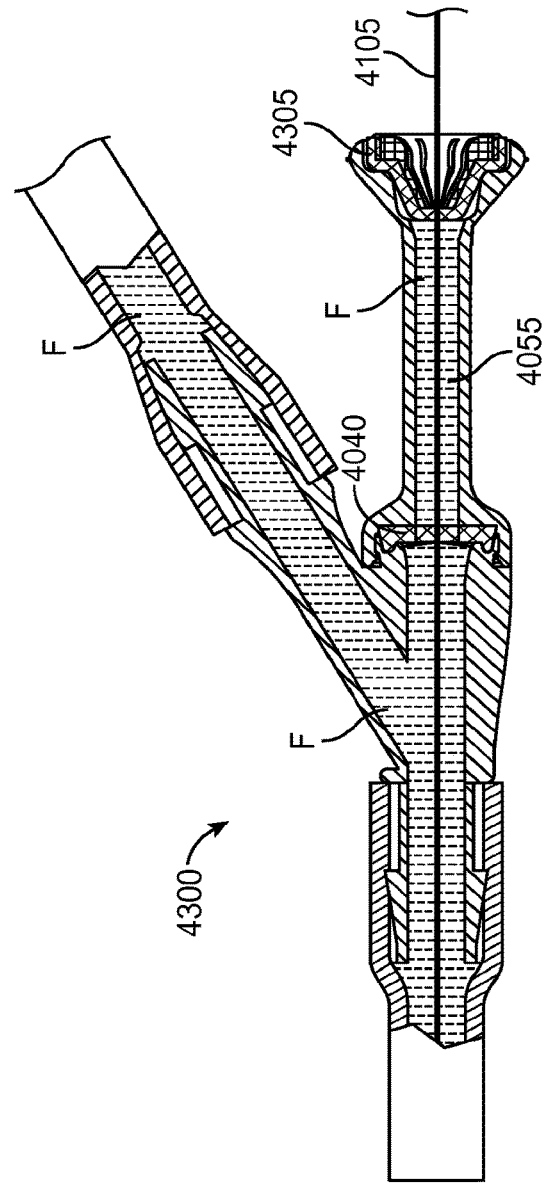
FIG. 134A
FIG. 134B

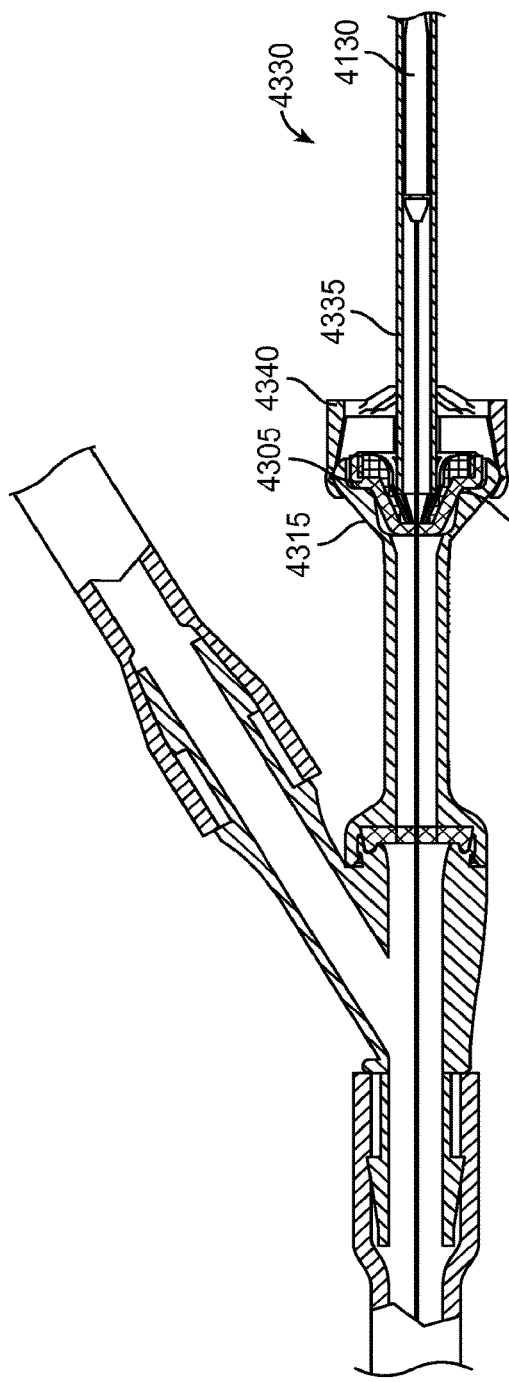
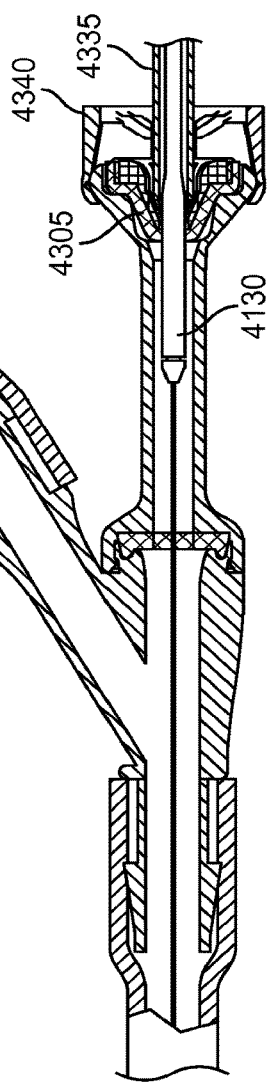
FIG. 134C
FIG. 134D

SYSTEMS AND METHODS FOR TREATING A CAROTID ARTERY

REFERENCE TO PRIORITY DOCUMENT

This application is a Continuation of U.S. National Phase patent application Ser. No. 13/816,670 entitled "SYSTEMS AND METHODS FOR TREATING ACAROTID ARTERY" filed on Apr. 11, 2013, which is a U.S. National Phase application of PCT Application No. PCT/US2011/046775, filed on Aug. 5, 2011, and claims priority of U.S. Provisional Patent Application Ser. No. 61/373,240 entitled SYSTEMS AND METHODS FOR TREATING A CAROTID ARTERY and filed on Aug. 12, 2010. The disclosure of the Provisional Patent Application is hereby incorporated by reference in its entirety.

BACKGROUND

The present disclosure relates generally to medical methods and devices. More particularly, the present disclosure relates to methods, systems and devices to treat carotid artery disease.

Carotid artery disease usually consists of deposits of plaque which narrow the internal carotid artery ICA at or near the junction between the common carotid artery and the internal carotid artery. These deposits increase the risk of embolic particles being generated and entering the cerebral vasculature, leading to neurologic consequences such as transient ischemic attacks TIA, ischemic stroke, or death. In addition, should such narrowings become severe, blood flow to the brain is inhibited with serious and sometimes fatal consequences.

Two principal therapies are employed for treating carotid artery disease. The first is carotid endarterectomy CEA, an open surgical procedure which relies on clamping the common, internal and external carotid arteries, surgically opening the carotid artery at the site of the disease (usually the carotid bifurcation where the common carotid artery divides into the internal carotid artery and external carotid artery), dissecting away and removing the plaque, and then closing the carotid artery with a suture. The risk of emboli release into the internal and external arteries is minimized. During the procedure while the artery is opened, all the carotid artery branches are clamped so particles are unable to enter the vasculature. The arteries are debrided and vigorously flushed before closing the vessels and restoring blood flow. Because the clinical consequence of emboli release into the external carotid artery is less significant, the common carotid and external carotid arteries are usually unclamped first, so that any embolic particles which remain in the bifurcation or in the common carotid artery are flushed from the common carotid artery into the external carotid artery. As a last step, the internal carotid artery clamp is opened to restore arterial flow throughout the carotid circulation.

The second procedure, carotid artery stenting CAS, relies on deployment and expansion of a metallic stent across the carotid artery stenosis, typically at or across the branch from the common carotid artery into the internal carotid artery, or entirely in the internal carotid artery, depending on the position of the disease. Usually, a self-expanding stent is introduced through a percutaneous puncture into the femoral artery in the groin and up the aortic arch into the target common carotid artery. If deemed necessary, a balloon dilatation of the stenosis is performed before the stent is inserted, to open the lesion and facilitate the placement of the stent delivery catheter and of other devices. In the majority of instances, a balloon dilatation is performed on the stenosis after the stent is placed, to optimize the luminal diameter of the stented segment. Usually, a guide wire remains in place across the stenosis during the entire intervention of the stenosis to facilitate the exchange of the various devices for pre-dilatation, stent delivery, and post-dilatation. The guide wire remains in place until a final angiogram confirms an acceptable outcome.

In carotid stenting procedures, adjunct embolic protection devices are usually used to at least partially alleviate the risk of emboli. One category of embolic protection devices is distal filters. These filters are positioned in the internal carotid artery distal to the region of stenting, prior to balloon dilatation and stent deployment. The filter is intended to capture the embolic particles to prevent passage into the cerebral vasculature. After the intervention is complete, the filter is retrieved from the vasculature.

Another category of embolic protection is flow occlusion or reversal in the internal carotid artery to prevent embolic debris entering the cerebral vasculature during the procedure. One example of flow occlusion is the method described by Henry et al. (1999) "Carotid stenting with cerebral protection: First clinical experience using the PercuSurge GuardWire System" *J. Endovasc. Surg.* 6:321-331, which is incorporated by reference herein in its entirety, whereby an occlusion balloon is placed in the ICA distal to the region of stenting and then inflated to occlude flow and prevent embolic particles from travelling to the brain. Prior to deflation of the distal occlusion balloon, a separate aspiration catheter is introduced into the treatment site to remove embolic debris.

In an alternate method proposed by Reimers and Coppi (Reimers et al. (2005) "Proximal endovascular flow blockage for cerebral protection during carotid artery stenting: Results from a prospective multicenter registry" *J. Endovasc. Ther.* 12:156-165, the common carotid artery and external carotid artery are occluded proximal to the treatment site using a dual balloon catheter inserted transfemorally to the target carotid artery. The distal-most balloon on the catheter is positioned in the external carotid artery and the proximal-most balloon is positioned in the common carotid artery. An opening in the catheter between the two balloons is used to deliver the interventional devices into the target internal carotid artery. During periods of the intervention and at the end of the intervention prior to establishing forward flow in the internal carotid artery, aspiration is performed between the two balloons to remove embolic debris.

In a reverse flow embolic protection method, an arterial access cannula is connected to a venous cannula in order to establish a reverse or retrograde flow from the internal carotid artery through the arterial cannula and away from the cerebral vasculature. Flow in the common carotid artery is occluded, typically by inflating a balloon on the distal tip of the cannula. Flow into the external carotid artery can also be occluded, typically using a balloon catheter introduced through the cannula. After such reverse or retrograde flow is established, the stenting procedure can be performed with a greatly reduced risk of emboli entering the cerebral vasculature.

All of the methods above rely on transfemoral access to position the embolic protection and interventional devices including the carotid artery stent. This access approach is well known for coronary interventions. However, in many patients, this approach to the carotid artery can involve traversing tortuous anatomy and/or diseased vessels, often leading to prolonged procedure times and can itself be a source of embolic complications. An alternate, trancervical access to the carotid arteries has been proposed for CAS procedures, either a direct, surgical access or percutaneous access to the cervical carotid artery, sometimes using distal filters. A transcervical reverse flow method utilizing a surgical approach can also be used. Such an approach eliminates complications associated with gaining transfemoral endovascular access to the common carotid artery, and allows the possibility of much shorter and potentially larger profile and/or more rigid interventional stent delivery devices. In addition, most relevant to the reverse flow methods, the shorter length reduces the flow resistance and thus increases the level of reverse flow achievable. This increased reverse flow reduces the need to occlude the external carotid artery by reducing the potential flow from the external carotid artery antegrade to the internal carotid artery during common carotid artery occlusion in the case of an external carotid artery to internal carotid artery pressure gradient. The elimination of the external carotid artery occlusion balloon greatly reduces the complexity, risk and potential complications of the procedure.

The transcervical access offers a potentially safer and more rapid access to carotid artery interventions. However, this access can have some drawbacks. One is that there is limited amount of sheath length that can be inserted. If the access sheath is inserted into the area of the bifurcation, it can interfere with deployment of the stent at the target site. In addition, the tip of the sheath can contact diseased material and cause embolic particles to be generated at the target site before any embolic protection system is employed. There is a need to limit the length of sheath insertion. However, if the access sheath is limited in the amount it can be inserted into the artery, there is a greater risk of inadvertent sheath removal during the procedure, especially as interventional devices are inserted and removed from the sheath creating forces on the sheath. Thus, there is also a need for features on the sheath which aid in prevention of over insertion and of sheath retention.

During a CAS procedure, there are periods of increased risk of release of embolic debris. These periods have been documented in studies using Transcranial Doppler (TCD) technology to measure the passage of embolic debris in the cerebral arteries during the CAS procedure. One of these periods is when a device, for example a dilatation balloon or stent delivery device, crosses the stenosis. Another example is when the post-stent dilatation balloon is deflated (presumably releasing embolic particles that have been generated during the dilatation). For reverse or static flow protocols where the common carotid artery is occluded, there is also an elevated risk of embolic particles when the common carotid artery is un-occluded. For these reasons, it would be desirable to provide methods and devices which would enable a CAS intervention with a reduction in the number of devices required to cross the stenosis. It would further be desirable to provide methods and devices which can offer augmented protection from embolic events during critical periods of intervention.

None of the cerebral protection devices and methods described offer protection after the CAS procedure. However, clinical and sub-clinical cerebral ischemia has been measured up to 48 hours post stent procedure. During CEA, flushing at the end of the procedure while blocking flow to the internal carotid artery can help reduce procedural and post-procedural emboli generation. Studies which have compared CAS and CEA procedures have documented a significantly higher level of micro-ischemic events during CAS procedures as measured by diffusion-weighted magnetic resonance imaging (DW-MRI). This suggests that the methods used to remove embolic debris and prevent embolic generation are more effective in CEA than in CAS procedures. It can be advantageous to provide a means to flush and/or aspirate the treated area during a CAS procedure to similar effect as is done in a CEA procedure, and further to isolate the internal carotid artery during removal of the common carotid artery occlusion so that any potential debris proximal to the common carotid artery occlusion or in the treatment zone is forward flushed via arterial blood flow into the external carotid artery before arterial flow is reestablished into the internal carotid artery.

SUMMARY

The disclosed methods, apparatus, and systems establish and facilitate a carotid artery stenting procedure utilizing a transcervical approach. These disclosed methods and devices include arterial access sheaths, closure devices, and interventional catheters. These methods and devices are useful for procedures utilizing any method of embolic protection, including distal filters, flow occlusion, retrograde flow, or combinations of these methods, or for procedures which do not use any method of embolic protection. Specific methods and devices for embolic protection are also described.

In particular, methods and devices are disclosed for enabling retrograde or reverse flow blood circulation in the region of the carotid artery bifurcation in order to limit or prevent the release of emboli into the cerebral vasculature, particularly into the internal carotid artery. Methods and devices are also described for enabling static flow in the region of the carotid artery bifurcation, or for reducing the level of antegrade flow in the internal carotid artery. These latter methods can be useful in providing embolic protection to patients who are not tolerant of reverse flow protocols and methods.

In one aspect, there are disclosed arterial access devices with features which are particularly useful for transcervical access to the carotid artery, including features for sheath retention and securement during the procedure and features which enable the user to introduce devices without subjecting his or her hands to the radiation from fluoroscopy.

In another aspect, there are disclosed features of the arterial access device which are particularly useful if reverse flow embolic protection methods are used, including connection to and optimization of a flow reversal circuit and automatic control of the flow circuit during contrast injection and/or active aspiration.

In another aspect, there are disclosed methods and devices for closure of the arterial access site which are particularly useful during transcervical access of the carotid artery. These method methods and devices include both suture-based and clip-based vessel closure embodiments.

In another aspect, interventional devices and methods are described for carotid intervention with features which are particularly useful for transcervical access to the carotid artery, including dimensional features and catheter flexibility and construction features. Other aspects of interventional devices and methods are also described.

In another aspect, access sheath hemostasis valves and valve connection devices are described which are particularly useful in interventional procedures where the sheath is subject to periods of negative pressure.

Methods and devices are also described for carotid artery interventional procedures, such as stenting, angioplasty, and atherectomy, performed through a transcervical or transfemoral approach into the common carotid artery, either using an open surgical technique or using a percutaneous technique, such as a modified Seldinger technique. Some of these methods and devices are particularly useful in procedures which use reverse or retrograde flow protocols.

In an aspect, there is disclosed a method for treating a carotid artery, comprising: forming a penetration in a wall of a common carotid artery; positioning an arterial access sheath through the penetration; causing retrograde blood flow from the carotid artery into the sheath; inserting a stent delivery catheter through the sheath into a treatment site comprised of the internal carotid artery or the bifurcation between the internal and external carotid arteries; and releasing the stent so that the stent expands and deploys at the treatment site. In this aspect, causing retrograde flow may comprise connecting the arterial access sheath to a passive flow reversal circuit, or it may comprise connecting the arterial access sheath to an active aspiration source such as a syringe or suction pump.

In another aspect, there is disclosed a method for treating a carotid artery, comprising: forming a penetration in a wall of a common carotid artery; positioning an arterial access sheath through the penetration wherein the sheath includes means for limiting the access distance into the artery, means for securing the sheath in position, and means for extending the proximal port of the sheath away from the radiation field; inserting a stent delivery catheter through the sheath into a treatment site comprised of the internal carotid artery or the bifurcation between the internal and external carotid arteries wherein the stent delivery device is dimensioned to be optimal for transcervical access of the carotid artery; and releasing the stent so that the stent expands and deploys at the treatment site.

In another aspect, there is disclosed a method for treating a carotid artery, comprising: inserting a guidewire into the common carotid artery through a puncture in the wall of the common carotid artery; inserting a suture delivery device over the guidewire into the common carotid artery such that a distal tip of the suture delivery device dilates an opening of an arteriotomy into the artery; drawing at least one end of a suture outside the body of the patient using the suture closure device such that the suture can be held until such time as the suture is to be tied off to create a permanent closure of the arteriotomy; removing the suture delivery device while leaving the guidewire in place; inserting an arterial access sheath over the guidewire into the common carotid artery; inserting a stent delivery catheter through the sheath into a treatment site comprised of the internal carotid artery or the bifurcation between the internal and external carotid arteries; releasing the stent so that the stent expands and deploys at the treatment site; removing the stent delivery catheter from the sheath; removing the sheath; and tying off the ends of the suture to close the arterial access site.

In another aspect, there is disclosed a method for treating a carotid artery, comprising: inserting a suture delivery device with a premounted sheath into the common carotid artery through an arteriotomy in the wall of the common carotid artery; drawing at least one end of a suture outside the body of the patient using the suture delivery device such that the suture can be held until such time as the suture is to be tied off to create a permanent closure of the arteriotomy; separating the suture from the body of the suture delivery device; advancing the premounted sheath through the arteriotomy into the common carotid artery; removing the suture delivery device; inserting a stent delivery catheter through the sheath into a treatment site comprised of the internal carotid artery or the bifurcation between the internal and external carotid arteries; releasing the stent so that the stent expands and deploys at the treatment site; removing the stent delivery catheter from the sheath; removing the sheath; and tying off the ends of the suture to close the arterial access site.

Other features and advantages should be apparent from the following description of various embodiments, which illustrate, by way of example, the principles of the invention.

BRIEF DESCRIPTION OF THE DRAWINGS

FIG. 8A illustrates an arterial access device useful in the methods and systems of the present disclosure.

FIG. 8B illustrates an additional arterial access device construction with a reduced diameter distal end.

FIGS. 9A and 9B illustrate a tube useful with the sheath of FIG. 8A.

FIG. 15A illustrates an additional arterial access device construction with an expandable occlusion element.

FIG. 15B illustrates an additional arterial access device construction with an expandable occlusion element and a reduced diameter distal end.

FIGS. 19A-19D, FIGS. 20A-20D, FIGS. 21A and 21B, FIGS. 22A-22D, and FIGS. 23A and 23B, illustrate different embodiments of a variable flow resistance component useful in the methods and systems of the present disclosure.

FIGS. 28A-28E illustrate examples of blood flow paths during a procedure for implanting a stent at the carotid bifurcation in accordance with the principles of the present disclosure.

FIGS. 51A and 51B show another embodiment of the shunt line shut off controller.

FIG. 54 shows a close-up view of a distal region of the closure device with the vessel wall locator in the deployed position.

FIGS. 57 and 58 show two embodiments of a pre-mounted sheath being advanced along the closure device after the suture has been placed across the arteriotomy.

FIGS. 86A, 86B, 87, and 88 show embodiments of a pre-tied closure device.

FIGS. 91A-91D and 92 show additional embodiments of combination closure devices.

FIGS. 93A-93C show a closure device with an embodiment of a delivery device.

FIGS. 95A-95B show a suction delivery system that is used to deliver a closure device.

FIGS. 104A-104D show a method of use of any of the catheters having a dilation balloon and stent delivery capabilities on a single system.

FIGS. 111A-111C show a catheter with a single balloon with a dual diameter.

FIGS. 115-121 show alternate embodiments of a stent delivery catheter.

FIGS. 122A-131 show various embodiments of sheath hemostasis valves

DETAILED DESCRIPTION

Figure 1:
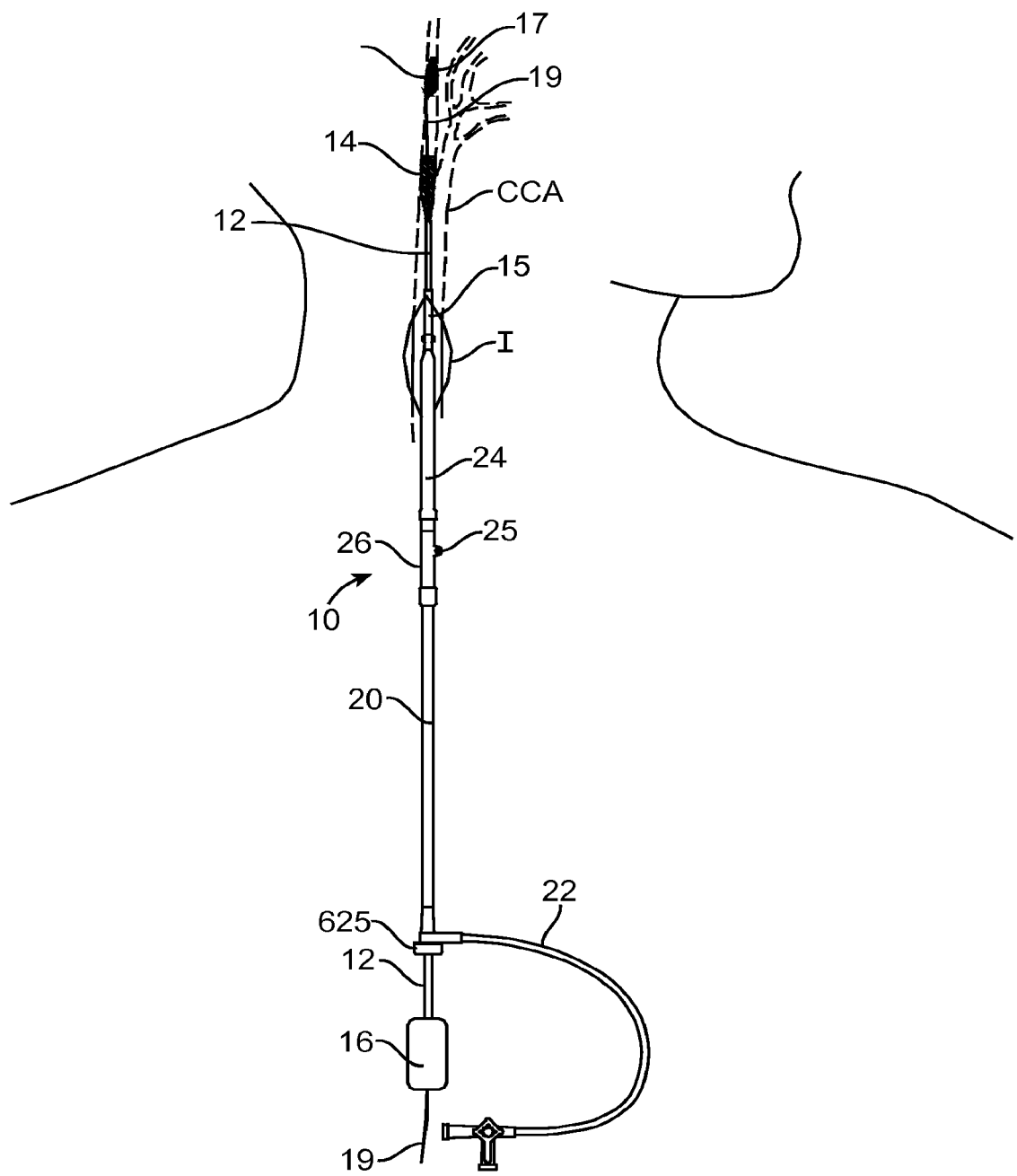
FIG. 1 is a schematic illustration of an access system and interventional device for transcervical carotid artery intervention.

FIG. 1 shows an embodiment of a transcervical access and stent delivery system that is adapted to provide transcervical access to the region of the carotid artery bifurcation and to deliver a treatment device such as a stent. The system includes an arterial access device 10 adapted to be inserted into the common carotid artery so as to provide access to the common carotid artery and associated regions via an internal lumen of the arterial access device 10. In an embodiment, transcervical access to the common carotid artery is achieved percutaneously via a puncture in the skin through which the arterial access device 10 is inserted. In an alternate embodiment, the arterial access device 110 accesses the common carotid artery CCA via a direct surgical incision I.

A stent delivery catheter 12 can be inserted into the arterial access device 10 via an access port such that a portion of the stent delivery catheter 12 can be guided through the arterial access device 10 into the common carotid artery. The distal region of the stent delivery catheter 12 can be guided into a desired location of the vasculature, such as into the internal carotid artery. A stent 14 can be located on the distal region of the stent delivery catheter 12 and can be deployed in the vasculature using an actuator 16. In an embodiment, the stent delivery catheter 12 has a working length that is particularly configured for insertion into the artery via a transcervical access location in the artery. Several embodiments of stent delivery catheters are described in detail below. An embolic protection device, such as a filter 17 or an occlusion balloon can be delivered to a location distal of the stent 14. In this regard, the filter 17 or occlusion balloon can be delivered using a separate delivery catheter or guidewire that is inserted into the artery via the arterial access device 10.

The arterial access device 10 can include a distal sheath 15, a connector 26, a proximal extension 20 that is optionally removable from the arterial access device 10. The connector may include a sheath securement member 25 such as a suture eyelet. The distal sheath 15 can be adapted to be introduced through the incision or puncture in the wall of the common carotid artery. The distal sheath 15 can have a stepped or other configuration having a reduced diameter insertion region or distal region, as described in detail below. The proximal extension 20 can have an inner lumen which is contiguous with an inner lumen of the distal sheath 15. A flush line 22 can be connected to a proximal end of the proximal extension 20. Optionally, the flush line 22 can be connected to the connector 26. The flush-line 22 can allow for the introduction of saline, contrast fluid, or the like, during a procedure.

Optionally, an external tube 24 can be provided which is coaxially received over the exterior of the distal sheath 15. The tube 24 can have a proximal end that engages a sheath connector 26. The length of the tube 24 can limit the introduction of the sheath 15 to the portion of the sheath 15 that extends distally out of the tube 24. In this regard, the tube 24 can have a dimension that is larger than the dimension of the puncture into the common carotid artery such that the tube cannot be inserted into the common carotid artery. Also, the tube 24 can engage a pre-deployed puncture closure device disposed in the carotid artery wall, if present, to permit the sheath 24 to be withdrawn without dislodging the closure device. Alternate embodiments of arterial access devices are described below for use with a retrograde flow system. The arterial access device 10 can be configured with any of the features of the arterial access devices described below.

Figure 2A:
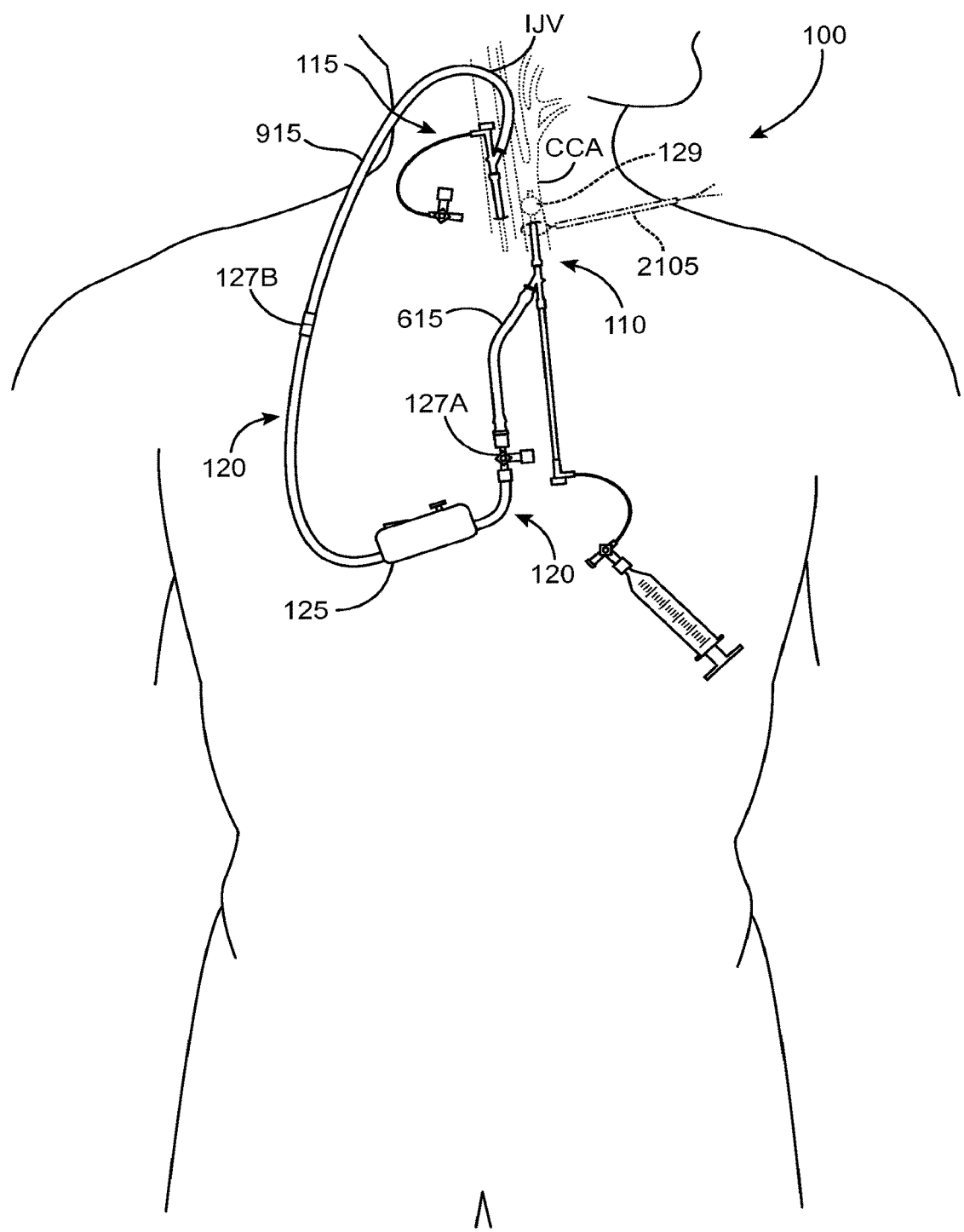
FIG. 2A is a schematic illustration of a system of devices for transcervical carotid artery stenting using a retrograde blood flow embolic protection system including a flow control assembly wherein an arterial access device accesses the common carotid artery via a transcervical approach and a venous return device communicates with the internal jugular vein.

FIG. 2A shows a first embodiment of a retrograde flow system 100 that is adapted to establish and facilitate retrograde or reverse flow blood circulation in the region of the carotid artery bifurcation in order to limit or prevent the release of emboli into the cerebral vasculature, particularly into the internal carotid artery. The system 100 interacts with the carotid artery to provide retrograde flow from the carotid artery to a venous return site, such as the internal jugular vein (or to another return site such as another large vein or an external receptacle in alternate embodiments.) The retrograde flow system 100 can include an arterial access device 110, a venous return device 115, and a shunt 120 that provides a passageway for retrograde flow from the arterial access device 110 to the venous return device 115. A flow control assembly 125 can interact with the shunt 120. The flow control assembly 125 can be adapted to regulate and/or monitor the retrograde flow from the common carotid artery to the internal jugular vein, as described in more detail below. The flow control assembly 125 can interact with the flow pathway through the shunt 120, either external to the flow path, inside the flow path, or both. The arterial access device 110 can at least partially insert into the common carotid artery CCA and the venous return device 115 at least partially inserts into a venous return site such as the internal jugular vein IJV, as described in more detail below. The arterial access device 110 and the venous return device 115 couple to the shunt 120 at connection locations 127a and 127b. When flow through the common carotid artery is blocked, the natural pressure gradient between the internal carotid artery and the venous system can cause blood to flow in a retrograde or reverse direction RG (FIG. 2A) from the cerebral vasculature through the internal carotid artery and through the shunt 120 into the venous system. The flow control assembly 125 can modulate, augment, assist, monitor, and/or otherwise regulate the retrograde blood flow.

In the embodiment of FIG. 2A, the arterial access device 110 can access the common carotid artery CCA via a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous aortic arch or common carotid artery anatomy. At least a portion of the venous return device 115 can be placed in the internal jugular vein IJV. In an embodiment, transcervical access to the common carotid artery is achieved percutaneously via an incision or puncture in the skin through which the arterial access device 110 is inserted. If an incision is used, then the incision can be about 0.5 cm in length. An occlusion element 129, such as an expandable balloon, can be used to occlude the common carotid artery CCA at a location proximal of the distal end of the arterial access device 110. The occlusion element 129 can be located on the arterial access device 110 or it can be located on a separate device. In an alternate embodiment, the arterial access device 110 accesses the common carotid artery CCA via a direct surgical transcervical approach. In the surgical approach, the common carotid artery can be occluded using a tourniquet 2105. The tourniquet 2105 is shown in phantom to indicate that it is a device that is used in the optional surgical approach.

Figure 2B:
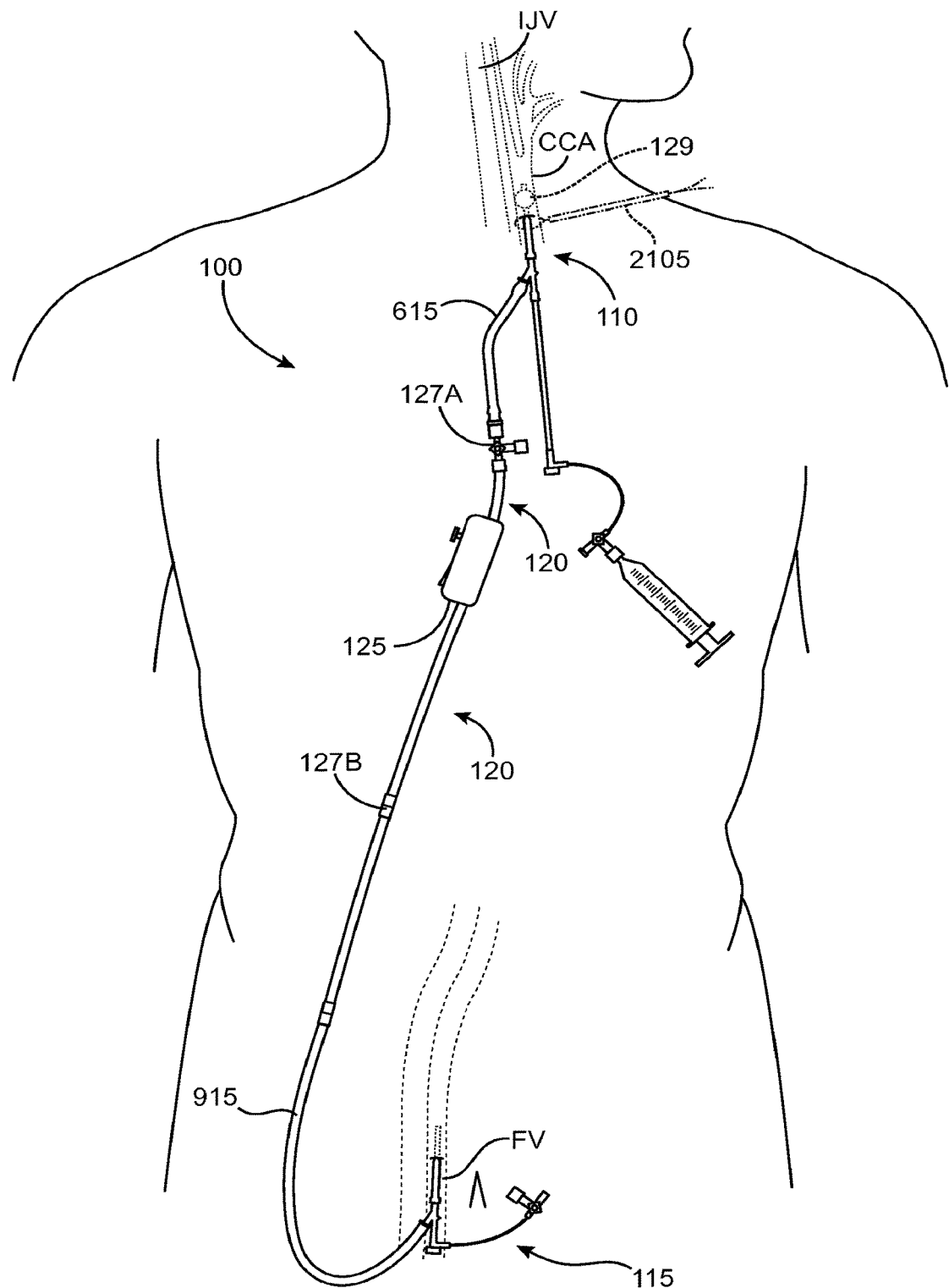
FIG. 2B is a schematic illustration of a system of devices for transcervical carotid artery stenting using a retrograde blood flow embolic protection system, system wherein an arterial access device accesses the common carotid artery via a transcervical approach and a venous return device communicates with the femoral vein.

In another embodiment, shown in FIG. 2B, the arterial access device 110 accesses the common carotid artery CCA via a transcervical approach while the venous return device 115 access a venous return site other than the jugular vein, such as a venous return site including the femoral vein FV. The venous return device 115 can be inserted into a central vein such as the femoral vein FV via a percutaneous puncture in the groin.

Figure 2C:
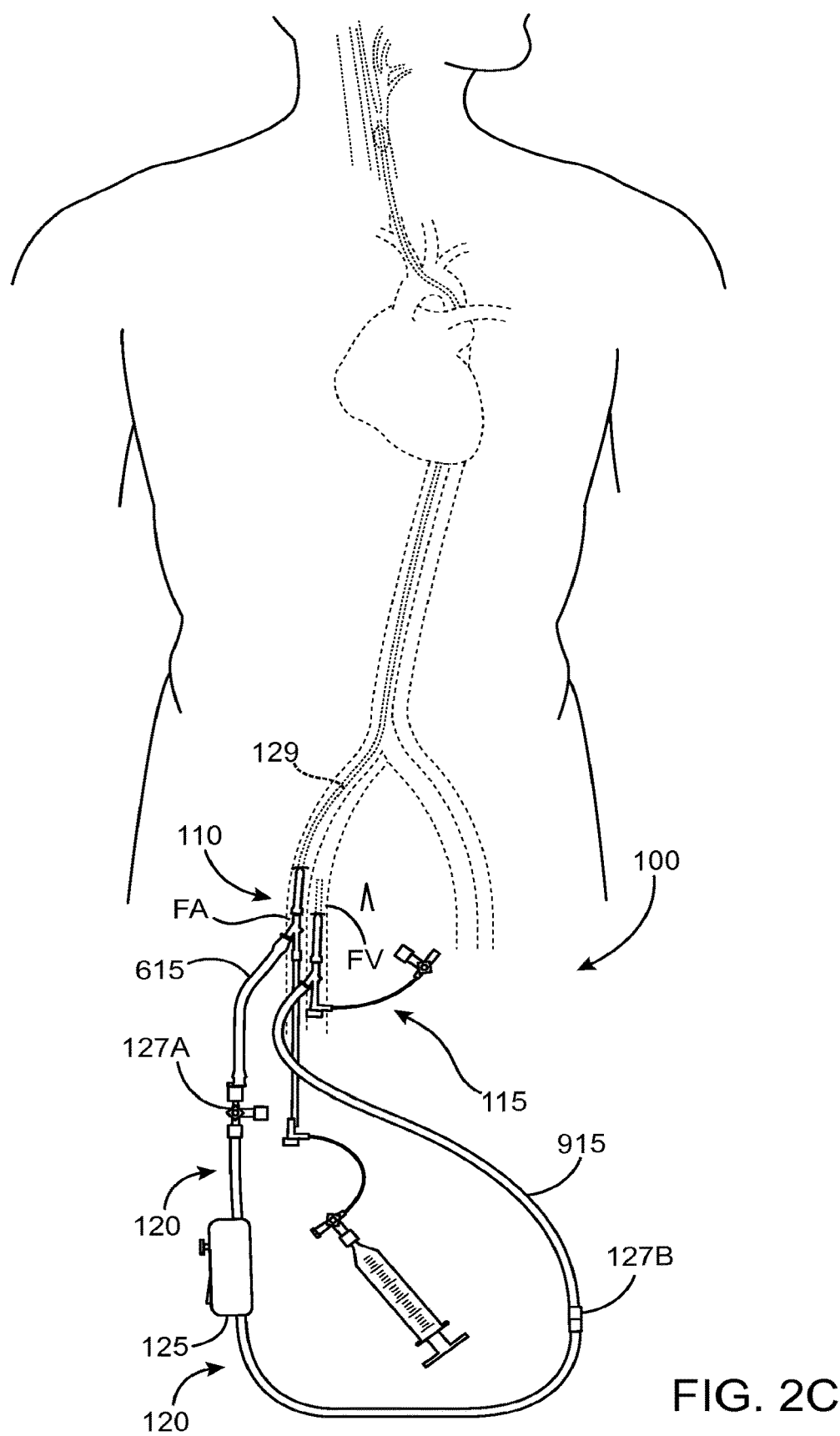
FIG. 2C is a schematic illustration of a system of devices for carotid artery stenting using a retrograde blood flow embolic protection system wherein an arterial access device accesses the common carotid artery via a transfemoral approach and a venous return device communicates with the femoral vein.

In another embodiment, shown in FIG. 2C, the arterial access device 110 accesses the common carotid artery via a femoral approach. According to the femoral approach, the arterial access device 110 approaches the CCA via a percutaneous puncture into the femoral artery FA, such as in the groin, and up the aortic arch AA into the target common carotid artery CCA. The venous return device 115 can communicate with the jugular vein JV or the femoral vein FV.

Figure 2D:
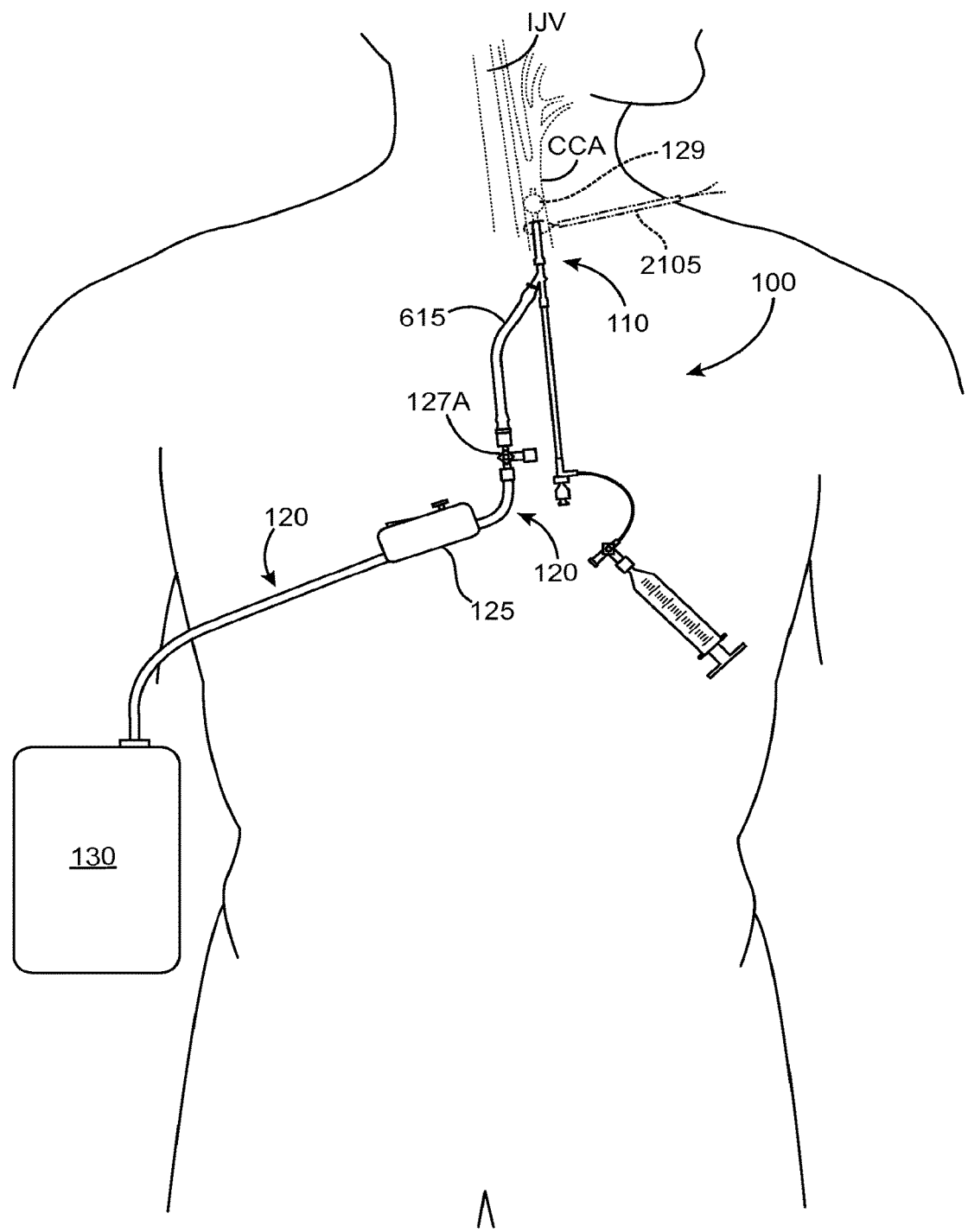
FIG. 2D is a schematic illustration of a retrograde blood flow system wherein retrograde flow is collected in an external receptacle.

FIG. 2D shows yet another embodiment, wherein the system provides retrograde flow from the carotid artery to an external receptacle 130 rather than to a venous return site. The arterial access device 110 can connect to the receptacle 130 via the shunt 120, which communicates with the flow control assembly 125. The retrograde flow of blood can be collected in the receptacle 130. If desired, the blood can be filtered and subsequently returned to the patient. The pressure of the receptacle 130 can be set at zero pressure (atmospheric pressure) or even lower by positioning the receptacle below the level of the patient, causing the blood to flow in a reverse direction from the cerebral vasculature to the receptacle 130. Optionally, to achieve or enhance reverse flow from the internal carotid artery, flow from the external carotid artery can be blocked, typically by deploying a balloon or other occlusion element in the external carotid artery just above the bifurcation with the internal carotid artery. FIG. 2D shows the arterial access device 110 arranged in a transcervical approach with the CCA although it should be appreciated that the use of the external receptacle 130 can also be used with the arterial access device 110 in a transfemoral approach.

Figure 3A:
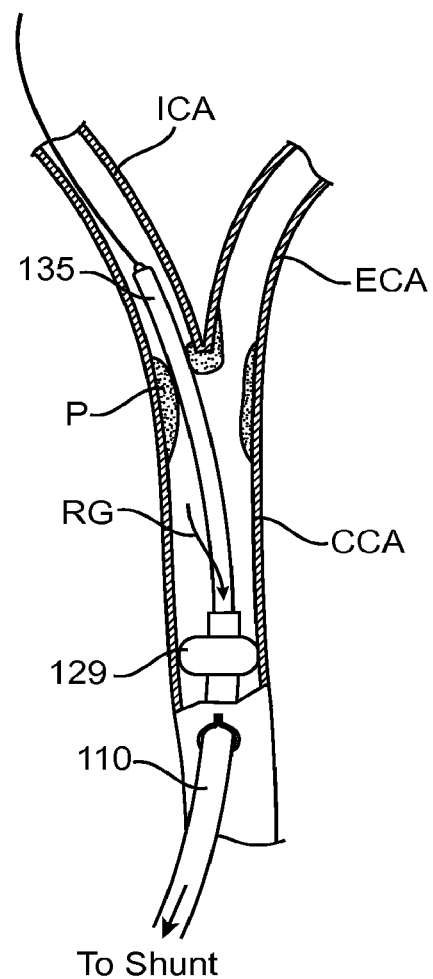
FIG. 3A is an enlarged view of the carotid artery wherein the carotid artery is occluded and connected to a reverse flow shunt via an arterial access device, and an interventional device, such as a stent delivery system or other working catheter, is introduced into the carotid artery via the arterial access device.

With reference to the enlarged view of the carotid artery in FIG. 3A, an interventional device, such as a stent delivery system 135 or other working catheter, can be introduced into the carotid artery via the arterial access device 110, as described in detail below. The stent delivery system 135 can be used to treat the plaque P such as to deploy a stent into the carotid artery. The arrow RG in FIG. 3A represents the direction of retrograde flow.

Figure 3B:
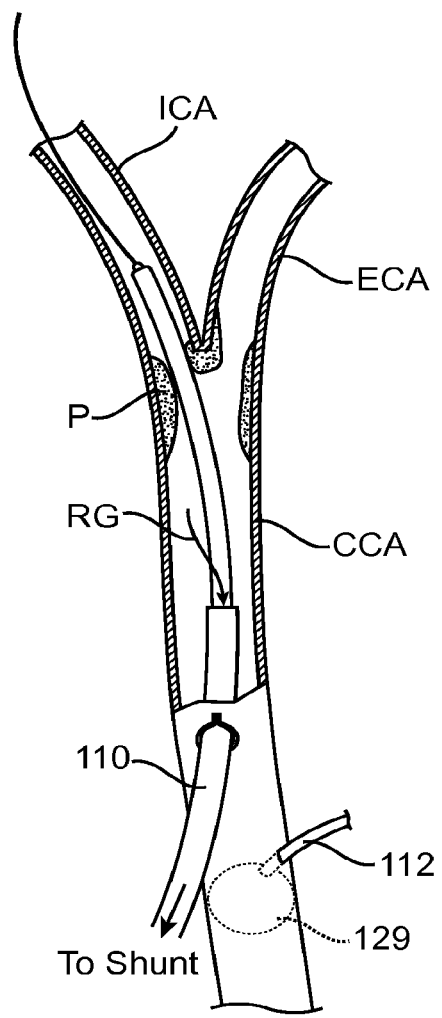
FIG. 3B is an alternate system wherein the carotid artery is connected to a reverse flow shunt and an interventional device, such as a stent delivery system or other working catheter, is introduced into the carotid artery via an arterial access device, and the carotid artery is occluded with a separate occlusion device.

FIG. 3B shows another embodiment, wherein the arterial access device 110 is used for the purpose of creating an arterial-to-venous shunt as well as introduction of at least one interventional device into the carotid artery. A separate arterial occlusion device 112 with an occlusion element 129 can be used to occlude the common carotid artery CCA at a location proximal to the distal end of the arterial access device 110.

Figure 3C:
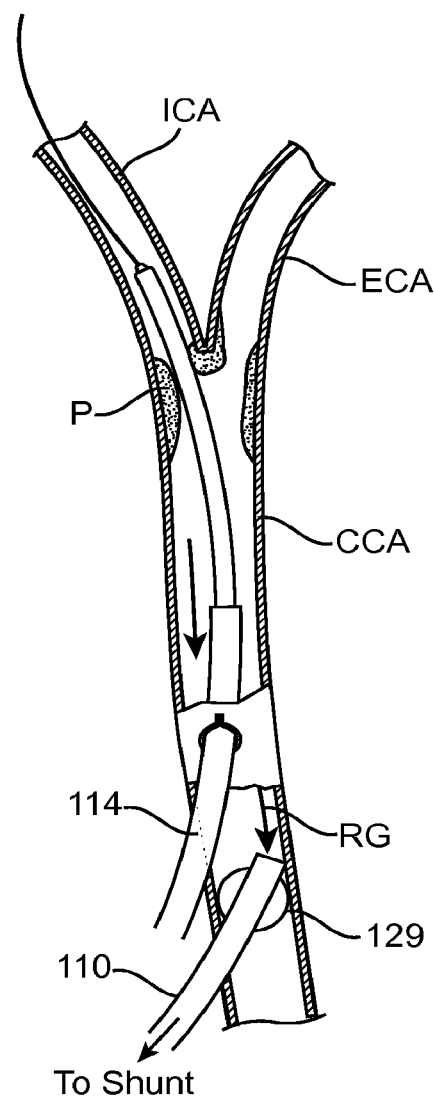
FIG. 3C is an alternate system wherein the carotid artery is occluded and the artery is connected to a reverse flow shunt via an arterial access device and the interventional device, such as a stent delivery system, is introduced into the carotid artery via an arterial introducer device.

FIG. 3C shows yet another embodiment wherein the arterial access device 110 is used for the purpose of creating an arterial-to-venous shunt as well as arterial occlusion using an occlusion element 129. A separate arterial introducer device can be used for the introduction of at least one interventional device into the carotid artery at a location distal to the arterial access device 110.

Description of Anatomy

Collateral Brain Circulation

The Circle of Willis CW is the main arterial anastomatic trunk of the brain where all major arteries which supply the brain, namely the two internal carotid arteries (ICAs) and the vertebral basilar system, connect. The blood is carried from the Circle of Willis by the anterior, middle and posterior cerebral arteries to the brain. This communication between arteries makes collateral circulation through the brain possible. Blood flow through alternate routes is made possible thereby providing a safety mechanism in case of blockage to one or more vessels providing blood to the brain. The brain can continue receiving adequate blood supply in most instances even when there is a blockage somewhere in the arterial system (e.g., when the ICA is ligated as described herein). Flow through the Circle of Willis ensures adequate cerebral blood flow by numerous pathways that redistribute blood to the deprived side.

The collateral potential of the Circle of Willis is believed to be dependent on the presence and size of its component vessels. It should be appreciated that considerable anatomic variation between individuals can exist in these vessels and that many of the involved vessels can be diseased. For example, some people lack one of the communicating arteries. If a blockage develops in such people, collateral circulation is compromised resulting in an ischemic event and potentially brain damage. In addition, an autoregulatory response to decreased perfusion pressure can include enlargement of the collateral arteries, such as the communicating arteries, in the Circle of Willis. An adjustment time is occasionally required for this compensation mechanism before collateral circulation can reach a level that supports normal function. This autoregulatory response can occur over the space of 15 to 30 seconds and can only compensate within a certain range of pressure and flow drop. Thus, it is possible for a transient ischemic attack to occur during the adjustment period. Very high retrograde flow rate for an extended period of time can lead to conditions where the patient's brain is not getting enough blood flow, leading to patient intolerance as exhibited by neurologic symptoms or in some cases a transient ischemic attack.

Figure 5:
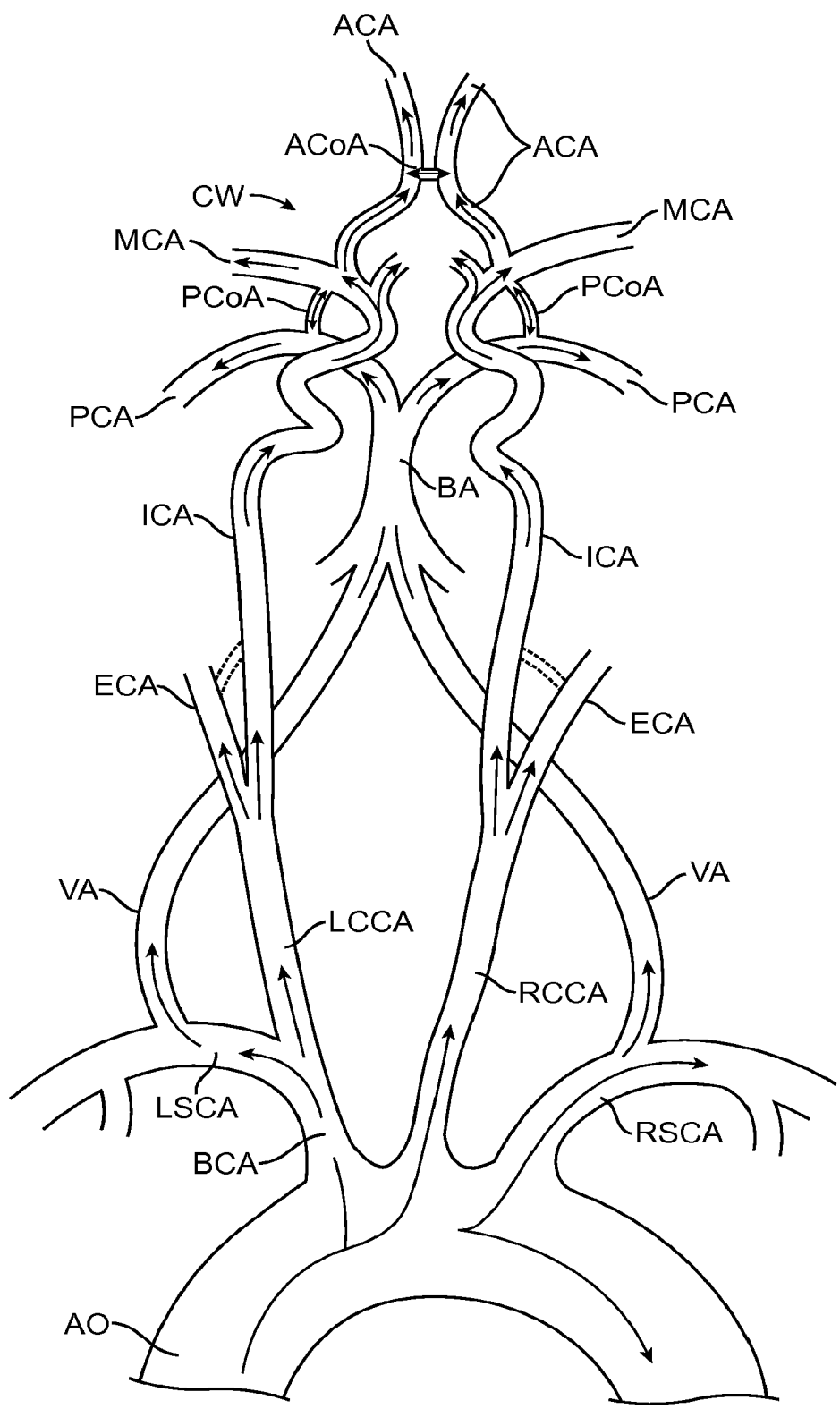
FIG. 5 illustrates a normal cerebral circulation diagram including the Circle of Willis CW.

FIG. 5 depicts a normal cerebral circulation and formation of Circle of Willis CW. The aorta AO gives rise to the brachiocephalic artery BCA, which branches into the left common carotid artery LCCA and left subclavian artery LSCA. The aorta AO further gives rise to the right common carotid artery RCCA and right subclavian artery RSCA. The left and right common carotid arteries CCA gives rise to internal carotid arteries ICA which branch into the middle cerebral arteries MCA, posterior communicating artery PcoA, and anterior cerebral artery ACA. The anterior cerebral arteries ACA deliver blood to some parts of the frontal lobe and the corpus striatum. The middle cerebral arteries MCA are large arteries that have tree-like branches that bring blood to the entire lateral aspect of each hemisphere of the brain. The left and right posterior cerebral arteries PCA arise from the basilar artery BA and deliver blood to the posterior portion of the brain (the occipital lobe).

Anteriorly, the Circle of Willis is formed by the anterior cerebral arteries ACA and the anterior communicating artery ACoA which connects the two ACAs. The two posterior communicating arteries PCoA connect the Circle of Willis to the two posterior cerebral arteries PCA, which branch from the basilar artery BA and complete the Circle posteriorly.

The common carotid artery CCA also gives rise to external carotid artery ECA, which branches extensively to supply most of the structures of the head except the brain and the contents of the orbit. The ECA also helps supply structures in the neck and face.

Carotid Artery Bifurcation

Figure 6:
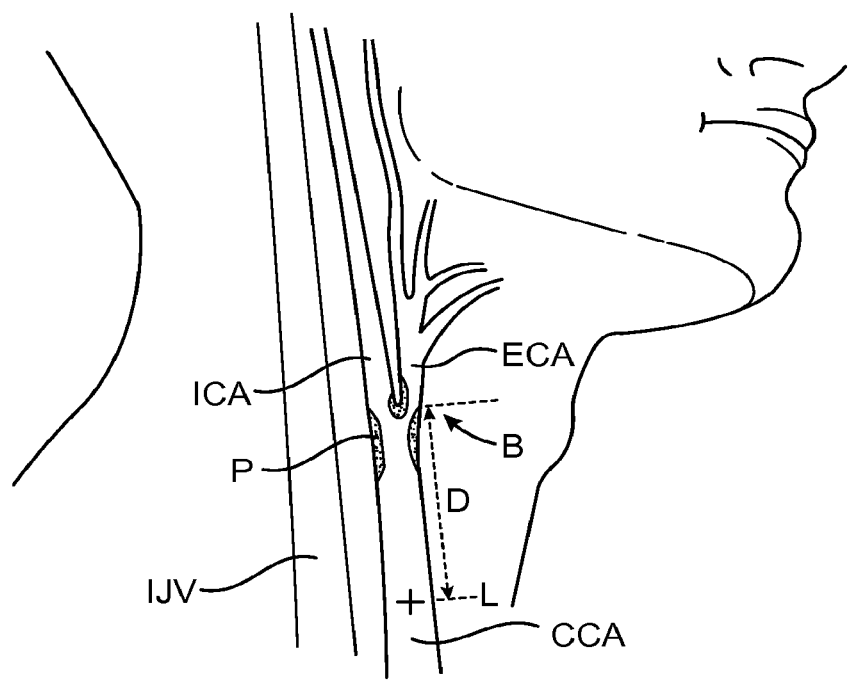
FIG. 6 illustrates the vasculature in a patient's neck, including the common carotid artery CCA, the internal carotid artery ICA, the external carotid artery ECA, and the internal jugular vein IJV.

FIG. 6 shows an enlarged view of the relevant vasculature in the patient's neck. The common carotid artery CCA branches at bifurcation B into the internal carotid artery ICA and the external carotid artery ECA. The bifurcation is located at approximately the level of the fourth cervical vertebra. FIG. 6 shows plaque P formed at the bifurcation B.

As discussed above, the arterial access device 110 can access the common carotid artery CCA via a transcervical approach. Pursuant to the transcervical approach, the arterial access device 110 can be inserted into the common carotid artery CCA at an arterial access location L, which can be, for example, a surgical incision or puncture in the wall of the common carotid artery CCA. There is typically a distance D of around 5 to 7 cm between the arterial access location L and the bifurcation B. When the arterial access device 110 is inserted into the common carotid artery CCA, it is undesirable for the distal tip of the arterial access device 110 to contact the bifurcation B as this can disrupt the plaque P and cause generation of embolic particles. In order to minimize the likelihood of the arterial access device 110 contacting the bifurcation B, in an embodiment only about 2-4 cm of the distal region of the arterial access device is inserted into the common carotid artery CCA during a procedure.

The common carotid arteries are encased on each side in a layer of fascia called the carotid sheath. This sheath also envelops the internal jugular vein and the vagus nerve. Anterior to the sheath is the sternocleidomastoid muscle. Transcervical access to the common carotid artery and internal jugular vein, either percutaneous or surgical, can be made immediately superior to the clavicle, between the two heads of the sternocleidomastoid muscle and through the carotid sheath, with care taken to avoid the vagus nerve.

At the upper end of this sheath, the common carotid artery bifurcates into the internal and external carotid arteries. The internal carotid artery continues upward without branching until it enters the skull to supply blood to the retina and brain. The external carotid artery branches to supply blood to the scalp, facial, ocular, and other superficial structures. Intertwined both anterior and posterior to the arteries are several facial and cranial nerves. Additional neck muscles can also overlay the bifurcation. These nerve and muscle structures can be dissected and pushed aside to access the carotid bifurcation during a carotid endarterectomy procedure. In some cases the carotid bifurcation is closer to the level of the mandible, where access is more challenging and with less room available to separate it from the various nerves which should be spared. In these instances, the risk of inadvertent nerve injury can increase and an open endarterectomy procedure may not be a good option.

Detailed Description of Transcervical Arterial Access Devices

Figure 7:
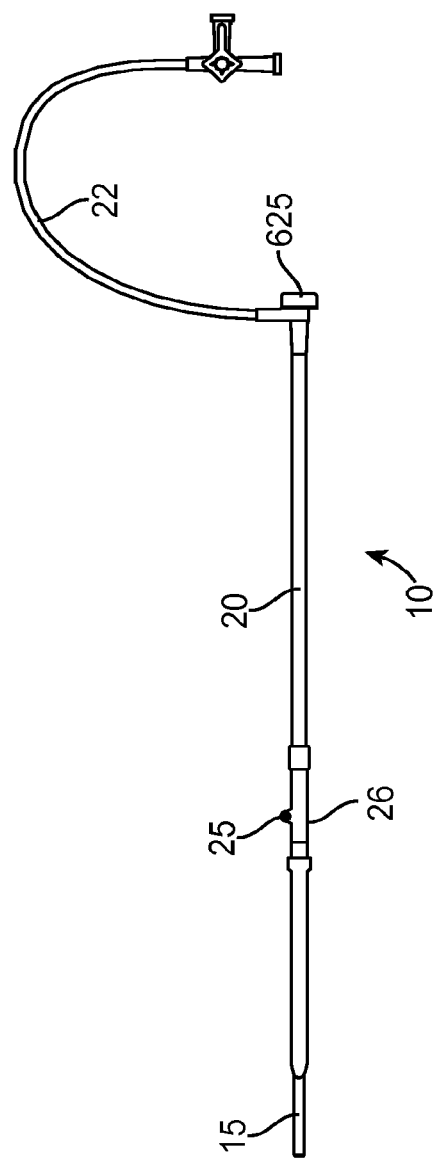
FIG. 7 illustrates an arterial access device useful in the methods and systems of the present disclosure.

FIG. 7 shows the arterial access device 10 of FIG. 1. As mentioned, the arterial access device 10 can include a distal sheath 15, a connector 26, a proximal extension 20 that is optionally removable from the arterial access device 10, and a hemostasis valve 625. The connector 26 can include a suture eyelet 25 that can be used to suture the arterial access device 10 to the patient's skin. If the proximal extension 20 is removable, there may be a second hemostasis valve located between the connector 26 and the proximal extension 20, to maintain hemostasis of the sheath upon removal of the proximal extension 20. The flush line 22 can be connected to a proximal end of the proximal extension 20, as shown, or to the connector 26, or two flush lines connected at both locations. The flush-line 22 allows for the introduction of saline, contrast fluid, or the like, during a procedure. As mentioned, an external tube 24 can be coaxially received over the exterior of the distal sheath 15. As mentioned, the arterial access device 10 can include any of the features of the other embodiments of the arterial access devices described below.

FIG. 8A shows an embodiment of the arterial access device 110 of FIG. 2A, which can include a distal sheath 605, a proximal extension 610, a hemostasis valve 625, a flow line 615 and an adaptor or Y-connector 620 for connecting the arterial access device to a flow reverse circuit (see below). For any of the embodiments of the arterial access device, the distal sheath 605 is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter can be in the range from 7 Fr (1 Fr=0.33 mm) to 10 Fr, usually being 8 Fr. Particularly when the sheath is being introduced through the transcervical approach, above the clavicle but below the carotid bifurcation, it is desirable that the sheath 605 be highly flexible while retaining hoop strength to resist kinking and buckling. Thus, the distal sheath 605 can be circumferentially reinforced, such as by braid, helical ribbon, helical wire, or the like.

The distal sheath 605 can have a stepped or other configuration having a reduced diameter insertion region or distal region 630, as shown in FIG. 8B, which shows an enlarged view of the distal region 630 of the sheath 605. The distal region 630 of the sheath can be sized for insertion into the carotid artery, typically having an inner diameter in the range from 2.16 mm (0.085 inch) to 2.92 mm (0.115 inch) with the remaining proximal region of the sheath having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B. Moreover, the reduced diameter section 630 also permits a reduction in size of the arteriotomy for introducing the sheath 605 into the artery while having a minimal impact in the level of flow resistance.

With reference again to FIG. 8A, the proximal extension 610 can have an inner lumen which is contiguous with an inner lumen of the sheath 605. The lumens can be joined by the Y-connector 620 which can also connect a lumen of the flow line 615 to the sheath. In the assembled system, the flow line 615 can connect to and form a first leg of the retrograde shunt 120 (FIG. 1). The proximal extension 610 can have a length sufficient to space the hemostasis valve 625 well away from the Y-connector 620, which is adjacent to the percutaneous or surgical insertion site. By spacing the hemostasis valve 625 away from a percutaneous insertion site, the physician can introduce a stent delivery system or other working catheter into the proximal extension 610 and sheath 605 while staying out of the fluoroscopic field when fluoroscopy is being performed.

A flush line 635 can be connected to the side of the hemostasis valve 625 and can have a stopcock 640 at its proximal or remote end. The flush-line 635 can allow for the introduction of saline, contrast fluid, or the like, during the procedures. The flush line 635 can also allow pressure monitoring during the procedure. A dilator 645 having a tapered distal end 650 can be provided to facilitate introduction of the distal sheath 605 into the common carotid artery. The dilator 645 can be introduced through the hemostasis valve 625 so that the tapered distal end 650 extends through the distal end of the sheath 605, as best seen in FIG. 9A. The dilator 645 can have a central lumen to accommodate a guide wire. Typically, the guide wire is placed first into the vessel, and the dilator/sheath combination travels over the guide wire as it is being introduced into the vessel.

Optionally, a tube 705 can be provided which is coaxially received over the exterior of the distal sheath 605, also as seen in FIG. 9A. The tube 705 has a flared proximal end 710 which engages the adapter 620 and a distal end 715. Optionally, the distal end 715 can be beveled, as shown in FIG. 9B. The tube 705 can serve at least two purposes. First, the length of the tube 705 can limit the introduction of the sheath 605 to the exposed distal portion of the sheath 605, as seen in FIG. 9A. Second, the tube 705 can engage a pre-deployed puncture closure device disposed in the carotid artery wall, if present, to permit the sheath 605 to be withdrawn without dislodging the closure device.

In an embodiment, the sheath 605 includes a retention feature that is adapted to retain the sheath within a blood vessel (such as the common carotid artery) into which the sheath 605 has been inserted. The retention feature reduces the likelihood that the sheath 605 will be inadvertently pulled out of the blood vessel. In this regard, the retention feature interacts with the blood vessel to resist and/or eliminate undesired pull-out. In addition, the retention feature can also include additional elements that interact with the vessel wall to prevent the sheath from entering too far into the vessel. The retention feature can also include sealing elements which help seal the sheath against arterial blood pressure at the puncture site.

The distal sheath 605 can be configured to establish a curved transition from a generally anterior-posterior approach over the common carotid artery to a generally axial luminal direction within the common carotid artery. The transition in direction is particularly useful when a percutaneous access is provided through the common carotid wall. While an open surgical access can allow for some distance in which to angle a straight sheath into the lumen of the common carotid artery, percutaneous access will generally be in a normal or perpendicular direction relative to the access of the lumen, and in such cases, a sheath that can flex or turn at an angle will find great use.

The sheath 605 can be formed in a variety of ways. For example, the sheath 605 can be pre-shaped to have a curve or an angle some set distance from the tip, for example 2 to 3 cm. The pre-shaped curve or angle can provide for a turn in the range from 20° to 90°, preferably from 30° to 70°. For initial introduction, the sheath 605 can be straightened with an obturator or other straight or shaped instrument such as the dilator 645 placed into its lumen. After the sheath 605 has been at least partially introduced through the percutaneous or other arterial wall penetration, the obturator can be withdrawn to allow the sheath 605 to reassume its pre-shaped configuration into the arterial lumen.

Other sheath configurations include having a deflection mechanism such that the sheath can be placed and the catheter can be deflected in situ to the desired deployment angle. In still other configurations, the catheter has a non-rigid configuration when placed into the lumen of the common carotid artery. Once in place, a pull wire or other stiffening mechanism can be deployed in order to shape and stiffen the sheath into its desired configuration. One particular example of such a mechanism is commonly known as a "shape-lock" mechanism as well described in medical and patent literature.

Another sheath configuration includes a curved dilator inserted into a straight but flexible sheath, so that the dilator and sheath are curved during insertion. The sheath can be flexible enough to conform to the anatomy after dilator removal.

In an embodiment, the sheath has built-in puncturing capability and atraumatic tip analogous to a guide wire tip. This eliminates the need for needle and wire exchange currently used for arterial access according to the micro-puncture technique, and can thus save time, reduce blood loss, and require less surgeon skill.

Figure 10:
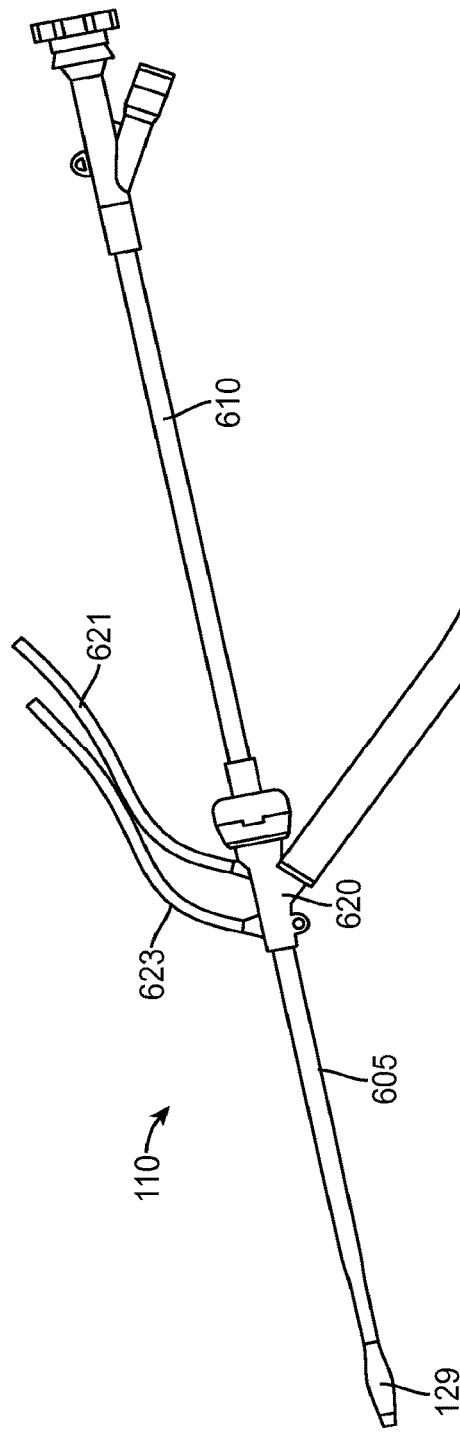
FIGS. 10 and 11 show an arterial access device embodiment with a removable proximal extension.
Figure 11:
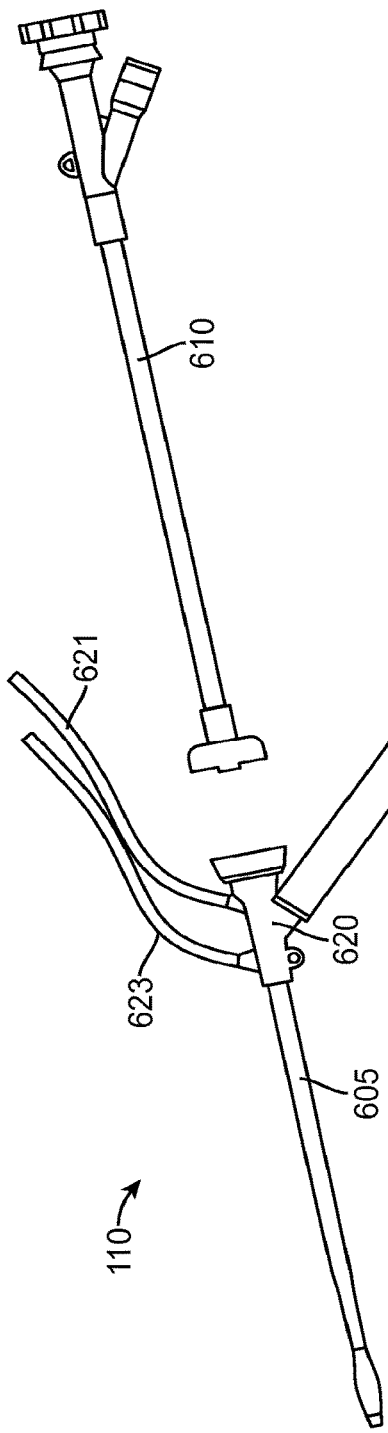

In an embodiment shown in FIGS. 10 and 11, the proximal extension 610 can be removably connected to the Y-arm connector 620 at a connection site. In this embodiment, an additional hemostasis valve 621 can be included at the connection site of the proximal extension 610 to the Y-arm connector 620, so that hemostasis is maintained when the proximal extension is not attached. FIG. 10 shows the arterial access sheath 605, with the proximal extension 610 attached to the Y-connector 620. FIG. 10 also shows an additional connection line 623 for balloon inflation of an occlusion element 129. FIG. 11 shows the proximal extension 610 removed from the Y-connector 620.) The Y-connector in these figures can be a flush, aspiration, and/or contrast line or can be a connection to a reverse flow shunt.

Figure 12:
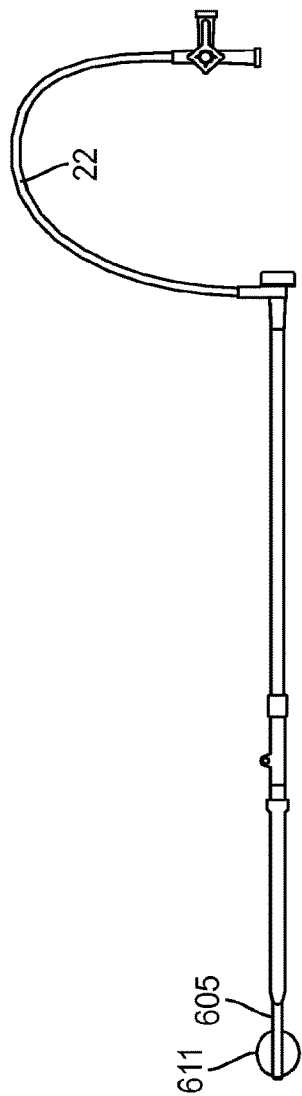
FIGS. 12, 13 and 14 show alternate embodiments of arterial access devices.

In another embodiment shown in FIG. 12, the distal sheath 605 includes an occlusion member 129 on the distal end. The occlusion member 129 can be any member that is configured to occlude a blood vessel, such as an inflatable balloon. The occlusion member 129 can allow for occlusion of the CCA and prevent antegrade flow from the CCA into the ICA and ECA during the procedure. Depending on the patient anatomy, this occlusion of the CCA can result in greatly reduced antegrade flow through the ICA from the ECA, static flow in the ICA, or slight reverse flow from the ICA into the ECA In addition, the sheath can include a flush line for attachment of an aspiration device so that active aspiration can be performed during certain, critical moments of the procedure.

Figure 13:
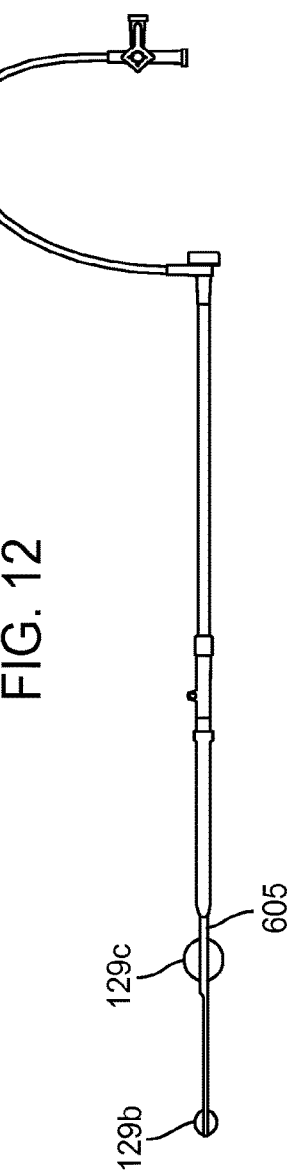

In another embodiment shown in FIG. 13, the distal sheath 605 includes two occlusion members 129a and 129b on a distal region of the sheath, wherein proximal occlusion member 129a and distal occlusion member 129b are spaced apart from one another such that one occlusion member can be positioned in the CCA and another can be positioned in the ECA. The occlusion members 129a and 129b enable occlusion of both the CCA and the ECA with a single device. The sheath can have an exit port distal to the proximal occlusion member 129a that enables a treatment device to exit the sheath and be positioned at the target site in the ICA or the carotid bifurcation.

Figure 14:
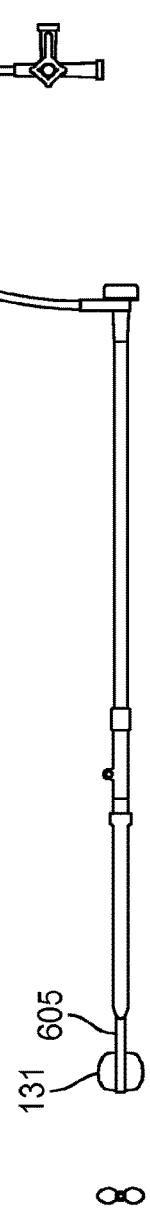

In another embodiment shown in FIG. 14, the distal sheath 605 includes a flow restriction member 131, such as an inflatable member which is sized and shaped to partially block but not totally occlude flow in the blood vessel. This can allow for the antegrade flow through the ICA to be reduced but not eliminated, and can be an alternative embolic protection method for patients who cannot tolerate reverse or static flow in the ICA and for whom distal protection methods are not possible.

Detailed Description of Retrograde Blood Flow System

As discussed, the retrograde flow system 100 can include the arterial access device 110, venous return device 115, and shunt 120 which provides a passageway for retrograde flow from the arterial access device 110 to the venous return device 115. The system also includes the flow control assembly 125, which interacts with the shunt 120 to regulate and/or monitor retrograde blood flow through the shunt 120. Embodiments of the components of the retrograde flow system 100 are described below.

Figure 4:
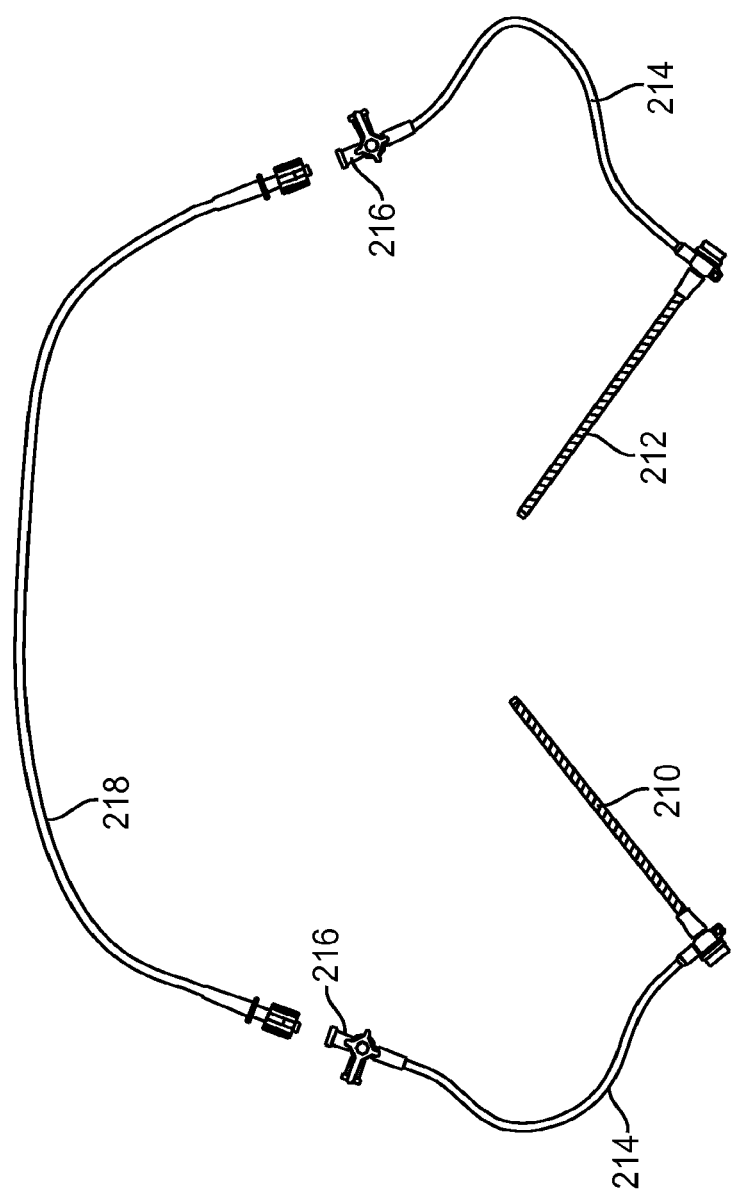
FIG. 4 illustrates a Criado flow shunt system.

It should be appreciated that the retrograde flow system can vary. For example, FIG. 4 shows a prior flow shunt system, referred to as the Criado system. The Criado system uses a flow shunt which includes an arterial sheath 210 and a venous sheath 212. Each sheath has a side arm 214, terminating in a stopcock 216. The two sheaths stopcocks are connected by a connector tubing 218, thus completing a reverse flow shunt from the arterial sheath 210 to the venous sheath 212. The arterial sheath can be placed in the common carotid artery CCA through an open surgical incision in the neck below the carotid bifurcation. Occlusion of the common carotid artery CCA can be accomplished using a temporary vessel ligation, for example using a Rummel tourniquet and umbilical tape or vessel loop. The venous return sheath 212 can be placed into the internal jugular vein IJV, such as via an open surgical incision. Retrograde flow from the internal carotid artery ICA and the external carotid artery ECA can then be established by opening the stopcock 216. The Criado protocol is an improvement over the earlier retrograde flow protocols since it eliminates the need for femoral access. This method can also utilize and arterial access sheath with the improvements described in the previous section.

Arterial Access Device

In addition to the features described in the previous section, the arterial access device can have features particularly useful in a retrograde blood flow system. As described above and shown in FIG. 8A, the arterial access device 110 can include a flow line 615 and Y-adaptor 620 to connect the sheath to a retrograde flow system. FIG. 15A shows another embodiment of the arterial access device 110. This embodiment similar is substantially the same as the embodiment shown in FIG. 8A, except that the distal sheath 605 includes an occlusion element 129 for occluding flow through, for example the common carotid artery. If the occluding element 129 is an inflatable structure such as a balloon or the like, the sheath 605 can include an inflation lumen that communicates with the occlusion element 129. The occlusion element 129 can be an inflatable balloon, but it can also be an inflatable cuff, a conical or other circumferential element which flares outwardly to engage the interior wall of the common carotid artery to block flow therepast, a membrane-covered braid, a slotted tube that radially enlarges when axially compressed, or similar structure which can be deployed by mechanical means, or the like. In the case of balloon occlusion, the balloon can be compliant, non-compliant, elastomeric, reinforced, or have a variety of other characteristics. In an embodiment, the balloon is an elastomeric balloon which is closely received over the exterior of the distal end of the sheath prior to inflation. When inflated, the elastomeric balloon can expand and conform to the inner wall of the common carotid artery. In an embodiment, the elastomeric balloon is able to expand to a diameter at least twice that of the non-deployed configuration, frequently being able to be deployed to a diameter at least three times that of the undeployed configuration, more preferably being at least four times that of the undeployed configuration, or larger.

As shown in FIG. 15B, the distal sheath 605 with the occlusion element 129 can have a stepped or other configuration having a reduced diameter distal region 630. The distal region 630 can be sized for insertion into the carotid artery with the remaining proximal region of the sheath 605 having larger outside and luminal diameters, with the inner diameter typically being in the range from 2.794 mm (0.110 inch) to 3.43 mm (0.135 inch). The larger luminal diameter of the proximal region can minimize the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B.

FIG. 3B shows an alternative embodiment, wherein the occlusion element 129 can be introduced into the carotid artery on a second sheath 112 separate from the distal sheath 605 of the arterial access device 110. The second or "proximal" sheath 112 can be adapted for insertion into the common carotid artery in a proximal or "downward" direction away from the cerebral vasculature. The second, proximal sheath can include an inflatable balloon 129 or other occlusion element, generally as described above. The distal sheath 605 of the arterial access device 110 can then be placed into the common carotid artery distal of the second, proximal sheath and generally oriented in a distal direction toward the cerebral vasculature. By using separate occlusion and access sheaths, the size of the arteriotomy needed for introducing the access sheath can be reduced.

FIG. 3C shows yet another embodiment of a two arterial sheath system, wherein the interventional devices are introduced via an introducer sheath 114 separate from the distal sheath 605 of the arterial device 110. A second or "distal" sheath 114 can be adapted for insertion into the common carotid artery distal to the arterial access device 110. As with the previous embodiment, the use of two separate access sheaths allows the size of each arteriotomy to be reduced.

Venous Return Device

Figure 16:
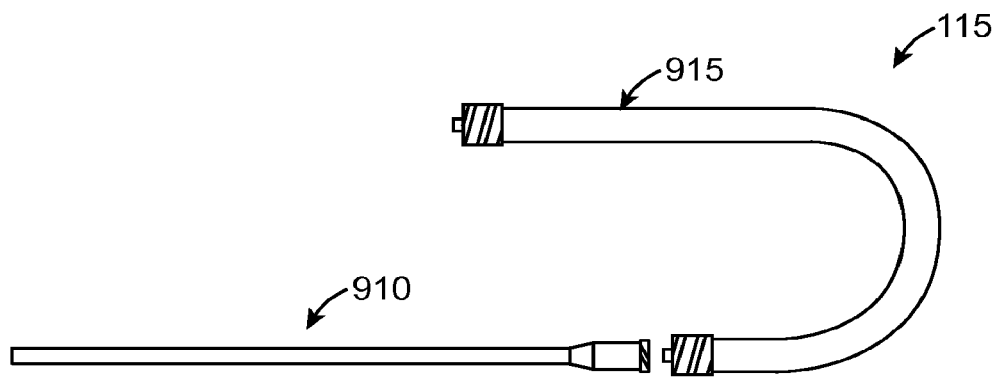
FIG. 16 illustrates a first embodiment of a venous return device useful in the methods and systems of the present disclosure.
Figure 17:
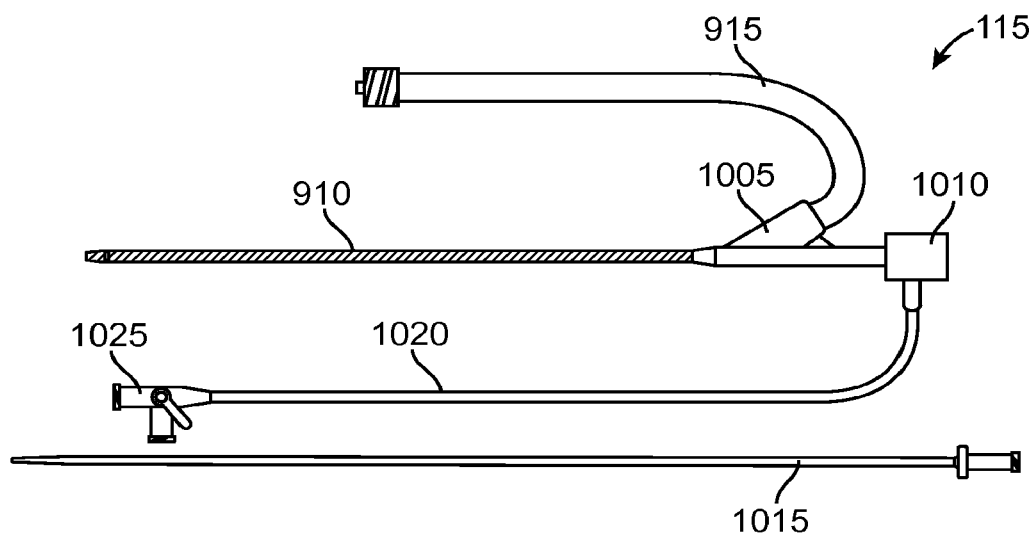
FIG. 17 illustrates an alternative venous return device useful in the methods and systems of the present disclosure.

Referring now to FIG. 16, the venous return device 115 can include a distal sheath 910 and a flow line 915, which connects to and forms a leg of the shunt 120 when the system is in use. The distal sheath 910 is adapted to be introduced through an incision or puncture into a venous return location, such as the jugular vein or femoral vein. The distal sheath 910 and flow line 915 can be permanently affixed, or can be attached using a conventional luer fitting, as shown in FIG. 16. Optionally, as shown in FIG. 17, the sheath 910 can be joined to the flow line 915 by a Y-connector 1005. The Y-connector 1005 can include a hemostasis valve 1010, permitting insertion of a dilator 1015 to facilitate introduction of the venous return device into the internal jugular vein or other vein. As with the arterial access dilator 645, the venous dilator 1015 can include a central guide wire lumen so the venous sheath and dilator combination can be placed over a guide wire. Optionally, the venous sheath 910 can include a flush line 1020 with a stopcock 1025 at its proximal or remote end.

In order to reduce the overall system flow resistance, the arterial access flow line 615 (FIG. 8A) and the venous return flow line 915, and Y-connectors 620 (FIG. 8A) and 1005, can each have a relatively large flow lumen inner diameter, typically being in the range from 2.54 mm (0.100 inch) to 5.08 mm (0.200 inch), and a relatively short length, typically being in the range from 10 cm to 20 cm. The low system flow resistance is desirable since it permits the flow to be maximized during portions of a procedure when the risk of emboli is at its greatest. The low system flow resistance also allows the use of a variable flow resistance for controlling flow in the system, as described in more detail below. The dimensions of the venous return sheath 910 can be generally the same as those described for the arterial access sheath 605 above. In the venous return sheath, an extension for the hemostasis valve 1010 is not required.

Retrograde Shunt

The shunt 120 can be formed of a single tube or multiple, connected tubes that provide fluid communication between the arterial access catheter 110 and the venous return catheter 115 to provide a pathway for retrograde blood flow therebetween. As shown in FIG. 2A, the shunt 120 connects at one end (via connector 127a) to the flow line 615 of the arterial access device 110, and at an opposite end (via connector 127b) to the flow line 915 of the venous return catheter 115.

In an embodiment, the shunt 120 can be formed of at least one tube that communicates with the flow control assembly 125. The shunt 120 can be any structure that provides a fluid pathway for blood flow. The shunt 120 can have a single lumen or it can have multiple lumens. The shunt 120 can be removably attached to the flow control assembly 125, arterial access device 110, and/or venous return device 115. Prior to use, the user can select a shunt 120 with a length that is most appropriate for use with the arterial access location and venous return location. In an embodiment, the shunt 120 can include one or more extension tubes that can be used to vary the length of the shunt 120. The extension tubes can be modularly attached to the shunt 120 to achieve a desired length. The modular aspect of the shunt 120 permits the user to lengthen the shunt 120 as needed depending on the site of venous return. For example, in some patients, the internal jugular vein IJV is small and/or tortuous. The risk of complications at this site can be higher than at some other locations, due to proximity to other anatomic structures. In addition, hematoma in the neck can lead to airway obstruction and/or cerebral vascular complications. Consequently, for such patients it can be desirable to locate the venous return site at a location other than the internal jugular vein IJV, such as the femoral vein. A femoral vein return site can be accomplished percutaneously, with lower risk of serious complication, and also offers an alternative venous access to the central vein if the internal jugular vein IJV is not available. Furthermore, the femoral venous return changes the layout of the reverse flow shunt such that the shunt controls can be located closer to the "working area" of the intervention, where the devices are being introduced and the contrast injection port is located.

In an embodiment, the shunt 120 has an internal diameter of 4.76 mm (³⁄₁₆ inch) and has a length of 40-70 cm. As mentioned, the length of the shunt can be adjusted.

Flow Control Assembly—Regulation and Monitoring of Retrograde Flow

The flow control assembly 125 can interact with the retrograde shunt 120 to regulate and/or monitor the retrograde flow rate from the common carotid artery to the venous return site, such as the internal jugular vein, or to the external receptacle 130. In this regard, the flow control assembly 125 enables the user to achieve higher maximum flow rates than existing systems and to also selectively adjust, set, or otherwise modulate the retrograde flow rate. Various mechanisms can be used to regulate the retrograde flow rate, as described more fully below. The flow control assembly 125 enables the user to configure retrograde blood flow in a manner that is suited for various treatment regimens, as described below.

In general, the ability to control the continuous retrograde flow rate allows the physician to adjust the protocol for individual patients and stages of the procedure. The retrograde blood flow rate will typically be controlled over a range from a low rate to a high rate. The high rate can be at least two-fold higher than the low rate, typically being at least three-fold higher than the low rate, and often being at least five-fold higher than the low rate, or even higher. In an embodiment, the high rate is at least three-fold higher than the low rate and in another embodiment the high rate is at least six-fold higher than the low rate. While it is generally desirable to have a high retrograde blood flow rate to maximize the extraction of emboli from the carotid arteries, the ability of patients to tolerate retrograde blood flow will vary. Thus, by having a system and protocol which allows the retrograde blood flow rate to be easily modulated, the treating physician can determine when the flow rate exceeds the tolerable level for that patient and set the reverse flow rate accordingly. For patients who cannot tolerate continuous high reverse flow rates, the physician can chose to turn on high flow only for brief, critical portions of the procedure when the risk of embolic debris is highest. At short intervals, for example between 15 seconds and 1 minute, patient tolerance limitations are usually not a factor.

In specific embodiments, the continuous retrograde blood flow rate can be controlled at a base line flow rate in the range from 10 ml/min to 200 ml/min, typically from 20 ml/min to 100 ml/min. These flow rates will be tolerable to the majority of patients. Although flow rate is maintained at the base line flow rate during most of the procedure, at times when the risk of emboli release is increased, the flow rate can be increased above the base line for a short duration in order to improve the ability to capture such emboli. For example, the retrograde blood flow rate can be increased above the base line when the stent catheter is being introduced, when the stent is being deployed, pre- and post-dilatation of the stent, removal of the common carotid artery occlusion, and the like.

The flow rate control system can be cycled between a relatively low flow rate and a relatively high flow rate in order to "flush" the carotid arteries in the region of the carotid bifurcation prior to reestablishing antegrade flow. Such cycling can be established with a high flow rate which can be approximately two- to six-fold greater than the low flow rate, typically being about three-fold greater. The cycles can typically have a length in the range from 0.5 seconds to 10 seconds, usually from 2 seconds to 5 seconds, with the total duration of the cycling being in the range from 5 seconds to 60 seconds, usually from 10 seconds to 30 seconds.

Figure 18:
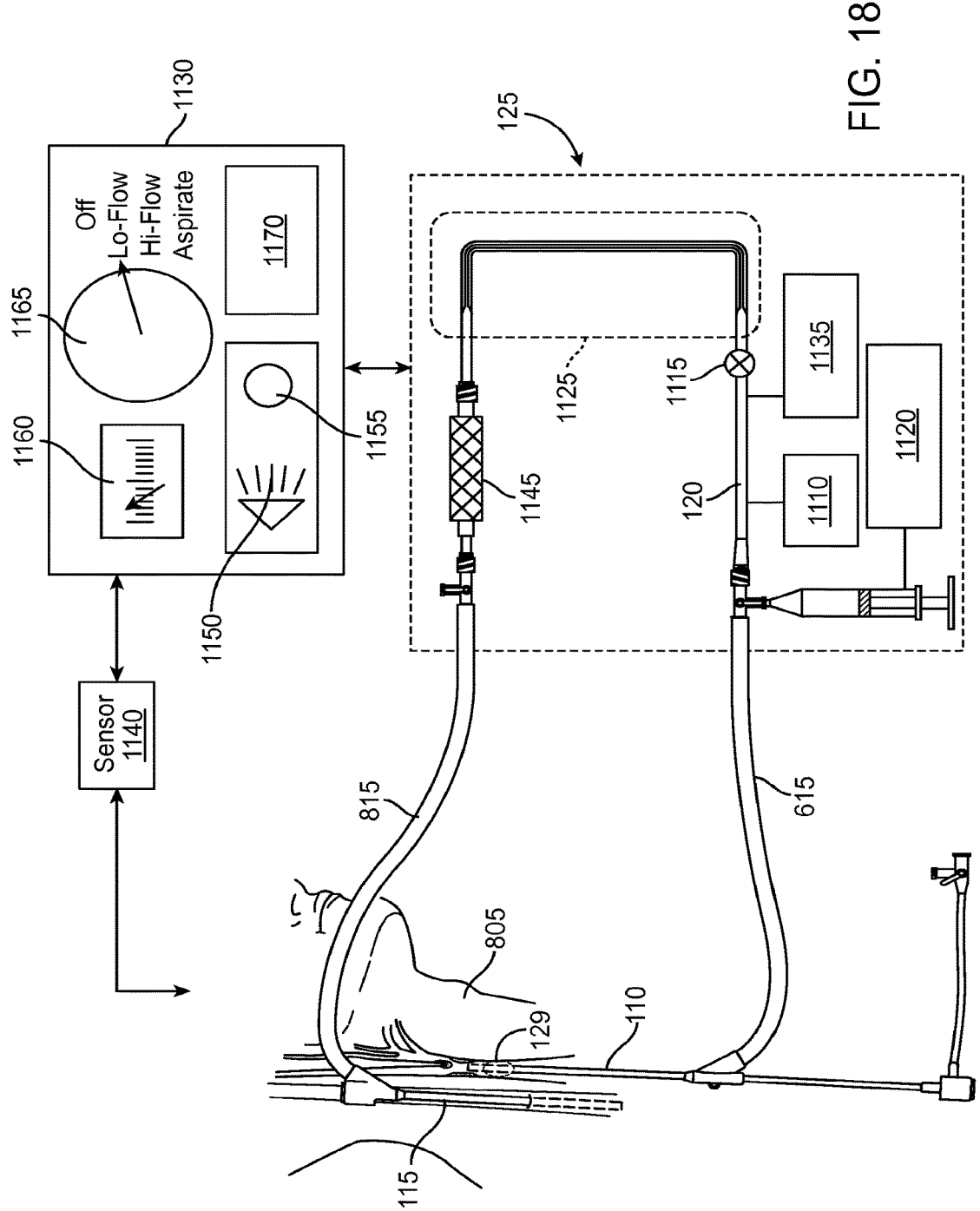
FIG. 18 illustrates the system of FIG. 2A including a flow control assembly.

FIG. 18 shows an example of the system 100 with a schematic representation of the flow control assembly 125, which is positioned along the shunt 120 such that retrograde blood flow passes through or otherwise communicates with at least a portion of the flow control assembly 125. The flow control assembly 125 can include various controllable mechanisms for regulating and/or monitoring retrograde flow. The mechanisms can include various means of controlling the retrograde flow, including one or more pumps 1110, valves 1115, syringes 1120 and/or a variable resistance component 1125. The flow control assembly 125 can be manually controlled by a user and/or automatically controlled via a controller 1130 to vary the flow through the shunt 120. For example, varying the flow resistance, the rate of retrograde blood flow through the shunt 120 can be controlled. The controller 1130, which is described in more detail below, can be integrated into the flow control assembly 125 or it can be a separate component that communicates with the components of the flow control assembly 125.

In addition, the flow control assembly 125 can include one or more flow sensors 1135 and/or anatomical data sensors 1140 (described in detail below) for sensing one or more aspects of the retrograde flow. A filter 1145 can be positioned along the shunt 120 for removing emboli before the blood is returned to the venous return site. When the filter 1145 is positioned upstream of the controller 1130, the filter 1145 can prevent emboli from entering the controller 1145 and potentially clogging the variable flow resistance component 1125. It should be appreciated that the various components of the flow control assembly 125 (including the pump 1110, valves 1115, syringes 1120, variable resistance component 1125, sensors 1135/1140, and filter 1145) can be positioned at various locations along the shunt 120 and at various upstream or downstream locations relative to one another. The components of the flow control assembly 125 are not limited to the locations shown in FIG. 18. Moreover, the flow control assembly 125 does not necessarily include all of the components but can rather include various sub-combinations of the components. For example, a syringe can optionally be used within the flow control assembly 125 for purposes of regulating flow or it can be used outside of the assembly for purposes other than flow regulation, such as to introduce fluid such as radiopaque contrast into the artery in an antegrade direction via the shunt 120.

Both the variable resistance component 1125 and the pump 1110 can be coupled to the shunt 120 to control the retrograde flow rate. The variable resistance component 1125 controls the flow resistance, while the pump 1110 provides for positive displacement of the blood through the shunt 120. Thus, the pump can be activated to drive the retrograde flow rather than relying on the perfusion stump pressures of the ECA and ICA and the venous back pressure to drive the retrograde flow. The pump 1110 can be a peristaltic tube pump or any type of pump including a positive displacement pump. The pump 1110 can be activated and deactivated (either manually or automatically via the controller 1130) to selectively achieve blood displacement through the shunt 120 and to control the flow rate through the shunt 120. Displacement of the blood through the shunt 120 can also be achieved in other manners including using the aspiration syringe 1120, or a suction source such as a VACUTAINER, VACULOK syringe, or wall suction can be used. The pump 1110 can communicate with the controller 1130.

One or more flow control valves 1115 can be positioned along the pathway of the shunt. The valve(s) can be manually actuated or automatically actuated (via the controller 1130). The flow control valves 1115 can be, for example one-way valves to prevent flow in the antegrade direction in the shunt 120, check valves, or high pressure valves which would close off the shunt 120, for example during high-pressure contrast injections (which are intended to enter the arterial vasculature in an antegrade direction).

The controller 1130 communicates with components of the system 100 including the flow control assembly 125 to enable manual and/or automatic regulation and/or monitoring of the retrograde flow through the components of the system 100 (including, for example, the shunt 120, the arterial access device 110, the venous return device 115 and the flow control assembly 125). For example, a user can actuate one or more actuators on the controller 1130 to manually control the components of the flow control assembly 125. Manual controls can include switches or dials or similar components located directly on the controller 1130 or components located remote from the controller 1130 such as a foot pedal or similar device. The controller 1130 can also automatically control the components of the system 100 without requiring input from the user. In an embodiment, the user can program software in the controller 1130 to enable such automatic control. The controller 1130 can control actuation of the mechanical portions of the flow control assembly 125. The controller 1130 can include circuitry or programming that interprets signals generated by sensors 1135/1140 such that the controller 1130 can control actuation of the flow control assembly 125 in response to such signals generated by the sensors.

The representation of the controller 1130 in FIG. 18 is merely an example. It should be appreciated that the controller 1130 can vary in appearance and structure. The controller 1130 is shown in FIG. 18 as being integrated in a single housing. This permits the user to control the flow control assembly 125 from a single location. It should be appreciated that any of the components of the controller 1130 can be separated into separate housings. Further, FIG. 18 shows the controller 1130 and flow control assembly 125 as separate housings. It should be appreciated that the controller 1130 and flow control regulator 125 can be integrated into a single housing or can be divided into multiple housings or components.

Flow State Indicator(s)

The controller 1130 can include one or more indicators that provide a visual and/or audio signal to the user regarding the state of the retrograde flow. An audio indication advantageously reminds the user of a flow state without requiring the user to visually check the flow controller 1130. The indicator(s) can include a speaker 1150 and/or a light 1155 or any other means for communicating the state of retrograde flow to the user. The controller 1130 can communicate with one or more sensors of the system to control activation of the indicator. Or, activation of the indicator can be tied directly to the user actuating one of the flow control actuators 1165. The indicator need not be a speaker or a light. The indicator can be a button or switch that visually indicates the state of the retrograde flow. For example, the button being in a certain state (such as a pressed or down state) can be a visual indication that the retrograde flow is in a high state. Or, a switch or dial pointing toward a particular labeled flow state can be a visual indication that the retrograde flow is in the labeled state.

The indicator can provide a signal indicative of one or more states of the retrograde flow. In an embodiment, the indicator identifies two discrete states: a state of "high" flow rate and a state of "low" flow rate. In another embodiment, the indicator identifies more than two flow rates, including a "high" flow rate, a "medium" flow rate, and a "low" rate. The indicator can be configured to identify any quantity of discrete states of the retrograde flow or it can identify a graduated signal that corresponds to the state of the retrograde flow. In this regard, the indicator can be a digital or analog meter 1160 that indicates a value of the retrograde flow rate, such as in ml/min or any other units.

In an embodiment, the indicator is configured to indicate to the user whether the retrograde flow rate is in a state of "high" flow rate or a "low" flow rate. For example, the indicator can illuminate in a first manner (e.g., level of brightness) and/or emit a first audio signal when the flow rate is high and then change to a second manner of illumination and/or emit a second audio signal when the flow rate is low. Or, the indicator can illuminate and/or emit an audio signal only when the flow rate is high, or only when the flow rate is low. Given that some patients can be intolerant of a high flow rate or intolerant of a high flow rate beyond an extended period of time, it can be desirable that the indicator provide notification to the user when the flow rate is in the high state. This would serve as a fail safe feature.

In another embodiment, the indicator provides a signal (audio and/or visual) when the flow rate changes state, such as when the flow rate changes from high to low and/or vice-versa. In another embodiment, the indicator provides a signal when no retrograde flow is present, such as when the shunt 120 is blocked or one of the stopcocks in the shunt 120 is closed.

Flow Rate Actuators

The controller 1130 can include one or more actuators that the user can press, switch, manipulate, or otherwise actuate to regulate the retrograde flow rate and/or to monitor the flow rate. For example, the controller 1130 can include a flow control actuator 1165 (such as one or more buttons, knobs, dials, switches, etc.) that the user can actuate to cause the controller to selectively vary an aspect of the reverse flow. For example, in the illustrated embodiment, the flow control actuator 1165 is a knob that can be turned to various discrete positions each of which corresponds to the controller 1130 causing the system 100 to achieve a particular retrograde flow state. The states include, for example, (a) OFF; (b) LO-FLOW; (c) HI-FLOW; and (d) ASPIRATE. It should be appreciated that the foregoing states are merely for example and that different states or combinations of states can be used. The controller 1130 can achieve the various retrograde flow states by interacting with one or more components of the system, including the sensor(s), valve(s), variable resistance component, and/or pump(s). It should be appreciated that the controller 1130 can also include circuitry and software that regulates the retrograde flow rate and/or monitors the flow rate such that the user need not actively actuate the controller 1130.

The OFF state corresponds to a state where there is no retrograde blood flow through the shunt 120. When the user sets the flow control actuator 1165 to OFF, the controller 1130 causes the retrograde flow to cease, such as by shutting off valves or closing a stop cock in the shunt 120. The LO-FLOW and HI-FLOW states correspond to a low retrograde flow rate and a high retrograde flow rate, respectively. When the user sets the flow control actuator 1165 to LO- FLOW or HI-FLOW, the controller 1130 interacts with components of the flow control regulator 125 including pump(s) 1110, valve(s) 1115 and/or variable resistance component 1125 to increase or decrease the flow rate accordingly. Finally, the ASPIRATE state corresponds to opening the circuit to a suction source, for example a VACUTAINER or suction unit, if active retrograde flow is desired.

The system can be used to vary the blood flow between various states including an active state, a passive state, an aspiration state, and an off state. The active state can correspond to the system using a means that actively drives retrograde blood flow. Such active means can include, for example, a pump, syringe, vacuum source, etc. The passive state can correspond to when retrograde blood flow is driven by the perfusion stump pressures of the ECA and ICA and possibly the venous pressure. The aspiration state corresponds to the system using a suction source, for example a VACUTAINER or suction unit, to drive retrograde blood flow. The off state can correspond to the system having zero retrograde blood flow such as the result of closing a stopcock or valve. The low and high flow rates can be either passive or active flow states. In an embodiment, the particular value (such as in ml/min) of either the low flow rate and/or the high flow rate can be predetermined and/or pre-programmed into the controller such that the user does not actually set or input the value. Rather, the user selects "high flow" and/or "low flow" (such as by pressing an actuator such as a button on the controller 1130) and the controller 1130 interacts with one or more of the components of the flow control assembly 125 to cause the flow rate to achieve the predetermined high or low flow rate value. In another embodiment, the user sets or inputs a value for low flow rate and/or high flow rate such as into the controller. In another embodiment, the low flow rate and/or high flow rate is not actually set. Rather, external data (such as data from the anatomical data sensor 1140) is used as the basis for affects the flow rate.

The flow control actuator 1165 can be multiple actuators, for example one actuator, such as a button or switch, to switch state from LO-FLOW to HI-FLOW and another to close the flow loop to OFF, for example during a contrast injection where the contrast is directed antegrade into the carotid artery. In an embodiment, the flow control actuator 1165 can include multiple actuators. For example, one actuator can be operated to switch flow rate from low to high, another actuator can be operated to temporarily stop flow, and a third actuator (such as a stopcock) can be operated for aspiration using a syringe. In another example, one actuator is operated to switch to LO-FLOW and another actuator is operated to switch to HI-FLOW. Or, the flow control actuator 1165 can include multiple actuators to switch states from LO-FLOW to HI-FLOW and additional actuators for fine-tuning flow rate within the high flow state and low flow state. Upon switching between LO-FLOW and HI-FLOW, these additional actuators can be used to fine-tune the flow rates within those states. Thus, it should be appreciated that within each state (i.e. high flow state and low flow states) a variety of flow rates can be dialed in and fine-tuned. A wide variety of actuators can be used to achieve control over the state of flow.

The controller 1130 or individual components of the controller 1130 can be located at various positions relative to the patient and/or relative to the other components of the system 100. For example, the flow control actuator 1165 can be located near the hemostasis valve where interventional tools are introduced into the patient in order to facilitate access to the flow control actuator 1165 during introduction of the tools. The location can vary, for example, based on whether a transfemoral or a transcervical approach is used, as shown in FIGS. 2A-C. The controller 1130 can have a wireless connection to the remainder of the system 100 and/or a wired connection of adjustable length to permit remote control of the system 100. The controller 1130 can have a wireless connection with the flow control regulator 125 and/or a wired connection of adjustable length to permit remote control of the flow control regulator 125. The controller 1130 can also be integrated in the flow control regulator 125. Where the controller 1130 is mechanically connected to the components of the flow control assembly 125, a tether with mechanical actuation capabilities can connect the controller 1130 to one or more of the components. In an embodiment, the controller 1130 can be positioned a sufficient distance from the system 100 to permit positioning the controller 1130 outside of a radiation field when fluoroscopy is in use.

The controller 1130 and any of its components can interact with other components of the system (such as the pump(s), sensor(s), shunt, etc) in various manners. For example, any of a variety of mechanical connections can be used to enable communication between the controller 1130 and the system components. Alternately, the controller 1130 can communicate electronically or magnetically with the system components. Electro-mechanical connections can also be used. The controller 1130 can be equipped with control software that enables the controller 1130 to implement control functions with the system components. The controller 1130 itself can be a mechanical, electrical or electro-mechanical device. The controller 1130 can be mechanically, pneumatically, or hydraulically actuated or electromechanically actuated (for example in the case of solenoid actuation of flow control state). The controller 1130 can include a computer, computer processor, and memory, as well as data storage capabilities.

Sensor(s)

As mentioned, the flow control assembly 125 can include or interact with one or more sensors, which communicate with the system 100 and/or communicate with the patient's anatomy. Each of the sensors can be adapted to respond to a physical stimulus (including, for example, heat, light, sound, pressure, magnetism, motion, etc.) and to transmit a resulting signal for measurement or display or for operating the controller 1130. In an embodiment, the flow sensor 1135 interacts with the shunt 120 to sense an aspect of the flow through the shunt 120, such as flow velocity or volumetric rate of blood flow. The flow sensor 1135 can be directly coupled to a display that directly displays the value of the volumetric flow rate or the flow velocity. Or the flow sensor 1135 can feed data to the controller 1130 for display of the volumetric flow rate or the flow velocity.

The type of flow sensor 1135 can vary. The flow sensor 1135 can be a mechanical device, such as a paddle wheel, flapper valve, rolling ball, or any mechanical component that responds to the flow through the shunt 120. Movement of the mechanical device in response to flow through the shunt 120 can serve as a visual indication of fluid flow and can also be calibrated to a scale as a visual indication of fluid flow rate. The mechanical device can be coupled to an electrical component. For example, a paddle wheel can be positioned in the shunt 120 such that fluid flow causes the paddle wheel to rotate, with greater rate of fluid flow causing a greater speed of rotation of the paddle wheel. The paddle wheel can be coupled magnetically to a Hall-effect sensor to detect the speed of rotation, which is indicative of the fluid flow rate through the shunt 120.

In an embodiment, the flow sensor 1135 is an ultrasonic or electromagnetic flow meter, which allows for blood flow measurement without contacting the blood through the wall of the shunt 120. An ultrasonic or electromagnetic flow meter can be configured such that it does not have to contact the internal lumen of the shunt 120. In an embodiment, the flow sensor 1135 at least partially includes a Doppler flow meter, such as a transonic flow meter, that measures fluid flow through the shunt 120. It should be appreciated that any of a wide variety of sensor types can be used including an ultrasound flow meter and transducer. Moreover, the system can include multiple sensors.

The system 100 is not limited to using a flow sensor 1135 that is positioned in the shunt 120 or a sensor that interacts with the venous return device 115 or the arterial access device 110. For example, an anatomical data sensor 1140 can communicate with or otherwise interact with the patient's anatomy such as the patient's neurological anatomy. In this manner, the anatomical data sensor 1140 can sense a measurable anatomical aspect that is directly or indirectly related to the rate of retrograde flow from the carotid artery. For example, the anatomical data sensor 1140 can measure blood flow conditions in the brain, for example the flow velocity in the middle cerebral artery, and communicate such conditions to a display and/or to the controller 1130 for adjustment of the retrograde flow rate based on predetermined criteria. In an embodiment, the anatomical data sensor 1140 includes a transcranial Doppler ultrasonography (TCD), which is an ultrasound test that uses reflected sound waves to evaluate blood as it flows through the brain. Use of TCD results in a TCD signal that can be communicated to the controller 1130 for controlling the retrograde flow rate to achieve or maintain a desired TCD profile. The anatomical data sensor 1140 can be based on any physiological measurement, including reverse flow rate, blood flow through the middle cerebral artery, TCD signals of embolic particles, or other neuromonitoring signals.

In an embodiment, the system 100 includes a closed-loop control system. In the closed-loop control system, one or more of the sensors (such as the flow sensor 1135 or the anatomical data sensor 1140) senses or monitors a predetermined aspect of the system 100 or the anatomy (such as, for example, reverse flow rate and/or neuromonitoring signal). The sensor(s) can feed relevant data to the controller 1130, which continuously adjusts an aspect of the system as necessary to maintain a desired retrograde flow rate. The sensors can communicate feedback on how the system 100 is operating to the controller 1130 so that the controller 1130 can translate that data and actuate the components of the flow control regulator 125 to dynamically compensate for disturbances to the retrograde flow rate. For example, the controller 1130 can include software that causes the controller 1130 to signal the components of the flow control assembly 125 to adjust the flow rate such that the flow rate is maintained at a constant state despite differing blood pressures from the patient. In this embodiment, the system 100 need not rely on the user to determine when, how long, and/or what value to set the reverse flow rate in either a high or low state. Rather, software in the controller 1130 can govern such factors. In the closed loop system, the controller 1130 can control the components of the flow control assembly 125 to establish the level or state of retrograde flow (either analog level or discreet state such as high, low, baseline, medium, etc.) based on the retrograde flow rate sensed by the sensor 1135.

In an embodiment, the anatomical data sensor 1140 (which measures a physiologic measurement in the patient) communicates a signal to the controller 1130, which adjusts the flow rate based on the signal. For example the physiological measurement can be based on flow velocity through the MCA, TCD signal, or some other cerebral vascular signal. In the case of the TCD signal, TCD can be used to monitor cerebral flow changes and to detect microemboli. The controller 1130 can adjust the flow rate to maintain the TCD signal within a desired profile. For example, the TCD signal can indicate the presence of microemboli ("TCD hits") and the controller 1130 can adjust the retrograde flow rate to maintain the TCD hits below a threshold value of hits. (See, Ribo, et al., "Transcranial Doppler Monitoring of Transcervical Carotid Stenting with Flow Reversal Protection: A Novel Carotid Revascularization Technique", *Stroke* 2006, 37, 2846-2849; Stejskal, et al., "Experience of 500 Cases of Neurophysiological Monitoring in Carotid Endarterectomy", *Acta Neurochir*, 2007, 149:681-689, which are incorporated by reference in their entirety.

In the case of the MCA flow, the controller 1130 can set the retrograde flow rate at the "maximum" flow rate that is tolerated by the patient, as assessed by perfusion to the brain. The controller 1130 can thus control the reverse flow rate to optimize the level of protection for the patient without relying on the user to intercede. In another embodiment, the feedback is based on a state of the devices in the system 100 or the interventional tools being used. For example, a sensor can notify the controller 1130 when the system 100 is in a high risk state, such as when an interventional catheter is positioned in the sheath 605. The controller 1130 then adjusts the flow rate to compensate for such a state.

The controller 1130 can be used to selectively augment the retrograde flow in a variety of manners. For example, it has been observed that greater reverse flow rates can cause a resultant greater drop in blood flow to the brain, most importantly the ipsilateral MCA, which may not be compensated enough with collateral flow from the Circle of Willis. Thus a higher reverse flow rate for an extended period of time can lead to conditions where the patient's brain is not getting enough blood flow, leading to patient intolerance as exhibited by neurologic symptoms. Studies show that MCA blood velocity less than 10 cm/sec is a threshold value below which patient is at risk for neurological blood deficit. There are other markers for monitoring adequate perfusion to the brains, such as EEG signals. However, a high flow rate can be tolerated even up to a complete stoppage of MCA flow for a short period, up to about 15 seconds to 1 minute.

Thus, the controller 1130 can optimize embolic debris capture by automatically increasing the reverse flow only during limited time periods which correspond to periods of heightened risk of emboli generation during a procedure. These periods of heightened risk include the period of time while an interventional device (such as a dilatation balloon for pre or post stenting dilatation or a stent delivery device) crosses the plaque P. Another period is during an interventional maneuver such as deployment of the stent or inflation and deflation of the balloon pre- or post-dilatation. A third period is during injection of contrast for angiographic imaging of treatment area. During lower risk periods, the controller can cause the reverse flow rate to revert to a lower, baseline level. This lower level can correspond to a low reverse flow rate in the ICA, or even slight antegrade flow in those patients with a high ECA to ICA perfusion pressure ratio.

In a flow regulation system where the user manually sets the state of flow, there is risk that the user may not pay attention to the state of retrograde flow (high or low) and accidentally keep the circuit on high flow. This can then lead to adverse patient reactions. In an embodiment, as a safety mechanism, the default flow rate is the low flow rate. This serves as a failsafe measure for patients that are intolerant of a high flow rate. In this regard, the controller 1130 can be biased toward the default rate such that the controller causes the system to revert to the low flow rate after passage of a predetermined period of time of high flow rate. The bias toward low flow rate can be achieved via electronics or software, or it can be achieved using mechanical components, or a combination thereof. In an embodiment, the flow control actuator 1165 of the controller 1130 and/or valve(s) 1115 and/or pump(s) 1110 of the flow control regulator 125 are spring loaded toward a state that achieves a low flow rate. The controller 1130 is configured such that the user can over-ride the controller 1130 such as to manually cause the system to revert to a state of low flow rate if desired.

In another safety mechanism, the controller 1130 includes a timer 1170 (FIG. 18) that keeps time with respect to how long the flow rate has been at a high flow rate. The controller 1130 can be programmed to automatically cause the system 100 to revert to a low flow rate after a predetermined time period of high flow rate, for example after 15, 30, or 60 seconds or more of high flow rate. After the controller reverts to the low flow rate, the user can initiate another predetermined period of high flow rate as desired. Moreover, the user can override the controller 1130 to cause the system 100 to move to the low flow rate (or high flow rate) as desired.

In an embodiment procedure, embolic debris capture can be optimized while not causing patient tolerance issues by initially setting the level of retrograde flow at a low rate, and then switching to a high rate for discreet periods of time during critical stages in the procedure. Alternately, the flow rate is initially set at a high rate, and then verifying patient tolerance to that level before proceeding with the rest of the procedure. If the patient shows signs of intolerance, the retrograde flow rate is lowered. Patient tolerance can be determined automatically by the controller based on feedback from the anatomical data sensor 1140 or it can be determined by a user based on patient observation. The adjustments to the retrograde flow rate can be performed automatically by the controller or manually by the user. Alternately, the user can monitor the flow velocity through the middle cerebral artery (MCA), for example using TCD, and then to set the maximum level of reverse flow which keeps the MCA flow velocity above the threshold level. In this situation, the entire procedure can be done without modifying the state of flow. Adjustments can be made as needed if the MCA flow velocity changes during the course of the procedure, or the patient exhibits neurologic symptoms.

Mechanisms to Regulate Flow

The system 100 is adapted to regulate retrograde flow in a variety of manners. Any combination of the pump 1110, valve 1115, syringe 1120, and/or variable resistance component 1125 can be manually controlled by the user or automatically controlled via the controller 1130 to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set VACULOK syringe, VACUTAINER, suction system, or the like), or any combination thereof.

In the situation of FIG. 2D where an external receptacle or reservoir is used, the retrograde flow can be augmented in various manners. The reservoir has a head height that is of the height of the blood inside the reservoir and the height of the reservoir with respect to the patient. Reverse flow into the reservoir can be modulated by setting the reservoir height to increase or decrease the amount of pressure gradient from the CCA to the reservoir. In an embodiment, the reservoir is raised to increase the reservoir pressure to a pressure that is greater than venous pressure. Or, the reservoir can be positioned below the patient, such as down to a level of the floor, to lower the reservoir pressure to a pressure below venous or atmospheric pressure.

The variable flow resistance in shunt 120 can be provided in a wide variety of ways. In this regard, flow resistance component 1125 can cause a change in the size or shape of the shunt to vary flow conditions and thereby vary the flow rate. Or, the flow resistance component 1125 can re-route the blood flow through one or more alternate flow pathways in the shunt to vary the flow conditions. Some embodiments of the flow resistance component 1125 are now described.

As shown in FIGS. 19A, 19B, 19C, and 19D, in an embodiment the shunt 120 has an inflatable bladder 1205 formed along a portion of its interior lumen. As shown in FIGS. 19A and 19C, when the bladder 1205 is deflated, the inner lumen of the shunt 120 remains substantially unrestricted, providing for a low resistance flow. By inflating the bladder 1205, however, as shown in FIGS. 19B and 19D, the flow lumen can be greatly restricted, thus greatly increasing the flow resistance and reducing the flow rate of atrial blood to the venous vasculature. The controller 1130 can control inflation/deflation of the bladder 1205 or it can be controlled manually by the user.

Rather than using an inflatable internal bladder, as shown in FIGS. 19A-19D, the cross-sectional area of the lumen in the shunt 120 can be decreased by applying an external force, such as flattening the shunt 120 with a pair of opposed plates 1405, as shown in FIGS. 20A-20D. The opposed plates are adapted to move toward and away from one another with the shunt 120 positioned between the plates. When the plates 1405 are spaced apart, as shown in FIGS. 20A and 20C, the lumen of the shunt 120 remains unrestricted. When the plates 1405 are closed on the shunt 120, as shown in FIGS. 20B and 20D, in contrast, the plates 1405 constrict the shunt 120. In this manner, the lumen remaining in shunt 120 can be greatly decreased to increase flow resistance through the shunt. The controller 1130 can control movement of the plates 1405 or such movement can be controlled manually by the user.

Referring now to FIGS. 21A and 21B, the available cross-sectional area of the shunt 120 can also be restricted by axially elongating a portion 1505 of the shunt 120. Prior to axial elongation, the portion 1505 will be generally unchanged, providing a full luminal flow area in the portion 1505, as shown in FIG. 21A. By elongating the portion 1505, however, as shown in FIG. 21B, the internal luminal area of the shunt 120 in the portion 1505 can be significantly decreased and the length increased, both of which have the effect of increasing the flow resistance. When employing axial elongation to reduce the luminal area of shunt 120, it will be advantageous to employ a mesh or braid structure in the shunt at least in the portion 1505. The mesh or braid structure provides the shunt 120 with a pliable feature that facilitates axial elongation without breaking. The controller 1130 can control elongation of the shunt 120 or it can be controlled manually by the user.

Referring now to FIGS. 22A-22D, instead of applying an external force to reduce the cross-sectional area of shunt 120, a portion of the shunt 120 can be manufactured having a small diameter, as shown in FIGS. 22A and 22C. The shunt 120 can pass through a chamber 1600 which is sealed at both ends. A vacuum can be applied within the chamber 1600 exterior of the shunt 120 to cause a pressure gradient. The pressure gradient can cause the shunt 120 to increase in size within the chamber 120, as shown in FIGS. 19B and 19D. The vacuum can be applied in a receptacle 1605 attached to a vacuum source 1610. Conversely, a similar system can be employed with a shunt 120 having resting configuration that is in the increased size. Pressure can be applied to the chamber to shrink or flatten the shunt to decrease the flow resistance. The controller 1130 can control the vacuum or it can be controlled manually by the user.

Figure 23A:
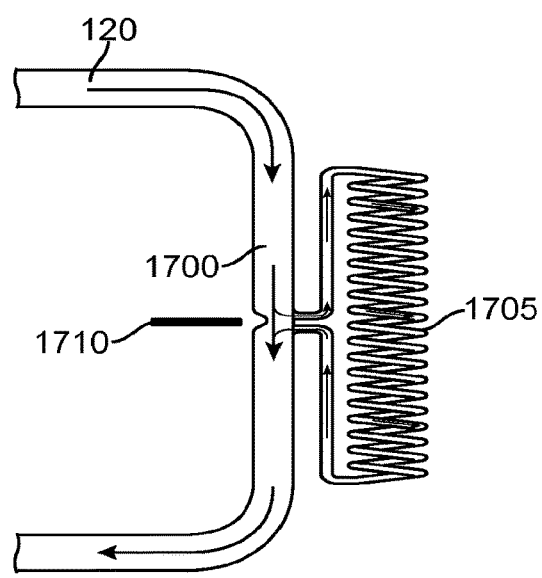
Figure 23B:
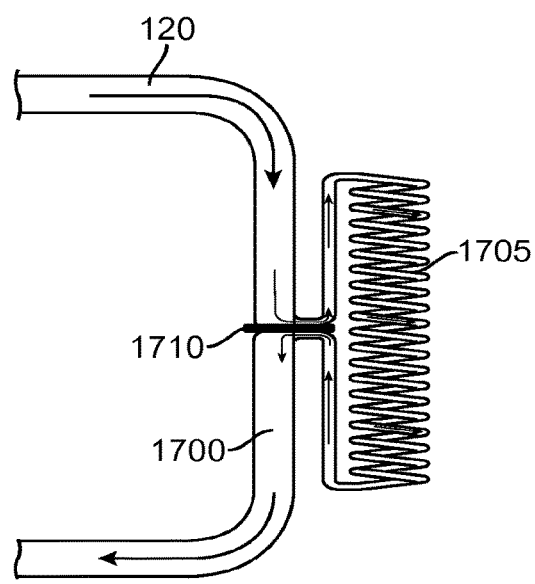

As yet another alternative, the flow resistance through shunt 120 can be changed by providing two or more alternative flow paths. As shown in FIG. 23A, the flow through shunt 120 can pass through a main lumen 1700 as well as secondary lumen 1705. The secondary lumen 1705 can be longer and/or have a smaller diameter than the main lumen 1700. Thus, the secondary lumen 1705 has higher flow resistance than the main lumen 1700. By passing the blood through both these lumens, the flow resistance will be at a minimum. Blood can flow through both lumens 1700 and 1705 due to the pressure drop created in the main lumen 1700 across the inlet and outlet of the secondary lumen 1705. This has the benefit of preventing stagnant blood. As shown in FIG. 23B, by blocking flow through the main lumen 1700 of shunt 120, the flow can be diverted to the secondary lumen 1705, thus increasing the flow resistance and reducing the blood flow rate. It will be appreciated that additional flow lumens can also be provided in parallel to allow for a three, four, or more discrete flow resistances. The shunt 120 can be equipped with a valve 1710 that controls flow to the main lumen 1700 and the secondary lumen 1705 with the valve 1710 being controlled by the controller 1130 or being controlled manually by the user. The embodiment of FIGS. 23A and 23B has an advantage in that this embodiment in that it does not require as small of lumen sizes to achieve desired retrograde flow rates as some of the other embodiments of variable flow resistance mechanisms. This is a benefit in blood flow lines in that there is less chance of clogging and causing clots in larger lumen sizes than smaller lumen sizes.

Figure 24A:
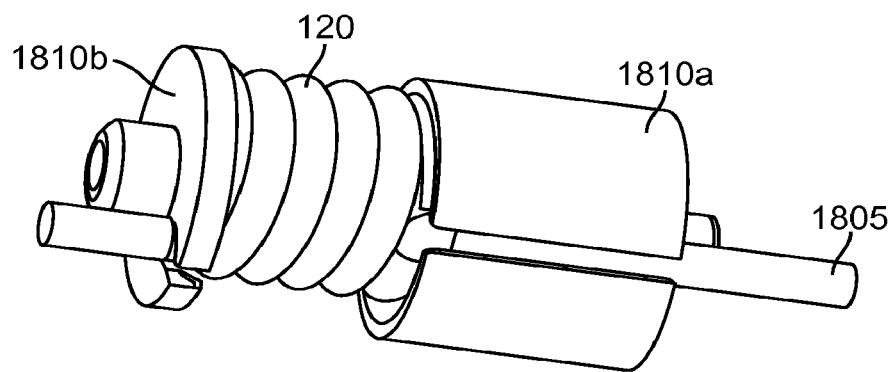
FIGS. 24A-24B, FIGS. 25A-25B, FIGS. 26A-26D, and FIGS. 27A-27B illustrate further embodiments of a variable flow resistance system useful in the methods and systems of the present disclosure.
Figure 24B:
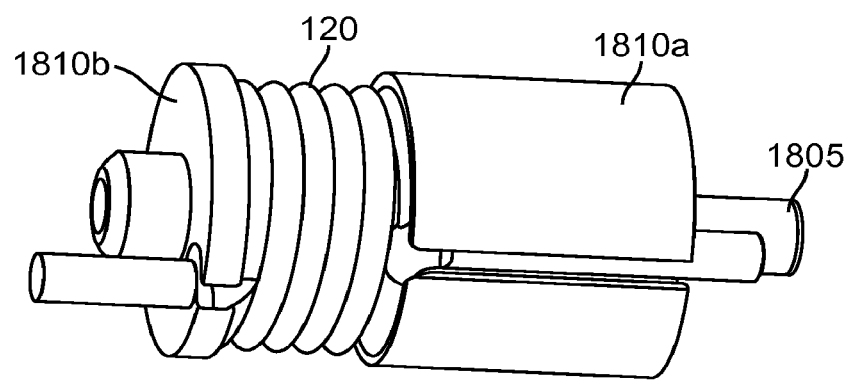

The shunt 120 can also be arranged in a variety of coiled configurations which permit external compression to vary the flow resistance in a variety of ways. Arrangement of a portion of the shunt 120 in a coil contains a long section of the shunt in a relatively small area. This allows compression of a long length of the shunt 120 over a small space. As shown in FIGS. 24A and 24B, a portion of the shunt 120 can be wound around a dowel 1805 to form a coiled region. The dowel 1805 can have plates 1810a and 1810b which can move toward and away from each other in an axial direction. When plates 1810a and 1810b are moved away from each other, the coiled portion of the shunt 105 is uncompressed and flow resistance is at a minimum. The shunt 120 is large diameter, so when the shunt is non-compressed, the flow resistance is low, allowing a high-flow state. To down-regulate the flow, the two plates 1810a and 1810b can be pushed together, compressing the coil of shunt 120. By moving the plates 1810a and 1810b together, as shown in FIG. 24B, the coiled portion of the shunt 120 can be compressed to increase the flow resistance. The controller 1130 can control the plates or they can be controlled manually by the user.

Figure 25A:
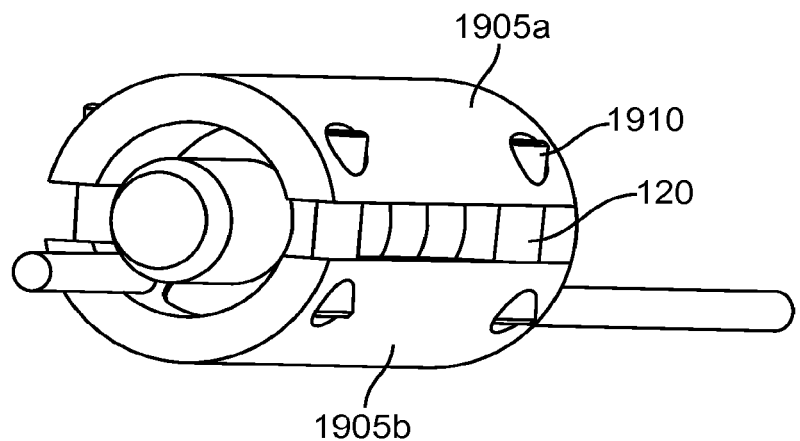
Figure 25B:
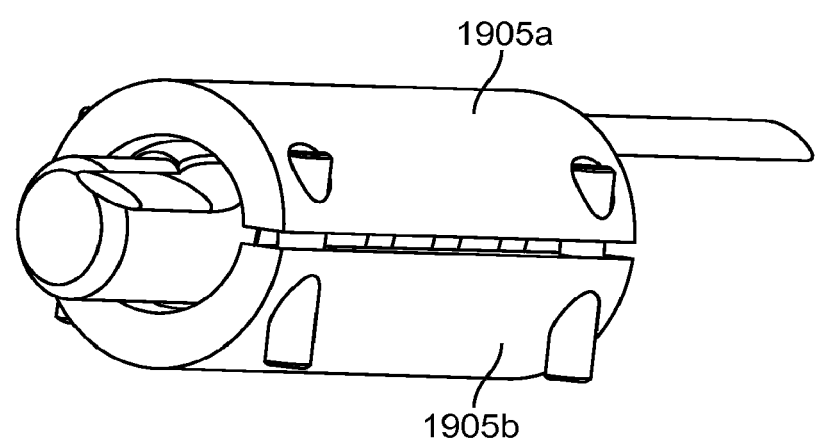

A similar compression apparatus is shown in FIGS. 25A and 25B. In this configuration, the coiled shunt 120 can be encased between two movable cylinder halves 1905a and 1905b. The halves 1905a and 1905b can slide along dowel pins 1910 to move toward and away from one another. When the cylinder halves 1905 are moved apart, the coiled shunt 120 is uncompressed and flow resistance is at a minimum. When the cylinder halves 1905 are brought together, the coiled shunt 120 is compressed circumferentially to increase flow resistance. The controller 1130 can control the halves 1905 or they can be controlled manually by the user.

Figure 26A:
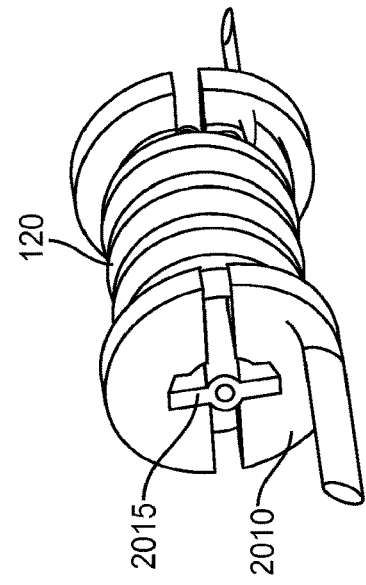
Figure 26B:
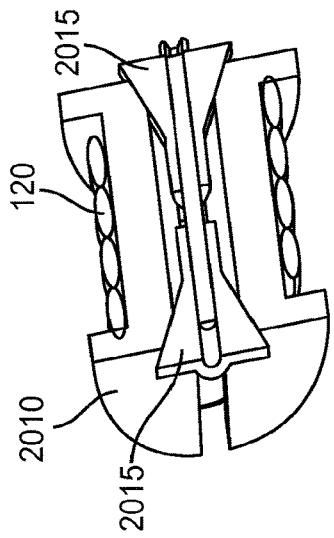
Figure 26C:
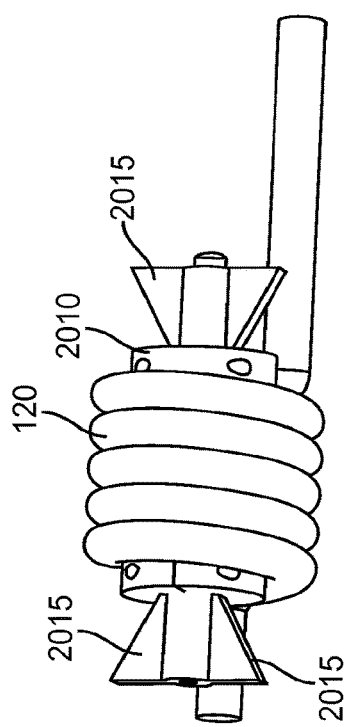
Figure 26D:
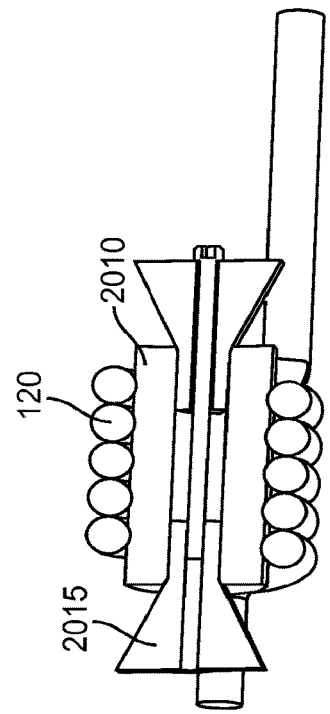

As shown in FIGS. 26A through 26D, the shunt 120 can also be wound around an axially split mandrel 2010 having wedge elements 2015 on opposed ends. By axially translating wedge elements 2015 in and out of the split mandrel 2010, the split portions of the mandrel can be opened and closed relative to one another, causing the coil of tubing to be stretched (when the mandrel portions 2010 are spread apart, FIG. 26C, 26D) or relaxed (when the mandrel portions 2010 are closed, FIG. 26A, 26B.) Thus, when the wedge elements 2015 are spaced apart, as shown in FIGS. 26A and 26B, the outward pressure on the shunt 120 is at a minimum and the flow resistance is also at a minimum. By driving the wedge elements 2015 inwardly, as shown in FIGS. 26C and 26D, the split mandrel halves 2020 are forced apart and the coil of shunt 120 is stretched. This has the dual effect of decreasing the cross sectional area of the shunt and lengthening the shunt in the coiled region, both of which can lead to increased flow resistance.

Figure 27A:
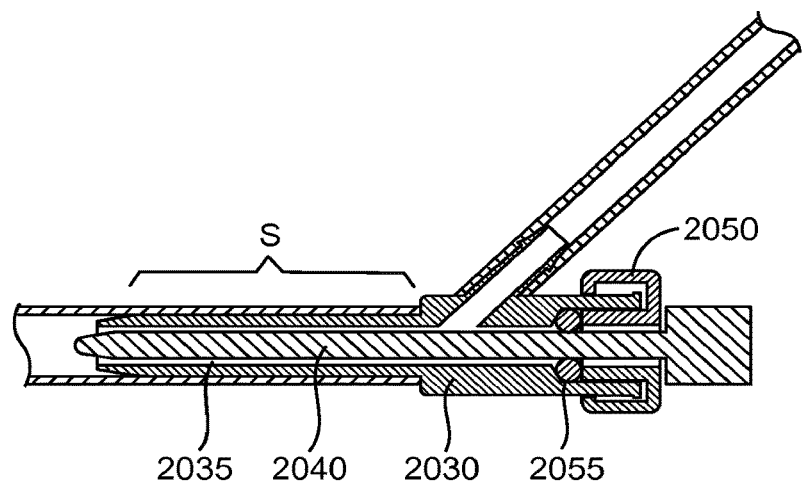
Figure 27B:
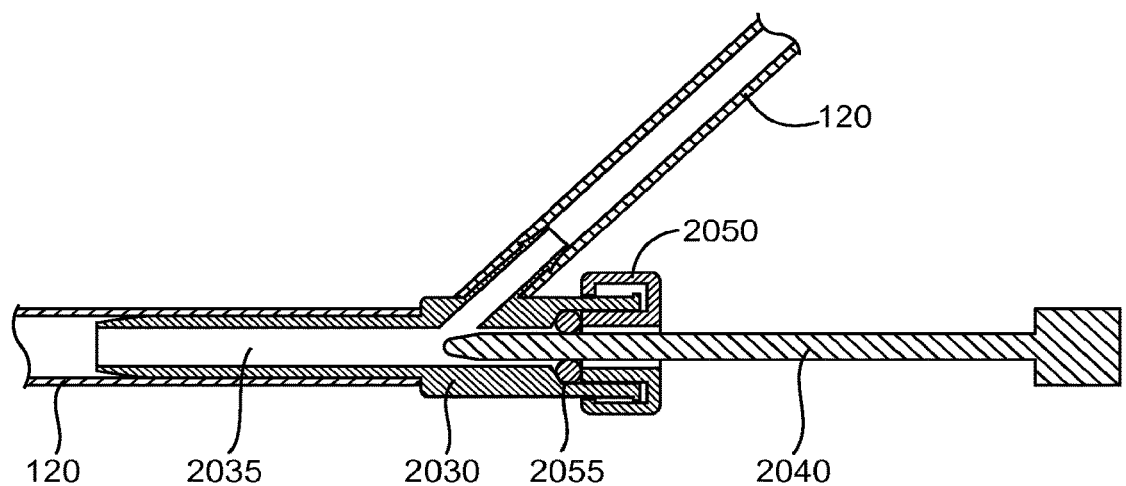

FIGS. 27A and 27B show an embodiment of the variable resistance component 1125 that uses a dowel to vary the resistance to flow. A housing 2030 can be inserted into a section of the shunt 120. The housing 2030 can have an internal lumen 2035 that is contiguous with the internal lumen of the shunt 120. A dowel 2040 can move into and out of a portion of the internal lumen 2035. As shown in FIG. 27A, when the dowel 2040 is inserted into the internal lumen 2035, the internal lumen 2035 is annular with a cross-sectional area that is much smaller than the cross-sectional area of the internal lumen 2035 when the dowel is not present. Thus, flow resistance increases when the dowel 2040 is positioned in the internal lumen 2035. The annular internal lumen 2035 has a length S that can be varied by varying the portion of the dowel 2040 that is inserted into the lumen 2035. Thus, as more of the dowel 2040 is inserted, the length S of the annular lumen 2035 increases and vice-versa. This can be used to vary the level of flow resistance caused by the presence of the dowel 2040.

The dowel 2040 can enter the internal lumen 2035 via a hemostasis valve in the housing 2030. A cap 2050 and an O-ring 2055 can provide a sealing engagement that seals the housing 2030 and dowel 2040 against leakage. The cap 2050 can have a locking feature, such as threads, that can be used to lock the cap 2050 against the housing 2030 and to also fix the position of the dowel 2040 in the housing 2040. When the cap 2050 is locked or tightened, the cap 2050 exerts pressure against the O-ring 2055 to tighten it against the dowel 2040 in a sealed engagement. When the cap 2050 is unlocked or untightened, the dowel 2040 is free to move in and out of the housing 2030.

Methods of Use

Referring now to FIGS. 28A-28E, flow through the carotid artery bifurcation at different stages of the methods of the present disclosure will be described. Initially, as shown in FIG. 28A, the distal sheath 605 of the arterial access device 110 is introduced into the common carotid artery CCA. As mentioned, entry into the common carotid artery CCA can be via a transcervical or transfemoral approach. After the sheath 605 of the arterial access device 110 has been introduced into the common carotid artery CCA, the blood flow will continue in antegrade direction AG with flow from the common carotid artery entering both the internal carotid artery ICA and the external carotid artery ECA, as shown in FIG. 28A.

The venous return device 115 can then be inserted into a venous return site, such as the internal jugular vein IJV (not shown in FIGS. 28A-28E). The shunt 120 can be used to connect the flow lines 615 and 915 of the arterial access device 110 and the venous return device 115, respectively (as shown in FIG. 2A). In this manner, the shunt 120 provides a passageway for retrograde flow from the atrial access device 110 to the venous return device 115. In another embodiment, the shunt 120 can connect to an external receptacle 130 rather than to the venous return device 115, as shown in FIG. 2C.

Once all components of the system are in place and connected, flow through the common carotid artery CCA can be stopped, such as using the occlusion element 129 as shown in FIG. 28B. The occlusion element 129 can be expanded at a location proximal to the distal opening of the sheath 605 to occlude the CCA. Alternately, the tourniquet 2105 (FIG. 2A) or other external vessel occlusion device can be used to occlude the common carotid artery CCA to stop flow therethrough. In an alternative embodiment, the occlusion element 129 can be introduced on second occlusion device 112 separate from the distal sheath 605 of the arterial access device 110, as shown in FIG. 3B. The ECA can also be occluded with a separate occlusion element, either on the same device 110 or on a separate occlusion device.

At that point retrograde flow RG from the external carotid artery ECA and internal carotid artery ICA can begin and can flow through the sheath 605, the flow line 615, the shunt 120, and into the venous return device 115 via the flow line 915. The flow control assembly 125 can regulate the retrograde flow as described above. FIG. 28B shows the occurrence of retrograde flow RG. While the retrograde flow is maintained, a stent delivery catheter 2110 can be introduced into the sheath 605, as shown in FIG. 28C. The stent delivery catheter 2110 can be introduced into the sheath 605 through the hemostasis valve 615 and the proximal extension 610 (not shown in FIGS. 28A-28E) of the arterial access device 110. The stent delivery catheter 2110 can be advanced into the internal carotid artery ICA and a stent 2115 deployed at the bifurcation B, as shown in FIG. 28D.

The rate of retrograde flow can be increased during periods of higher risk for emboli generation for example while the stent delivery catheter 2110 is being introduced and optionally while the stent 2115 is being deployed. The rate of retrograde flow can be increased also during placement and expansion of balloons for dilitation prior to or after stent deployment. An atherectomy can also be performed before stenting under retrograde flow.

Still further optionally, after the stent 2115 has been expanded, the bifurcation B can be flushed by cycling the retrograde flow between a low flow rate and high flow rate. The region within the carotid arteries where the stent has been deployed or other procedure performed can be flushed with blood prior to reestablishing normal blood flow. In particular, while the common carotid artery remains occluded, a balloon catheter or other occlusion element can be advanced into the internal carotid artery and deployed to fully occlude that artery. The same maneuver can also be used to perform a post-deployment stent dilatation, which can be done in self-expanding stent procedures. Flow from the common carotid artery and into the external carotid artery can then be reestablished by temporarily opening the occluding means present in the artery. The resulting flow can flush the common carotid artery which was exposed to slow, turbulent, or stagnant flow during carotid artery occlusion into the external carotid artery. In addition, the same balloon can be positioned distally of the stent during reverse flow and forward flow then established by temporarily relieving occlusion of the common carotid artery and flushing. Thus, the flushing action occurs in the stented area to help remove loose or loosely adhering embolic debris in that region.

Optionally, while flow from the common carotid artery continues and the internal carotid artery remains blocked, measures can be taken to further loosen emboli from the treated region. For example, mechanical elements can be used to clean or remove loose or loosely attached plaque or other potentially embolic debris within the stent, thrombolytic or other fluid delivery catheters can be used to clean the area, or other procedures can be performed. For example, treatment of in-stent restenosis using balloons, atherectomy, or more stents can be performed under retrograde flow. In another example, the occlusion balloon catheter can include flow or aspiration lumens or channels which open proximal to the balloon. Saline, thrombolytics, or other fluids can be infused and/or blood and debris aspirated to or from the treated area without the need for an additional device. While the emboli thus released can flow into the external carotid artery, the external carotid artery is generally less sensitive to emboli release than the internal carotid artery. By prophylactically removing potential emboli which remain when flow to the internal carotid artery is reestablished the risk of emboli release is even further reduced. The emboli can also be released under retrograde flow so that the emboli flows through the shunt 120 to the venous system, a filter in the shunt 120, or the receptacle 130.

After the bifurcation has been cleared of emboli, the occlusion element 129 or alternately the tourniquet 2105 can be released, reestablishing antegrade flow, as shown in FIG. 28E. The sheath 605 can then be removed.

In another embodiment, carotid artery stenting can be performed after the sheath is placed and an occlusion balloon catheter deployed in the external carotid artery. The stent having a side hole or other element intended to not block the ostium of the external carotid artery can be delivered through the sheath with a guidewire or a shaft of an external carotid artery occlusion balloon received through the side hole. Thus, as the stent is advanced, typically by a catheter being introduced over a guidewire which extends into the internal carotid artery, the presence of the catheter shaft in the side hole will ensure that the side hole becomes aligned with the ostium to the external carotid artery as the stent is being advanced. When an occlusion balloon is deployed in the external carotid artery, the side hole can prevent trapping the external carotid artery occlusion balloon shaft with the stent, which can be a disadvantage of the other flow reversal systems. This approach also avoids "jailing" the external carotid artery, and if the stent is covered with a graft material, avoids blocking flow to the external carotid artery.

In another embodiment, stents can be placed that have a shape which substantially conforms to any preexisting angle between the common carotid artery and the internal carotid artery. Due to significant variation in the anatomy among patients, the bifurcation between the internal carotid artery and the external carotid artery can have a wide variety of angles and shapes. By providing a family of stents having differing geometries, or by providing individual stents which can be shaped by the physician prior to deployment, the physician can choose a stent that matches the patient's particular anatomy prior to deployment. The patient's anatomy can be determined using angiography or by other conventional means. As a still further alternative, the stent can have sections of articulation. These stents can be placed first and then articulated in situ in order to match the angle of bifurcation between a common carotid artery and internal carotid artery. Stents can be placed in the carotid arteries where the stents have a sidewall with different density zones.

In another embodiment, a stent can be placed where the stent is at least partly covered with a graft material at either or both ends. Generally, the stent can be free from graft material and the middle section of the stent that can be deployed adjacent to the ostium to the external carotid artery to allow blood flow from the common carotid artery into the external carotid artery.

In another embodiment, a stent delivery system can be optimized for transcervical access by making them shorter and/or more rigid than systems designed for transfemoral access. These changes can improve the ability to torque and position the stent accurately during deployment. In addition, the stent delivery system can be designed to align the stent with the ostium of the external carotid artery, either by using the external carotid occlusion balloon or a separate guide wire in the external carotid artery, which is especially useful for stents with side holes or for stents with curves, bends, or angulation where orientation is critical. In an embodiment, a catheter of the stent delivery system has a working length that is particularly configured for insertion into the artery via a transcervical access location in the artery. In an embodiment, the working length is within the range of approximately 40-60 cm. In another embodiment, the working length is within the range of approximately 40-75 cm. In another embodiment, the working length is in the range of 25 cm to 60 cm. This embodiment may be suitable for use with an arterial access device that does not have a proximal extension.

In certain embodiments, the shunt is fixedly connected to the arterial access sheath and the venous return sheath so that the entire assembly of the replaceable flow assembly and sheaths can be disposable and replaceable as a unit. In other instances, the flow control assembly can be removably attached to either or both of the sheaths.

In an embodiment, the user first determines whether any periods of heightened risk of emboli generation can exist during the procedure. As mentioned, some examples of periods of heightened risk include (1) during periods when the plaque P is being crossed by a device; (2) during an interventional procedure, such as during delivery of a stent or during inflation or deflation of a balloon catheter or guidewire; (3) during injection or contrast. The foregoing are merely examples of periods of heightened risk. During such periods, the user can set the retrograde flow at a high rate for a discreet period of time. At the end of the high risk period, or if the patient exhibits any intolerance to the high flow rate, then the user can revert the flow state to baseline flow. If the system has a timer, the flow state can automatically revert to baseline flow after a set period of time. In this case, the user can re-set the flow state to high flow if the procedure is still in a period of heightened embolic risk.

In another embodiment, if the patient exhibits an intolerance to the presence of retrograde flow, then retrograde flow can be established only during placement of a filter in the ICA distal to the plaque P. Retrograde flow can then be ceased while an interventional procedure is performed on the plaque P. Retrograde flow can then be re-established while the filter is removed. In another embodiment, a filter can be placed in the ICA distal of the plaque P and retrograde flow established while the filter is in place. This embodiment combines the use of a distal filter with retrograde flow.

Detailed Description of Sheath Retention

Various embodiments of the arterial access device 110 including the distal sheath 605 are now described. In these particular embodiments, the sheath 605 can include a retention feature that is adapted to retain the sheath within a blood vessel (such as the common carotid artery) into which the sheath 605 has been inserted. The retention feature reduces the likelihood that the sheath 605 will be inadvertently pulled out of the blood vessel. In this regard, the retention feature can interact with the blood vessel to resist and/or eliminate undesired pull-out. In addition, the retention feature can also include additional elements that interact with the vessel wall to prevent the sheath from entering too far into the vessel. The retention feature can also include sealing elements which help seal the sheath against arterial blood pressure at the puncture site. The structure of the retention feature can vary and some examples of retention features are described below.

Figure 29A:
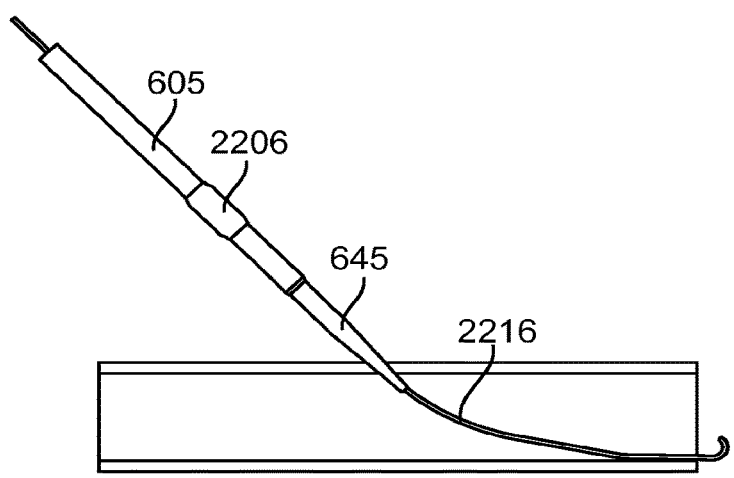
FIGS. 29A-29C show an embodiment of the sheath that has a retention feature that includes an expandable member that expands through inflation.
Figure 29B:
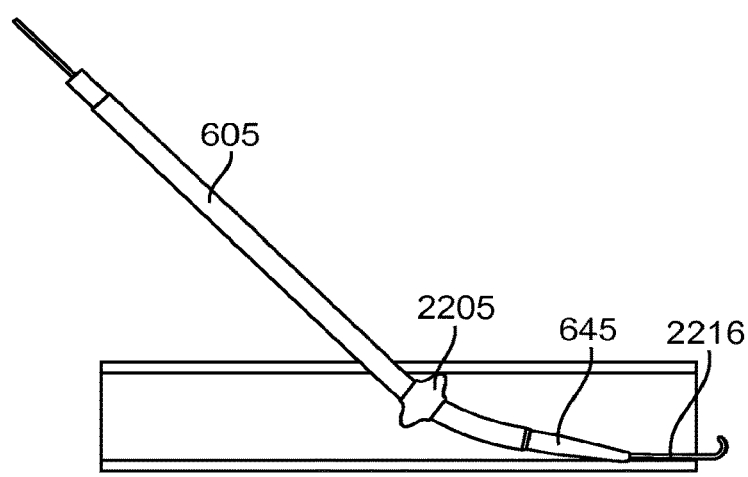
Figure 29C:
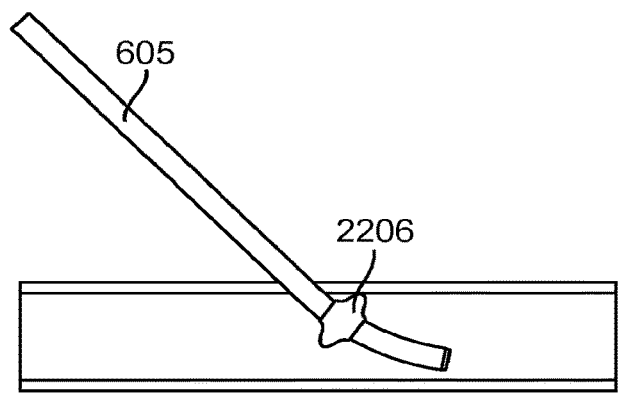

FIGS. 29A-29C show an embodiment of the sheath 605 that has a retention feature 2206 that includes an expandable member that expands through inflation such as via an inflation lumen in the sheath 605. The retention feature 2206 can be an inflatable balloon, bladder, or any other structure that expands via inflation. The retention feature 2206 can be positioned on the sheath 605 such that the retention feature 2206 can be located inside the blood vessel when the sheath 605 is moved distally into the blood vessel via a puncture. FIG. 29A shows the sheath 605 and a dilator 645 being inserted over a guidewire 2216 that has been positioned at least partially in the blood vessel. The dilator 645 can be positioned through a puncture in the blood vessel.

FIG. 29B shows the sheath 605 positioned in the blood vessel with the dilator 645 and guidewire 2216 still in place. The retention feature 2206 has been expanded (relative to its size in FIG. 29A) and positioned such that it is lodged against the interior surface of the blood vessel wall. The retention feature 2206 is expanded to a size that is greater than the size of the opening through which the sheath 605 was inserted into the blood vessel. In this manner, the retention feature 2206 resists being pulled out of the blood vessel through the opening. FIG. 29C shows the sheath 605 after the dilator 645 and guidewire 2216 have been removed.

Figure 30:
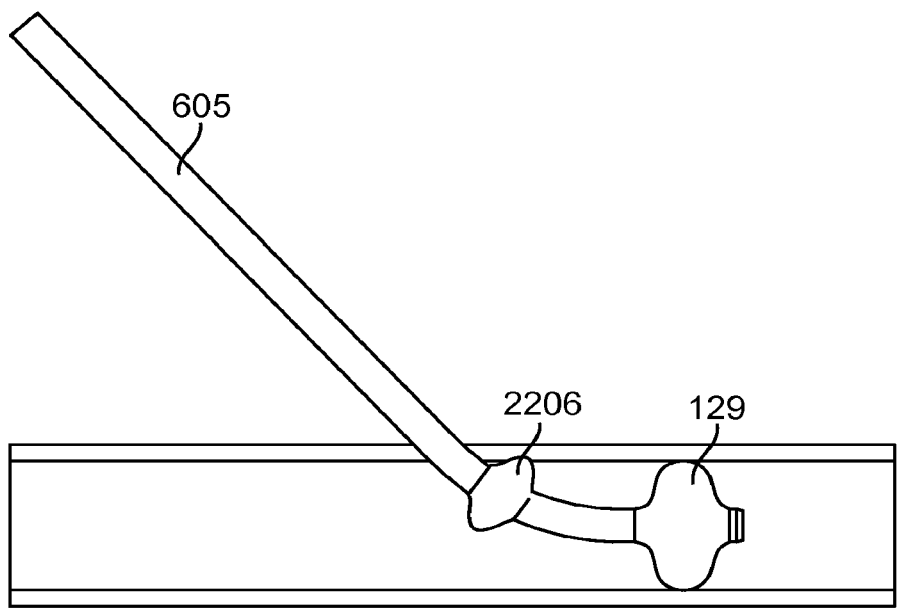
FIG. 30 shows an embodiment of the sheath that includes an occlusion element and a separate retention feature that includes an inflatable balloon.

As shown in FIGS. 15A and 15B, the sheath 605 can include an occlusion element 129 that occludes the blood vessel when the sheath 605 is positioned in the blood vessel. FIG. 30 shows an embodiment of the sheath 605 that includes an occlusion element 129 and a separate retention feature 2206 that includes an inflatable balloon. The sheath 605 can be positioned in the blood vessel such that the occlusion element 129 is expanded to a size that occludes the blood vessel and the retention feature 2206 can be expanded and positioned such that it is lodged against the interior surface of the blood vessel wall. The retention feature 2206 can be expanded to a size that is greater than the size of the opening through which the sheath 605 was inserted into the blood vessel. The two features can include separate inflation lumens and be independently inflatable, such that the retention feature can be expanded during the entire time the sheath is in the artery, whereas the occlusion element can be inflated and deflated as dictated by the procedure.

Figure 31:
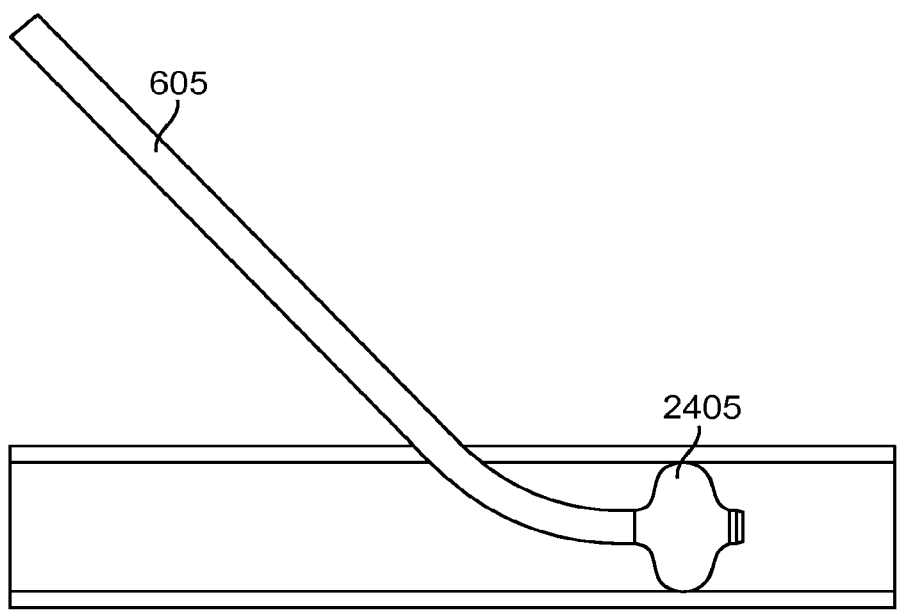
FIG. 31 shows another embodiment where the occlusion element and retention feature are combined into a single expandable balloon.

FIG. 31 shows another embodiment where the occlusion element and retention feature are combined into a single expandable balloon 2405. The balloon 2405 can expand to a size such that it lodges against the interior wall of the blood vessel to occlude the blood vessel. The balloon 2405 can exert a force on the interior wall of the blood vessel that is sufficient to retain the sheath 605 in a fixed position relative to the blood vessel to resist and/or eliminate undesired pull-out of the sheath 605.

Figure 32:
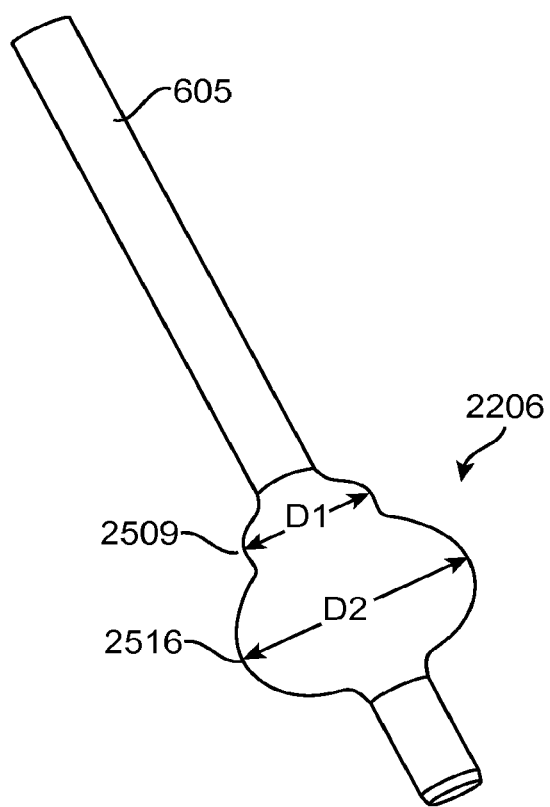
FIG. 32 shows another embodiment of a retention feature that includes an inflatable balloon that has a first section that enlarges to a first diameter and a second section that enlarges to a second diameter.

FIG. 32 shows another embodiment of a retention feature 2206 that includes an inflatable balloon that has a first section 2509 that enlarges to a first diameter D1 and a second section 2516 that enlarges to a second diameter D2 larger than the first diameter D1. The larger diameter section 2516 expands to a size that occludes the blood vessel, while the smaller diameter section 2509 expands to a size that is greater than the size of the opening through which the sheath 605 was inserted into the blood vessel. The dual diameter balloon can inflate to the first diameter when exposed to a first inflation pressure and to a second diameter when exposed to a second inflation pressure. Thus it can be inflated to a first lower pressure when sheath retention is desired, and to a second, higher pressure when vessel occlusion is desired.

Figure 33A:
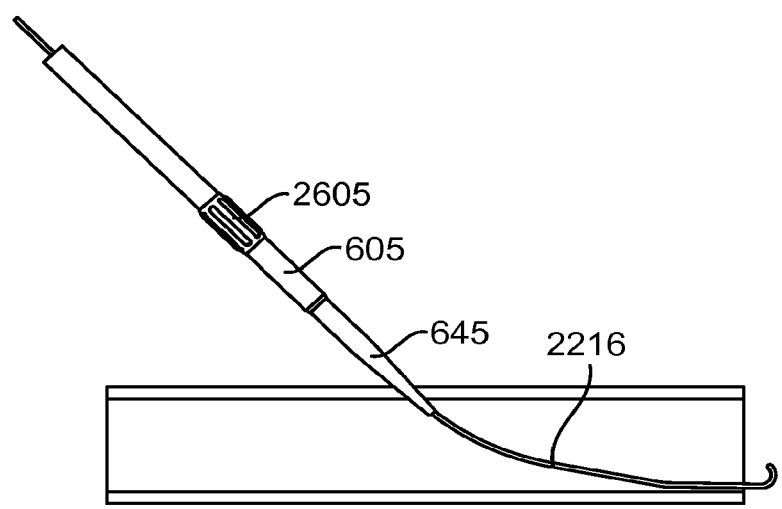
FIGS. 33A-33C show an embodiment of the sheath that has a retention feature that includes an expandable member that expands when shortened along the axial length of the sheath.
Figure 33B:
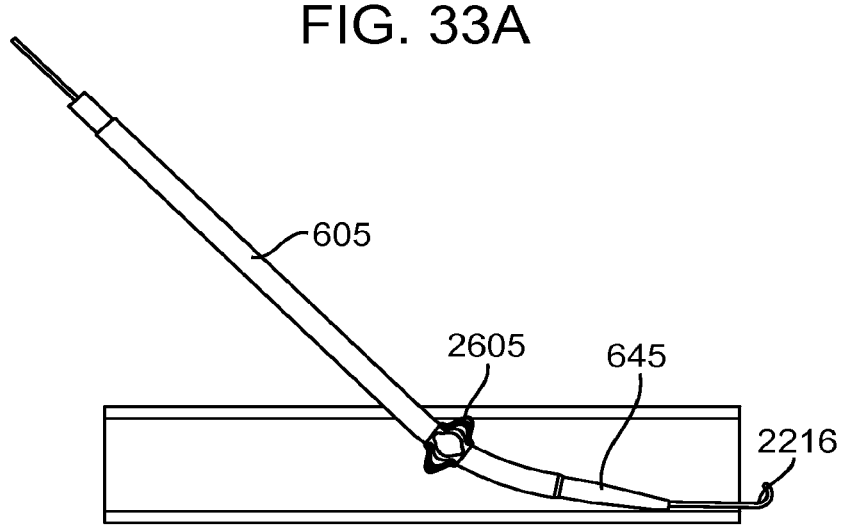
Figure 33C:
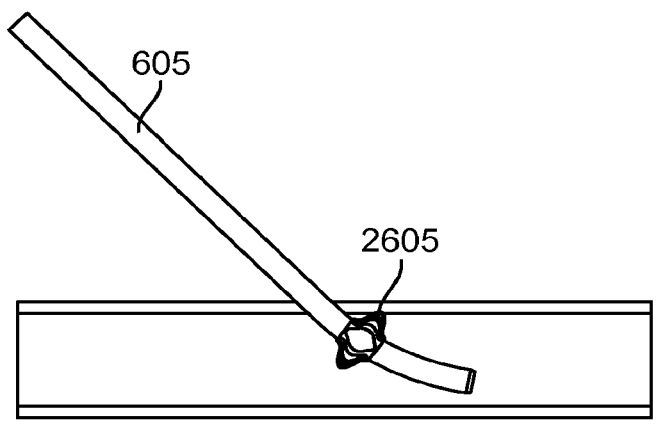

FIGS. 33A-33C show an embodiment of the sheath 605 that has a retention feature 2605 that includes an expandable member that expands when shortened along the axial length of the sheath 605. When shortened, the retention feature 2605 expands radially outward. The retention feature 2605 can be formed of a tubular member with a plurality of axially-extending elongate members (such as ribbons) that deform radially outward when axially-shortened. The retention feature 2605 can be positioned on the sheath 605 such that the retention feature 2605 can be located inside the blood vessel when the sheath 605 is moved distally into the blood vessel via a puncture. FIG. 33A shows the sheath 605 and a dilator 645 being inserted over a guidewire 2216 that has been positioned at least partially in the blood vessel. The dilator 645 can be positioned through a puncture in the blood vessel.

FIG. 33B shows the sheath 605 positioned in the blood vessel with the dilator 645 and guidewire 2216 still in place. The retention feature 2605 has been expanded radially outward (relative to its size in FIG. 33A) and positioned such that it is lodged against the interior surface of the blood vessel wall. The retention feature 2605 can be expanded to a size that is greater than the size of the opening through which the sheath 605 was inserted into the blood vessel. FIG. 33C shows the sheath 605 after the dilator 645 and guidewire 2216 have been removed.

Figure 34A:
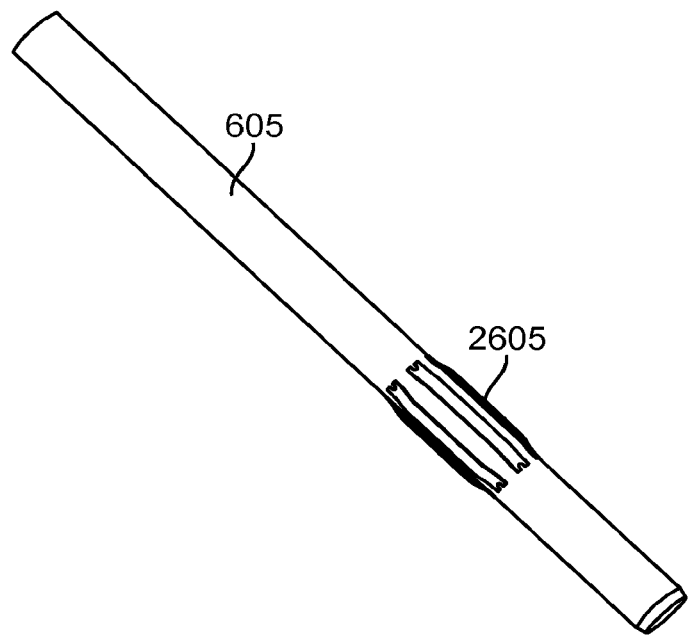
FIGS. 34A and 34B show an embodiment of a sheath having a retention feature with more than two elongate members.
Figure 34B:
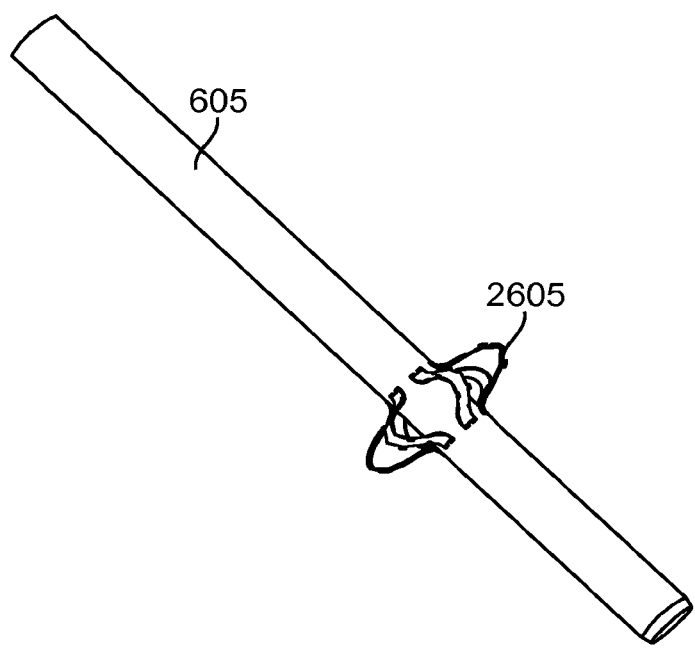
Figure 35A:
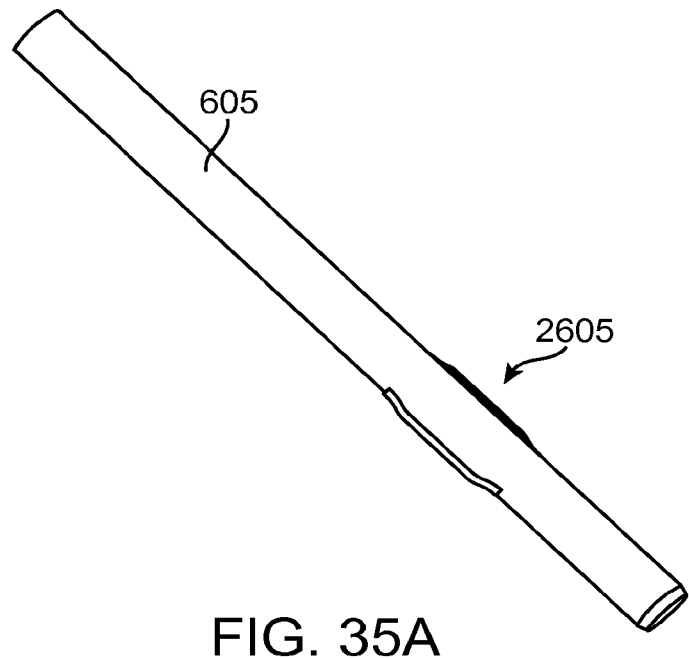
FIGS. 35A and 35B show an embodiment of a sheath having a retention feature with only two elongate members.
Figure 35B:
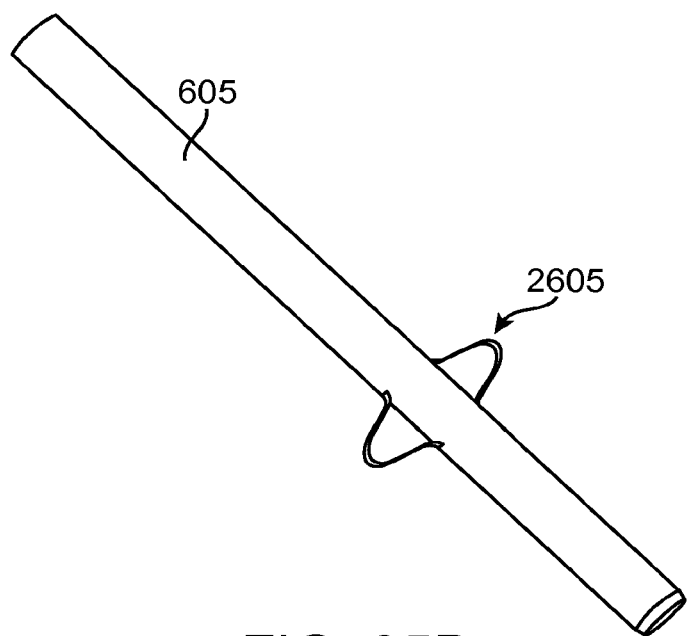

The retention feature 2605 can be shortened and expanded in various manners. The sheath 605 can include an actuator (such as a pull wire or pull tube) that can be pulled on to cause longitudinal shortening of the retention feature 2605 and radial expansion of the elongate members. The retention feature 2605 can include one or more elongate members that deform when shortened to expand radially outward. For example, FIGS. 34A and 34B show the retention feature 2605 with more than two elongate members in the non-expanded state (FIG. 34A) and in the expanded state (FIG. 34B). FIGS. 35A and 35B show the retention feature 2605 with only two elongate members in the non-expanded state (FIG. 34A) and in the expanded state (FIG. 34B). In the embodiment of FIGS. 35A and 35B, the elongate members are positioned 180 degrees apart from one another although variations in the spacing between the elongate members are possible.

Figure 36:
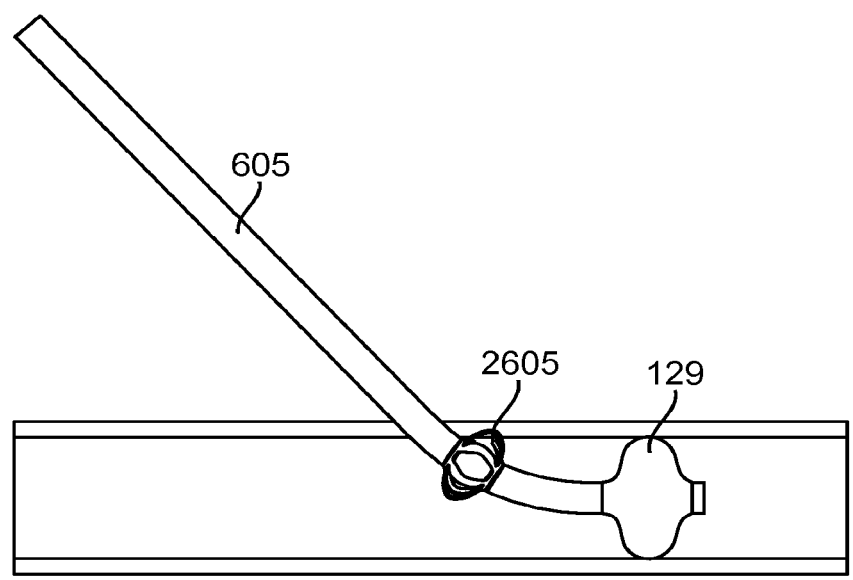
FIG. 36 shows an embodiment of the sheath that includes an occlusion element and a retention feature that expands when shortened.

FIG. 36 shows an embodiment of the sheath 605 that includes an occlusion element 129 and a retention feature 2605 that expands when shortened. It should be appreciated that any of the embodiments of retention features described herein can be used in combination with a sheath having an occlusion element. Moreover, any of the retention elements described herein can also be an occlusion element for occluding the blood vessel. The retention features can be configured such that they expand to a first, larger diameter sufficient to occlude the blood vessel, and a second, smaller diameter sufficient to prevent or resist pull out of the sheath 605 from the blood vessel.

Figure 37A:
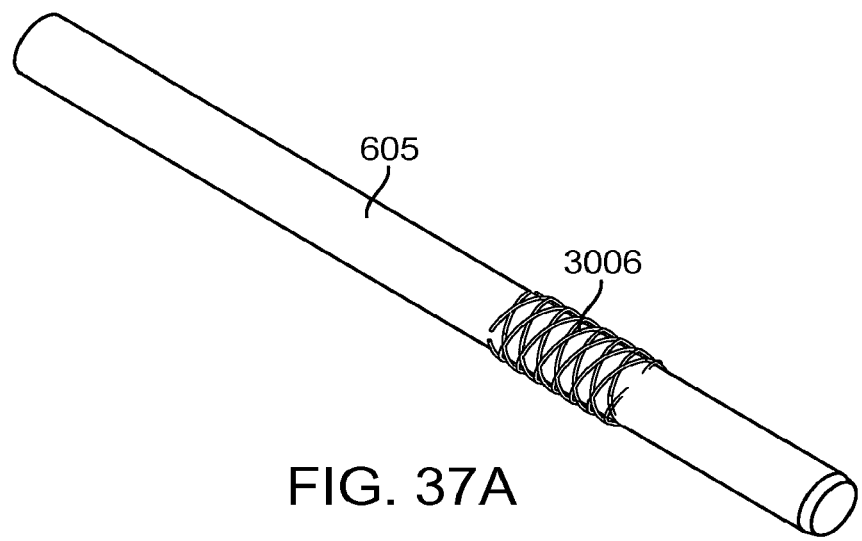
FIGS. 37A and 37B shows another embodiment of a sheath with a retention feature that expands when shortened along the axial length of the sheath.
Figure 37B:
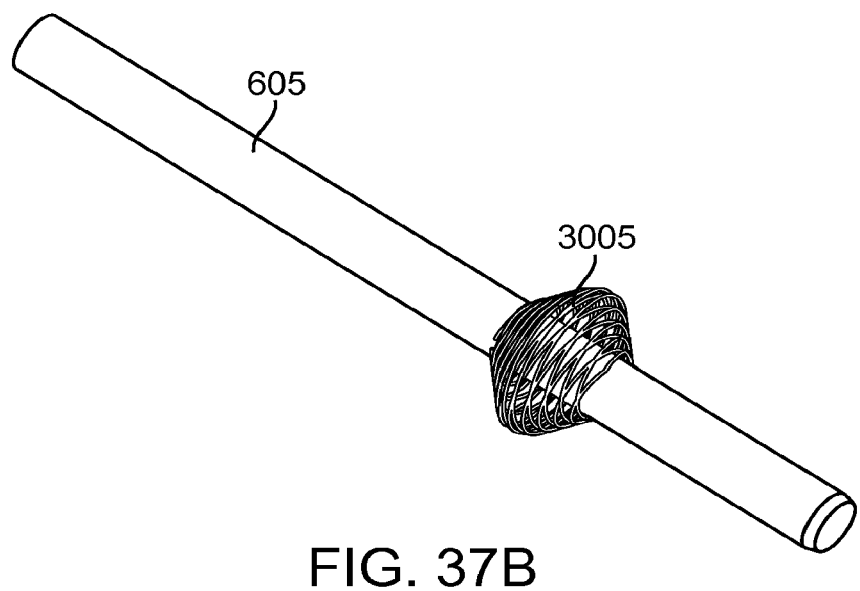

FIG. 37A shows another embodiment of a sheath with a retention feature 3006 that expands when shortened along the axial length of the sheath 605. The retention feature 3006 can be an expandable element that can be formed of one or more strands of material (such as wire or ribbon). The element can be a single strand wound in a helical configuration, or multiple strands that are braided together, for example. When the opposite longitudinal ends of the retention feature 3006 are shortened toward one another, the strands of the retention feature 3006 can expand radially outward, as shown in FIG. 37B.

Figure 38A:
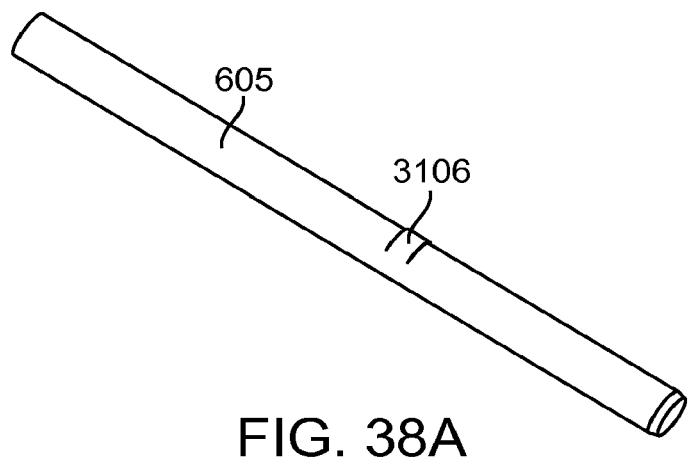
FIGS. 38A-38C show another embodiment of a sheath with a retention feature formed of one or more strips of material that follow the circumference of the sheath.
Figure 38B:
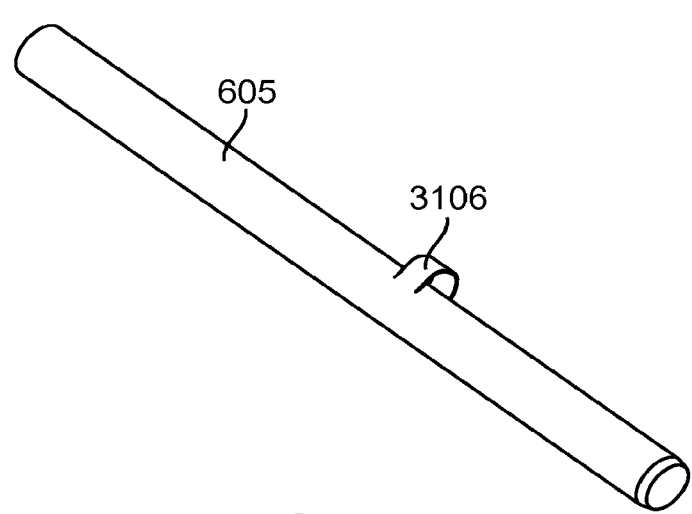
Figure 38C:
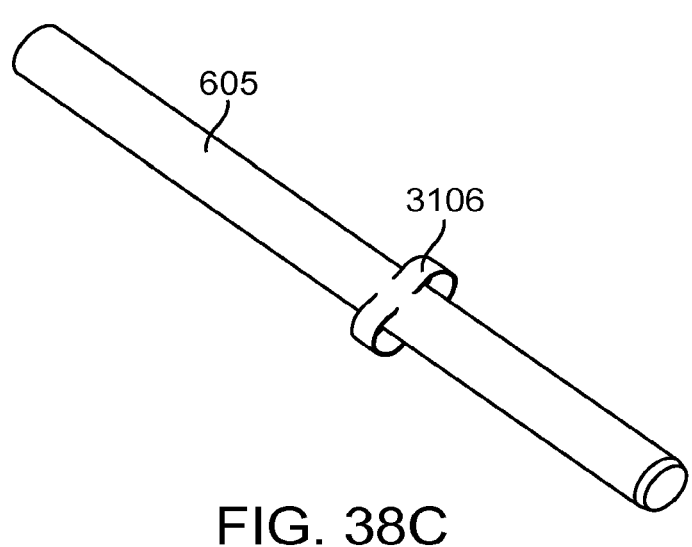

FIGS. 38A-38B show another embodiment of a sheath 605 with a retention feature 3106 formed of one or more strips of material that follow or wrap entirely or partially around the circumference of the sheath 605. The strips of material can be attached at one end to the sheath 605 and at an opposite end to a rotation member that can be rotated relative to the sheath 605. The strips can expand radially outward when the rotation member is rotated relative to a portion of the sheath 605. The rotation member can be rotated (about the longitudinal axis of the sheath) relative to the sheath 605. As shown in FIG. 38B, the relative rotation can cause the strip to expand radially outward. The rotation element can be a tube coaxially attached to the sheath 605. The rotation element can be a flexible tube that transmits torque to the retention feature 3106. FIG. 38C shows another embodiment of the retention feature 3106 that includes two strips of material.

Figure 39:
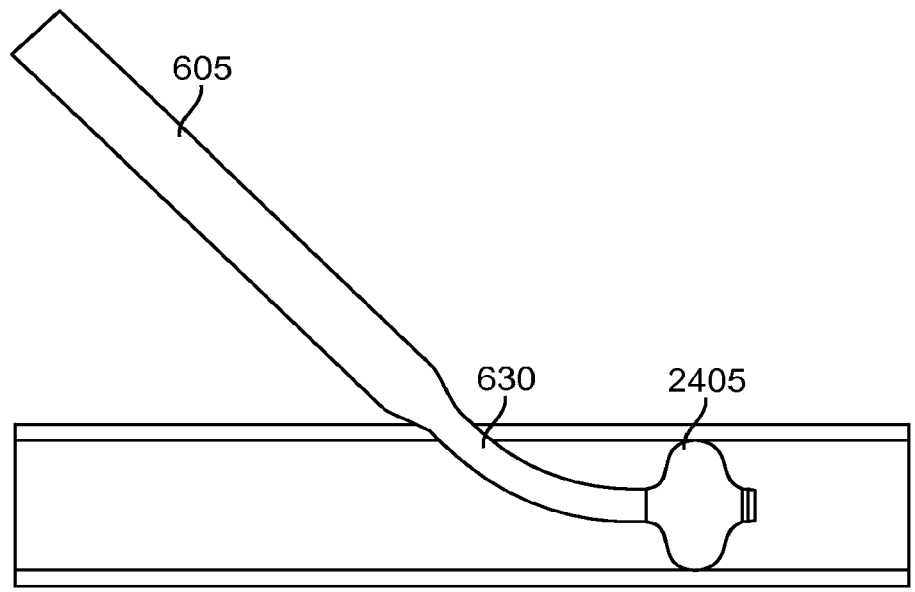
FIG. 39 shows a sheath with a with a retention feature having a reduced diameter distal region.

Any of the embodiments of the retention feature can be positioned at various locations along the sheath 605, such as at the distal tip of the sheath 605 or at a predetermined distance from the distal tip. Moreover, any of the embodiments of the retention feature can be used on a stepped sheath of the type described above with respect to FIG. 8B. For example, FIG. 39 shows a sheath 605 with a stepped or other configuration having a reduced diameter distal region 630. The sheath can include a single expandable balloon 2405. The balloon 2405 expands to a size such that it lodges against the interior wall of the blood vessel to occlude the blood vessel. The balloon 2405 exerts a force on the interior wall of the blood vessel that is sufficient to retain the sheath 605 in a fixed position relative to the blood vessel to resist and/or eliminate undesired pull-out of the sheath 605.

Figure 40:
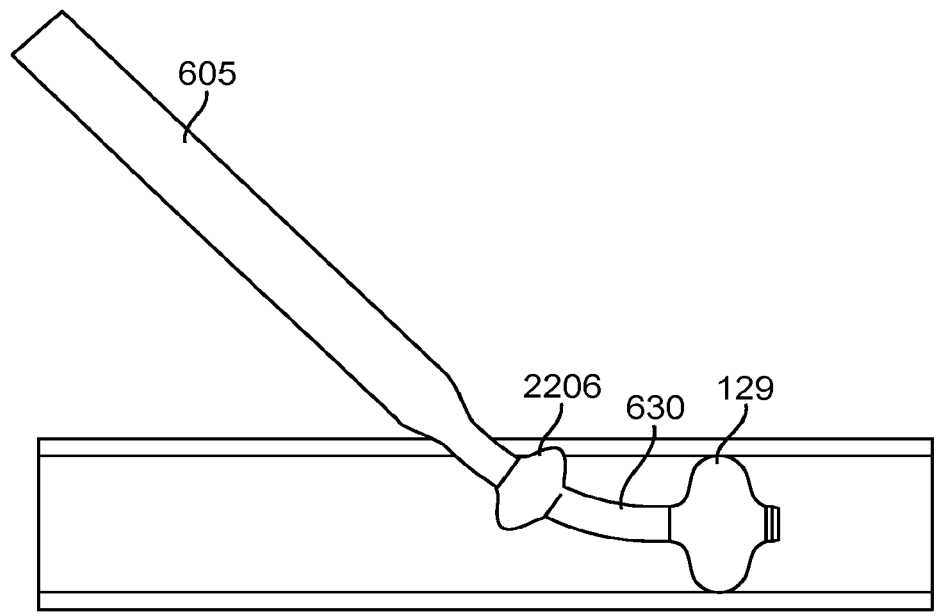
FIG. 40 shows another embodiment of a sheath with a with a retention feature having a reduced diameter distal region.

FIG. 40 shows another embodiment of a sheath 605 with a stepped or other configuration having a reduced diameter distal region 630. The sheath 605 can include an occlusion element 129 and a separate retention feature 2206 that includes an inflatable balloon. The sheath 605 can be positioned in the blood vessel such that the occlusion element 129 is expanded to a size that occludes the blood vessel and the retention feature 2206 can be expanded and positioned such that it is lodged against the interior surface of the blood vessel wall. The retention feature 2206 can be expanded to a size that is greater than the size of the opening through which the sheath 605 was inserted into the blood vessel.

Figure 41A:
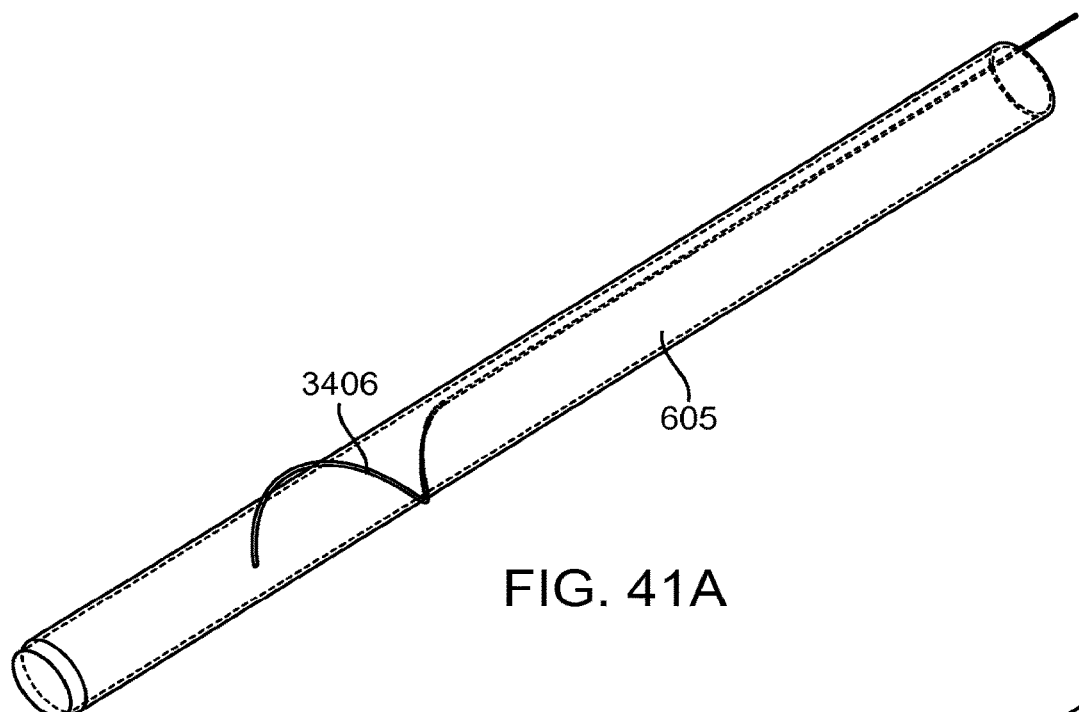
FIGS. 41A and 41B show another embodiment of a sheath having a retention feature that includes a wire that is expanded outward.
Figure 41B:
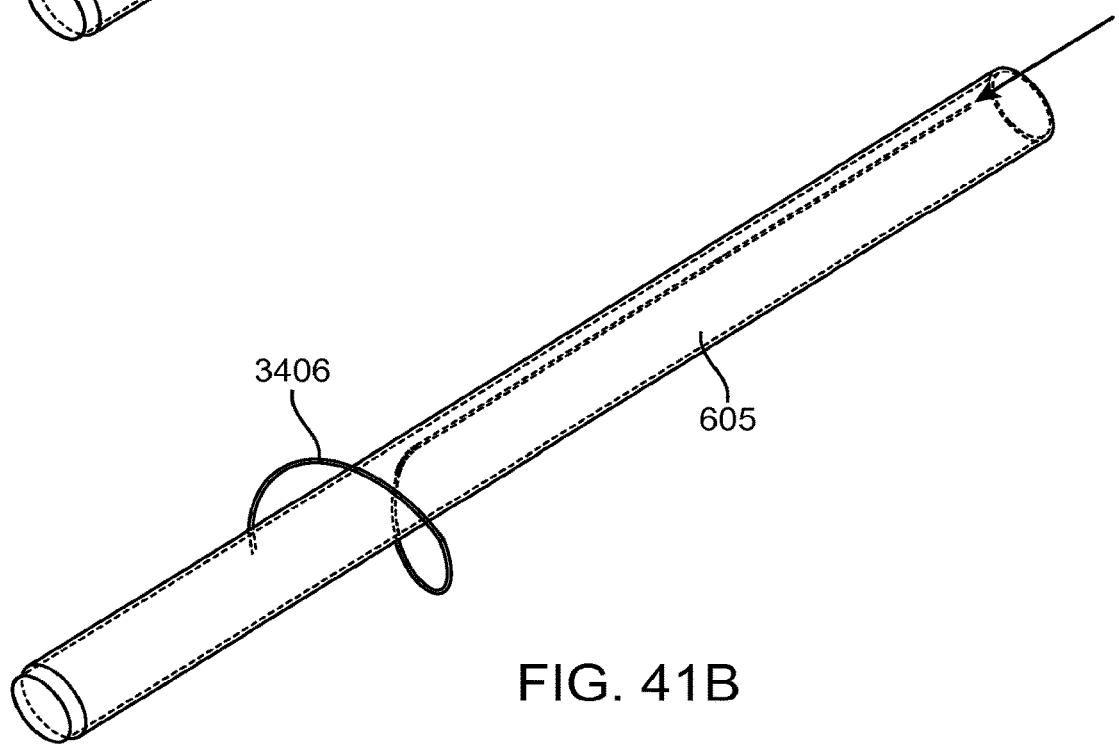

FIGS. 41A and 41B show another embodiment of a sheath 605 having a retention feature that includes a wire 3406 that expands outward, as described below. The wire 3406 can have a distal end that is fixed to the sheath 605 while the remainder of the wire 3406 is free to move relative to the sheath. A distal region of the wire 3406 can be wound about the circumference of the sheath 605 with a portion of the wire 3406 slidably embedded into a groove that extends along the length of the sheath 605. In a retracted state (shown in FIG. 41A), the wire 3406 can be wound tightly against the outer surface of the sheath 605 such that the wire does not significantly contribute to the outer dimension of the sheath 605. As shown in FIG. 41B, the wire 3406 can be pushed distally to cause the distal region of the wire 3406 to expand outward relative to the sheath 605. The expanded region of the wire 3406 can serve as a retention feature that is greater than the size of the opening through which the sheath 605 was inserted into the blood vessel.

Figure 42:
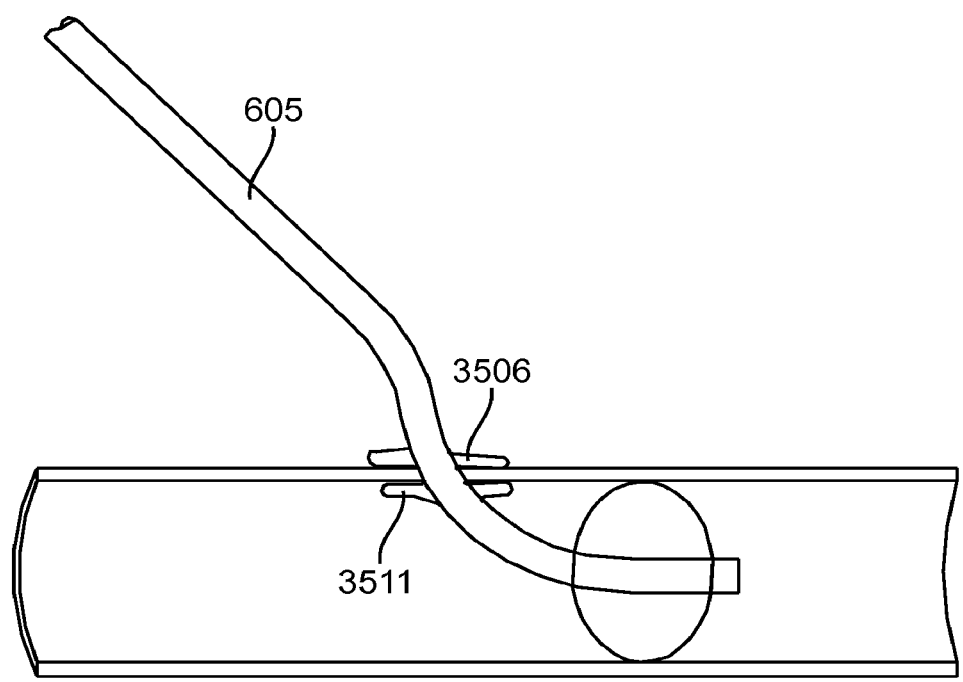
FIG. 42 shows another embodiment of a sheath with a dual expandable feature including a first expandable element and a second expandable element.

FIG. 42 shows another embodiment of a sheath with a dual expandable feature including a first expandable element 3506 and a second expandable element 3511. The expandable elements 3506 and 3511 can expand on both sides of the vessel wall. This construction serves the dual purpose of preventing the sheath from inadvertent removal, and inadvertent advancement too far into the carotid artery. The expandable elements 3506 and 3511 can be expanded at the same time, for example with one inflation lumen or one rotatable or retractable actuator, or be independently actuated.

The inflatable retention features can also serve the purpose of sealing the puncture site of the arterial sheath. When the retention feature is expanded against the vessel wall, the arterial blood pressure can have the effect of pressing this feature against the inner wall which in effect assists the sealing function. If the retention feature is mechanical, for example a single or multiple wire loops, these features can be covered by a sealing membrane to enable the sealing function of the retaining feature. This sealing function can be optimized when applied to both sides of the vessel wall, as shown in FIG. 42.

Detailed Description of Contrast Control

There are now described various embodiments of a retrograde flow system having a shunt valve that automatically actuates and shuts off flow through the shunt 120 in response to injection of a contrast into the flush line 635 and also aspiration from the flush line 635 of the arterial access device 110 or access port 2230.

Figure 43:
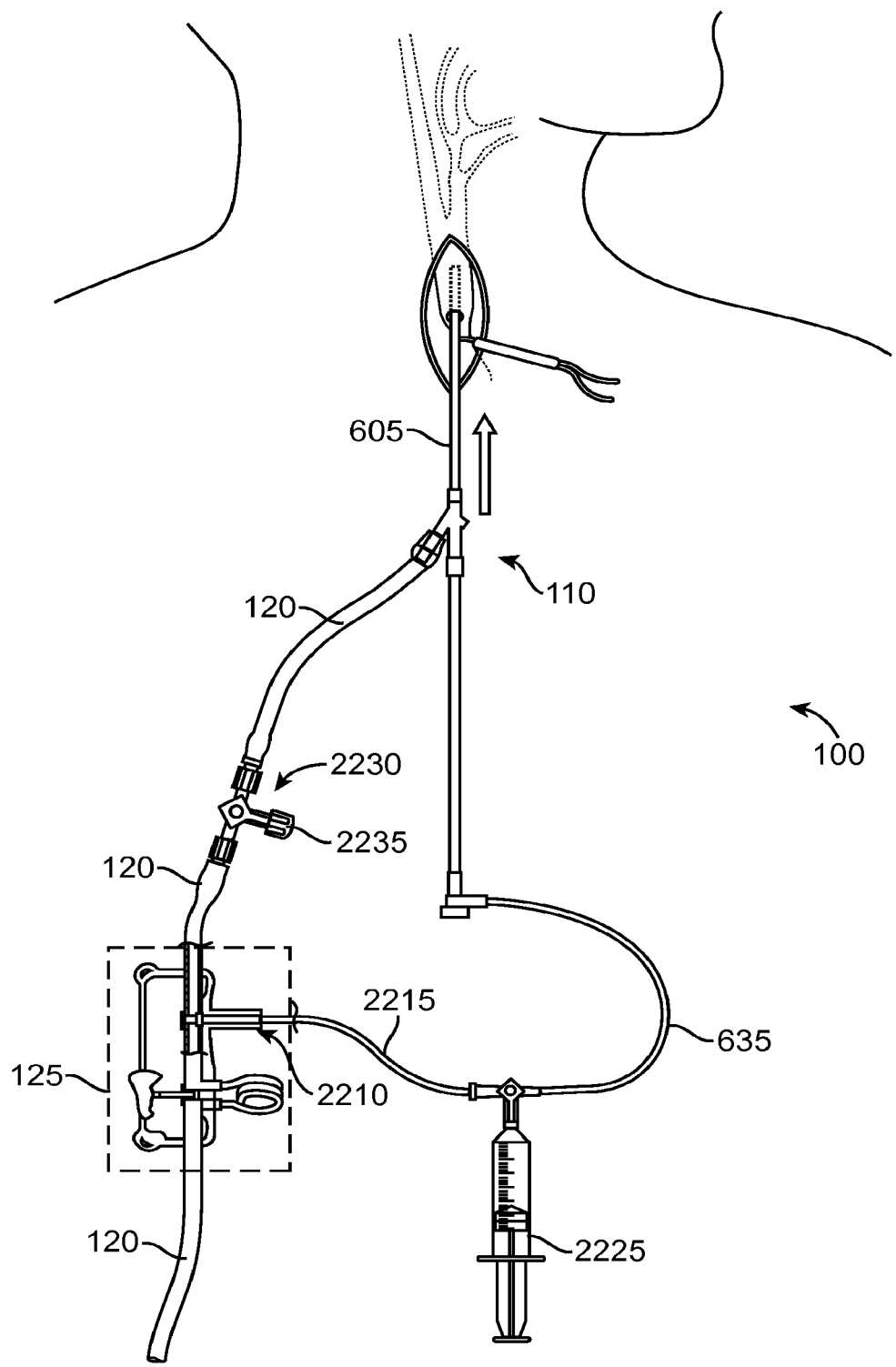
FIG. 43 illustrates a modified retrograde blood flow system including a flow control assembly with an automatic shunt valve that is connected to a flush line.

FIG. 43 show a first embodiment of a retrograde flow system 100 with a flow control assembly 125 that contains a shunt valve assembly or shut-off valve assembly having an automatic shunt valve 2210 (also referred to as a shut-off valve) that regulates fluid flow through the shunt 120. In an embodiment, the flow control assembly 125 can be a single housing that contains the various components described herein. The automatic shunt valve 2210 can actuate in response to injection of a fluid such as a contrast fluid into the flush line 635 of the arterial access device 110. That is, the shunt valve 2210 automatically closes and prevents flow through the shunt 120 when contrast is injected into the flush line 635 of the arterial access device 110. The automatic nature of the shut-off valve assembly permits the user to inject the contrast fluid using a single hand without requiring the user to use a second hand to close and/or open a device such as a stopcock while fluid is being injected. The shut-off valve assembly may also permit the user to aspirate fluid from the arterial access device 110 with an aspiration device such as a syringe 2225 using a single hand without requiring the user to use a second hand to close and/or open a device such as a stopcock while fluid is being aspirated. The shut-off valve also eliminates the possibility of the user forgetting to open the stopcock and re-establish flow through the shunt 120 after either flushing or aspirating.

The automatic shunt valve 2210 can be fluidly connected via a fluid line 2215 to the flush line 635 of the arterial access device 110. Both the fluid line 2215 and the flush line 635 have internal lumens through which fluid can flow. A syringe 2225 can be fluidly coupled to the flush line 635 and the fluid line 2215. The fluid line 2215 can provide a fluid connection between the syringe 2225 and flush line 635 to the automatic shunt valve 2210. The syringe 2225 can contain contrast and can deliver contrast into the flush line 635 and the arterial access sheath 605 and into the artery. The syringe 2225 can be coupled to the flush line 635 and/or fluid line 2215 via a stopcock or a needless access device. When contrast or other solution is injected, a pressure change in the fluid line 2215 can be communicated to the automatic shunt valve 2210. That is, injection of the contrast increases the pressure within the fluid line 2215 to a level that causes the shunt valve 2210 to automatically close and prevent fluid flow through the shunt 120. When the injection is done, the pressure in the syringe 2225 and fluid line 2215 can reduce to a lower pressure relative to the pressure in the shunt 120. As a result, the shunt valve 2210 can open to again permit flow through the shunt 120.

FIG. 43 also shows a port 2230 in the shunt 120. The port 2230 can be used to connect an aspiration device, such as a syringe, an aspiration pump, or other aspiration source, to the shunt 120. The port 2230 as shown in FIG. 43 is a stopcock, which can require actuation, such as a manual turn of the stopcock valve 2235, to connect the port 2230 to the arterial side of the shunt. The port 2230 can also contain a valve which automatically opens when a device is connected to it, and shuts off when the device is removed. These types of valves are called needleless or needle-free access ports. The automatic opening and closing of the valve permits the user to use a single hand to aspirate while not needing to use a second hand to actuate the stopcock or other mechanism.

Figure 44A:
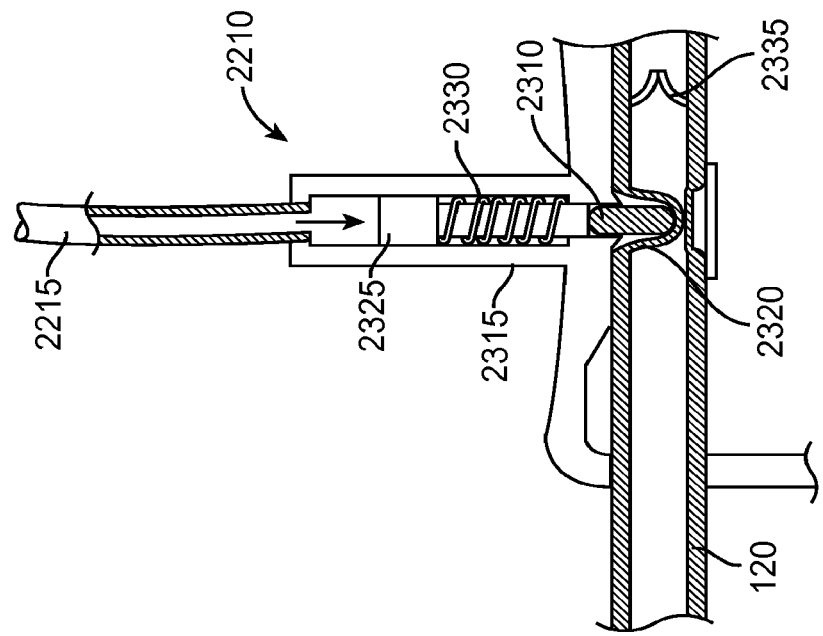
FIGS. 44A, 44B, 45A, and 45B illustrate examples of contrast pressure actuated shunt valves.
Figure 44B:
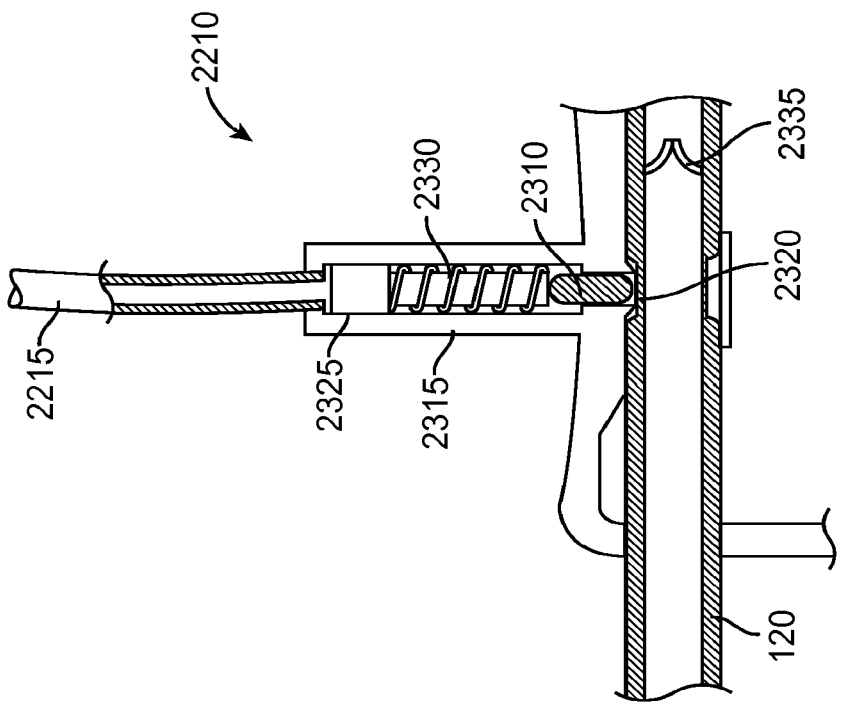

FIGS. 44A and 44B show an embodiment of an automatic shunt valve 2210. In FIG. 44A, the shunt valve 2210 is in an open state such that it permits fluid to flow through the shunt 120. The shunt valve 2210 can include a movable blocking member such as an anvil 2310 that is slidably positioned in a housing 2315 that communicates with the fluid line 2215 of the shunt 120, as described below. The anvil 2310 can be situated adjacent to a thin-walled segment 2320 of the shunt 120. A plunger 2325 can be positioned above the anvil 2310 within the housing 2315. An upper end of the plunger 2325 can be sealably connected to an end of the fluid line 2215 such that fluid from the syringe 2225 cannot flow past the plunger into the shunt 120. When the pressure in the fluid line 2215 increases as a result of the syringe 2225 injecting contrast, the pressure increase can cause the shunt valve 2210 to transition to a closed state that prevents fluid flow through the shunt 120, as shown in FIG. 44B. That is, the pressure increase pushes the plunger 2325 forward (toward the shunt 120). The plunger 2325 in turn can push the anvil 2310 toward the thin walled segment 2320 of the shunt 120 to pinch off the thin-walled segment 2320 of the shunt 120 and prevent flow through the shunt 120. A biasing member 2330, such as a spring, in the housing 2315 can urge the plunger and anvil toward the open position when there is no pressure in the fluid line.

A one-way valve 2335 can also be located in the shunt 120. During aspiration from the flush line 635 via the syringe 2225, or via the aspiration port 2230, the valve 2335 can close to prevent aspiration from the venous side of the shunt 120 and instead enables aspiration entirely from the sheath 605 of the arterial access device 110.

Figure 45B:
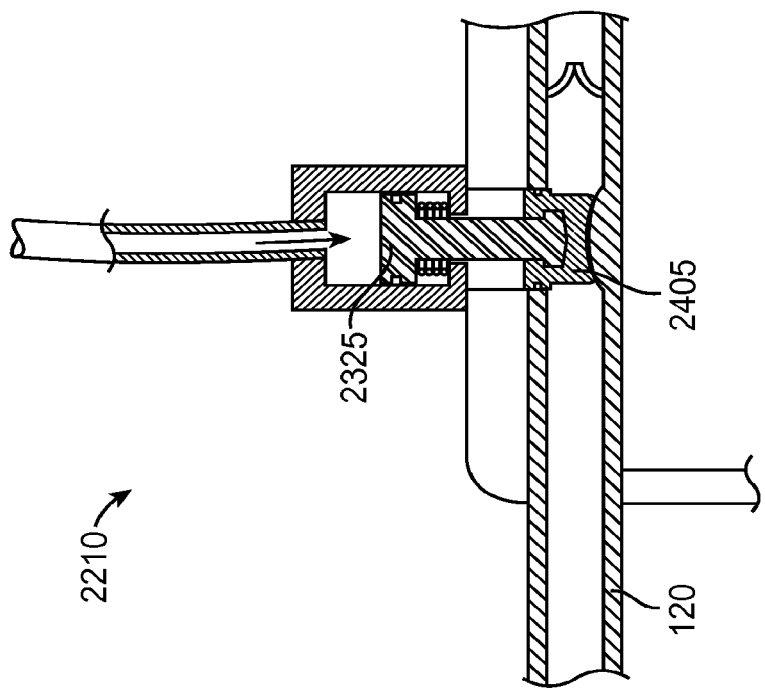
Figure 45A:
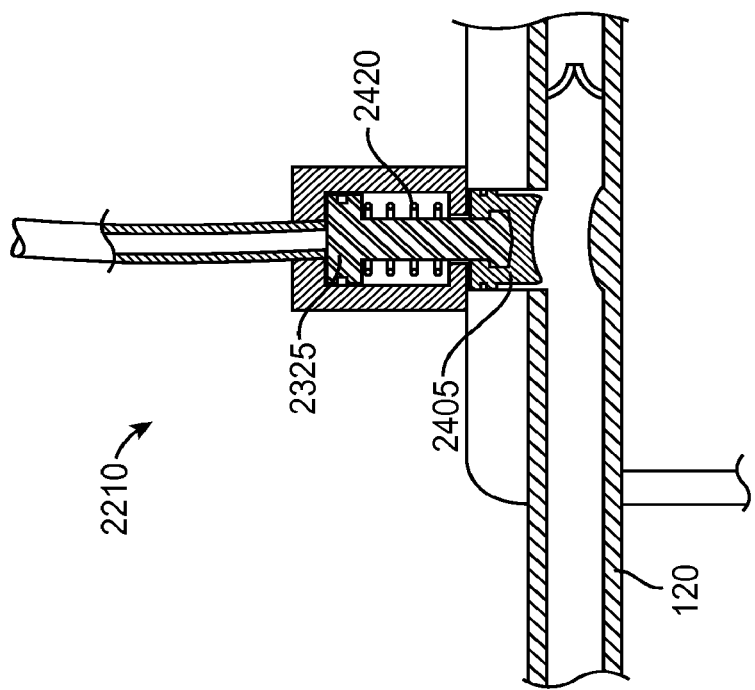

FIGS. 45A and 45B show another embodiment of the shunt valve 2210. FIG. 45A shows the shunt valve 2210 in the open state and FIG. 45B shows the shunt valve 2210 in the closed state. In this embodiment, the plunger 2325 can include a seal member 2405 on the lower end of the plunger 2325. When fluid pressure pushes the plunger 2325 downward (as a result of injection of contrast), the attached seal member 2405 also can move downward into the lumen of the shunt 120 to directly shut off the fluid flow in the shunt 120. The seal member 2405 can be sized and shaped to form a sealed engagement with the internal walls of the shunt 120 such that fluid cannot flow past the seal member 2405 when it is properly positioned in the shunt 120. As in the previous embodiment, a spring member 2420 can maintain the plunger and seal in the open position when there is no increased pressure in the fluid line 2215.

In another embodiment, the contrast injection between the syringe 2225 and the fluid line 2215 can be coupled to a pressure sensor, having an output connected to a solenoid coupled to the shunt valve 2210. The solenoid actuates the shunt valve 2210 to close the valve 2210 in response to a predetermined pressure increase. This can move the plunger 2325 in the automatic shunt valve 2210 to close the shunt 120. This embodiment is more complex than a direct fluid connection, but can enable a better control between contrast injection pressure and valve actuation.

Figure 46A:
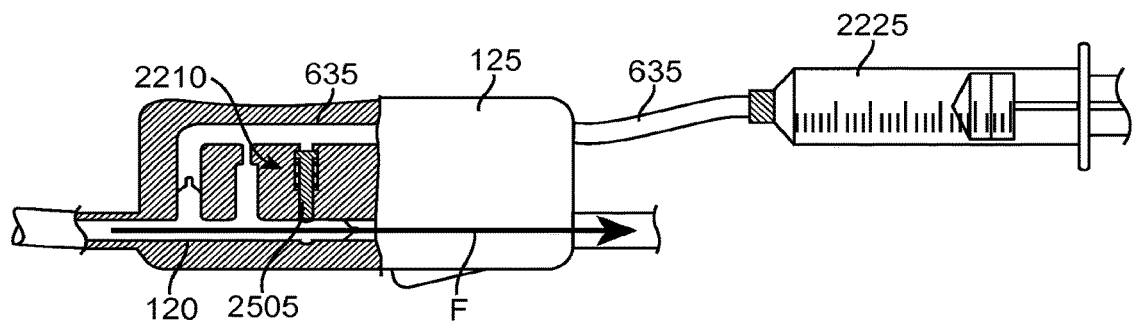
FIGS. 46A-46C illustrate yet another embodiment of a retrograde flow system including a flow control assembly with an automatic shunt valve that is connected to the flush line that is built in to the flow control assembly.
Figure 46B:
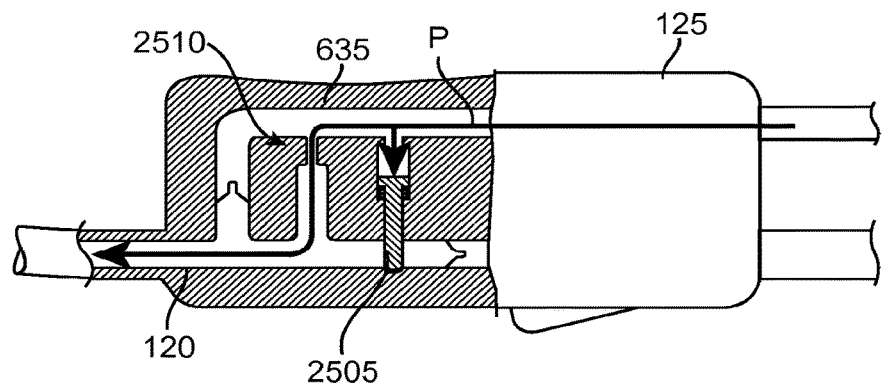
Figure 46C:
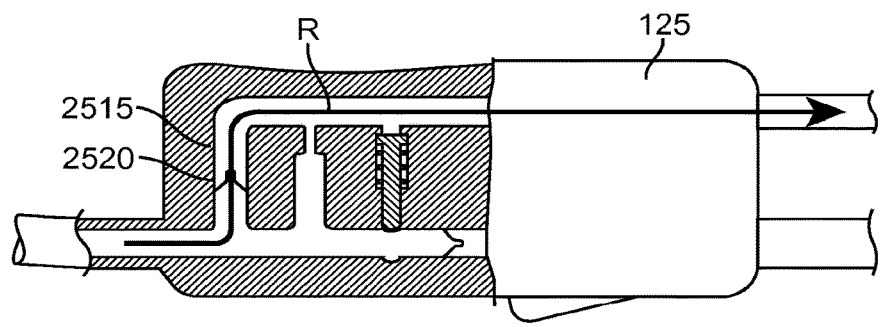

FIGS. 46A-46C shows an alternate layout of the automatic shunt valve 2210. In this layout, the flush line 635 can connect directly to the flow control assembly 125 such that the syringe 2225 injects fluid directly into the flow control assembly 125 via the flush line 635, which communicates with the shunt 120. The shunt valve 2210 can be positioned inside the flow control assembly 125. The shunt valve 2210 can include a spring-loaded plunger 2505. In a default, open state, the plunger 2505 can be positioned outside of the shunt 120 such that it does not interfere with fluid flow through the shunt, as shown in FIG. 46A. Thus, fluid can flow unimpeded through the shunt, as represented by fluid flow line F in FIG. 46A.

When contrast is injected into the flush line 635, as shown in FIG. 46B, pressure increases in the flush line 635, which can cause the plunger 2505 to move toward and into the shunt 120. The plunger 2505 can block flow through the shunt 120, shutting off the shunt 120 and directing the contrast towards the sheath 605 of the arterial access device 110. The contrast can flow along a flow pathway as represented by line P in FIG. 46B. The contrast flow pathway can include a narrowed region 2510, which acts as a throttle to increase the pressure on the plunger 2505 during injection. The flow control assembly 125 also can include a less-restrictive, parallel flow pathway 2515 through which fluid can flow in an opposite direction during aspiration, as represented by line R in FIG. 46C. A one-way valve 2520 in the aspiration flow pathway can prevent solution from flowing in this opposite direction during an injection.

Figure 47:
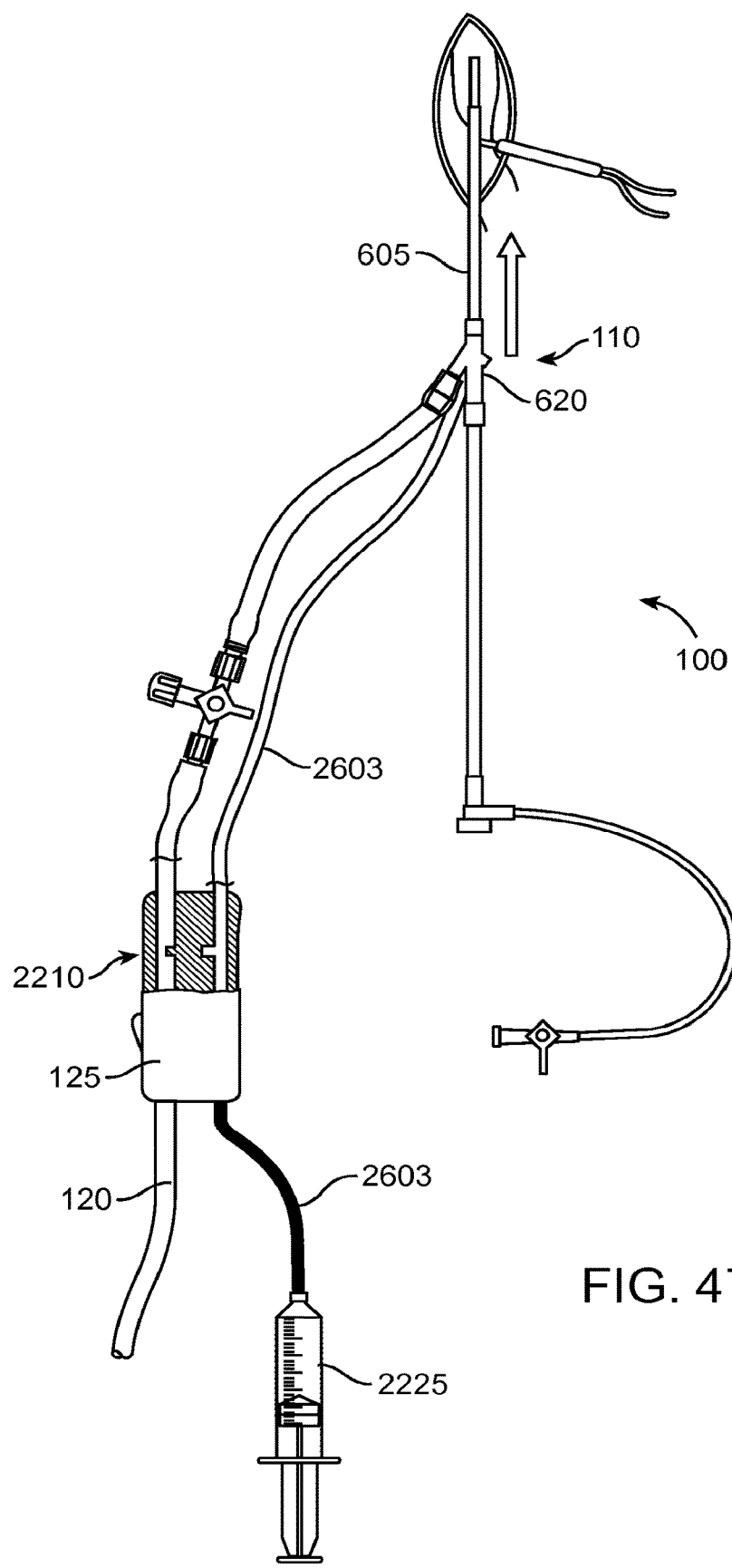
FIGS. 47 and 48A-48C illustrate another embodiment of a retrograde flow system with an automatic shunt valve connected to a flush line.

FIG. 47 shows an alternate layout of a retrograde flow system 100 with an automatic shunt valve 2210. In this layout, the syringe 2225 can fluidly communicate with a fluid line that can include a flush line 2603 that passes through a single housing of the flow control assembly 125 and connects directly to the Y-arm 620 of the arterial access device 110, but is parallel to the shunt line 120. The flush line 2603 can be separate from the flush line 635 of the arterial access device 110. At least a portion of the shunt 120 and a portion of the flush line 2603 can pass through the housing of the flow control assembly 125. The internal lumen of the flush line 2603 can have a smaller diameter than the internal lumen of the shunt 120. In this arrangement, the amount of contrast entering the shunt 120, and subsequently the patient, is minimized.

Figure 48A:
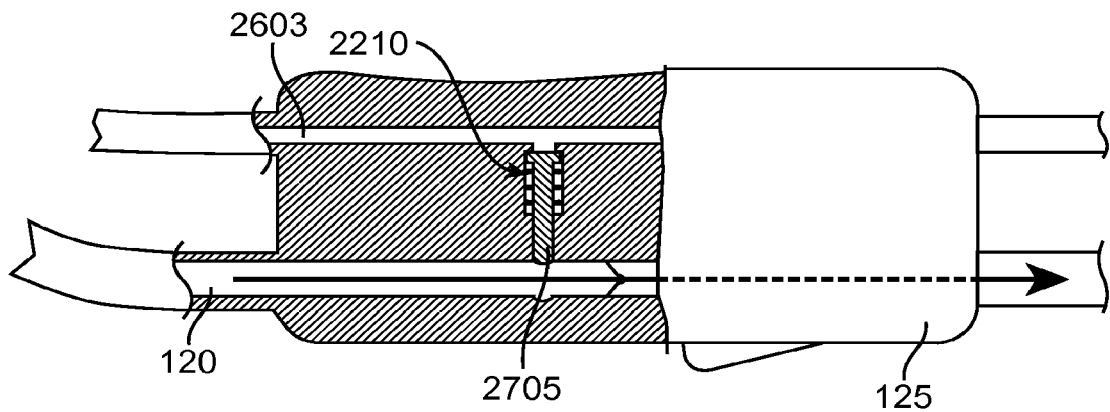
Figure 48B:
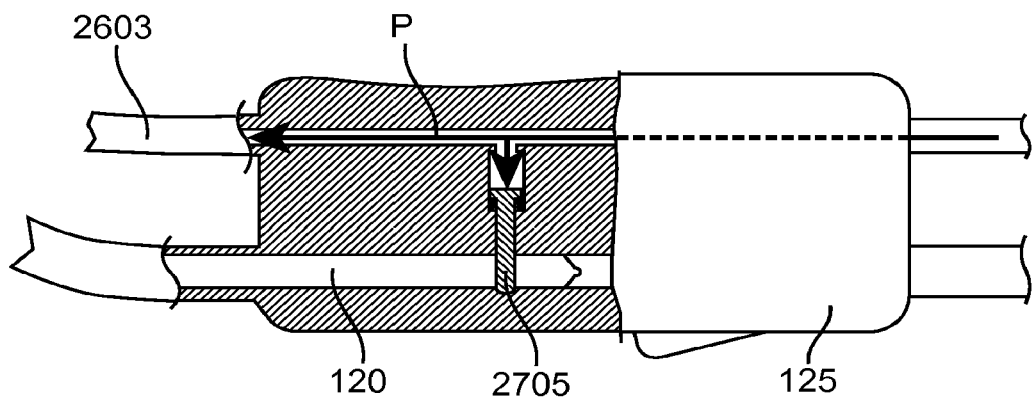
Figure 48C:
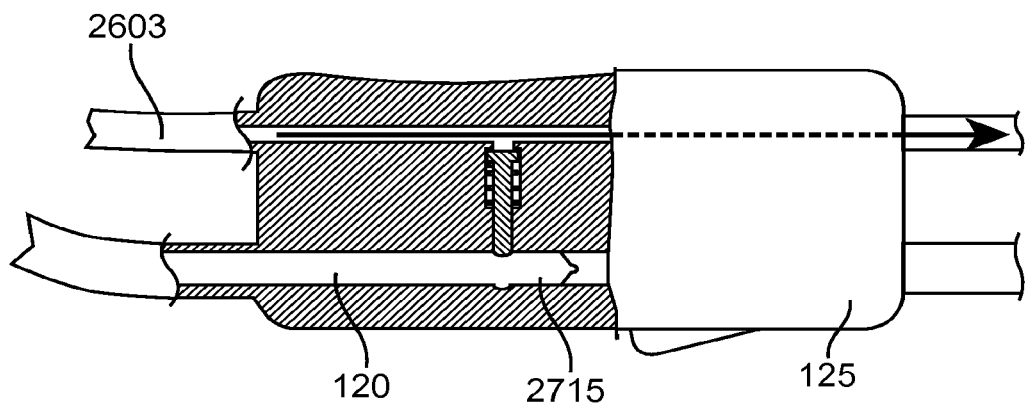

FIGS. 48A-48C show cross-sectional views of the flow control assembly 125 in FIG. 47. The shunt valve 2210 can include a spring-loaded plunger 2705 that is in the shunt-open position when there is no increased pressure in the flush line 2603. That is, in a default, open state, the plunger 2705 can be positioned outside the shunt 120 such that it does not interfere with fluid flow through the shunt, as shown in FIG. 48A. When contrast is injected into the flush line 2603, as shown in FIG. 48B, pressure increases in the flush line 2603, which can cause the plunger 2705 to move toward and into the shunt 120. The plunger 2705 can block flow through the shunt 120, shutting off the shunt 120. Contrast thus flows through the separate flush line 2603 (as represented by line P in FIG. 48B) into the Y-arm 620 of the sheath 605, and subsequently the artery, rather than into the shunt 120. A one way valve 2715 in the shunt 120 can prevent suction from the shunt line during aspiration, as shown in FIG. 48C. Thus, aspiration can occur entirely from the arterial sheath 605.

Figure 49:
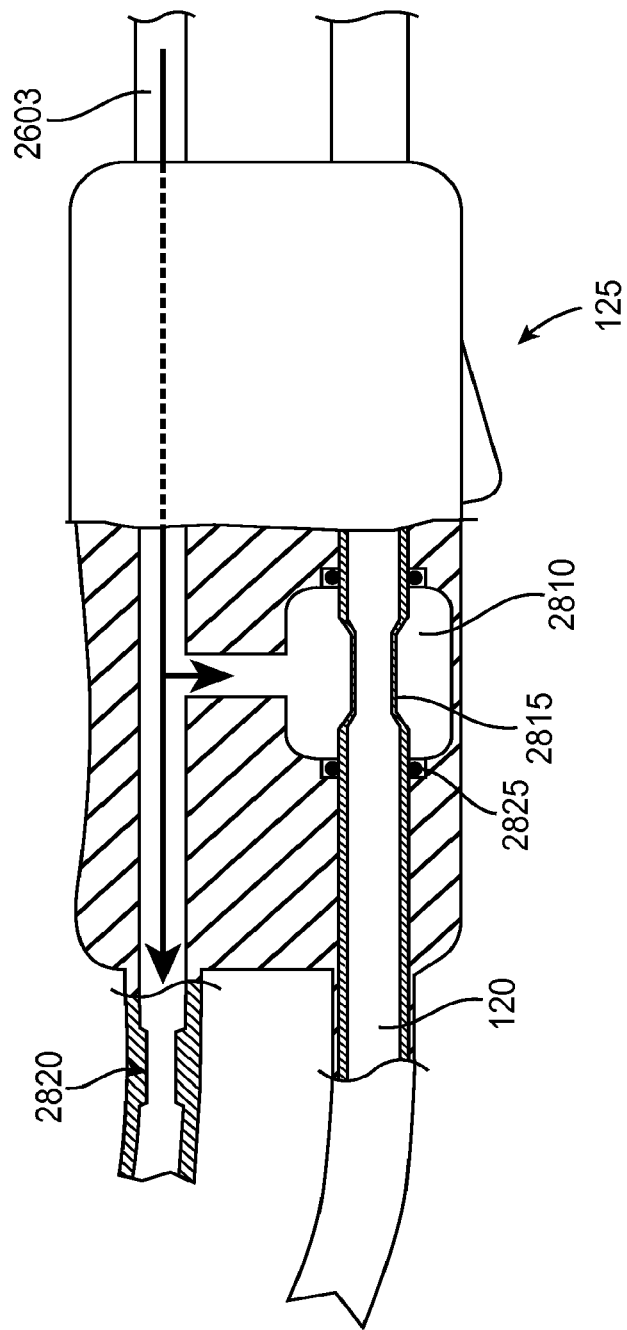
FIG. 49 shows another embodiment of a flow control assembly.

FIG. 49 shows another embodiment of a flow control assembly 125 that can be used in the layout shown in FIG. 47. The flush line 2603 can communicate with a supply of fluid such as contrast. The flush line 2603 also can communicate with a chamber 2810 that is in contact with a thin-walled section 2815 of the shunt 120. When the contrast is injected into the flush line 2603, the pressure within the chamber 2810 can increase. The pressure increase can be sufficiently high to pinch closed the thin-walled section 2815 of the shunt 120 and prevent flow through the shunt 120.

The chamber 2810 can be made of a material that maintains its shape sufficiently to be pressurized up to a maximum injection pressure. In an embodiment, the material can be rigid plastic such as polycarbonate or ABS and the maximum pressure can be about 320 kPa, although different materials and pressures can be used. The material used for the chamber 2810 can be rigid, semi-flexible or flexible. The chamber 2810 can be coupled to one or more seal members 2825 that creates a seal with the outside of the shunt 120. An O-ring or a clamping mechanism, for example, can be used as the seal member. The thin-walled section 2815 of the shunt 120 can be made of flexible tubing having a wall thickness that allows it to be collapsed when exposed to an injection pressure some level below the maximum pressure. A throttle 2820 can be utilized in the flush line 2603 to increase the pressure exerted onto the shunt 120. In an embodiment, the thin-walled section 2815 collapses under a pressure less than 320 kPa.

Figure 50A:
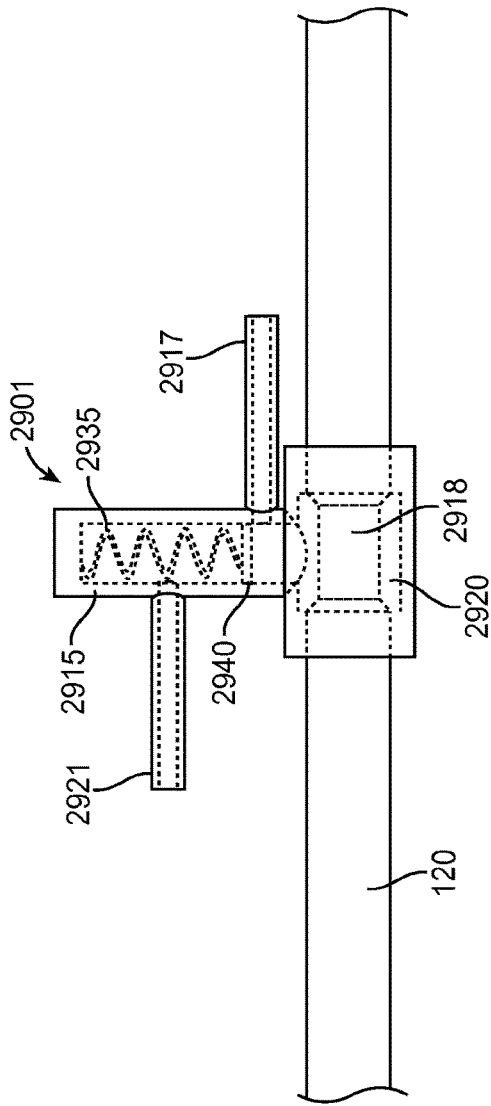
FIGS. 50A-50C show a schematic view of a shunt line shut-off controller for automatically shutting off the shunt when contrast is injected.
Figure 50B:
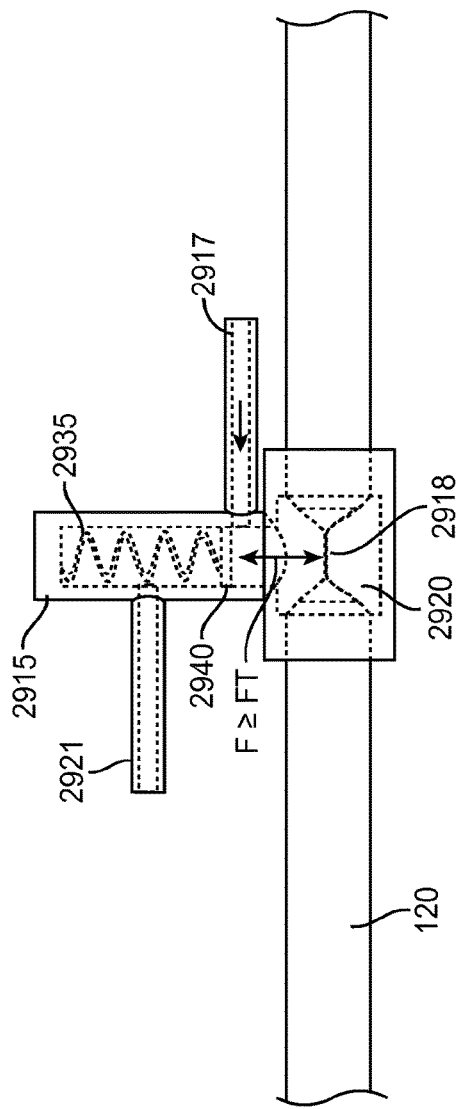
Figure 50C:
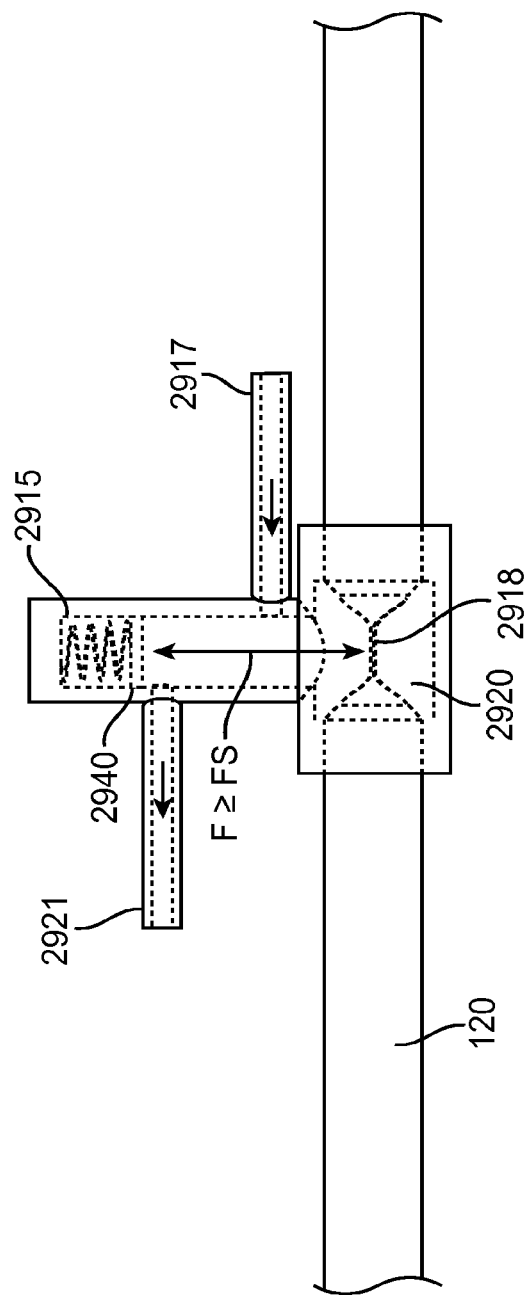

In a scenario where the contrast is injected under low pressure, the flow control assembly as shown in FIG. 49 can allow contrast to flow without exerting enough force to shut off the flow line. FIGS. 50A-50C shows a schematic view of another embodiment of a shut-off valve assembly that includes a shut-off valve 2901 in flow control assembly 125 which prevents this. A valve housing 2915 can be fluidly connected to a chamber 2920. The chamber 2920 can be in contact with a thin-walled section 2918 of the flow shunt 120. A first leg 2917 of the flush line can enter the housing 2915 and a second leg 2921 of the flush line can exit the housing 2915. A spring 2935 can be positioned in the housing 2915 and exert a force FS onto a plunger 2940 inside the housing 2915. In a default state as shown in FIG. 50A, the plunger 2940 can be positioned inside the housing 2915 to block off communication between the first leg 2917 and the second leg 2921 of the flush line.

FIG. 50B shows the control assembly 2910 as contrast is injected into the first leg 2917 of the flush line. When contrast is first injected into the valve housing 2915, the pressure is increased inside the chamber 2920 and exerts a force FT which pinches off the thin-walled section 2918 of shunt 120. As the contrast is continued to be injected, as shown in FIG. 50C, the pressure inside the chamber 2920 increases further, and eventually overcomes the spring force FS. The spring-loaded plunger 2940 can then be pushed to above the opening to the second leg 2921. In this position, the plunger 2940 no longer blocks communication between the first leg 2917 and the second leg 2921 of the flush line. The contrast in the first leg 2917 and chamber 2915 is now free to flow into the second leg 2921 and toward the arterial access device 110. The valve can be designed such that the force FT to shut off the tubing is less that the force FS to compress the spring. In this manner, the shunt 120 is always shut off before contrast can be injected into the arterial access device.

The valve housing 2915 and the shunt housing 2920 can be made of a material of suitable rigidity, such as a rigid plastic or high durometer elastomer. The spring 2935 can be any force resisting member with a resisting force FS greater than the force FT required to collapse completely the thin-walled region 2918 of the shunt 120. In addition, the housing 2915 can include a section of reduced diameter that acts as a throttle which raises the level of pressure inside the housing 2915 that is exerted on the plunger 2940 during injection of fluid.

FIGS. 51A and 51B show a variation of the previous embodiment of the shut-off valve 2901 in the flow control assembly 125. This variation includes an actuator for enabling aspiration, such as a button 2933 that communicates with the spring 2935 in a manner that permits a user to exert a force onto the spring 2935 and the plunger 2940. As shown in FIG. 51A, when the aspiration button 2933 is not depressed, the valve 2901 behaves as in the previous embodiment to shut off the flow shunt 120 during contrast injections. The user can aspirate from the first leg 2917 of the flow line by pushing on the button 2933 to move the plunger to a location below where the first leg 2917 of the flush line connects to the housing 2915. In this state, the first and second legs of the flush line can be in fluid communication with each other, but not with chamber 2920 and the aspiration device is able to aspirate from the access device via the second leg 2921. In this variation, the first leg 2917 of the flush line can be connected to an aspiration device for aspirating through the shunt line.

Figure 52A:
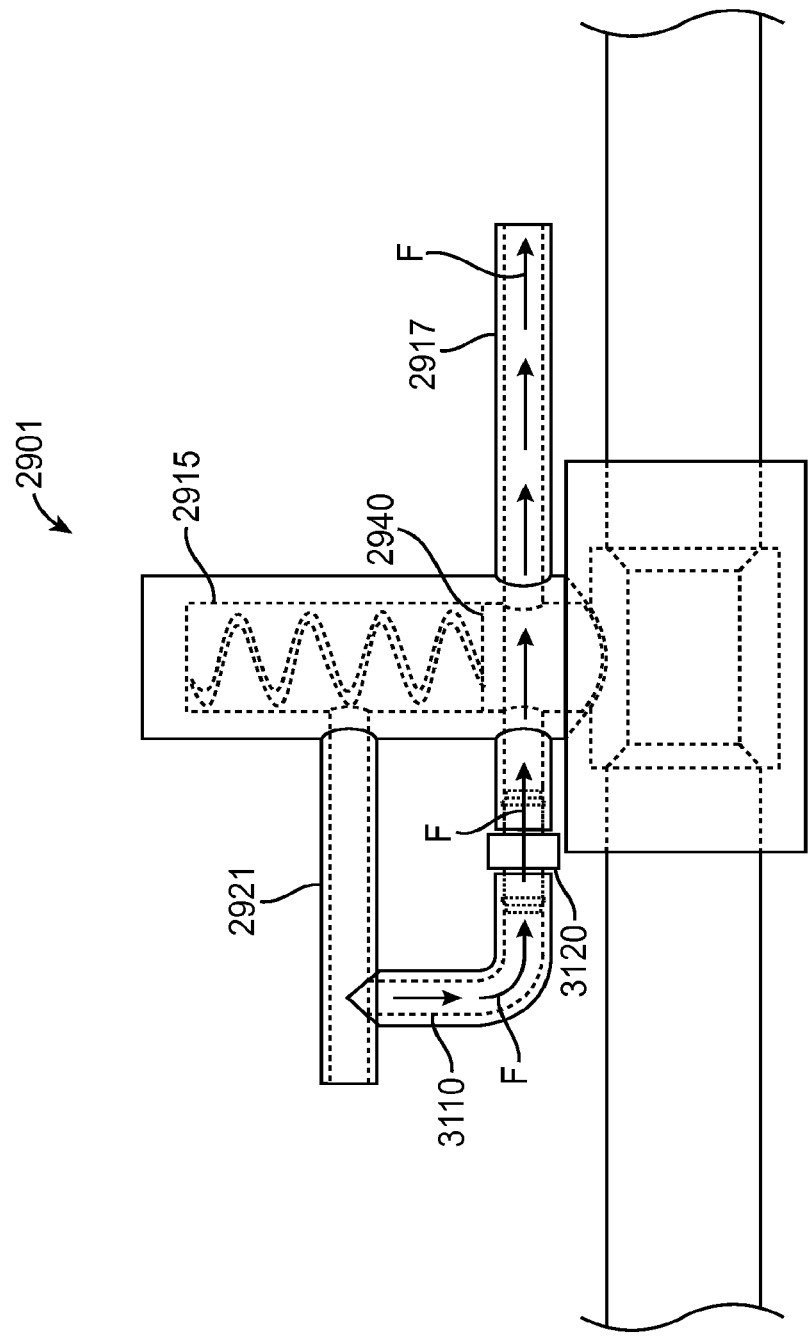
FIGS. 52A-52B show yet another embodiment of the shunt line shut off controller.
Figure 52B:
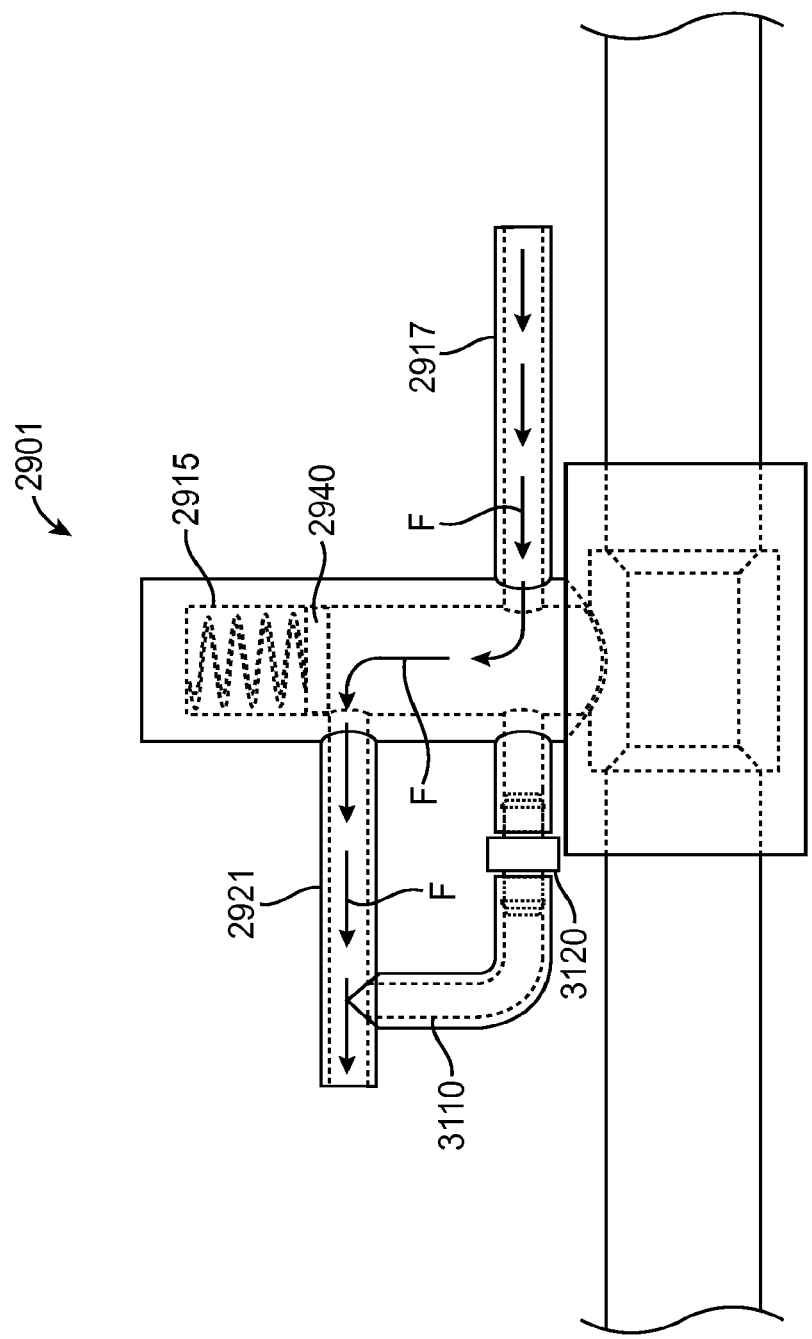

In yet another embodiment of the shunt line shut-off valve 2901, shown in FIGS. 52A and 52B, the valve can include a bypass 3110 of the second leg 2921. The bypass 3110 can connect at one end to the housing 2915 at a location below the plunger 2940 when the device is in a default state, and at the other end to the second leg 2921. Thus, the bypass 3110 always communicates with the first leg 2917. A one-way valve 3120 can be positioned in the bypass 3110 such that during aspiration fluid can be drawn from the second leg 2921 via the bypass 3110 and through the check valve 3120 to the first leg 2915, as represented by the flow arrows F in FIG. 52A. When contrast is injected via the first leg 2917, as in FIG. 52B, the check valve 3120 can prevent flow via the bypass 3110 into second leg 2921. Instead, pressure is built up in housing 2915 until the resulting pressure increase eventually overcomes the spring force FS and the spring-loaded plunger 2940 is then pushed to above the opening to the second leg 2921 (as described above with reference to FIG. 50C). The contrast is then free to flow from the first leg 2917 to the second leg 2921, as represented by the flow arrows F in FIG. 52B.

Detailed Description of Suture Preclose Devices

Disclosed is a suture-based blood vessel closure device that can perform the dilation of an arteriotomy puncture, and therefore does not require previous dilation of the arteriotomy puncture by a separate device or by a procedural sheath dilator. The suture-based vessel closure device can place one or more sutures across a vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of a procedural sheath and can also maintain temporary hemostasis after withdrawal of the procedural sheath but before tying off the suture. A suture-based vessel closure device also desirably can provide rapid access and control of suture ends in the instance of inadvertent sheath removal as well as provide a highly reliable hemostatic closure of the access site.

Figure 53A:
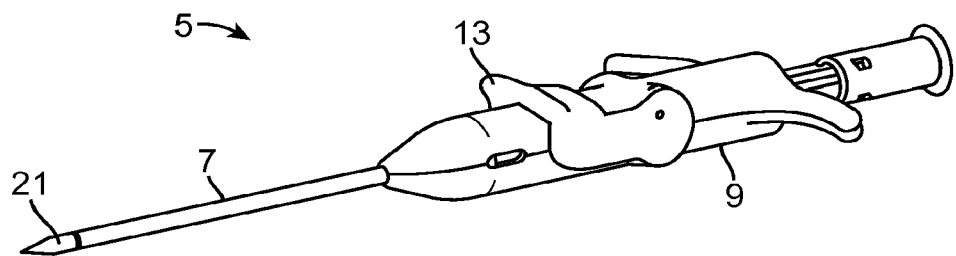
FIGS. 53A-53C show a suture-based vessel closure device or suture delivery device that can be used to position a loop of suture across a puncture in a blood vessel.

FIG. 53A shows a suture-based vessel closure device or suture delivery device 5 that can be used to position a loop of suture across a puncture in a blood vessel. The suture delivery device 5 generally includes a body that includes a delivery shaft 7 attached to a proximal housing 9 having control elements such as a movable actuation handle 11 and/or actuation lever 13. The type, number, and shape of the control elements can vary. In an embodiment, the actuation handle 11 controls movement of a pair of suture capture rods 15 (shown in FIG. 53C). The actuation lever 13 controls positioning of a vessel wall locator 17 (shown in FIGS. 53B and 53C). At least one of the suture capture rods 15 is coupled to a suture 19 (FIG. 54) in a manner that permits a loop of the suture to be positioned across an arteriotomy for closure of the arteriotomy. The delivery device 5 can be at least partially configured in the manner described in U.S. Pat. No. 7,001,400, which is incorporated herein by reference in its entirety. As used herein, the term "proximal" means closer to the user and the term "distal" means further from the user.

Figure 53B:
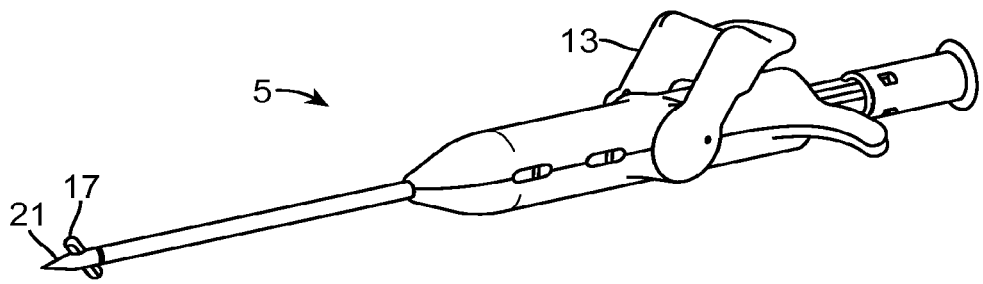
Figure 53C:
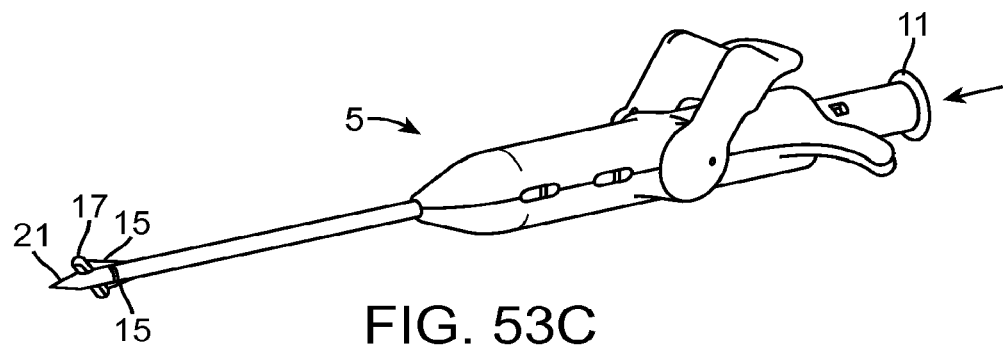

With reference still to FIG. 53A-53C, the device 5 includes a distal tip 21 that extends distally of a distal end of the delivery shaft 7. As described in detail below, in an embodiment the distal tip 21 can be adapted to dilate an arteriotomy. A guidewire lumen can extend entirely through the suture delivery device 5 from the distal end of the distal tip 21 to a proximal exit port of the delivery device 5. The guidewire lumen can permit the entire delivery device 5 to be placed over a guidewire, for example, a 0.035 or a 0.038 inch guidewire. The axis of the delivery shaft 7 need not be straight, as the shaft can curve somewhat.

With reference to FIG. 53B, a vessel wall locator 17 in the form of a foot can be movably positioned near the distal end of the delivery shaft 7. The vessel wall locator 17 can move between a stored position, in which the vessel wall locator 17 is substantially aligned along an axis of the delivery shaft 7 (as shown in FIG. 53A), and a deployed position, in which the vessel wall locator 17 extends laterally from the delivery shaft 7 (as shown in FIGS. 53B and 53C). In the stored position, the vessel wall locator 17 can be disposed within a receptacle of the delivery shaft 7 so as to minimize the cross-section of the device adjacent the vessel wall locator 17 prior to deployment.

The vessel wall locator 17 can be coupled via a control element such as a control wire to the actuation element 13 on the handle 9. As shown in FIGS. 53A-53C, movement of the actuation element 13 can cause movement of the vessel wall locator 17 between the stored position and deployed position. Actuation of the actuation element 13 can slide the control wire (contained within the delivery shaft 7) proximally, pulling the vessel wall locator 17 from the stored position to the deployed position.

Suture capture rods 15 (FIG. 53C) can be coupled to the actuation handle 11. Actuation of the actuation handle 11 can cause the capture rods 15 to move between a non-deployed position wherein the capture rods 15 are contained in the delivery shaft 7 (shown in FIGS. 53A and 53B), and a deployed position (shown in FIG. 53C) wherein the capture rods advance distally outward of the delivery shaft 7 toward the vessel wall locator 17. In the deployed position, distal ends of the capture rods 15 can mate with suture capture collars contained in lateral ends of the vessel wall locator 17.

Movement of the suture capture rods 15 to the deployed position causes at least one end of the suture to couple to the suture capture rods 15. The suture capture rods 15 can then be used to proximally draw the ends of the sutures through the vessel wall for forming a suture loop around the arteriotomy. At the end of the procedure after a procedural sheath has been removed, the suture can be tied in a knot and tightened distally against the arteriotomy to seal the arteriotomy. This can be achieved in various manners, some of which are described in U.S. Pat. No. 7,001,400, which is incorporated by reference in its entirety. In an embodiment, a short length of flexible filament 29 (FIG. 54) can extend substantially directly between suture capture elements in the vessel wall locator 17. One suture capture rod can attach a suture 19 to one end of flexible filament. In this manner, the flexible filament links the suture 19 to the opposing suture capture rod. As the rods are drawn back using actuator 11, the flexible filament pulls the suture 19 through the vessel wall on one side of the arteriotomy, across the arteriotomy, and out the other side. When the actuator 11 has fully pulled out the suture rods 15, both ends of the suture 19 can be retrieved.

FIG. 54 shows a close-up view of a distal region of the delivery device 5 with the vessel wall locator 17 in the deployed position. The delivery device 5 is shown in partial cross-section to illustrate the internal components. The distal tip 21 can taper smoothly to the diameter of the delivery shaft 7 to permit the distal tip 21 to be used as a dilator. As mentioned, the tapered distal tip 21 can dilate the arteriotomy as the delivery device 5 enters the blood vessel. In this regard, the distal tip 21 can have features that are particularly adapted for dilating an arteriotomy. Such features include size, shape, materials, and/or material properties that are specifically adapted to dilate an arteriotomy. For example, the dilating distal tip 21 can be constructed from materials and dimensions to reproduce the dilating function of a standard sheath dilator. For example, at least a portion of the tip can have a taper angle of 3° to 7° relative to a longitudinal midline axis of the suture closure device. In an embodiment, the distal tip has an equivalent stiffness and smoothness to polyethylene material. In an embodiment, the tapered portion of the tip 21 extends over a length of about 1 to 3 cm or about 1 to 2 cm. The tapered portion can taper outward from the distal-most location of the distal tip 21. It should be appreciated that the distal tip 21 is not required to be a dilating tip.

In addition, the distal tip 21 can include a guidewire lumen 31. As shown in FIG. 54, the guidewire lumen can extend through the entire device, or alternately through the entire distal region and delivery shaft 7 and exit distal to the proximal handle 9. In yet another alternate embodiment, the guidewire lumen can extend through the dilator tip to a point on one side of the distal region of the suture delivery device distal to the vessel wall locator. In this latter case, the guidewire rides only over the distal region of the suture delivery device, rather than through the delivery shaft.

The guidewire lumen 31 can form an opening or exit at the distal end of the distal tip 21. The distal exit of the guidewire lumen 31 can provide a smooth transition to the guidewire, so the device can smoothly and atraumatically be inserted into the vessel over the guidewire. Thus the diameter of the guidewire lumen can be close to the diameter of the guidewire itself when it exits the dilating tip. For example, for compatibility with a 0.035" or 0.038" guidewire, the dilating tip of the device can have a guidewire lumen of from 0.039" to 0.041" as it exits the tip (although it can be slightly larger for the remainder of the device). In addition, the leading edge of the dilating tip can be radiused, for example 0.050" to 0.075" radius, so there are no abrupt transitions as the device enters the vessel. Thus, as mentioned, a separate dilator is not needed to dilate the arteriotomy before deployment of the delivery device 5 through the arteriotomy. In an embodiment, the distal tip is located about 3 cm beyond the stitch delivery location, thus, about 3 cm distal of the vessel wall locator 17.

The distal portion of the delivery shaft 7 can include a position verification lumen that extends proximally from a position verification port just proximal to the vessel wall locator 17 to a position indicator at the housing 9. When the vessel wall locator 17 is properly positioned within the blood vessel, blood pressure causes blood to flow proximally into the position verification port, through the position verification lumen, and to the position indicator in the housing 9. Presence of blood in the position indicator provides an indication that the vessel wall locator 17 has entered the blood vessel and can be actuated to the "open" position (as in FIG. 53B). The position indicator can include a blood exit port, a clear receptacle in which blood is visible, or the like. It should be understood that a wide variety of alternative position verifications sensors might be used, including electrical pressure sensors, electrolytic fluid detectors, or the like.

With reference still to FIG. 54, a guidewire 33 can slidably extend through the guidewire lumen 31 via an opening in the center of the distal tip 21 of the device 5. At a distal-most location, the guidewire lumen 31 can be centered in the distal tip 21. That is, the guidewire 31 is aligned with the longitudinal midline or center-axis of the distal tip 21. The guidewire lumen 31 can transition toward an off-center position moving proximally through the delivery shaft 7. That is, at a location proximal of the distal most location of the distal tip 21, the guidewire lumen transitions to a position that is offset from the longitudinal center-axis of the delivery shaft 7. The vessel wall locator 17 can be positioned on the delivery shaft 7 such that the suture placement site is centered around the delivery shaft 7. Thus, the sutures can be placed at the center of the vessel puncture even though the guidewire 33 is off-center in the delivery shaft 7. Alternately, the guidewire lumen can be positioned in the central axis of the delivery shaft, and the vessel wall locator and suture placement sites are centered offset from the shaft central axis.

Figure 55A:
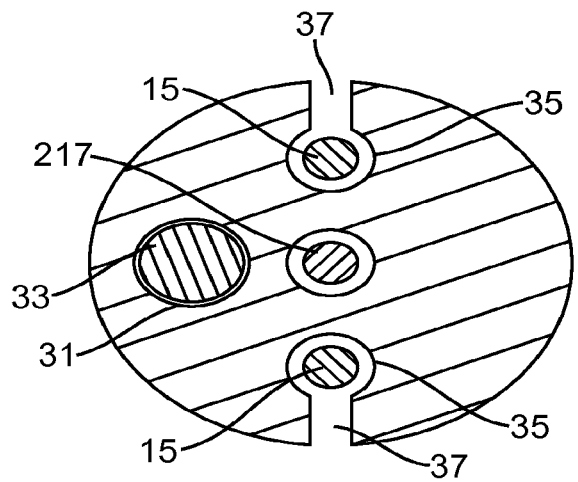
FIGS. 55A and 55B show cross-sectional views of the delivery shaft of the closure device along line 55A-55A of FIG. 54.
Figure 55B:
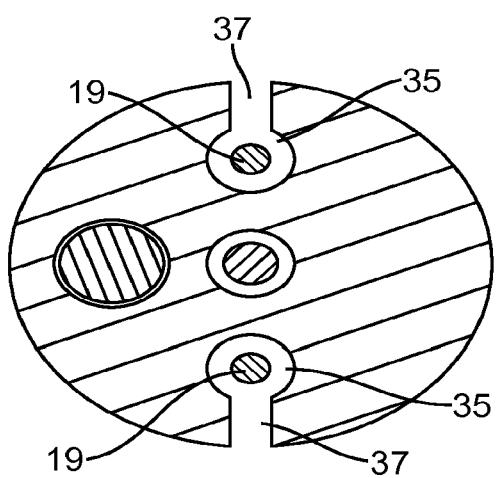

FIGS. 55A and 55B show a cross-sectional view of the delivery shaft 7 along line 55A-55A of FIG. 54. A pair of channels 35 can extend longitudinally through the delivery shaft 7 near the outer surface of the delivery shaft. Each of the channels 35 communicates with a slot 37 that provides external access to the respective channel 35. In FIG. 55A, a suture capture rod 15 can be positioned within each of the channels 35. The slot can be sized and shaped such that the suture capture rod 15 is securely contained within the channel 35. In FIG. 55B, the suture capture rods have been pulled proximally, pulling the suture 19 with them; thus the figure shows the suture 19 positioned within each of the channels 35. As shown in FIG. 55B, the slots are larger than the suture 19 such that the suture 19 can be removed through the slots 37, such as by being peeled out of the slots 37.

Figure 56A:
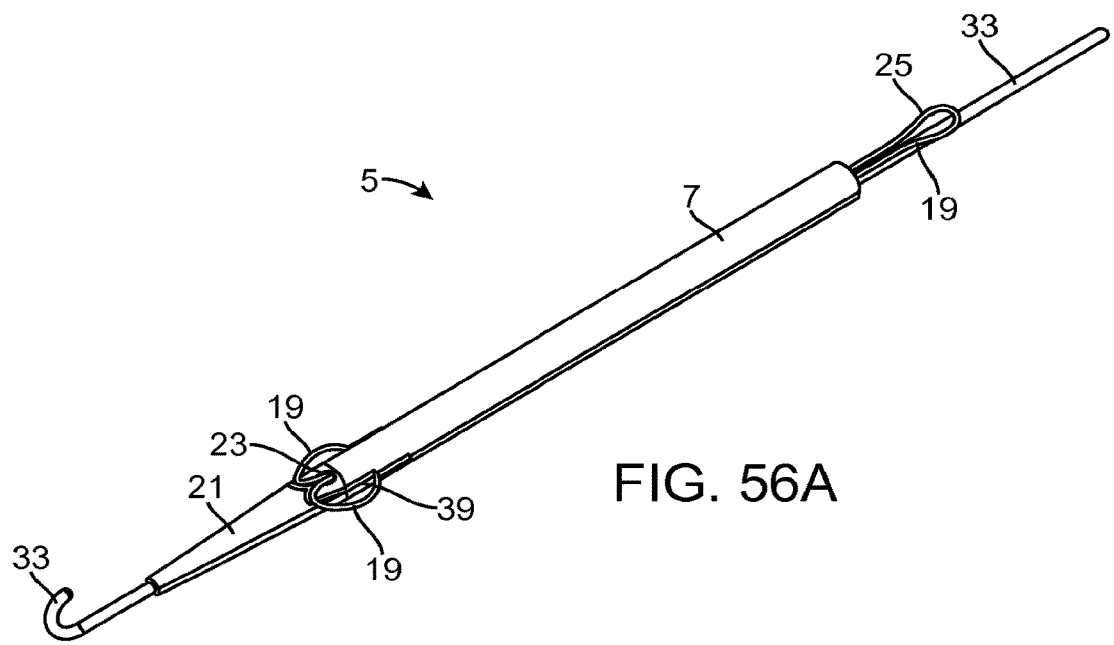
FIGS. 56A and 56B show a close-up view of an alternate embodiment of the distal portion of a suture delivery device that can be used to position a loop of suture across a puncture in a blood vessel.
Figure 56B:
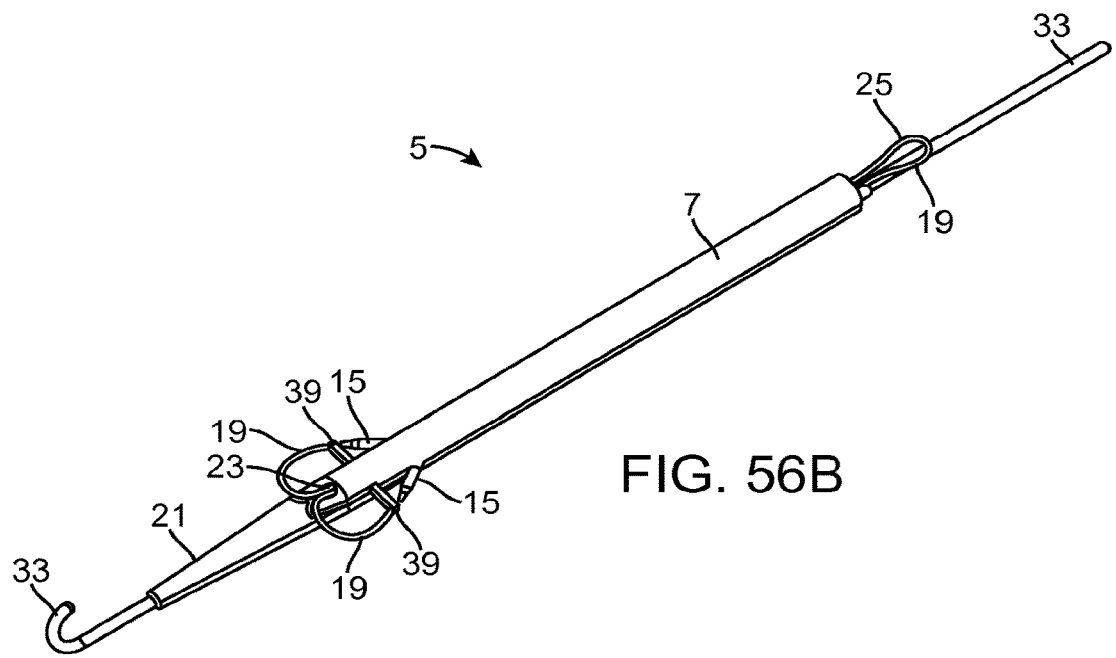

FIGS. 56A and 56B show a close-up view of an alternate embodiment of the distal portion of a suture delivery device 5 that can be used to position a loop of suture across a puncture in a blood vessel. A similar device is described in U.S. Pat. No. 7,004,952, which is incorporated by reference in its entirety. FIGS. 56A and 56B show the device 5 with a body that includes the shaft 7 truncated in order to illustrate features of the device 5. The vessel wall locator is in the form of two extendable arms 39. As with the previous embodiment, the vessel wall locator can be coupled via a rod or other coupler to an actuation element 13 on a handle 9. A loop of suture 19 can be positioned down the center of the delivery shaft 7 such that both ends of the suture 19 exit out a distal port 23 of the delivery shaft 7. The middle 25 of the loop of suture 19 can exit out the proximal end of the delivery device 5. Each end of the suture loop can be attached to the end of each extendable arm 39. As with the previous embodiment, the device can include a distal tip 21 with a central lumen for a guide wire 33. The distal tip 21 can optionally be a dilating tip as described above in the previous embodiment. Also as in the previous embodiment, the guide wire lumen can extend along the entire length of the delivery device, such that a guidewire can ride along the entire length of the suture delivery device 5 and exit out the proximal end, or can exit at a point in the delivery shaft distal to the proximal handle 9.

FIG. 56A shows the device with the extendable arms 39 in the retracted position. In this configuration, the delivery device 5 can be advanced over a guidewire into an arterial puncture. Once the device is in place, the extendable arms 39 can be extended outward which allows the device to be positioned accurately with respect to the vessel wall. FIG. 56B shows the device with the arms 39 in the extended position, with the ends of the suture loop 19 now also extended outwards. The suture capture rods 15 can now be extended and pierce the vessel wall to each side of the arterial puncture through which the delivery shaft 7 is located. The suture capture rods 15 can be configured to capture each end of the suture loop 19. When the capture rods 15 are retracted, they draw the suture loop 19 through the vessel wall across the arterial puncture, until the loop of suture is entirely in the vessel wall and no length of suture loop remains in the delivery shaft. The extendable arms 39 can now be retracted to enable removal of the device from the arterial puncture.

In a method of use, the ends of the suture 19 can be held in tension during removal of the suture delivery device 5 while the guidewire 33 remains in place. A procedural sheath and dilator can then be placed over the guidewire and through the pre-placed sutures into the vessel. The guidewire and dilator can be removed, and the procedural sheath can remain in place. The sutures can be relaxed during the subsequent procedure. However, they can be tagged or anchored in some manner so that they can be grasped and held in tension to achieve rapid hemostasis in the case of inadvertent sheath removal. After completion of the procedure, the sutures can be again held in tension during removal of the procedural sheath. The ends of the suture can be tied and the knot pushed against the arteriotomy to achieve permanent hemostasis.

In an embodiment shown in FIG. 57, a sheath 41 can be pre-mounted on the suture delivery device 5 (which can be any of the embodiments of delivery devices described herein). The sheath 41 can be an elongated body, such as a tubular body, having an internal lumen sized to receive the delivery shaft 7 of the suture delivery device 5. The pre-mounted sheath 41 can be initially positioned in a parked configuration wherein the sheath 41 is located on the proximal end or proximal region of the delivery shaft 7. The sheath 41 can remain in the parked configuration during suture placement. After the suture is deployed across the arteriotomy, the ends of the suture can be captured and peeled away from the delivery shaft 7. The sheath 41 can then slide distally over the delivery device 5 into the arteriotomy. FIG. 57 shows the pre-mounted sheath being advanced after the suture 19 has been placed across the arteriotomy. Alternately, the step of advancing the pre-mounted sheath 41 can facilitate peeling away the sutures from the delivery shaft 7 in that the sheath 41, as it moves, physically abuts the sutures to cause the sutures to peel away. Once the pre-mounted sheath has been advanced into the arteriotomy, the delivery device 5 can then be removed through the sheath 41.

In an embodiment, the pre-mounted sheath 41 can be an exchange sheath that provides a means for maintaining hemostasis of the arteriotomy while removing the suture delivery device 5 and then inserting a separate procedural sheath (such as the arterial access sheath 605 described below) for performing a procedure in the blood vessel. Once the suture is deployed across the arteriotomy, the exchange sheath 41 can be positioned through the arteriotomy and then the suture delivery device 5 can be removed. The procedural sheath can then be inserted into the blood vessel through the exchange sheath 41. Once the procedural sheath is placed, the exchange sheath 41 can be removed. In an embodiment, the exchange sheath 41 is configured to be removed from the procedural sheath in a peel-away fashion. The pre-mounted sheath 41 can have a hemostasis valve either on its distal end or on its proximal end to prevent bleeding during this exchange. The hemostasis valve can be in the form of a closed end or membrane, with a slit or cross slit, or other expandable opening. The membrane is normally closed and opens to allow passage of a procedural sheath therethrough.

In another embodiment, the pre-mounted sheath 41 is an outer sheath which remains in place during the procedure. The outer sheath 41 can include an occlusion element 129, as shown in FIG. 58, that is adapted to increase in size within the blood vessel to occlude the blood vessel. Once the pre-mounted outer sheath 41 sheath is positioned in the vessel, the procedural sheath can be inserted through the outer sheath 41 into the blood vessel. The procedural sheath can then be used to introduce one or more interventional devices into the blood vessel. In an embodiment, the procedural sheath is a sheath such as the sheath 605 (described below), which is used to connect the blood vessel to a reverse flow shunt, such as the reverse flow shunt described below. The occlusion element 129 on the sheath 41 can be used to occlude the blood vessel during the procedure. The intravascular occlusion element can be an inflatable balloon, an expandable member such as a braid, cage, or slotted tube around which is a sealing membrane, or the like. The outer sheath 41 can also include a sheath retention element such as an inflatable structure or an expandable wire, cage, or articulating structure which prevents inadvertent sheath removal when deployed.

This dual sheath configuration allows the pre-mounted sheath to be relatively short compared to the procedural sheath. The procedural sheath can require an extended proximal section such that the proximal adaptor where interventional devices are introduced into the sheath are at a site distance from the vessel access site, which can be advantageous in procedures where the vessel access site is near the fluoroscopy field. By keeping the pre-mounted sheath relatively short, the delivery shaft 7 can be kept shorter.

In another embodiment, the pre-mounted sheath 41 is the procedural sheath itself, such that use of an exchange or outer sheath is not necessary. The procedural sheath 41 can have a hemostasis valve, such as on the proximal end of the procedural sheath. Thus, when the suture delivery device 5 is removed, hemostasis is maintained. If a procedural sheath 41 is used which requires a proximal extended section, an extension can be added to the proximal end of the procedural sheath 41 after removal of the suture delivery device 5. Alternately, the delivery shaft 7 can have an extended length to allow pre-mounting of both the procedural sheath and proximal extension. The procedural sheath 41 can include an intravascular occlusion element for procedures requiring arterial occlusion. The intravascular occlusion element can be an inflatable balloon, an expandable member such as a braid, cage, or slotted tube around which is a sealing membrane, or the like. The procedural sheath can also include a sheath retention element such as an inflatable structure or an expandable wire, cage, or articulating structure which prevents inadvertent sheath removal when deployed.

An example of a method of use of the suture delivery device 5 of FIGS. 53A-53C is now described. A puncture can be formed into a blood vessel to provide access to the interior of the vessel. After accessing the blood vessel, a guidewire can be inserted so that the guidewire extends into the skin and down through tissue along tissue tract. The suture delivery device 5 can be advanced over the guidewire via the guidewire lumen 31 (FIG. 54) such that the guidewire directs the suture delivery device 5 along the tissue tract and into the vessel through the arteriotomy. As mentioned, the distal tip of the delivery device can act as a dilator such that it dilates the arteriotomy to facilitate entry. The distal tip of the delivery device can be used to dilate the arteriotomy without using any separate dilator device to dilate the arteriotomy. The delivery shaft 7 can include a position verification lumen. When the vessel wall locator 17 enters the blood vessel, blood flows through the position verification lumen to the proximal indicator to notify the operator that the vessel wall locator has entered the blood vessel.

When the vessel wall locator 17 is positioned inside the blood vessel, the actuation lever 13 on the handle 9 can be actuated to move the vessel wall locator 17 to the deployed position inside the blood vessel. The deployed vessel wall locator 17 can extend laterally from the delivery shaft 7, so that the vessel wall locator 17 can be drawn up against the vessel wall by pulling the delivery shaft 7.

The actuation handle 11 can then be actuated to deploy the suture capture rods 15 toward the vessel wall locator 17. The suture capture rods can mate with ends of the flexible link 29 contained in lateral ends of the vessel wall locator 17. This couples at least one end of the suture 19 to one end of the flexible link 29, and a suture capture rod 15 to the other end of the flexible link. The suture capture rods 15 can then be used to proximally draw the flexible link, and with it the suture 19, through the vessel wall for forming a suture loop across the arteriotomy. Alternately, the suture capture rods 15 can mate directly with ends of the suture 19, which are located in the lateral ends of the vessel locator. The suture capture rods 15 can then be used to draw the ends of the suture 19 through the vessel wall to form a suture loop across the arteriotomy. The suture capture rods then can pull the suture ends out of the tissue tract above the skin, where then can be retrieved by the user.

As the suture ends are held in tension to maintain hemostasis, the suture delivery device 5 can be removed over the guidewire, and exchanged for the procedure sheath. Manual compression can be applied over the arteriotomy site if needed for additional hemostasis control during the exchange of the suture delivery device 5 for the procedure sheath.

At the conclusion of the procedure, the procedure sheath can be removed and the pre-placed suture ends can be knotted and the knot pushed in place, in a similar manner to standard percutaneous suture closure devices. The suture ends can be pre-tied in a knot, in which case the knot is simply pushed into place. The tied suture ends are then trimmed.

In variation to this method, the suture delivery device 5 can be inserted into the artery and the sutures placed across the arteriotomy and drawn out of the tissue tract and above the skin, where they can be retrieved by the user, as described above. The sutures can then be separated from the delivery shaft 7. Prior suture delivery devices do not allow the sutures to "peel away" from the delivery shaft. Instead, in prior devices, the sutures can be pulled out through the proximal end of the delivery device. The delivery device 5 disclosed herein can permit the sutures to be peeled from the side of the delivery shaft 7. As mentioned, the sutures and suture capture rods can be disposed in open-sided channels in the delivery shaft 7, as shown in FIGS. 55A and 55B. The channels can be sized relative to the sutures such that the sutures can be lifted or pulled out of the channels. The suture capture rods still can exit out the proximal end of the delivery device 5. The suture end that is attached to the suture capture rod can be extracted from the delivery shaft 7 using a hook or pre-applied loop, and cut free of the suture capture rods. The other suture end can be pulled out of the side channels 35. The suture can have a pre-tied knot, as is disclosed in prior art. In this configuration, the knot can be located outside the body of the patient such that both ends of the suture can be grasped below the knot after the suture ends are retrieved.

With the suture free from the delivery device 5, the delivery device 5 can then be removed from the vessel while the guidewire 33 remains in the vessel. As mentioned, the guidewire channel extends entirely through the delivery device 5 to permit the delivery device to be easily removed from the guidewire. Prior to removing the delivery device 5, a pre-mounted sheath 41 is slid distally from the parked position (on the proximal end of the delivery shaft 7) into the tissue tract and through the arteriotomy. The act of pushing the sheath 41 forward can assist in pushing the sutures out of the channels 35 and away from the delivery shaft 7. As described above, the pre-mounted sheath can be an exchange sheath, an outer sheath for a dual-sheath configuration, or the procedural sheath itself. The sheath can further contain an intravascular occlusion element.

A variation on this configuration is to insert the suture delivery device 5 in the opposite direction from the ultimate direction of the sheath 41. This method can be used if there are anatomic restraints on the amount of blood vessel which can be entered, for example in a transcervical approach to carotid artery stenosis treatment. In this retrograde delivery, the delivery device can be inserted into the vessel in a more perpendicular approach, so that the tissue tract from the skin to the artery created by the initial wire puncture and subsequently the suture delivery device can also be used to approach the artery with the procedural sheath in the opposite direction. Once the suture has been deployed and the suture ends have been retrieved, the suture delivery device can be removed while keeping the guidewire in place. The guidewire can then be re-positioned such that the tip is now in the opposite direction. The guidewire can be advanced enough to provide support for the procedural sheath, which can now be advanced over the guidewire and inserted into the vessel. As it is critical not to lose the position of the guidewire during this change in guidewire direction, a feature can be added to the guidewire which prevents it from being removed from the vessel, for example an expandable element as described below.

In an embodiment, the suture delivery device 5 and the sheath 41 can be used to gain access to the common carotid artery pursuant to treatment of a carotid artery stenosis, or an intracerebral arterial procedure such as treatment of acute ischemic stroke, intracerebral artery stenosis, intracerebral aneurysm, or other neurointerventional procedure. In another embodiment, the suture delivery device 5 and the sheath 41 can be used to gain access to the common carotid artery pursuant to treatment of a vascular or cardiac structure such as transcatheter aortic valve replacement. In this particular embodiment, the sheath 41 can be directed in a proximal or caudal direction. In an embodiment, transcervical access to the common carotid artery can be achieved percutaneously via an incision or puncture in the skin through which the arterial access device 110 is inserted. However, it should be appreciated that the suture delivery device as well as any of the devices and methods described herein can be used with a variety of interventional procedures.

In another embodiment, the suture delivery device does not have a dilating tip and does not have a premounted sheath. Rather, the suture delivery device can be configured as described, for example, in U.S. Pat. No. 7,001,400, which is incorporated by reference in its entirety. The suture delivery device can be used to suture an arteriotomy performed in the common carotid artery via transcervical access. In this embodiment, shown in FIGS. 59A and 59B, the suture delivery device generally can have a shaft 7 having a proximal end 14 and a distal end 16. A proximal housing 18 can support a needle actuation handle 20. A flexible, atraumatic monorail guidebody 22 can extend distally of distal end 16 of shaft 12.

Figure 59A:
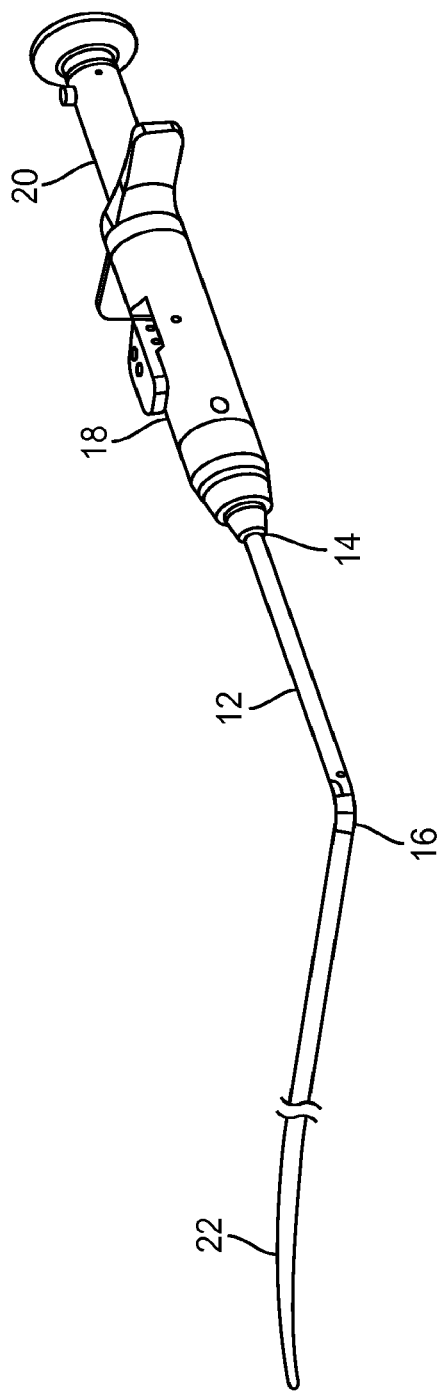
FIGS. 59A-59B show another embodiment of a suture-based vessel closure device or suture delivery device.
Figure 59B:
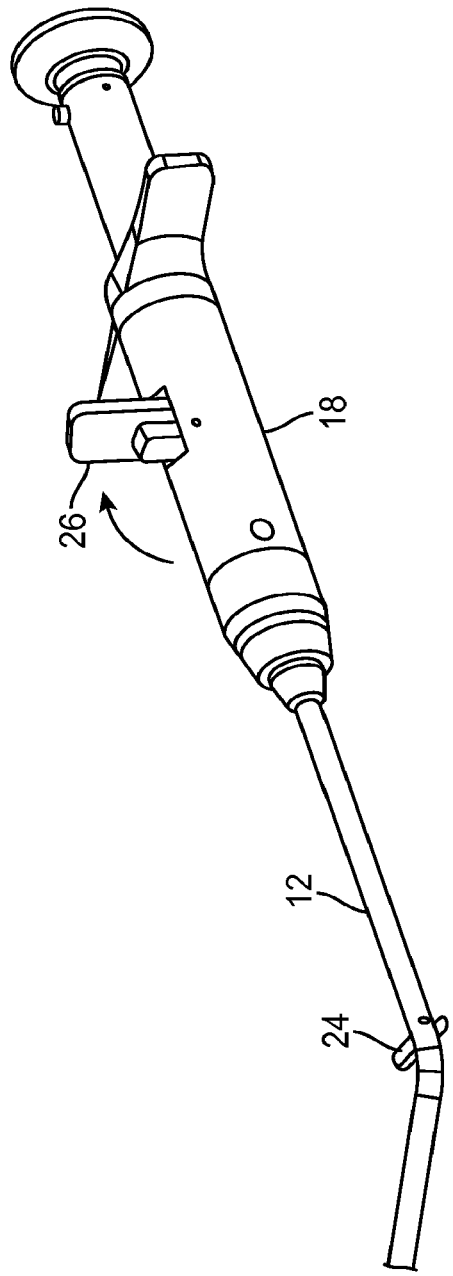

As shown in FIG. 59B, a foot 17 can be articulatably mounted near the distal end of shaft 12. The foot 17 can move between a low profile configuration, in which the foot is substantially aligned along an axis of shaft 12 (as illustrated in FIG. 59A), to a deployed position, in which the foot extends laterally from the shaft, upon actuation of a foot actuation handle 26 disposed on proximal housing 18. The suture delivery device shown in FIGS. 56A-59B can deliver the sutures in a similar manner to the way that the suture delivery device of FIGS. 53A-53C delivers the suture.

Figure 60:
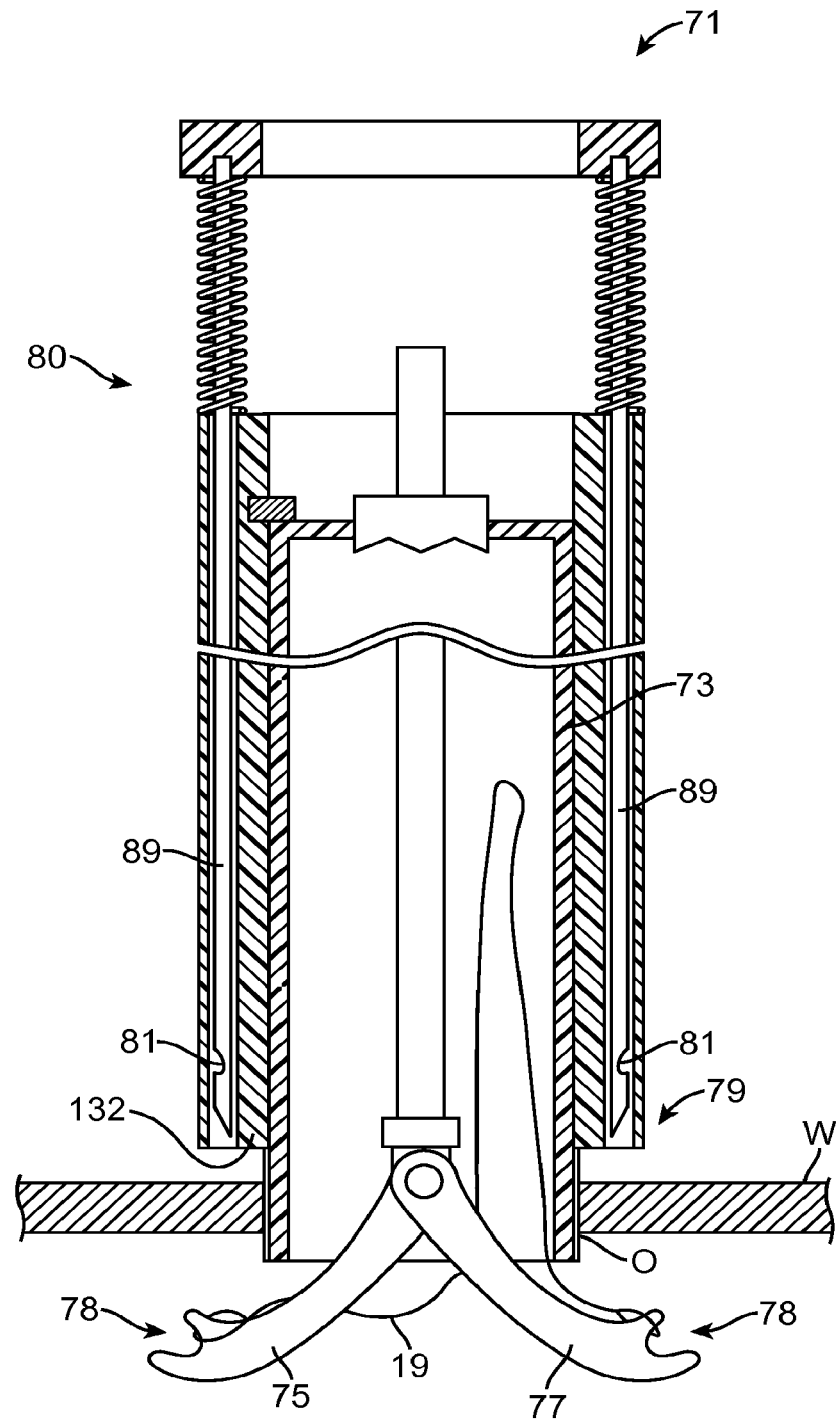
FIGS. 60 and 61 show portions of another embodiment of a suture delivery device.

FIG. 60 shows another embodiment of a suture delivery device, generally designated 71, for suturing vessel walls and other biological tissue. The device can be for use in suturing an arterial vessel walls W. The device 71 can include a suture introducer housing 73 for insertion into an opening O in the arterial wall W. Vessel wall locators in the form of suture clasp arms 75, 77 can be deployably housed in the housing during insertion and after insertion into the vessel, the arms can be deployed to the position shown in FIG. 60. When deployed, the suture clasp arms can extend outside the circumference of the suture introducer housing 73. Each arm can have at least one means, generally designated 78 and schematically illustrated, for clasping a suture 19. A penetrating mechanism, generally designated 79, with needles 89 can be provided for penetrating the vessel wall W. The penetrating mechanism can be provided on either the suture introducer housing 73 or on a suture catch assembly, generally designated 80. When, as shown in FIG. 60, the penetrating mechanism can be part of the suture catch assembly 80, the penetrating mechanism also can include a suture catch 81 for catching the suture 19 and dislodging it from the clasping means 78. The suture catch assembly can operate to pull the suture held by the suture catch through the vessel wall. After the ends of the suture are pulled outside the vessel, the introducing housing can be removed and the suture tied to close the vessel.

Figure 61:
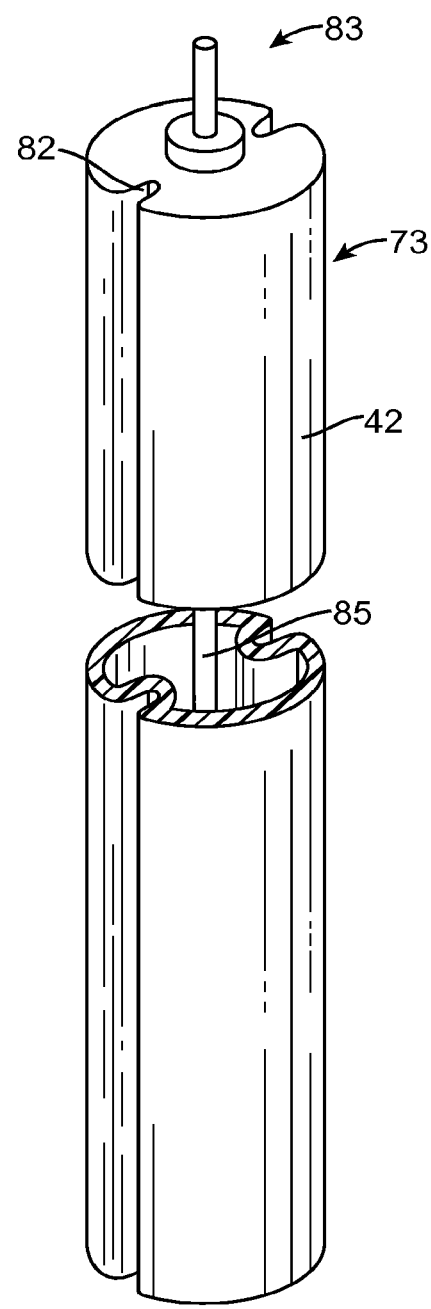

In an embodiment shown in FIG. 61, the suture introducer housing 73 can be a generally cylindrical and thin walled hypo tube such as a hollow elongated cylindrical member with a thin wall such that the inner diameter and outer diameter vary by a relatively small amount in the range of few thousandths of an inch to tens of thousandths of an inch. The outer surface 42 of the housing can include a key way groove 82 (exaggerated for clarity) to align the housing with a key on the inner surface of the suture catch assembly 80 (FIG. 60). An arm actuation assembly 83 for deploying the suture clasp arms can protrude from the proximal end of the housing, and an actuating rod 85 can extend from the actuation assembly through the housing to the suture clasp arms. U.S. Pat. Nos. 5,860,990 and 7,004,952, both of which are incorporated by reference in their entirety, described suture delivery devices.

The suture delivery device of FIGS. 60 and 61 generally works by actuating an arm on the suture delivery device from a first position wherein the arm is within the suture delivery device to a second position wherein the arm is extended away from the elongate body. The arm holds a portion of a suture. At least one of the needles 89 is advanced in a proximal to distal direction along at least a portion of the suture delivery device toward the arm, the needle being advanced through tissue of the artery. A portion of the needle is engaged with the portion of the suture and the needle is retracted in a distal to proximal direction to draw the suture through the artery tissue.

Figure 62A:
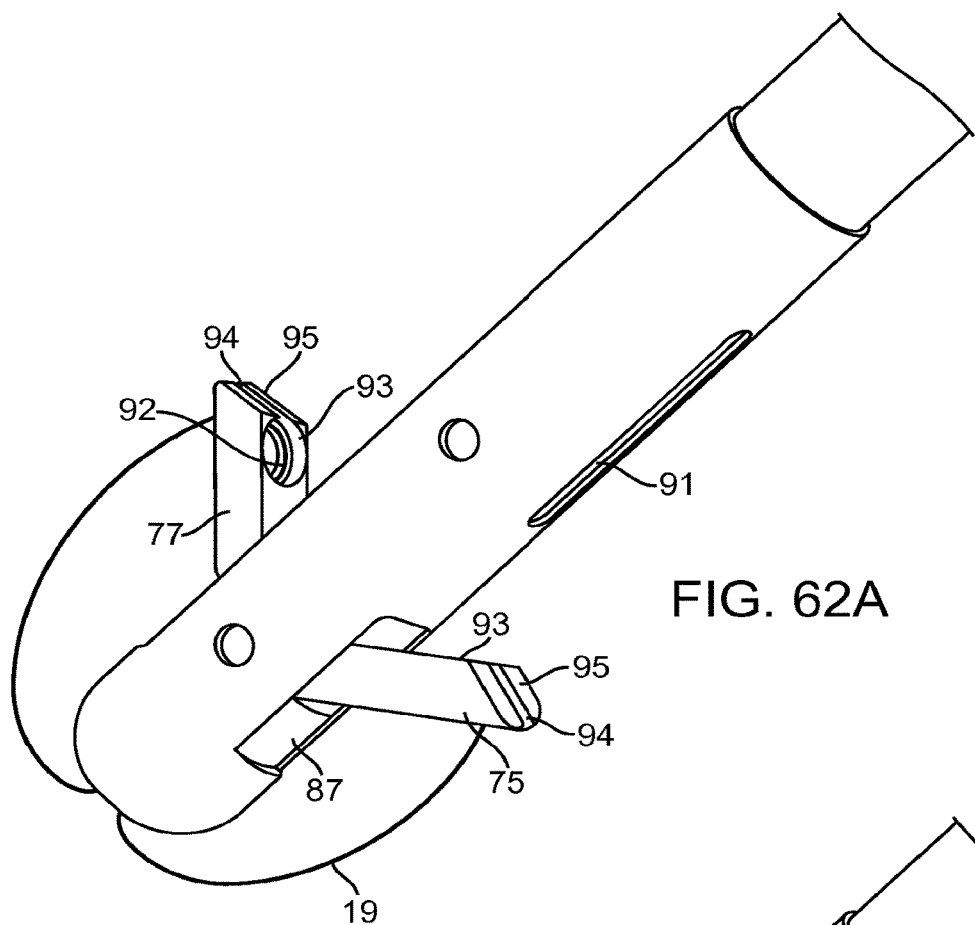
FIG. 62A is a perspective view of an embodiment of a distal region of a suture delivery device with the suture clasp arms partially deployed.
Figure 62B:
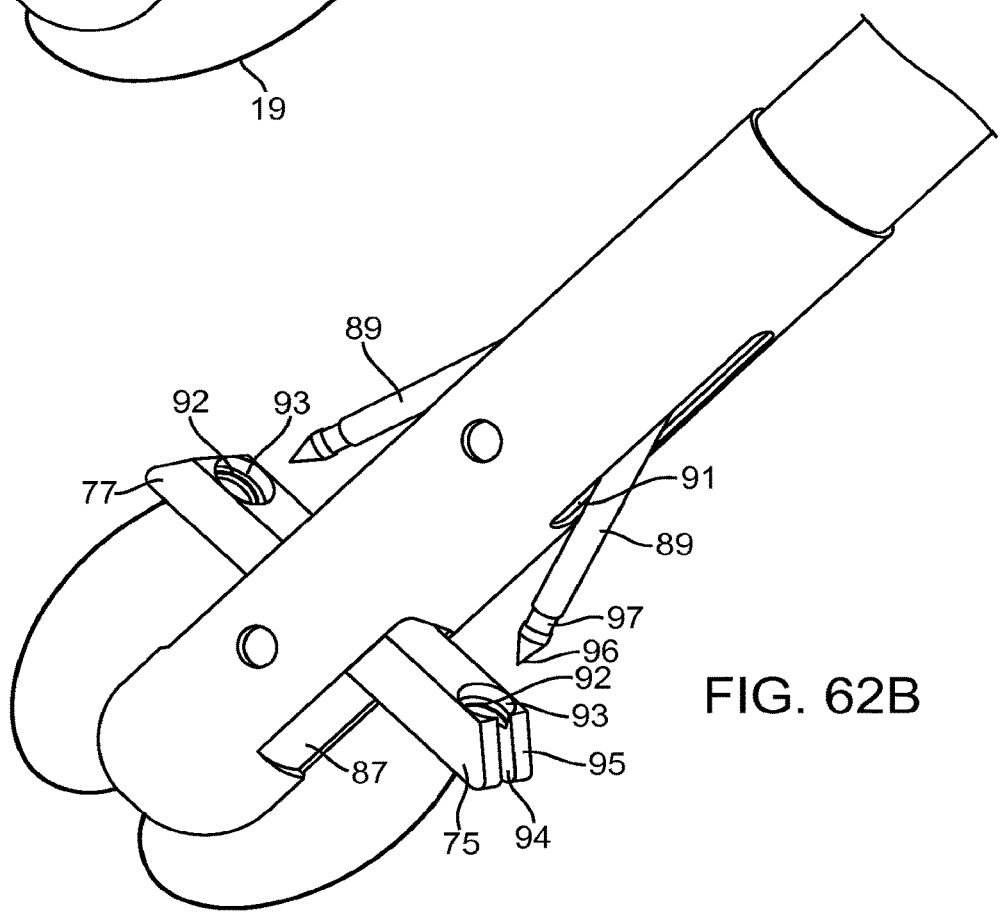
FIG. 62B is a perspective view of the suture delivery device with the suture clasp arms fully deployed.
Figure 62C:
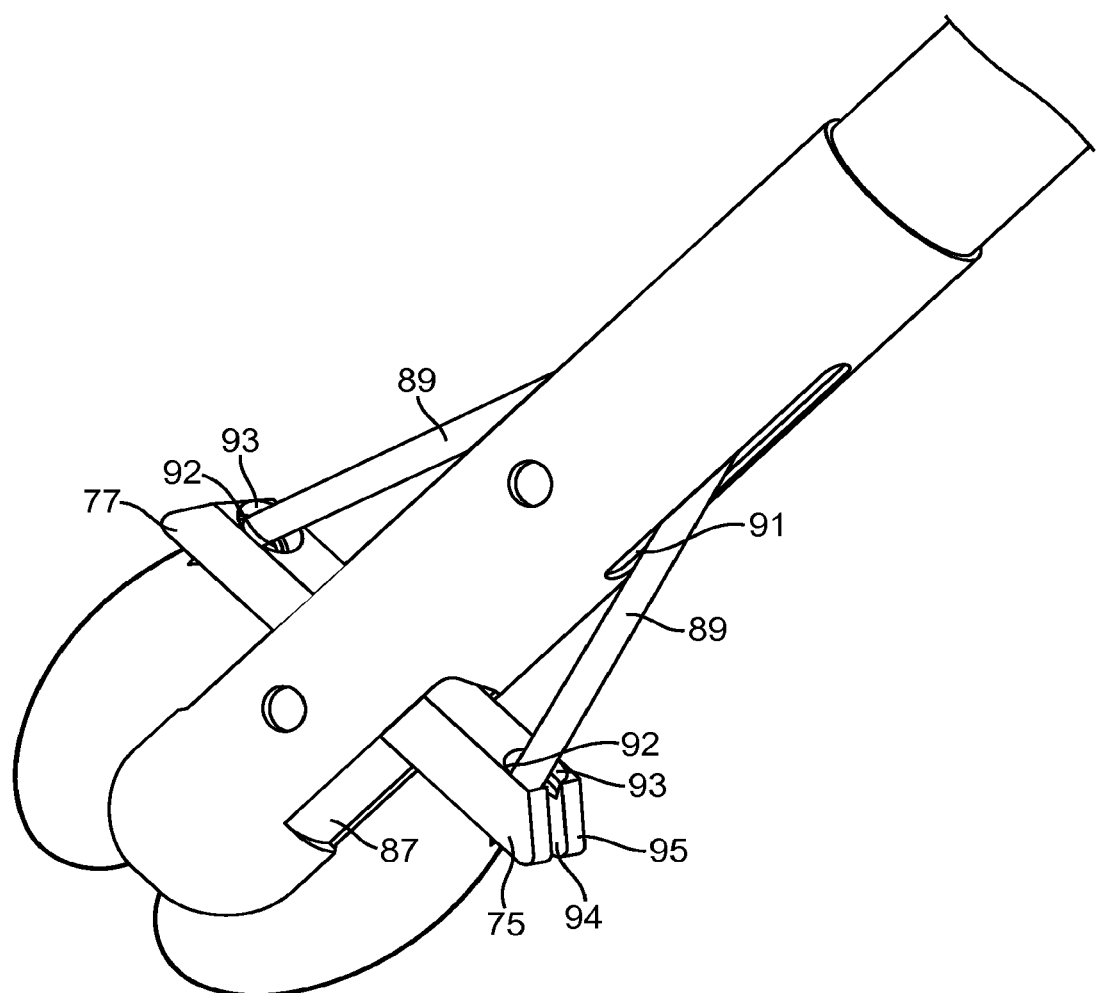
FIG. 62C shows two flexible needles extending out of needle apertures and engaging the suture clasp arms.

FIG. 62A is a perspective view of an embodiment of a distal region of a suture delivery device with the suture clasp arms 75, 77 partially deployed out of apertures 87. FIG. 62B is a perspective view of the suture delivery device with the suture clasp arms 75, 77 fully deployed. FIG. 62C shows two flexible needles 89 extending out of needle apertures 91 and engaging the suture clasp arms 75, 77. The device of FIGS. 62A-62C is not shown with a dilating tip although it should be appreciated that the device can be configured with a dilating tip pursuant to this disclosure.

The ends of the suture 19 can be provided with loops 92 that are configured to engage with the needles 89. The suture clasp arms 75, 77 each include an annular recess 93 for holding the suture looped end 92, a slit 94 for the length of the suture 19, and a sloped end 95. Each of the flexible needles 89 can include an extended shaft, a penetrating distal tip 96, and a groove 97 near the distal tip 96. The needle groove 97 can act as a detent mechanism or suture catch. In an embodiment, the grooves 97 can extend around the complete circumference of the needles 89. In other embodiments, the grooves 97 can be partially circumferential along the radial edge of the needles 89. The loops 92 can correspond generally in diameter to grooves 97 of the needles 89, but can be sufficiently resilient to expand in diameter in response to the downward force of the needles 89.

The general use and operation of the suture clasp arms 75, 77 is now described. The looped ends 92 of the suture 19 can be placed within the annular recess 93 of the suture clasp arms 75, 77. The distal end of the device can be inserted into biological tissue, and the suture clasp arms 75, 77 are deployed radially outward, as shown in FIG. 62B. The penetrating flexible needles 89 can pass distally through the biological tissue (e.g., artery tissue) to be sutured and engage the suture clasp arms 75, 77, as shown in FIG. 62C.

When the distal tips 96 pass through the looped ends 92 of the suture 19, the looped ends 92 can flex radially outward momentarily. As the needles 89 continue to advance distally, the looped ends 92 can come in contact with the grooves 97. The looped ends flex radially inward and fasten around the needle grooves 97, such that pulling the needles 89 proximally causes the suture ends 92 to follow the proximal movement of the needles 89 to draw the suture proximally through the artery tissue.

Methods of Use, Vessel Closure

Figure 72A:
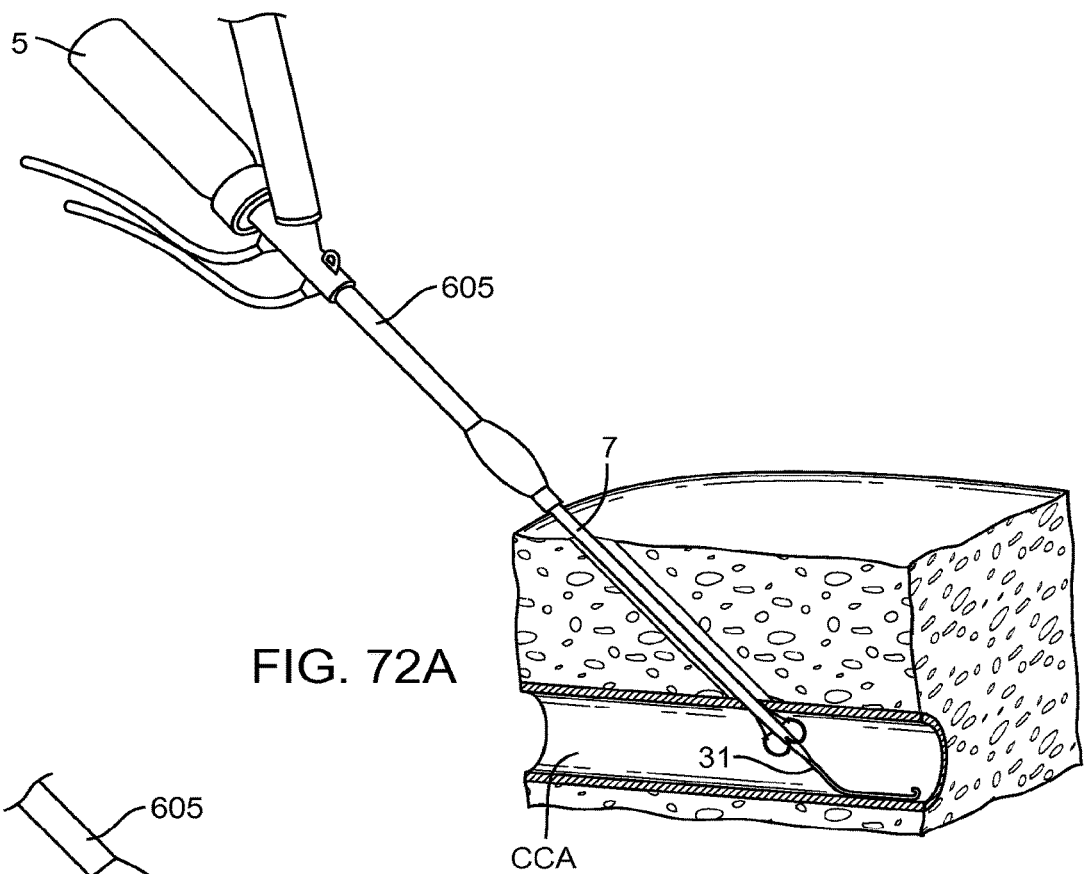
FIGS. 72A-72E, 73, and 74A-74F show operations in an embodiment of an interventional procedure.

Referring now to FIGS. 72A-72E, 73, and 74A-74F, an example method of use of a suture delivery device in connection with an interventional procedure is described. The procedure is described in the context of the carotid artery stenting procedure of FIGS. 28A-28E, above, although it should be appreciated that the suture delivery devices described herein can be used with various types of interventional procedures. Initially, as shown in FIG. 72A, the suture delivery device 5 with a pre-mounted distal sheath 605 can be inserted into the common carotid artery CCA over a pre-placed guidewire 31. The suture delivery device 5 can be positioned relative to the premounted sheath 605 such that a distal region of the suture delivery device's shaft 7 protrudes out of the distal end of the sheath 605 to provide access to the blood vessel wall for the suture delivery device 5.

Figure 72B:
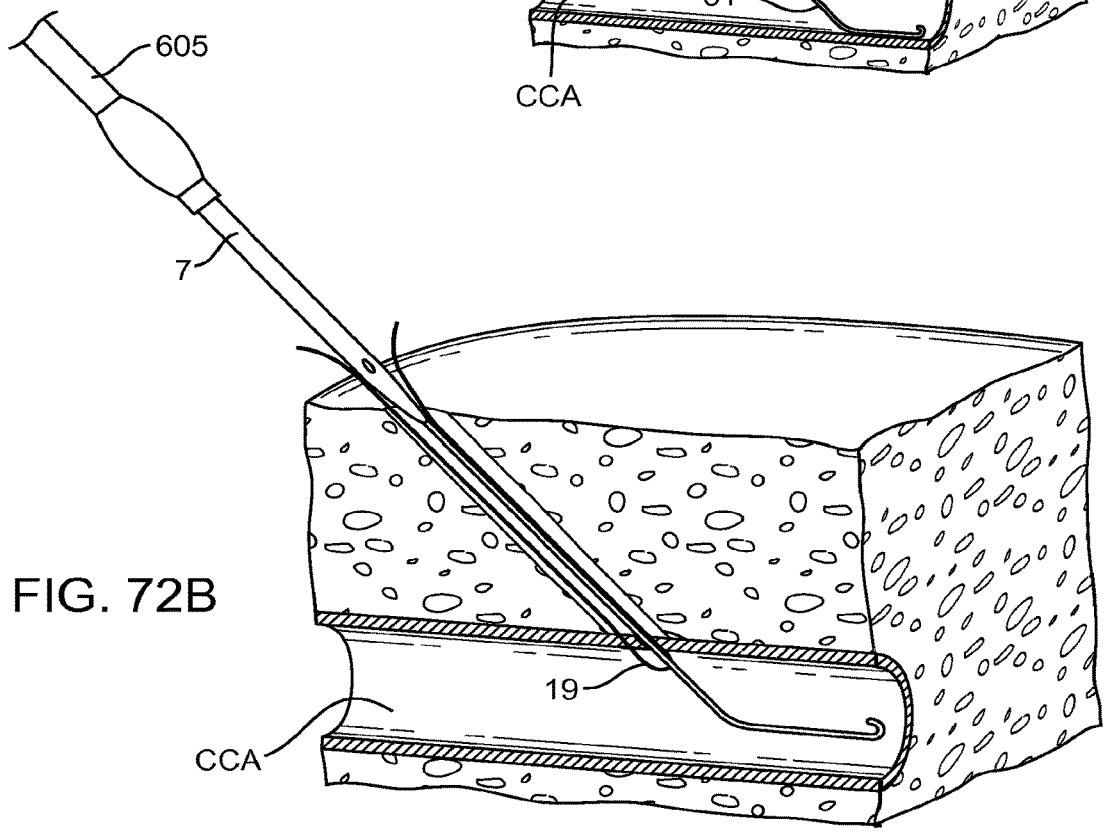
Figure 72C:
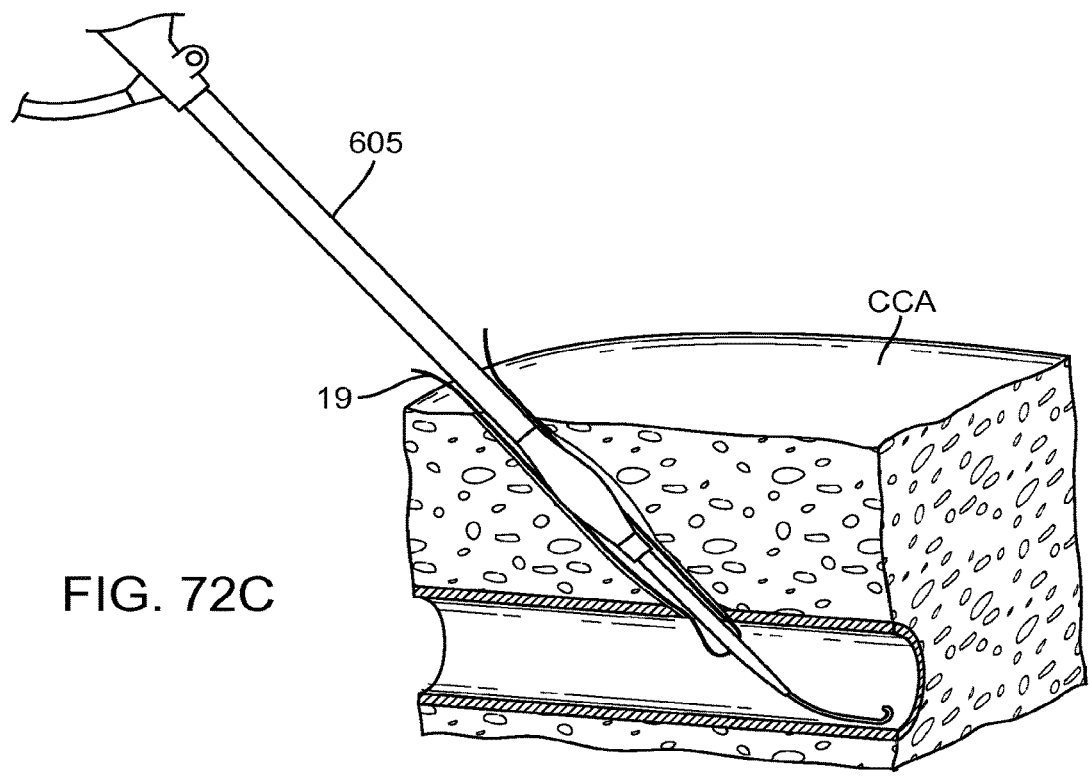

With reference to FIG. 72B, the suture delivery device 5 can then be used to deploy closing suture 19 into the vessel wall as described above to achieve pre-placement of the closing suture prior to insertion of the sheath 605 into the vessel. At least one end of the suture 19 can be drawn outside the body of the patient using the suture delivery device such that the suture 19 can be held until such time as the suture is to be tied off to create a permanent closure of the arteriotomy. With the suture 19 placed, the distal sheath 605 can then be advanced distally over the shaft 7 of the suture delivery device 5 into the vessel such that the distal end of the sheath 605 is positioned in the vessel and a proximal end of the sheath 605 protrudes out of the patient, as shown in FIG. 72C. In this manner, the sheath 605 can provide access to the inside of the vessel.

Figure 72D:
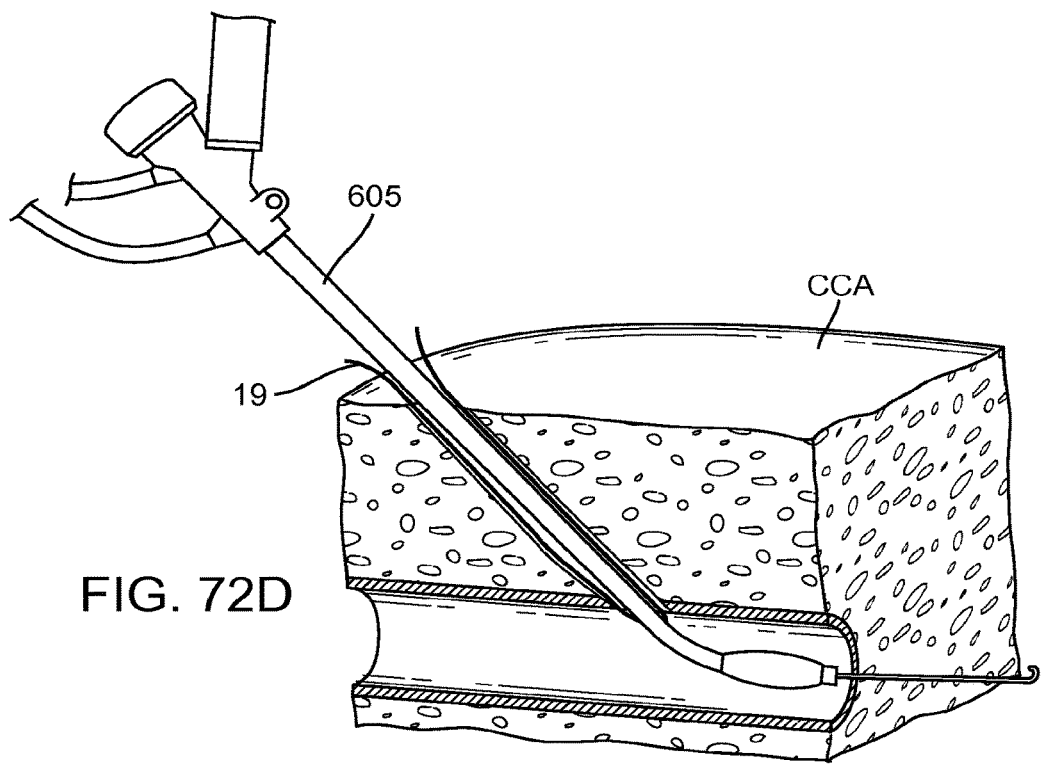
Figure 72E:
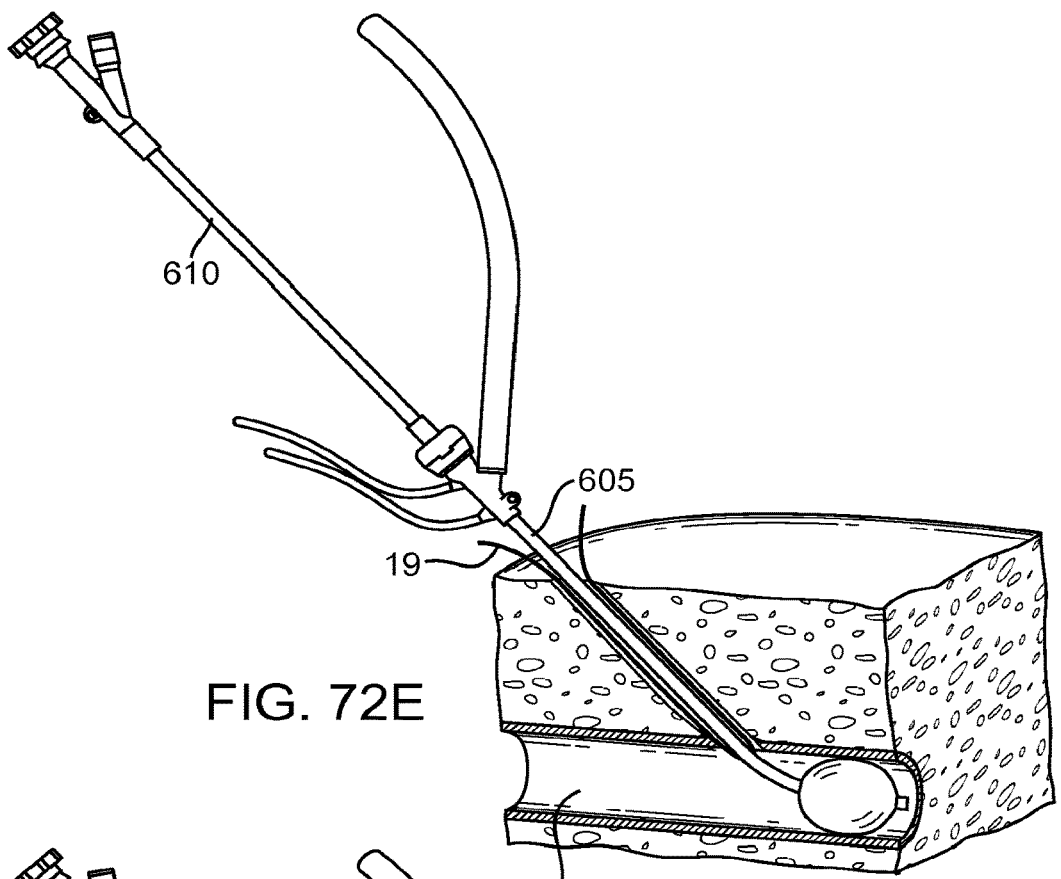

The suture delivery device 5 can then be removed from the sheath 605. FIG. 72D shows the sheath 605 positioned to provide access to the interior of the vessel with the suture delivery device removed. In an embodiment, a detachable proximal extension tube 610 can then be attached to the procedural sheath, as shown in FIG. 72E.

Figure 73:
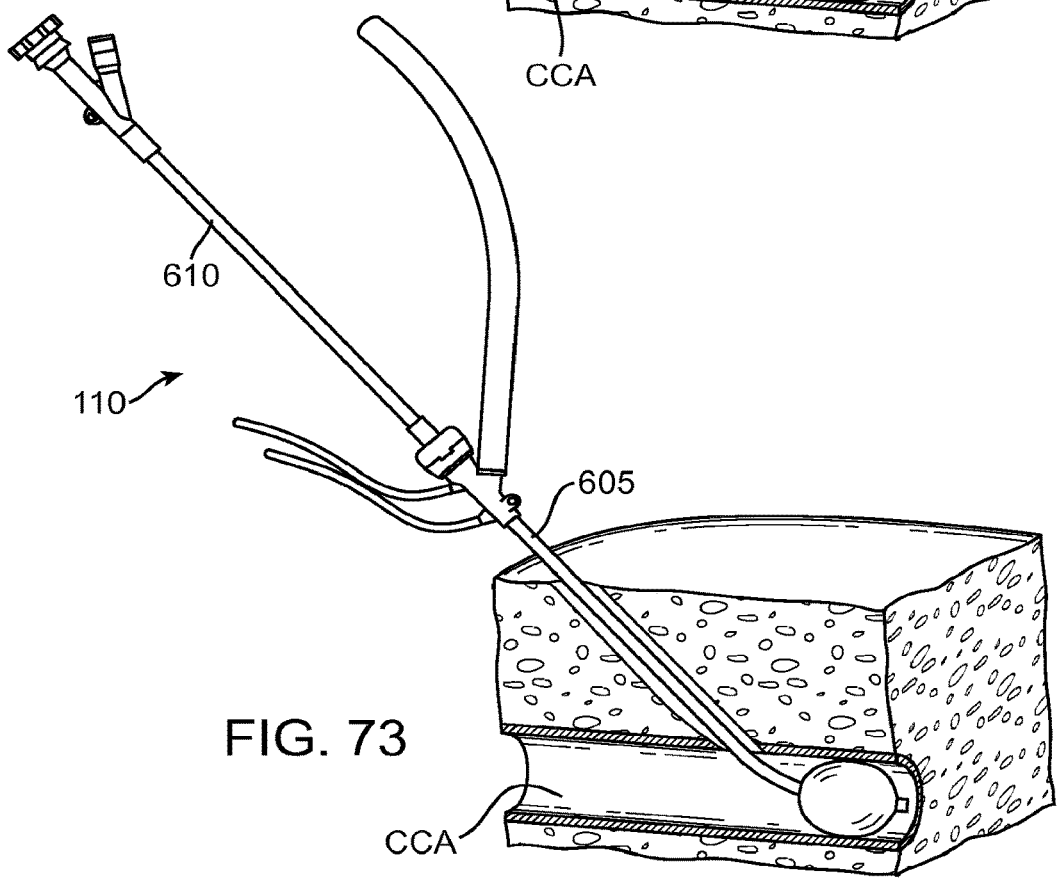

Alternately, as shown in FIG. 73, the arterial access device 110, with the proximal extension tube 610 pre-attached or permanently affixed to the distal sheath 610, can be inserted into the common carotid artery CCA without pre-placement of closing sutures, using either a direct surgical access or a percutaneous access. After the sheath 605 of the arterial access device 110 has been introduced into the common carotid artery CCA, the blood flow can continue in antegrade direction AG with flow from the common carotid artery entering both the internal carotid artery ICA and the external carotid artery ECA, as shown in FIG. 28A. The steps described with respect to FIGS. 28B-28E can then be performed.

Figure 74A:
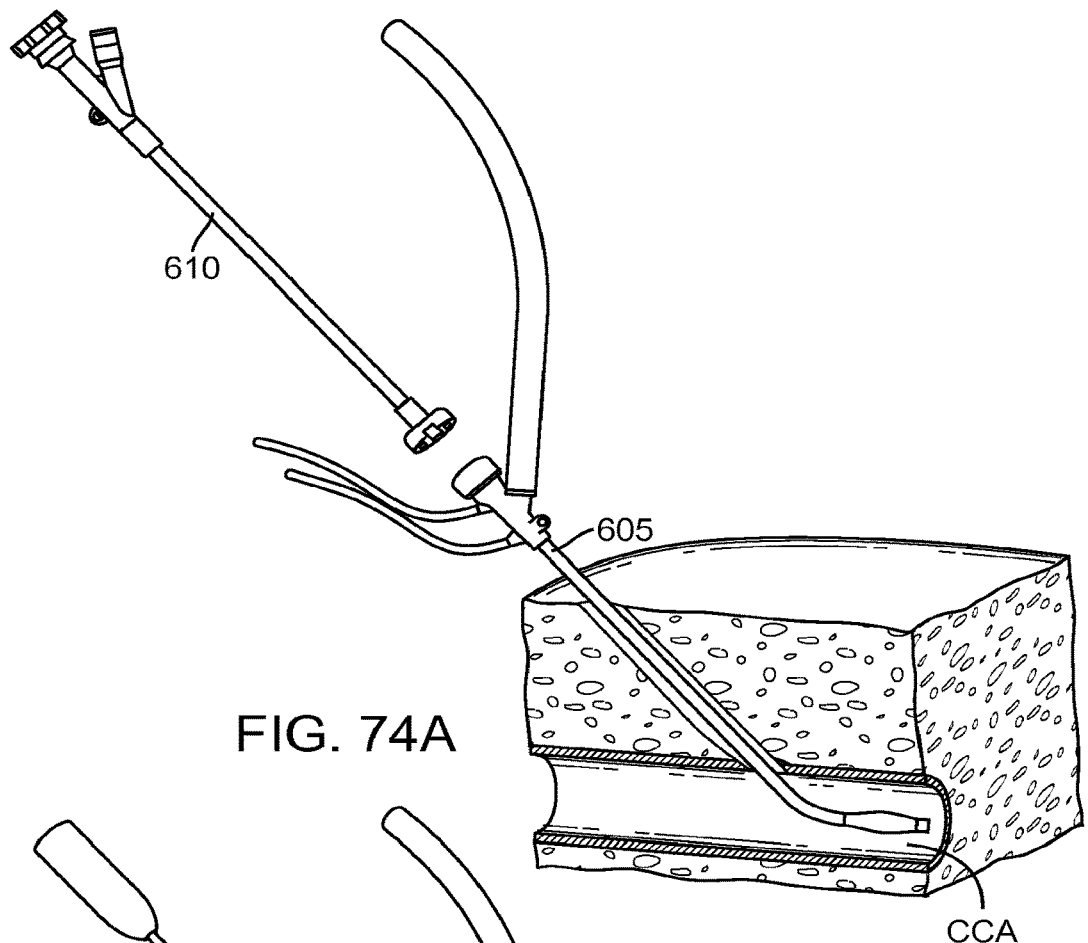
Figure 74B:
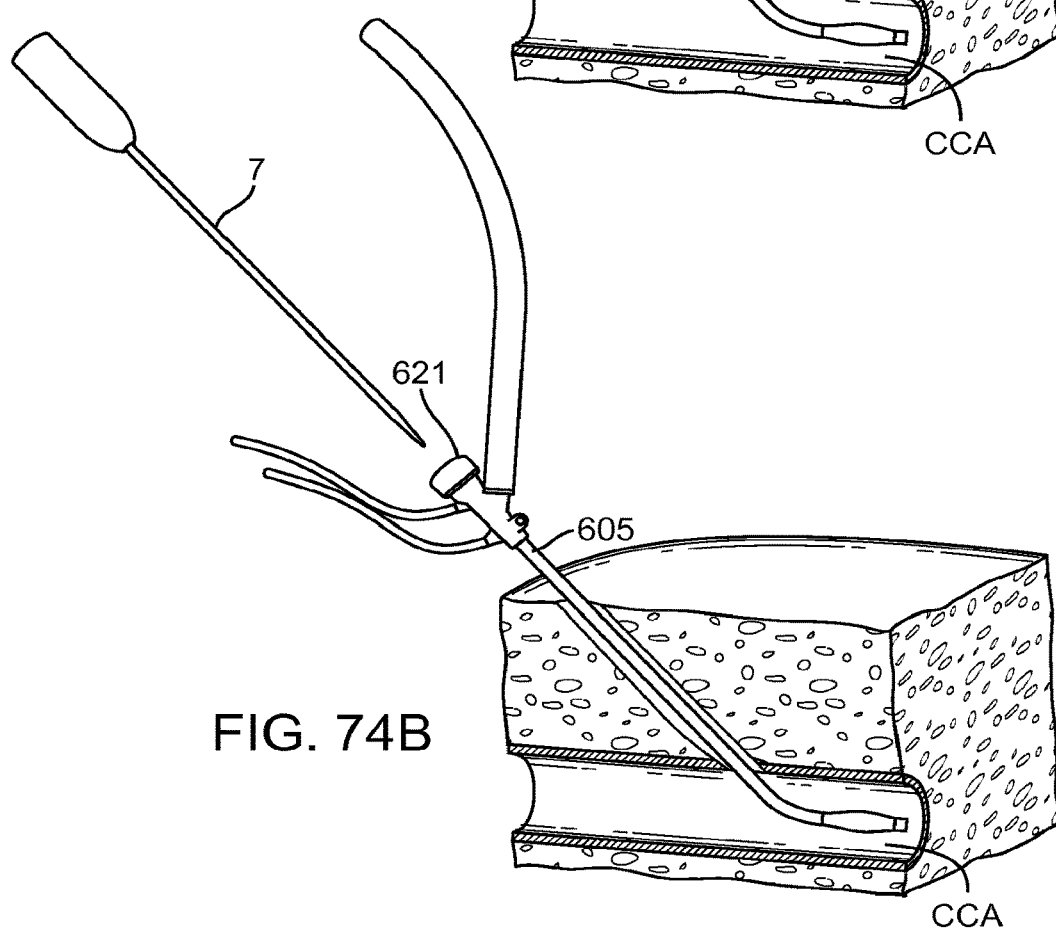
Figure 74C:
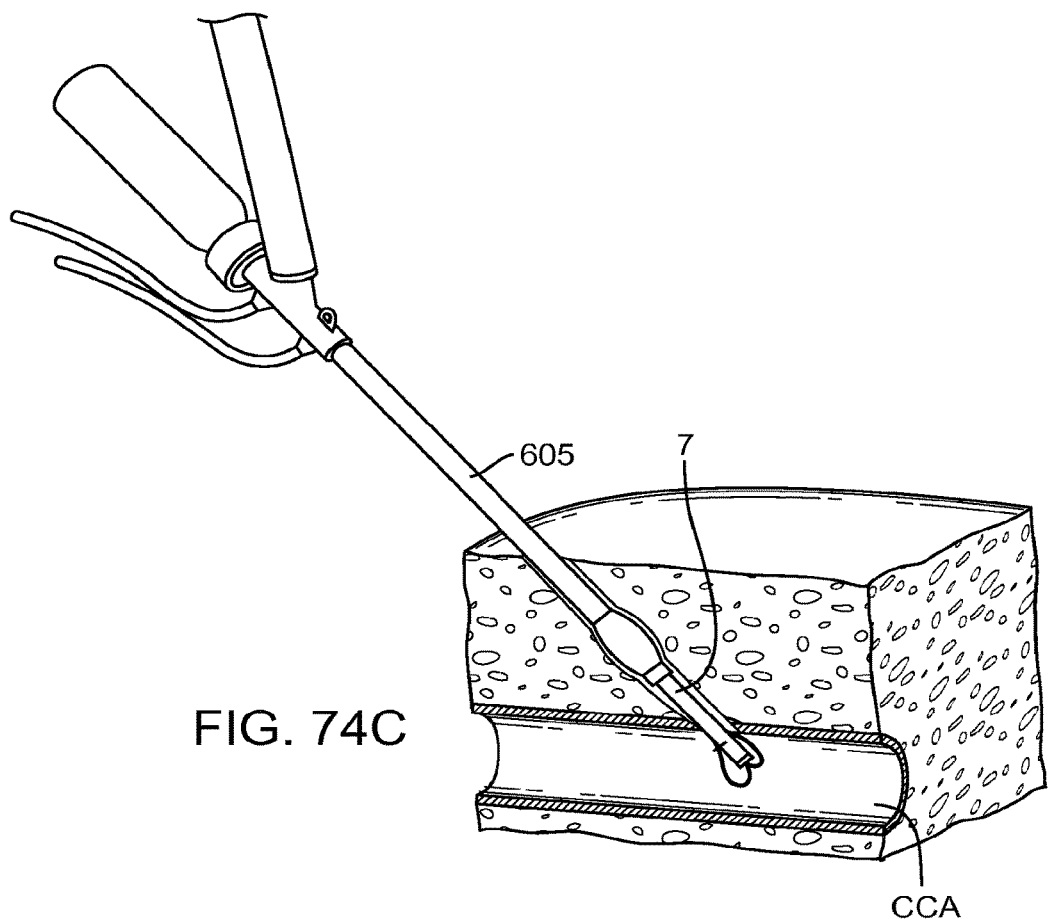
Figure 74D:
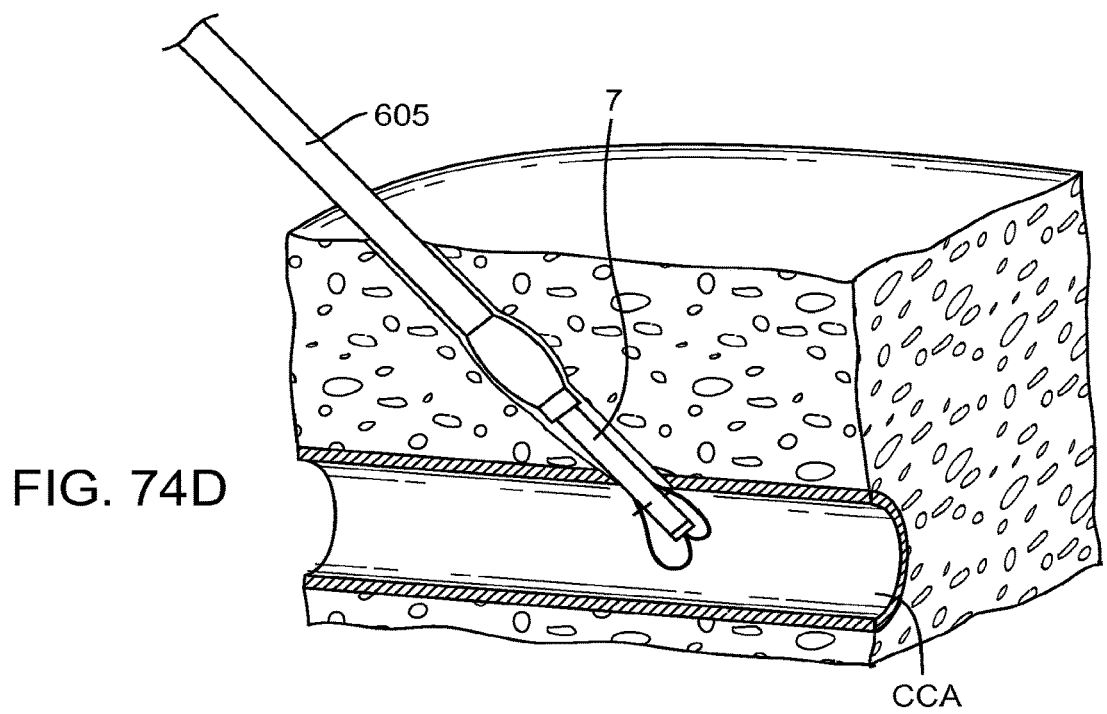
Figure 74E:
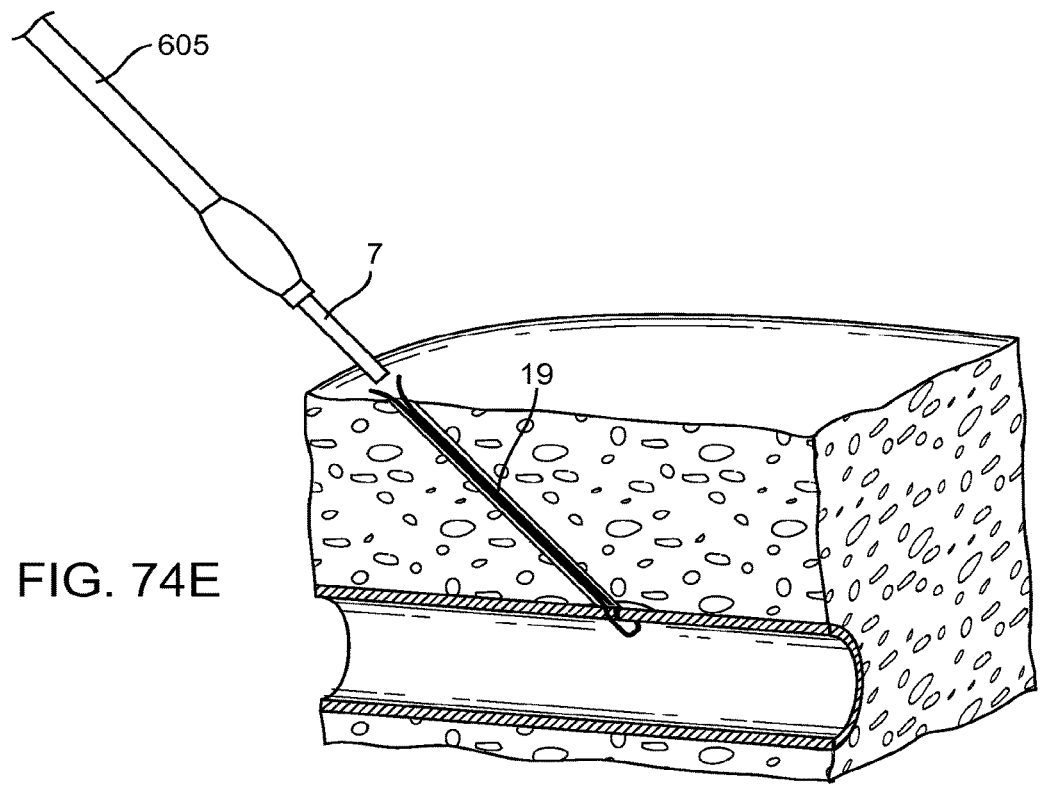
Figure 74F:
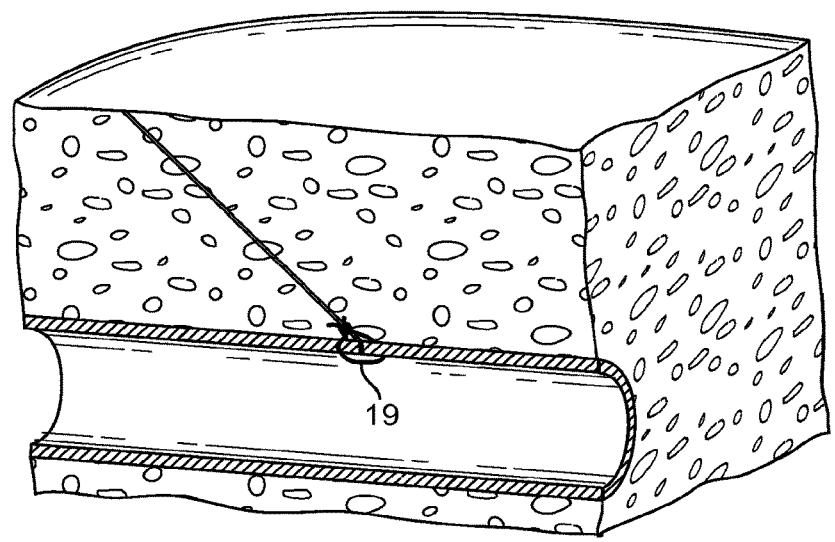

If closing sutures were not preplaced in the vessel at the beginning of the procedure, they can be placed when the occlusion element 129 or alternately the tourniquet 2105 is released. If the proximal extension tube 610 was attached to the sheath 605 (as shown in FIG. 73), the proximal extension tube 610 is detached from the sheath 605, as shown in FIG. 74A. A suture-based vessel closure device such as described herein can be inserted through the hemostasis valve 621 on the distal sheath 605 and into the vessel. As shown in FIG. 74C, the distal sheath 605 can then be withdrawn proximally to expose the distal region of the suture-based vessel closure device to the vessel wall. This is shown in more detail in the enlarged view of FIG. 74D. The closing suture 19 can then be inserted into the vessel wall and the suture-based vessel closure device as well as the sheath 605 are removed from the blood vessel, as shown in FIG. 74E. The suture ends can be tied off to achieve hemostasis of the arterial access site, as shown in FIG. 74F.

A self-closing element can be deployed about the penetration in the wall of the common carotid artery prior to withdrawing the sheath 605 at the end of the procedure. Usually, the self-closing element will be deployed at or near the beginning of the procedure, but optionally, the self-closing element can be deployed as the sheath is being withdrawn, often being released from a distal end of the sheath onto the wall of the common carotid artery. Use of the self-closing element is advantageous since it affects substantially the rapid closure of the penetration in the common carotid artery as the sheath is being withdrawn. Such rapid closure can reduce or eliminate unintended blood loss either at the end of the procedure or during accidental dislodgement of the sheath. In addition, such a self-closing element can reduce the risk of arterial wall dissection during access. Further, the self-closing element can be configured to exert a frictional or other retention force on the sheath during the procedure. Such a retention force is advantageous and can reduce the chance of accidentally dislodging the sheath during the procedure. A self-closing element eliminates the need for vascular surgical closure of the artery with suture after sheath removal, reducing the need for a large surgical field and greatly reducing the surgical skill required for the procedure.

The disclosed systems and methods can employ a wide variety of self-closing elements, typically being mechanical elements which include an anchor portion and a self-closing portion. The anchor portion can include hooks, pins, staples, clips, tines, sutures, or the like, which are engaged in the exterior surface of the common carotid artery about the penetration to immobilize the self-closing element when the penetration is fully open. The self-closing element can also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it can be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, clotting factors, or other clot-promoting agents. Alternatively, the tissue or self-closing element can be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane can have an inner opening such as a slit or cross cut, which would be normally closed against blood pressure. Any of these self-closing elements can be designed to be placed in an open surgical procedure, or deployed percutaneously.

Additional Embodiments of Closure Devices

Figure 63A:
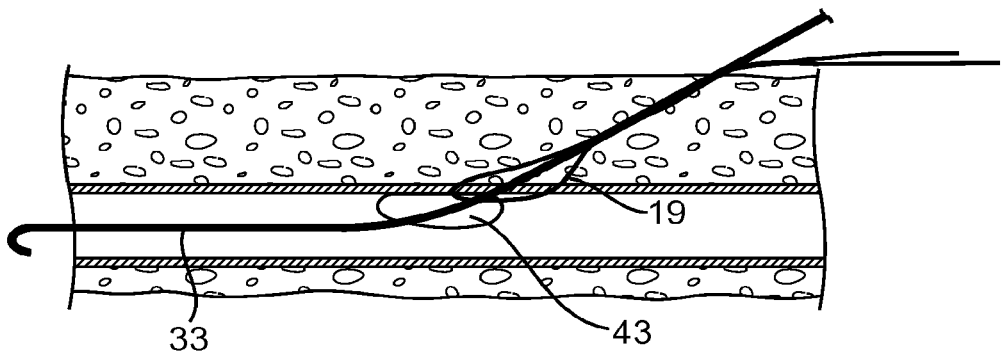
FIGS. 63A-63C, 64, and 65 show a guidewire with deployment of an expandable sealing element or elements to be used with a closure device

In another embodiment, the guidewire 33 can include at least one expandable sealing element 43 mounted on the guidewire. The expandable element 43, shown in FIGS. 63A-63C, can expand against the interior vessel wall to maintain hemostasis of the vessel access site, such as during exchange of the suture delivery device 5 for the procedural sheath, and during removal of procedural sheath. Alternately, the guidewire can be used to maintain hemostasis if the suture delivery device did not adequately place the suture in the tissue, and the device is needed to be exchanged for another vessel closure device. The second vessel closure device can be another suture delivery device, or can be another type of vessel closure device. This guidewire with sealing element can be used to exchange vessel closure devices either if the sutures are placed before the procedural sheath is placed or at the end of the procedure after sheath removal.

The expandable element 43 can be positioned a predetermined distance proximal from the distal tip of the guidewire. In an embodiment, the expandable element 43 is positioned about 3 cm proximal of the distal tip of the guidewire. This ensures that the distal tip of the guidewire is inserted a predetermined distance beyond the expandable element 43.

The expandable element can be collapsed when the suture delivery device is inserted into the vessel. The dilator tip 21 of the suture delivery device 5 can have an indicator lumen 45 for a blood mark. Thus, as soon as the dilator tip 21 of the delivery device 5 enters the blood vessel, an indication can be provided to the operator so that the operator knows to deflate or collapse the expandable element 43 on the guidewire. The expandable element 43 can vary in structure. For example, the expandable element 43 can be a balloon, an expandable member such as a braid, cage, or slotted tube around which is a sealing membrane, or the like.

Figure 63B:
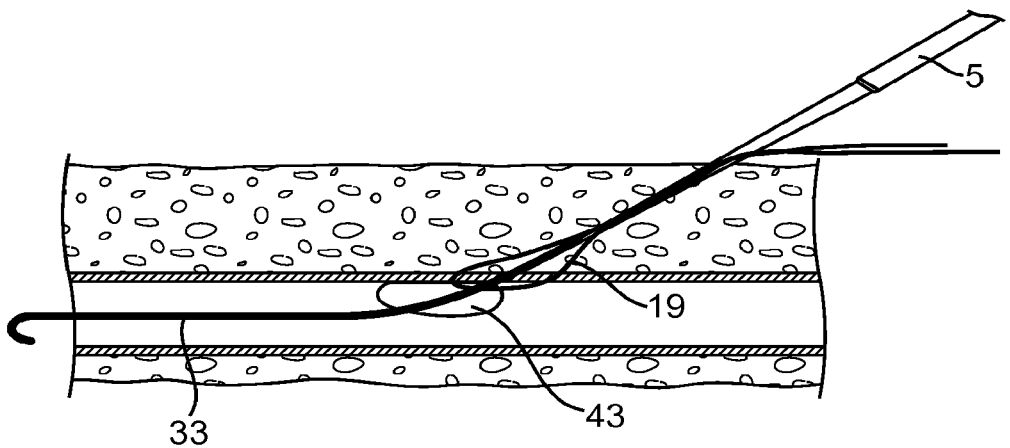
Figure 63C:
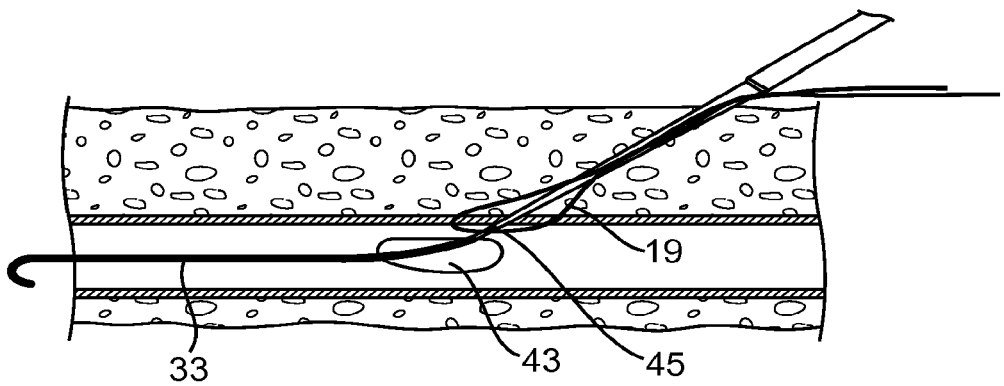
Figure 64:
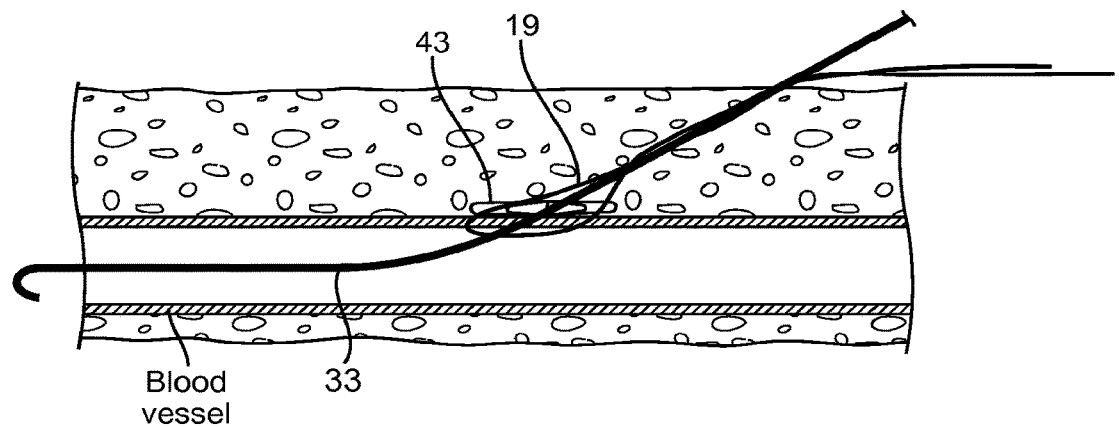

As shown in FIGS. 63B-63C, the expandable sealing element 43 can be positioned inside the blood vessel during use. Once the expandable element 43 is positioned in the blood vessel, the operator can pull it back proximally such that the expandable element 43 is sealed against the interior vessel wall. Arterial blood pressure within the vessel can also help exert pressure of the sealing element against the interior vessel wall, so that only a small amount of force, if any, can be needed to maintain hemostasis. In another embodiment, shown in FIG. 64, the expandable element 43 can be positioned outside the blood vessel. The operator can push the expandable element forward against the exterior vessel wall such that the expandable element 43 exerts pressure against the exterior vessel wall to achieve and maintain hemostasis.

Figure 65:
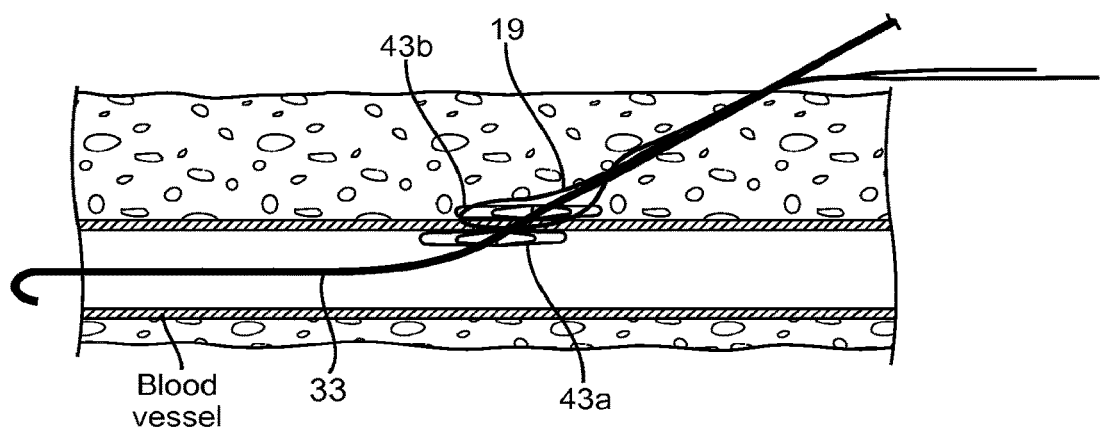

In yet another embodiment, the guidewire can include a pair of expandable sealing elements 43a and 43b, as shown in FIG. 65. During use the blood vessel wall is interposed between the expandable elements 43a and 43b with the expandable elements 43 exerting pressure on the vessel wall. This advantageously locks the position of the guidewire against movement relative to the vessel wall. The expandable elements 43a and 43b can be spring-loaded toward each other to achieve the pressure on the vessel wall. In a variation of the multi-expandable element embodiment, the expandable elements 43 can be inflatable balloons. During use, care can be taken that expandable portion does not increase the size of the arteriotomy, unless it is to be used to "pre-dilate" the arteriotomy.

Figure 66:
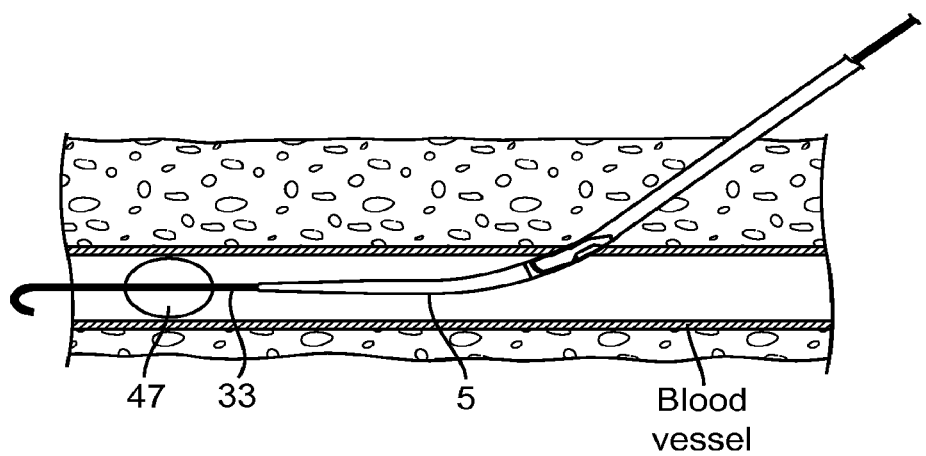
FIG. 66 shows a guidewire embodiment having an intra-vascular anchor.

In another embodiment, the guidewire can include an intravascular anchor that maintains the position of the guidewire relative to the blood vessel during insertion of the delivery device 5 and/or the procedural sheath into the blood vessel. As shown in FIG. 66, the anchor 47 can be, for example, an inflatable balloon, expandable cage or braid, or other element that secures to the interior vessel wall. In the case of an expandable or inflatable anchor 47, the anchor 47 can expand to a size such that the anchor 47 exerts sufficient force against the vessel wall to secure the anchor 47 in place.

In an embodiment, the expandable element can serve as both an expandable sealing element and an intravascular anchor. For example, if the expandable element was a balloon, inflation at one diameter can be sufficient to create a seal around the arteriotomy as well as anchor the guidewire in the vessel. Alternately, the expandable element can be inflated to one diameter to seal the arteriotomy, and a greater diameter to anchor against the vessel wall. Similarly, a mechanically expandable element can be expanded to both seal and anchor, or be expanded to one state sufficient to create a seal, and expanded further to anchor against the vessel wall. The device can need to be repositioned between the sealing expansion and the anchor expansion states.

Figure 67:
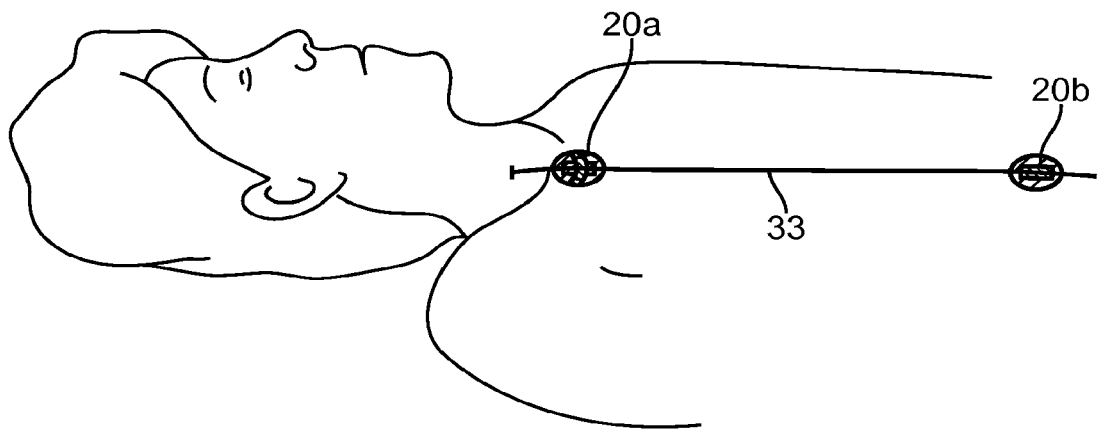
FIGS. 67-69 show another guidewire anchor embodiment wherein the guidewire attaches to one or more clips that can be secured to the skin of the patient to hold the guidewire in place.

FIG. 67 shows another embodiment wherein the guidewire 33 attaches to one or more clips 51 that can be secured to the skin of the patient to hold the guidewire in place. The clips 51 can be secured to the patient using various means including an adhesive backing. The clips 51 can be positioned on the patient's skin in any of a variety of configurations. In the embodiment of FIG. 67, two clips 51 are used including one clip 51a near the entry location into skin and another clip 51b further from the entry location. The clips 51 can serve to hold the guidewire in place at all times. The clip 51b can be released as the delivery device 5 is loaded onto wire, then re-clipped and the clip 51a is released as the delivery device 5 inserted into skin and positioned into the blood vessel. In a similar fashion, the clips can be used to maintain the guidewire 33 position while the delivery device is removed, and while the procedural sheath is inserted into the blood vessel.

Figure 68:
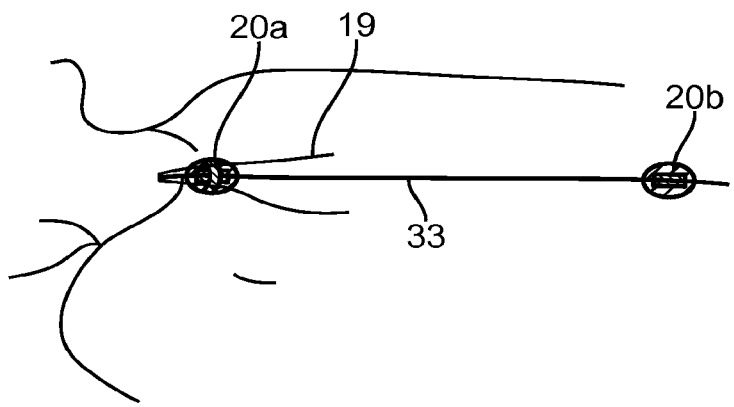
Figure 69:
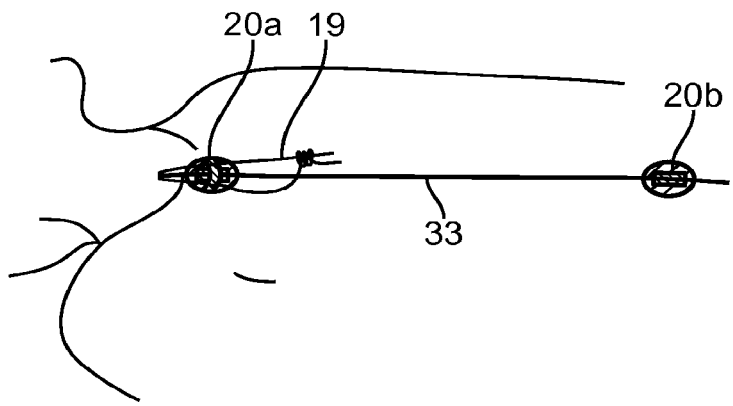

The clips 51 can also be used for management of the closure suture 19. The clips 51 can include one or more attachment means, such as slots, into which the suture can be inserted and held. FIGS. 68 and 69 show an example wherein the suture is not pre-tied (FIG. 68) and when the suture is pre-tied (FIG. 69). The sutures can also be both placed to the same side of the clip 51. The clips 51 can be configured to hold the suture in tension, such as during times when hemostasis is needed to keep sutures in tension to maintain hemostasis until procedural sheath can be placed. In this case, the knot is either not pre-tied or tied but far enough back that it is outside the skin and both sides of the stitch can be held in tension. The suture can be held in tension either manually, or with a clip or cleat on the skin. The suture back end can be attached to a tag or handle, or preattached to the clip or cleat which is then secured to the skin, to make this process easier. The sutures can either be kept in this clip or cleat during the intervention, or be removed if they are in the way, then reinserted after sheath removal but before knot tying. Or, the sutures can be manually held in tension and then the knot tied immediately afterwards. Or, if the knot is pre-tied, the knot can simply be pushed down in to place.

Figure 70A:
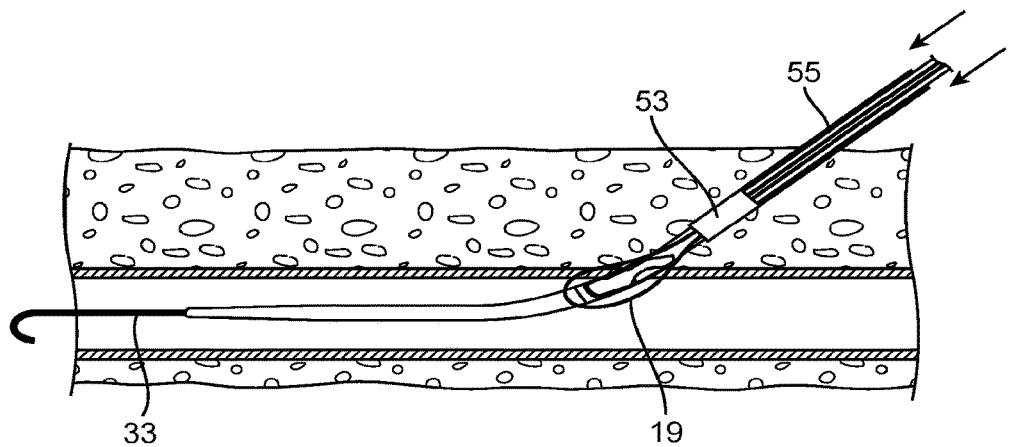
FIGS. 70A-70C show an embodiment of the closure device wherein a self closing material is pre-loaded on a proximal region of the delivery shaft.
Figure 70B:
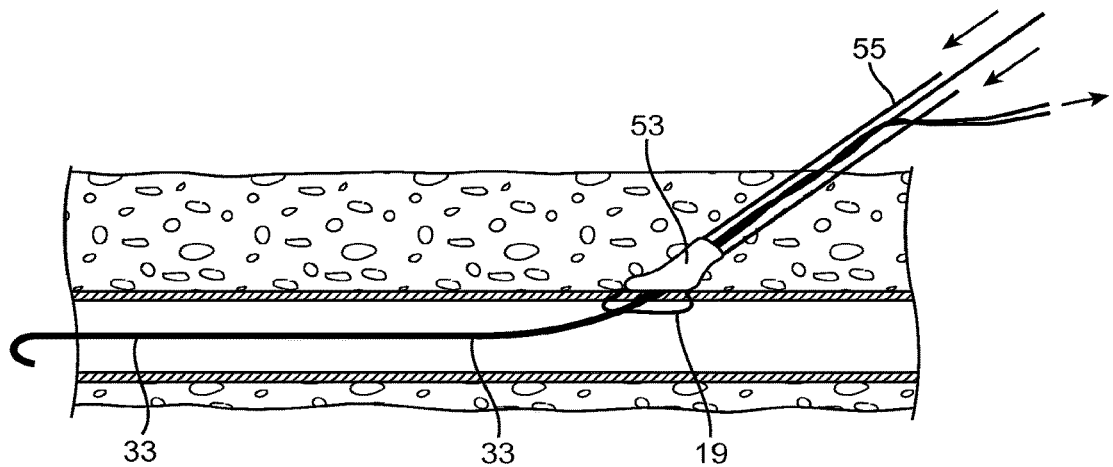
Figure 70C:
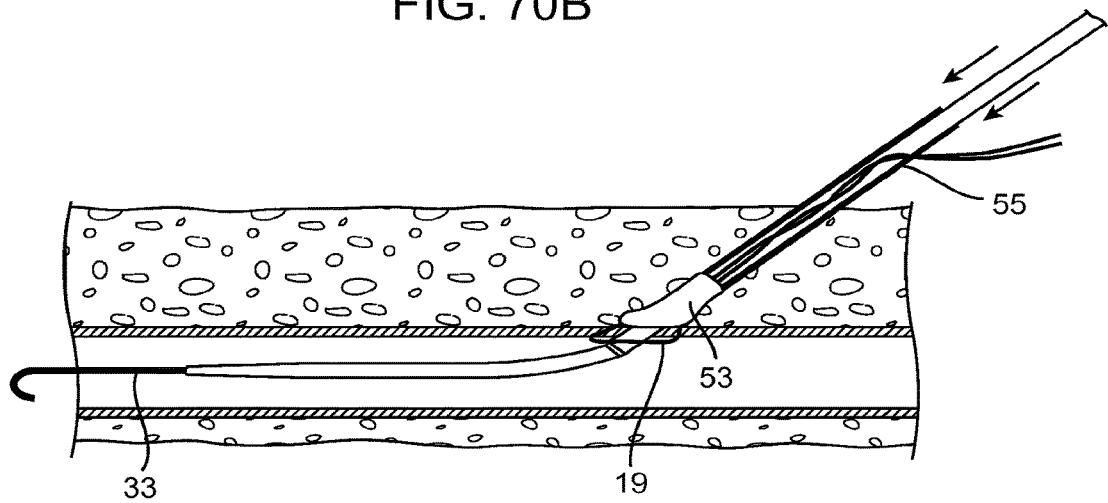

In another embodiment, shown in FIGS. 70A-70C, a self-closing material 53 is pre-loaded on a proximal region of the delivery shaft 7. A hole can extend through the center of the self-closing material and the delivery shaft 7 can be positioned through the hole. The self-closing material can be configured to automatically close over the hole when the delivery device 5 is pulled out of the hole. The self-closing material can be a rubber plug or membrane with a hole, slit, cross slit, duck-bill valve, or a compressible material such as a foam, or simply a pair of spring members (such as a wire or a flat spring) that close over the arteriotomy when the device 5 is pulled out. The self-closing material can also be a collagen plug, a bioabsorbable polymer, a non-bioabsorbable polymer such as Dacron or ePTFE, or other appropriate biocompatible material. If the self-closing material is temporary, the material can be a soft elastomer, such as silicone rubber, or polyurethane.

Just prior to removing the delivery device 5 from the arteriotomy, the self-closing material can be pushed distally over the arteriotomy such as with a pushing element 55 such as push rod or tube, as shown in FIG. 70A. The pushing element 55 can be integral to the delivery device 5 or it can be a separate accessory item. The self-closing material can be held in compression over the arteriotomy to maintain hemostasis, as shown in FIG. 70B. The sutures 19 that were just placed, as well as the guidewire which can remain in place, can pass through the center opening of the self-closing material. The procedural sheath can then be placed over the guidewire through the self-closing material, through the arteriotomy and into the blood vessel, as shown in FIG. 70C. The pusher holding the self-closing material in compression against outside of vessel wall can then be relaxed. After the procedure is completed, the pusher can again be pushed to apply compression to arteriotomy until a knot is tied in the suture. Where the pusher is a rigid sleeve, the pusher can double as a means to provide a channel for facilitating device exchange through tissue tract.

In a variation of this embodiment, the self-closing material remains in place to act as a hemostasis material at the end of the procedure. The material can be pre-loaded on the delivery shaft, and the suture capture rods can be threaded through locations to each side of the delivery shaft. Thus, when the sutures are pulled out of the delivery shaft, they can also be pulled through two side holes of the self-closing material. As above, the material can be pushed into place and acts as temporary hemostasis during device exchange. However, at the end of the procedure, the material remains in place when the suture ends are tied off to achieve permanent hemostasis.

Figure 71A:
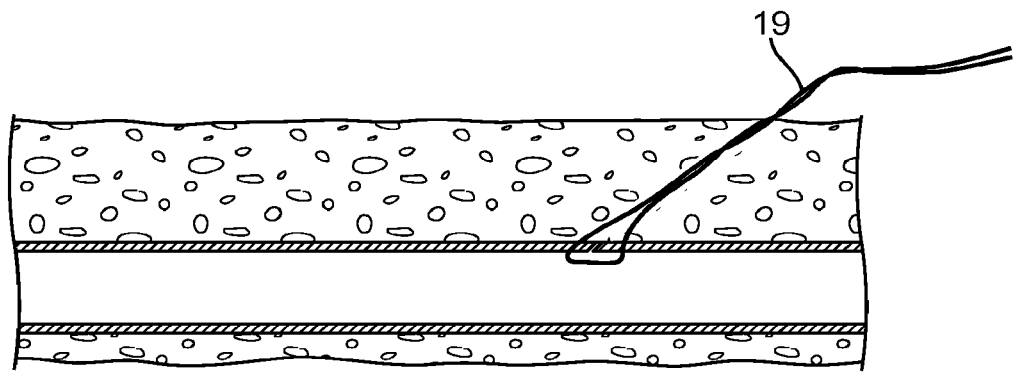
FIGS. 71A-71C show an embodiment wherein a hemostasis material is positioned over the arteriotomy location after removal of a procedural sheath.
Figure 71B:
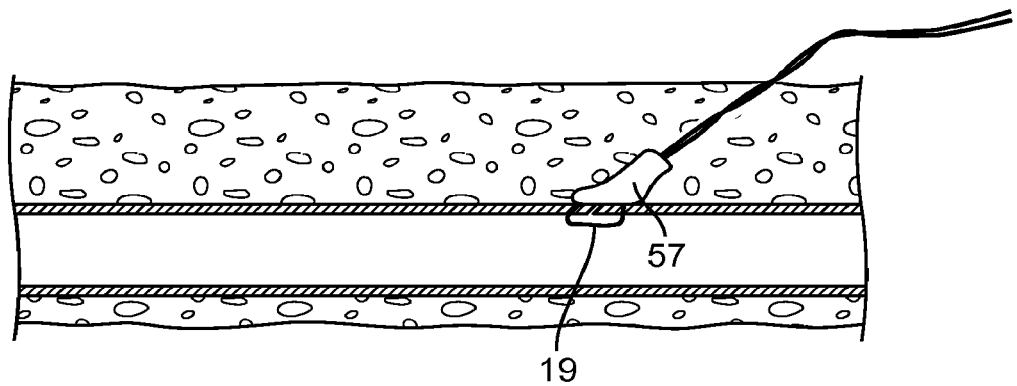
Figure 71C:
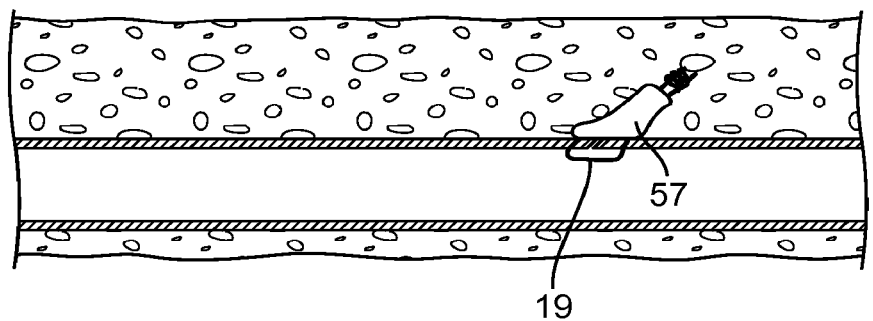

In another embodiment, shown in FIGS. 71A-71C, a hemostasis material 57 can be positioned over the arteriotomy location after removal of the procedural sheath. The hemostasis material 57 can be placed over the suture 19 before the suture knot is tied or during the tying of the suture knot. The knot can secure the hemostasis material in place over the arteriotomy. Alternately, the hemostasis material can be inserted over the arteriotomy after the suture knot is tied, and either another tie or a clip can be used to hold the hemostasis material against the arteriotomy. The hemostasis material can be, for example, a collagen plug, a bioabsorbable polymer, a non-bioabsorbable polymer such as Dacron or ePTFE, or other appropriate biocompatible material. The hemostasis material can be a temporary or a permanent material. U.S. Pat. No. 5,549,633, which is incorporated herein by reference in its entirety, described examples of devices and methods for coupling a sealing material to a suture.

Detailed Description of Clip Closure Devices

Disclosed herein are clip-based vascular closure devices that are configured to be pre-applied to a blood vessel prior to insertion of a vascular access device (such as a procedural sheath) through an incision, puncture, penetration or other passage through the blood vessel. The clip-based vascular closure devices can also be applied to the blood vessel after insertion of the vascular access device but before removal of the vascular access device, or after removal of the vascular access device. The closure devices can achieve rapid hemostasis upon either deliberate or inadvertent sheath removal. The disclosed devices require minimal entry into the vessel to be deployed. Furthermore, the devices leave minimal material or no material inside the vessel and have an extremely reliable means of achieving hemostasis, making the chance of a hematoma remote. In an embodiment, the disclosed closure device can be applied in a carotid artery via a transcervical access such as by forming an incision in the patient's neck to in order to access the blood vessel or other body lumen.

Figure 75:
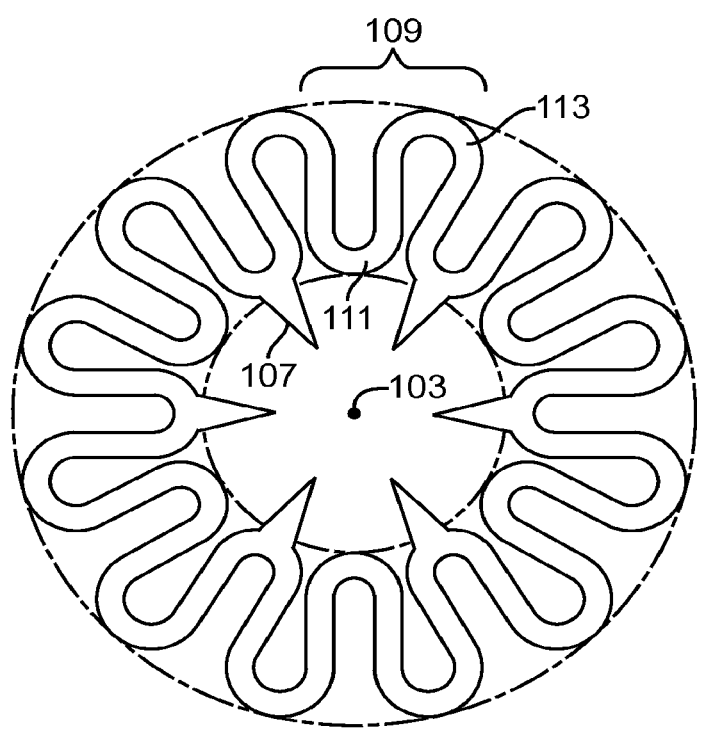
FIG. 75 shows an example of a closure device.

An existing closure device is described in U.S. Pat. No. 6,623,510 and an embodiment is shown in FIG. 75. U.S. Pat. No. 6,623,510 is incorporated herein by reference in its entirety. The existing closure device includes a clip for closing an incision, puncture, penetration, or other passage through a blood vessel or other body lumen. The clip can be adapted to transition between a cylindrical configuration and a flat or planar configuration, as described more fully below. FIG. 75 shows the clip in the planar configuration. The clip can include a body, which can be generally annular in shape and which surrounds a central axis 103. The central axis 103 can extend outward normal to the plane of FIG. 75 and can be at the center of a central opening of the body. The clip can further include a plurality of attachment features such as tines 107 extending from the body. The tines 107 can extend along an axis that intersects or abuts the central axis 103. U.S. Patent Application Publication Nos. 2004-0153122, 2004-0153123, 2006-0020270, 2008-0004636, 2008-0312666 describe examples of closure devices and delivery systems. These applications are incorporated by reference in their entirety.

The annular body can include a plurality of looped or curved elements 109 that are connected to one another to form the body. Each looped element 109 can include an inner or first curved region 111 and an outer or second curved region 113. In an embodiment, the first and second curved regions 111, 113 can be out of phase with one another and can be connected alternately to one another, thereby defining an endless sinusoidal pattern. When the clip is in the substantially flat or planar configuration, as shown in FIG. 75, the first curved regions 111 can define an inner periphery of the body and the clip, and the second curved regions 113 can define an outer periphery of the body. A disadvantage of the clip shown in FIG. 75 and the clips described in U.S. Pat. No. 6,623,510 is that the tines 107 of the clip are arranged in a manner that tends to interfere with passage of a vascular access device such as a procedural sheath through the center of the clip.

Figure 76A:
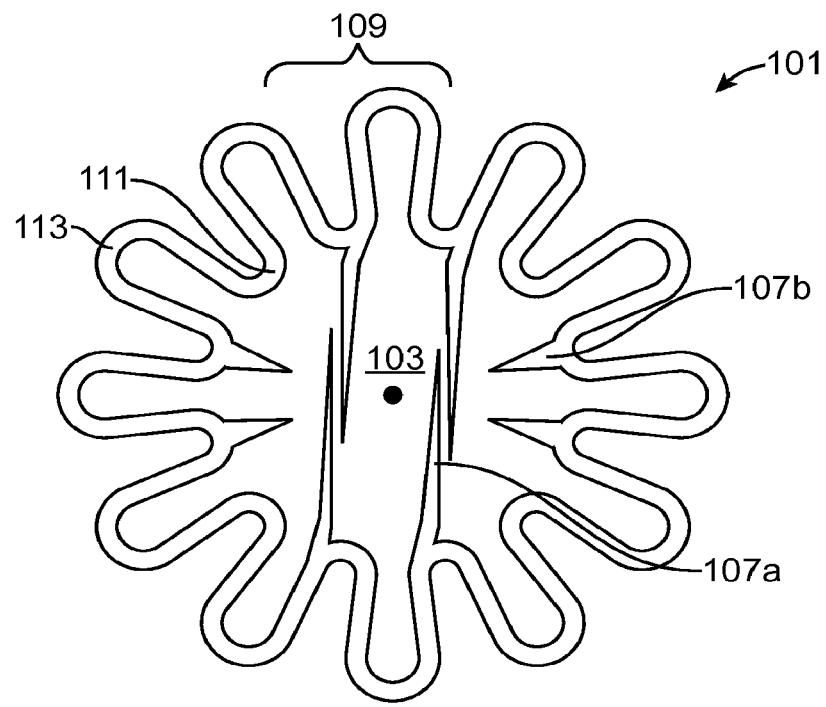
FIG. 76A shows another embodiment of a closure device.

FIG. 76A shows an improved embodiment of a closure device that includes a clip 101. The annular body of the clip 101 can have a central opening that is configured to receive a procedural sheath that can be inserted into a blood vessel, as described more fully below. The tines 107 can be arranged in a manner such that they do not interfere with, impede or interrupt insertion and/or removal of the procedural sheath through the body. The body can include any hollow body, for example, including one or more structures surrounding an opening, whether the body is substantially flat or has a significant thickness or depth. Thus, although an annular-shaped body can be circular, it can include other noncircular shapes as well, such as elliptical or other shapes that are asymmetrical about a central axis.

The plurality of tines 107 can be biased to extend generally inwardly towards one another and such that the tines do not intersect the central axis 103. Thus, the tines 107 extend along an axis that is offset or angled away from the central axis 103. The tines 107 can be disposed on the first curved regions 111 generally toward the body's central region but not intersecting the central axis 103 when the clip 101 is in the planar configuration. In an embodiment, the tines 107 can be provided in pairs opposite from one another or provided otherwise symmetrically with respect to the central axis 103.

In the embodiment of FIG. 76A, the tines 107 can include one or more major tines 107a that are of a longer length as well as one or more minor tines 107b that are shorter in length than the major tines 107a. The major tines 107a can extend along an axis that is offset a distance from intersection with the central axis 103. For example, the major tines 107a can be offset a distance of 0.010" to 0.030" from the central axis 103. Such a configuration can minimize or eliminate interference with the sheath that is inserted through the center of the body. For example, two pairs of major tines 107a can extend inwardly toward the center of the body but offset from the central axis 103. The longer length of the major tines 107a can make them more likely to interfere with passage of the procedural sheath through the body so it is desirable that the major tines 107a have a maximum amount of offset from the central axis 103 while still preserving the function of compressing the vessel wall around the area of an arteriotomy to provide hemostasis after removal of the access device.

Figure 76B:
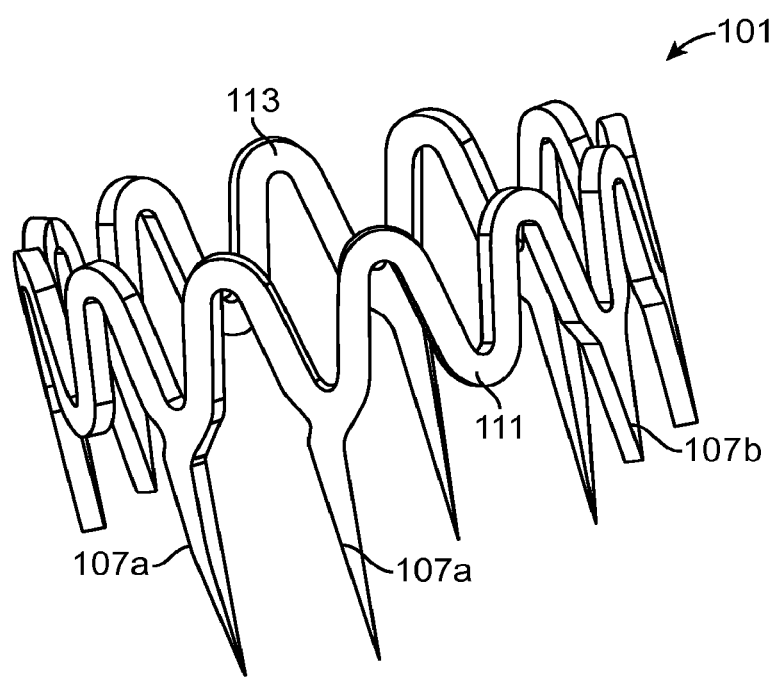
FIG. 76B shows a perspective view of the closure device of FIG. 76A during deployment.
Figure 76C:
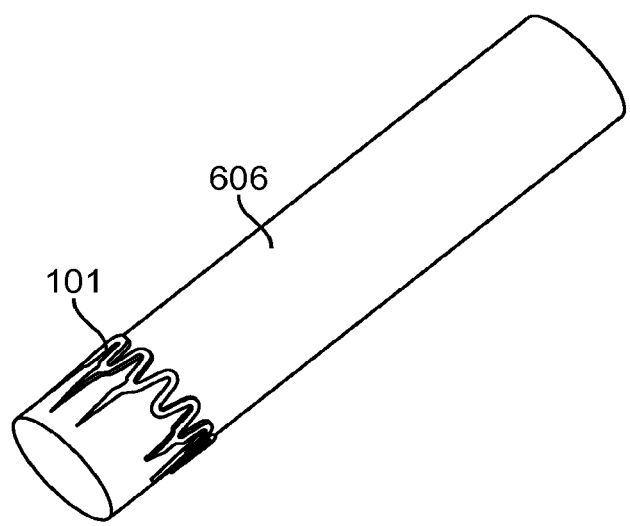
FIG. 76C shows the closure device of FIG. 76A mounted on a delivery system.

As shown in FIG. 76B, the annular body and/or the tines 107 can be deflected into a cylindrical configuration such that the tines 107 are oriented parallel to the central axis 103 and the body can have a generally annular shape having a length that extends generally parallel to the central axis 103, and corresponds generally to an amplitude of the zigzag pattern. The body can be sufficiently flexible so that the clip 101 can assume a generally circular or elliptical shape, such that it can be placed around the exterior surface of a central shaft 606 of a delivery system, as shown in FIG. 76C. As discussed below, the central shaft of the delivery system can be a procedural sheath or other vascular access device.

In an embodiment, the tines 107 and/or body can be biased to move from the cylindrical configuration (shown in FIG. 76B) towards the planar configuration (shown in FIG. 76A). Thus, with the tines 107 in the cylindrical configuration, the tines 107 can penetrate and/or be engaged with tissue at a puncture site. When the clip 101 is released, the tines 107 can attempt to return towards one another as the clip 101 moves towards the planar configuration, thereby drawing the engaged tissue together and substantially closing and/or sealing the puncture site, as explained further below.

Figure 77:
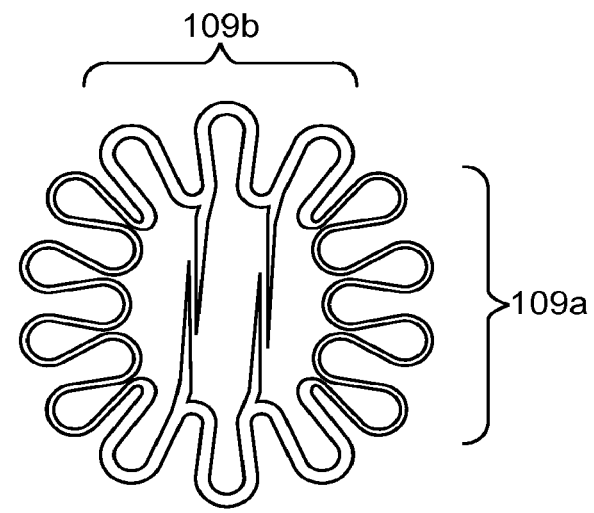
FIGS. 77, 78, 79A, and 79B show alternate embodiments of closure devices.

In another embodiment shown in FIG. 77, the loops 109a around two opposing sections of the clip 101 are thinner than the remainder of the loops 109b. Thus, the loops 109a can deform more easily than the loops 109b. In this embodiment, the clip 101 can act as a spring with a closing force is not radially uniform but rather directed linearly towards the arteriotomy.

Figure 78:
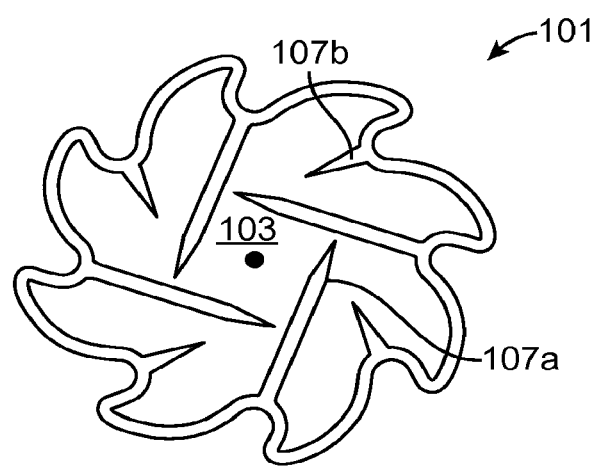

FIG. 78 shows another embodiment wherein all of the tines 107 (including the major tines 107a and minor tines 107b) extend along respective axes that do not intersect the central axis 103. In the planar configuration, at least one of the tines can extend along an axis that intersects an axis of another tine. None of the axes of the attachment features intersect the central axis. The tines 107 can point off-center from the central point 103 of the opening when the device is in the planar configuration. In this manner, the tines 107 can be arranged in an iris-like configuration around the central axis 103. This configuration reduces the likelihood that the tines 107 will interfere with the sheath during insertion and removal through the central axis 103.

The tines 107 can include a variety of pointed tips, such as a bayonet tip, and/or can include barbs for penetrating or otherwise engaging tissue. For example, to increase the penetration ability of the clip 101 and/or to lower the insertion force required to penetrate tissue, each tine 107 can include a tapered edge extending towards the tip along one side of the tine 107. Alternatively, each tine 107 can be provided with a tapered edge on each side of the tine 107 extending towards the tip.

Additionally, the tines 107 can be disposed on alternating first curved regions 111. Thus, at least one period of a zigzag pattern can be disposed between adjacent tines 107, which can enhance flexibility of the clip 101.

The looped elements 109 can distribute stresses in the clip 101 as it is deformed between the cylindrical and the planar configurations, thereby minimizing localized stresses that can otherwise plastically deform, break, or otherwise damage the clip 101 during delivery. To manufacture the clip 101 (or, similarly, any of the other clips described herein), the body and the tines 107 can be integrally formed from a single sheet of material, e.g., a superelastic alloy, such as a nickel-titanium alloy ("Nitinol"). Portions of the sheet can be removed using conventional methods, such as laser cutting, chemical etching, photo chemical etching, stamping, using an electrical discharge machine (EDM), and the like, to form the clip. The tines 107 can be sharpened to a point, i.e., tips can be formed on the tines 107 using conventional methods, such as machining, mechanical grinding, and the like.

The clip 101 can be polished to a desired finish using conventional methods, such as electro-polishing, chemical etching, tumbling, sandblasting, sanding, and the like. Polishing can perform various functions depending on the method used to form the clip 101. For a clip formed by laser cutting or using an EDM, polishing can remove heat affected zones (HAZ) and/or burrs from the clip. For a clip formed by photo chemical etching, polishing can create a smoother surface finish. For a clip formed by stamping, polishing can remove or reduce burrs from the bottom side of the clip, and/or can smooth the "roll" that can result on the topside of the clip from the stamping process.

Figure 79A:
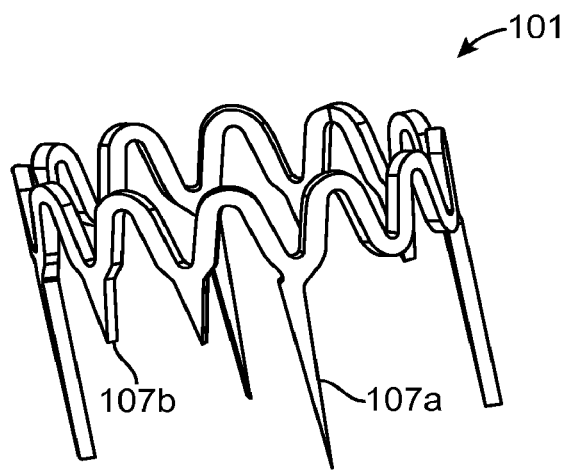
Figure 79B:
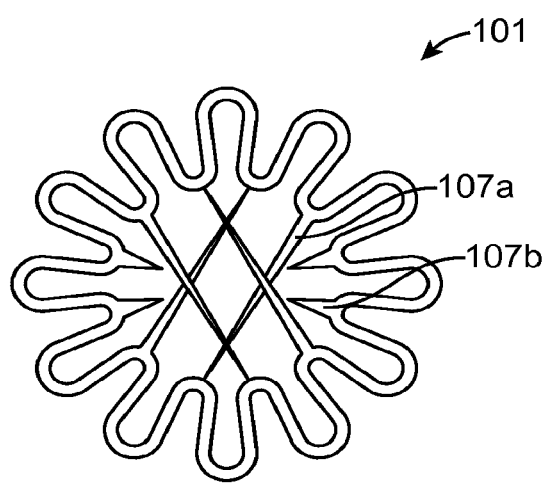

FIGS. 79A and 79B show another embodiment of the clip 101 in the cylindrical and planar states, respectively. In this embodiment, the major tines 107a can have an increased length with respect to the previous embodiments. The increased length of the major tines 107a reduces the likelihood that the major tines 107a will interfere with a sheath as the tines would tend to deflect to one or the other side of the sheath as the sheath is inserted through the central axis 103. Because the tines overlap in the planar configuration in this embodiment (as shown in FIG. 79B), the clip can be manufactured from a tube 3135 ather than a flat sheet, as shown in FIG. 79A. After the cutting and polishing process is complete, the clip can be flattened and heat set to the planar state of FIG. 79B, such as by using Nitinol processing methods well known in the art. The annular body can also include one or more upwardly extending bars (not shown) that can be used to assist in flattening the clip to the planar state during the flattening and heat-set process. The bars can be removed from the clip after the heat set process is complete.

Linear Compressive Sprint Embodiments

Figures 80A, 80B:
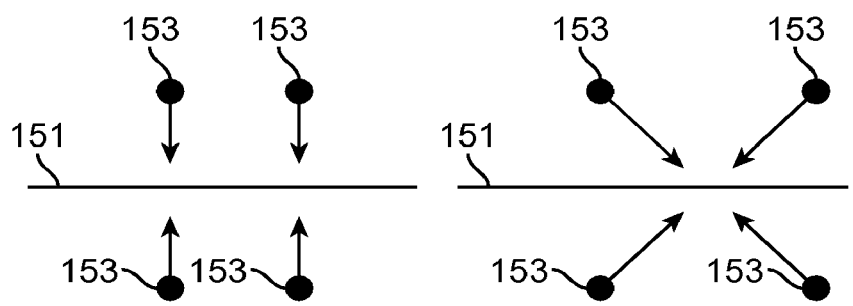
FIGS. 80A and 80B show a schematic representation of an arteriotomy including an incision.

Additional clip embodiments are now described wherein the clip provides closure force(s) that are linear across the pathway of the arteriotomy in the same or similar manner that a suture would apply closing forces. FIGS. 80A and 80B show a schematic representation of an arteriotomy including an incision 151. The arrows show the direction of force caused by conventional suture closure. FIG. 80A shows the forces created by two interrupted sutures, and FIG. 80B shows the force of a suture placed in a Z-configuration. The following clip embodiments recreate these forces on the arteriotomy. In a first embodiment, the clip applies closure forces that are directed linearly across the incision 151, as in FIG. 80A. In another embodiment, the clip applies closure forces along vectors that intersect one another as in FIG. 80B. The attachment locations 153 of the clip to the blood vessel tissue are positioned out of the entry pathway of the procedural sheath as the sheath enters the blood vessel. This minimizes interference of the clip with the sheath.

Figure 81A:
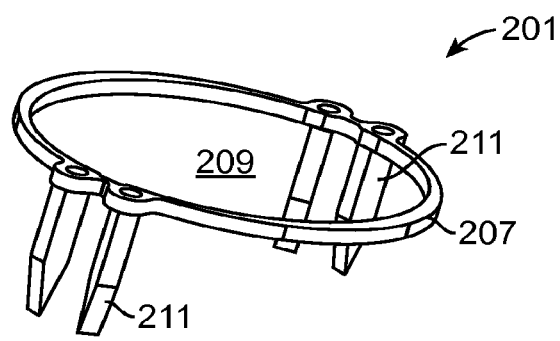
FIGS. 81A-81B show a first embodiment of a closure device that applies linear closing forces.
Figure 81B:
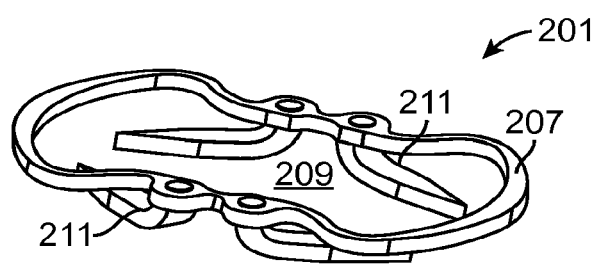

FIGS. 81A-81B show a first embodiment of the clip 201 that applies linear closing forces as described above. That is, the clip has a spring force that closes the annular body of the clip from the cylindrical configuration to the planar configuration pursuant to a generally linear rather than radial bias. The clip 201 can include an annular body that includes a ring member 207, and a set of attachment tines 211 that are configured to be positioned on either side of the arteriotomy such as in the arrangement of the attachment locations 153 shown in FIGS. 80A and 80B. The ring member 207 can be of an annular or partially annular configuration in that it surrounds a central opening 209 for receipt of the procedural sheath. The ring member 207 can be biased from an expanded state toward a radially inward state or compressed state relating to a decreased size of the opening 209 to provide a closing force to the arteriotomy when the procedural sheath or delivery shaft is removed. As shown in FIG. 81A, during delivery the clip 201 can be fully expanded such that the ring member 207 is round or substantially round, and the attachment tines 211 are constrained to be pointing downwards. The clip can be biased inward. When the delivery shaft is removed from the center of the clip, the clip can collapse inward and the attachment tines 211 deflect to their biased state parallel to the vessel wall to anchor the clip, as shown in FIG. 81B. As the clip 201 collapses, the clip 201 can provide a linear closing force to the arteriotomy. That is, the tines move toward one another in pairs along a linear vector, such as in the manner shown in FIG. 80A or 80B. The tines thereby draw the arteriotomy closed. A procedural sheath can then be inserted through the clip such that the clip re-expands to accept the sheath. When the procedural sheath is removed, the clip can revert to its biased, radially inward state to provide a closing force on the arteriotomy.

Figure 82A:
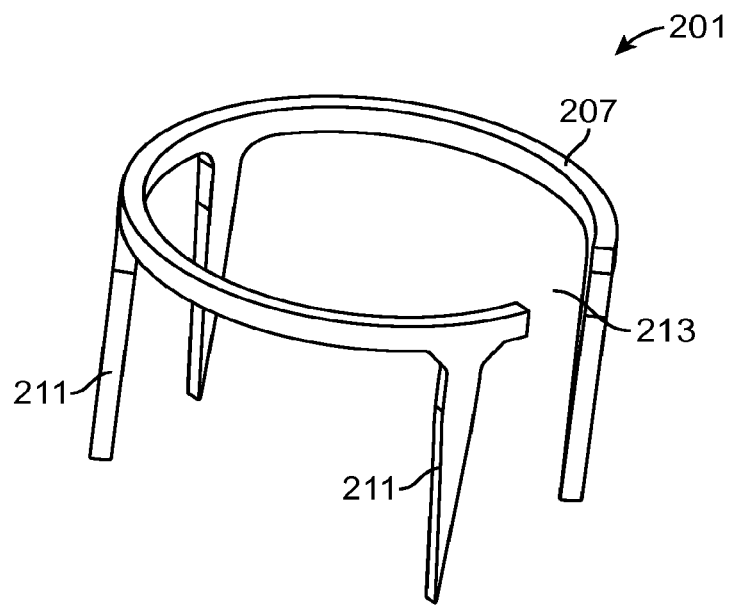
FIGS. 82A-82B show another embodiment of a closure device that applies linear closing forces.
Figure 82B:
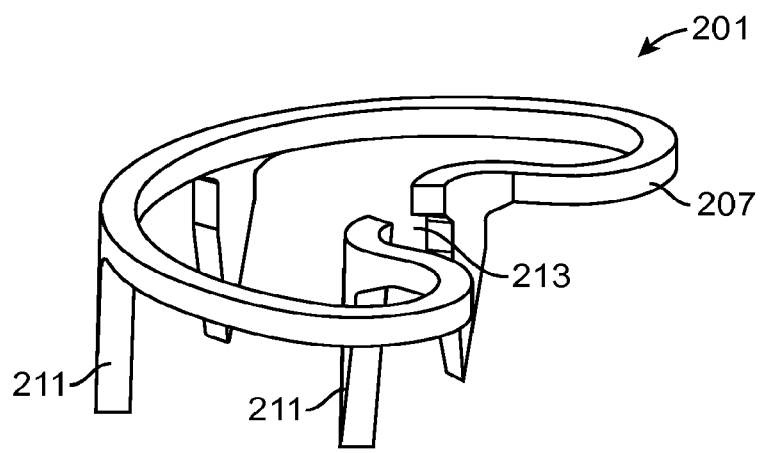

FIGS. 82A and 82B show another embodiment wherein the linear closure clip 201 is of a partially annular configuration. FIG. 82A shows the clip 201 with the ring member 207 in an expanded or non-collapsed state. In this embodiment, the ring 207 is not fully enclosed but rather has an opening 213 that permits the ring 207 to collapse, as shown in FIG. 82B. It should be appreciated that variations on the configuration of the ring 207 are possible.

Seal Attachment Embodiments

In another embodiment of the closure device, a seal member can be pre-attached to a clip. The clip can attach to the blood vessel via tines and provide a closure force to the arteriotomy. In conjunction with the closure force provided by the clip, the seal member can act as a compressive seal to the arteriotomy. The seal can be pre-cut and/or a self-sealing material.

Figure 83A:
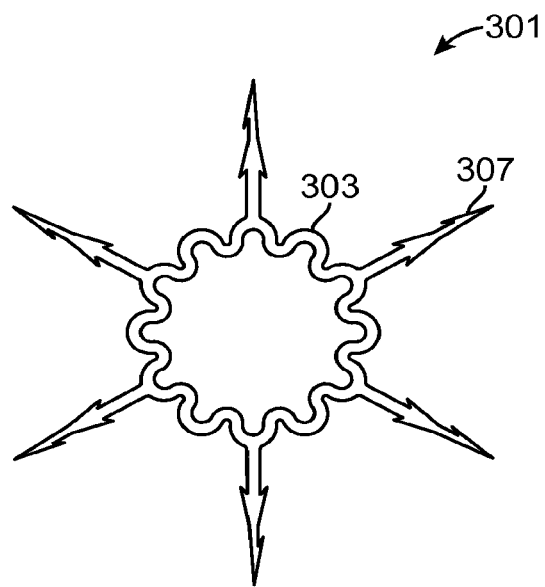
FIGS. 83A and 83B show an embodiment of a sealing closure device.
Figure 83B:
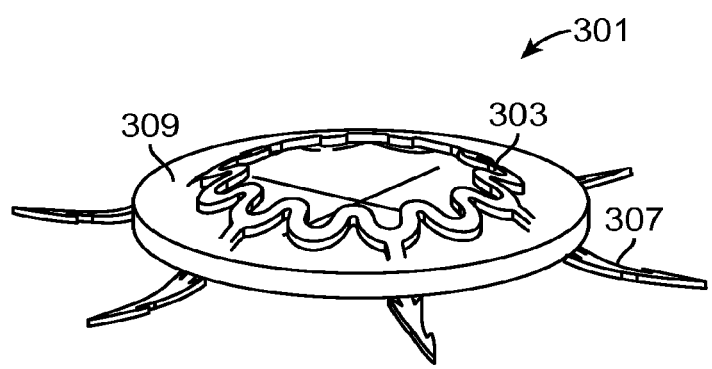

FIG. 83A shows a first embodiment of a sealing clip 301 that includes an annular body formed of a central ring 303, and a plurality of tines 307. The central ring 303 can have an opening through which the procedural sheath can be inserted. As shown in FIG. 83B, a seal member 309 can be coupled to the clip 301 such that the ring 303 inserts through the seal member 309 via the tines 307. The seal member 309 can have a pre-cut opening that permits the procedural sheath to be inserted through the seal member 309. In use, the sealing clip 301 can flatten when deployed onto the blood vessel wall and splay outward into the vessel wall, as shown in FIG. 83B. In this manner, the central ring 303 and tines 307 provide a closing force to the arteriotomy while anchoring the seal member to the vessel wall, while the seal member 309 provides additional sealing force to the arteriotomy.

Figure 84:
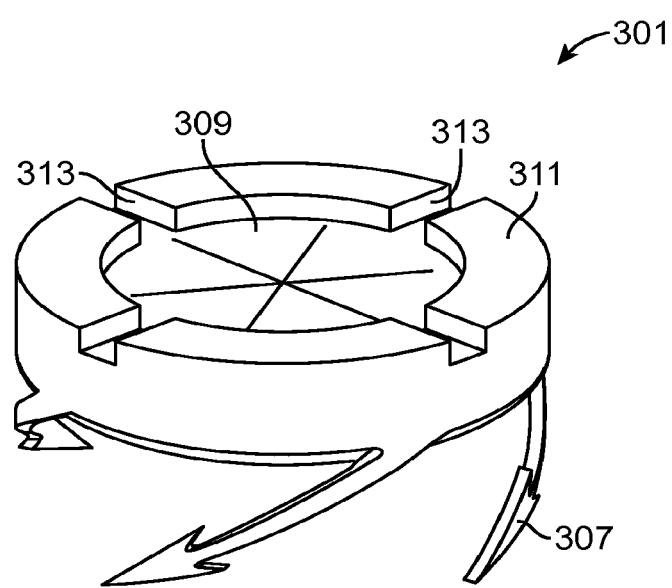
FIG. 84 shows another embodiment of a sealing closure device.

FIG. 84 shows another embodiment of a sealing clip 301. In this embodiment, the sealing clip 301 includes an annular body 311 having one or more tines 307 extending therefrom. The tines 307 can be arranged in a manner that permits them to be screwed into the tissue of the vessel. For example, the tines 307 can be arranged in a spiral or "cork-screw" configuration. The annular body 307 can include one or more engagement features 313, such as one or more slots or other engagement features that can be coupled to a torquing tool. The tool can then be used to apply a rotational force to the annular body 311 for screwing the clip into the vessel wall.

A seal member 309 can be coupled to the annular body 311. The seal member 309 can have a pre-cut opening that permits the procedural sheath to be inserted through the seal member 309 and through the center of the annular body 311. The seal member material and design in relation to the annular body can be configured such that the seal is "self-sealing". In other words when the delivery device or procedural sheath is removed from the central opening, the seal member can provide a hemostatic seal over the arteriotomy. For example, the seal member material can be a soft elastomer such as silicone rubber or polyurethane and the seal member can be in a slight compressed state when assembled in the annular body. As in the previous embodiment, the annular body 311 and tines 307 can attach the seal member to the vessel wall, while the seal member 309 seals the arteriotomy.

Figure 85A:
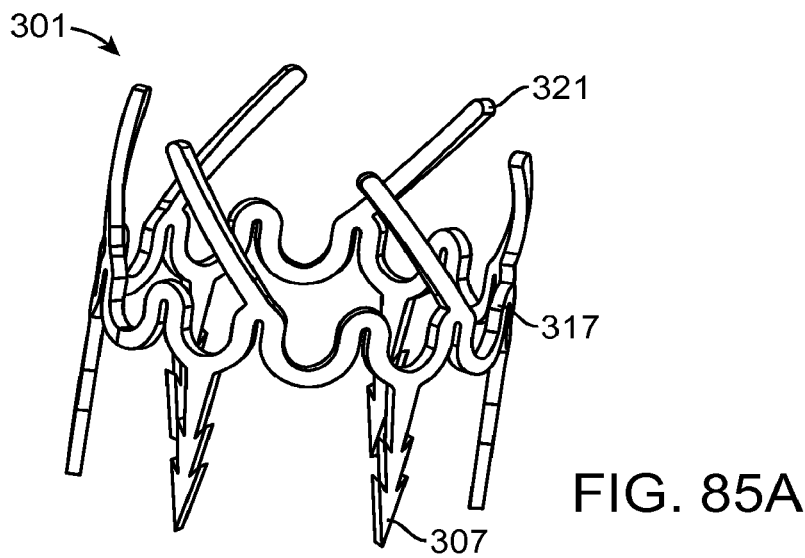
FIGS. 85A-85C show another embodiment of a sealing closure device.

FIG. 85A shows another embodiment of a sealing clip 301. In this embodiment, the sealing clip 301 can include an annular body 317 having one or more tines 307 extending therefrom. The annular body 317 has a similar configuration to the undulating loop annular body described above with reference to FIG. 76 although it should be appreciated that the configuration of the annular body can vary. A plurality of upwardly-extending posts 321 extend from the annular body and can be arranged in a spiral or cork-screw configuration. A seal member can be positioned on the posts for sealing the arteriotomy. As described below, the sealing clip 301 can collapse when deployed such that the posts 321 collapse and fold in an iris pattern over the arteriotomy. That is, the posts 321 can cause the seal to close in a circular, contractile manner.

Figure 85B:
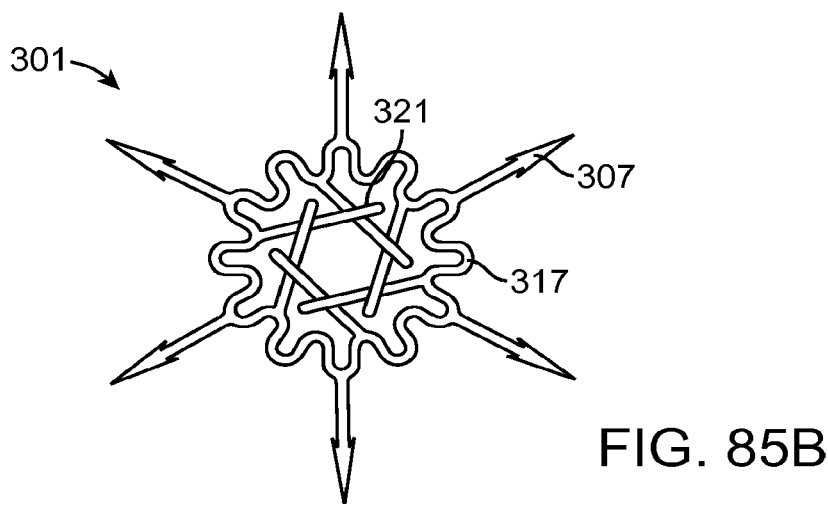

The clip 301 of FIG. 85A can be manufactured by cutting it out of a tube such that it has the configuration shown in FIG. 85A. The clip 301 can then be flattened to the achieve the configuration shown in FIG. 85B such that the tines 307 splay outward into the vessel wall. When flattened, the spiral arrangement of the posts 321 causes them to fold over one another in an iris fashion such that they fold over the arteriotomy.

Figure 85C:
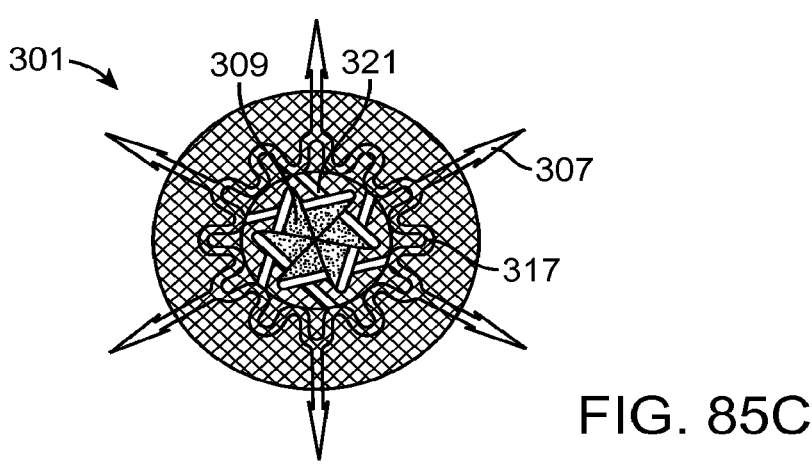

FIG. 85C shows the clip 301 in the planar state with the seal member 309 mounted on the clip. The seal member 309 can be mounted over the clip 301 such that a region of the seal member 309 is coupled to the posts 321. As the posts 321 fold downward, they pull the seal member 309 over the arteriotomy. The seal member 309 can fold over itself to create a compressive iris-style seal. The iris-style seal can be stretched open during insertion of a procedural sheath through the central opening, and then re-seal over the arteriotomy once the sheath is removed.

Pre-Tied Closure Clip Embodiments

In another embodiment, a clip has a pre-attached suture. The clip can attach to the vessel wall in a pattern around the arteriotomy location, for example with deflectable attachment tines as shown in FIGS. 81A and 81B. The suture can be threaded through the clip (such as through one or more eyelets) in a manner that permits tightening of the suture. For example, the suture can be arranged in a purse-string or X pattern relative to the clip. This embodiment varies from the previous embodiments in that there is no automatic hemostasis or sheath retentions force. The sutures act as "preclose" sutures as described in the introduction, but can be applied in more limited incision areas and require less surgical skill. After the procedural sheath is removed from the clip, the pre-threaded suture can be tied off, to accomplish hemostasis.

FIGS. 86A and 86B show a first embodiment of the pre-tied clip wherein a single clip 401 (formed of an annular body) has at least one tissue attachment member such as a tine for attaching to tissue and one or more sutures 403 threaded through the clip, such as through eyelets 407 in the clip member 401. FIG. 86A shows the clip member 401 in a first, untightened state such that the clip 401 is round or otherwise enlarged. A tightening force can be applied to clip 401 by pulling on the one or more sutures 403. The suture 403 can exert sufficient force to cause the clip member 401 to collapse and thereby close the arteriotomy to which it is attached, as shown in FIG. 86B In another embodiment shown in FIGS. 87 and 88, the pre-tied clip can include a pair of clip members 401a and 401b that are attached to one another by one or more sutures 403 threaded through the clip members 401. The clip members 401a and 401b can have any of a variety of shapes including curved clip members 401 (shown in FIG. 87), straight clip members 401 (shown in FIG. 88) and/or curvilinear clip members. The suture 403 can be tightened to draw the clip members 401a and 401b toward one another so as to apply a closure force to the arteriotomy. Any quantity of clip members can be used in combination with one or more sutures.

Spring/Clip and Sealing Material Combination Embodiments

Another embodiment of the closure device is a combination of a clip and separate seal member. The clip can anchor to the vessel wall and include features which capture the seal member over the arteriotomy after removal of the procedural sheath. The seal member can be any hemostatic material such as Dacron, collagen or other biologic matrix, bioabsorbable polymer, or other known hemostatic material.

Figure 89C:
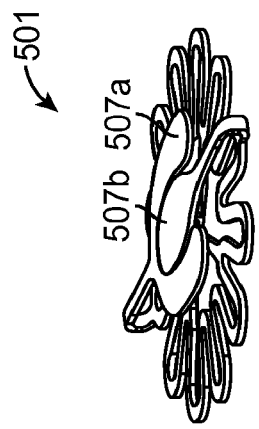
FIGS. 89A-89C show an embodiment of a combination closure device that combines a closure clip with a spring-loaded sealing element.
Figure 89B:
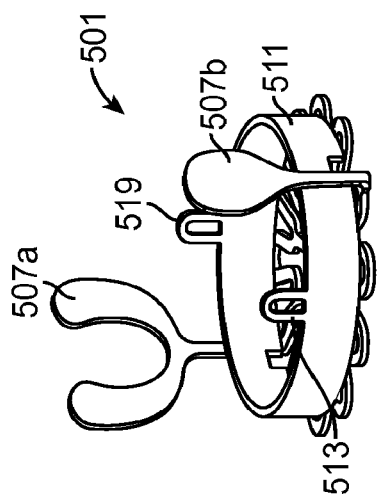
Figure 89A:
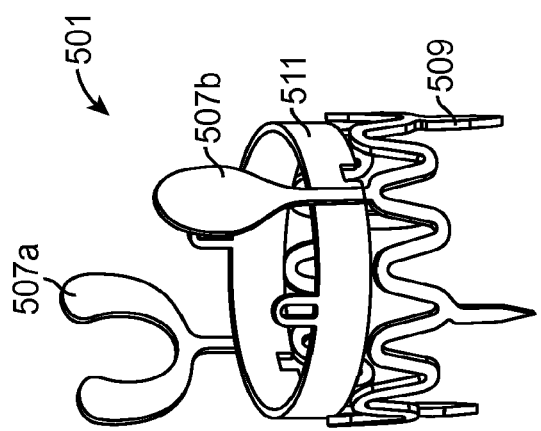

FIGS. 89A-89C show an embodiment of a combination clip 501 that combines a closure clip with a spring-loaded sealing element 507. The clip 501 can be configured the same as or similar to the clip 101 described above or the clip 501 can be a ring. Thus, the clip 501 can include an annular body, which can be generally annular in shape and which surrounds a central axis, and a plurality of tines 509 extending from the body. The body can be configured to receive a procedural sheath that can be inserted into a blood vessel, as described more fully below. The sealing element 507 can be an element that is adapted to seal with the wall of the blood vessel. The sealing element 507 can include one or more parts. In the embodiment of FIGS. 89A-989C, the sealing element 507 can include a first sealing element 507a that includes a U-shaped member that extends upwardly from the clip body. A second sealing element 507b also extends upward from the clip body and has a shape that fits within the cavity between the arms of the U-shaped first sealing element 507a.

FIG. 89A shows the clip 501 in a pre-deployed state as it would be configured during delivery over a central shaft of a delivery system. The sealing element 507 can be retained in an open position such that it does not interfere with the central passageway in the clip 501, thereby permitting a procedural sheath to be positioned in the central passageway. The sealing element 507 (both the first sealing element 507a and the second sealing element 507b) can be spring-loaded or otherwise biased to a position where it extends into the central passageway or opening and seals the arteriotomy as described more fully below.

With reference still to FIG. 89A, a retaining ring 511 can be removably coupled to the clip 501 in a manner that interferes with the sealing element 507. That is, the retaining ring 511 can prevent the sealing element 507 from moving into the central passageway of the clip and thereby retains the sealing element 507 in the pre-deployed state. This permits the delivery sheath to be passed through the clip 501 without interference from the sealing elements 507. In an embodiment, one or more tethers (not shown) are attached to eyelets 519 in the retaining ring to prevent potential loss of the ring in the body cavity during removal. The tether or tethers can also be used to remove the retaining ring.

FIG. 89B shows the clip 501 after it has deployed in the vessel wall over the arteriotomy. The annular body of the clip 501 has achieved the planar state so that it exerts a closure force onto the arteriotomy. One or more removal elements, such as tethers (not shown) can be attached to eyelets 519 on the retaining ring 511 for exerting a removal force thereon. After the delivery sheath is removed from the clip, the tethers can be pulled to disengage the retaining ring 511 from the clip 511 and the sealing elements 507. The sealing elements 507 can then spring to the deployed state shown in FIG. 89C. In the deployed state, the sealing elements 507 can mate with one another to seal the arteriotomy. Note that the second sealing element 507b fits within the cavity in the first sealing element 507a.

Figure 90B:
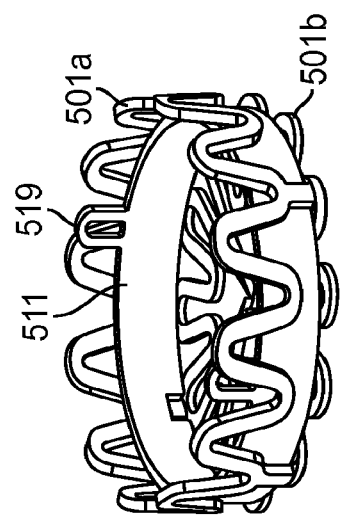
FIGS. 90A-90D show another embodiment of a closure device that includes an upper clip member positioned over a lower clip member and trapping a sealing member.
Figure 90A:
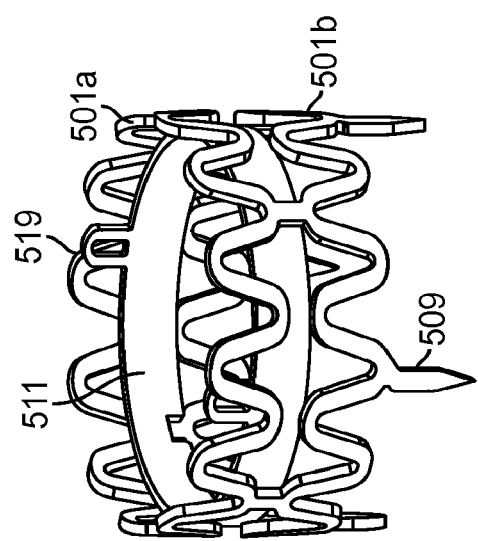

FIGS. 90A-90D show another embodiment of a clip that includes an upper clip member 501a positioned over a lower clip member 501b. As discussed below, the upper clip member can act as fastener element that fastens a seal member to the clip. Each of the clip members 501a and 501b can be formed of an annular body with an undulating loop configuration in the manner described above with reference to FIG. 76. One or more tines 509 can extend downward from the lower clip member 501b. FIG. 90A shows the clip in a pre-deployed state as it would be configured during delivery over a central shaft of a delivery system. A retaining ring 511 can couple to the clips 501a and 501b to maintain the clips in the cylindrical or open state. In use, the bottom clip member 501b can insert into the blood vessel wall via the tines 509. The bottom clip member 501b can then be permitted to collapse into the planar state, as shown in FIG. 90B. A procedural sheath can then be inserted through the center of the upper and lower clip members into the blood vessel. After the procedural sheath is removed, the retaining ring 511 can maintain the upper clip member 501a in the open or cylindrical state, as shown in FIG. 90B.

Figure 90D:
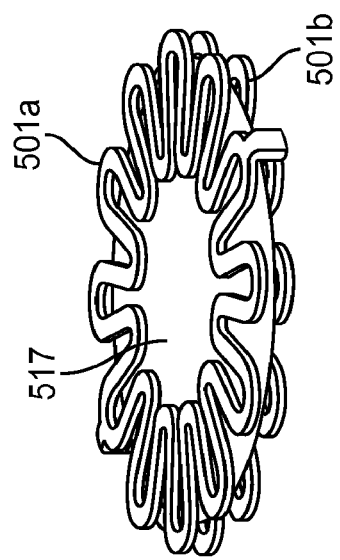
Figure 90C:
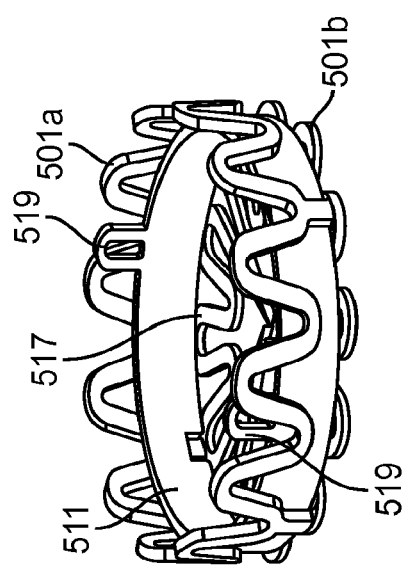

With reference to FIG. 90C, a sealing member 517 can then be positioned between the lower clip member 501b and the upper clip member 501a such that the sealing member 517 can be positioned over the arteriotomy. The retaining ring 511 can then be removed such as by pulling on the retaining ring 511 using a tether attached to eyelets 519. The removal of the retaining ring 511 removes interference with the upper clip member 501a such that the upper clip member 501a can collapse over the sealing member 517, as shown in FIG. 90D. The upper clip member 501a and lower clip member 501b thus can capture and retain the sealing member 517 in a fixed position over the arteriotomy.

Figure 91B:
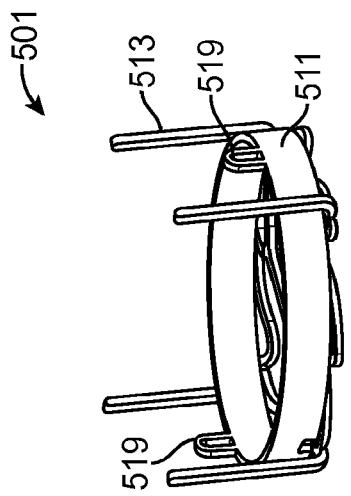
Figure 91A:
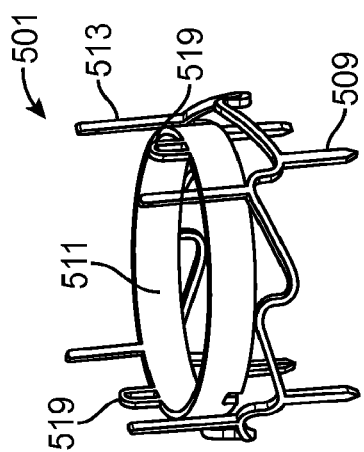

FIGS. 91A-91D shows yet another embodiment of a combination clip 501 having an annular body that includes one or more tines 509. The tines 509 can insert into and attach to the blood vessel wall. The clip 501 also can include one or more upwardly extending fasteners that include prongs 513 that are configured to couple or fasten to a sealing element 517 (FIG. 91C) such as by inserting through holes in the sealing element 517. A retaining ring 511 can interfere with and retains the prongs 513 in an open state as shown in FIG. 91A.

FIG. 91B shows the clip 501 as it is when deployed in the vessel wall so as to apply a closure force to the arteriotomy in the manner described above with reference to the clip 101. The prongs 513 can still be retained in the open position by the presence of the retaining ring 511. The procedural sheath can then be inserted into and out of the clip 501. After the procedural sheath is removed, a sealing element 517 can be loaded onto the prongs 513, as shown in FIG. 91C. With the sealing element 517 in place, the retaining ring 511 can then be removed such as by pulling on a tether attached to eyelets 519. The prongs 513 can then be allowed to transition downward into a closed state onto the sealing element 517. The prongs 513, when in the downward position or closed state, retain the sealing element 517 in place as shown in FIG. 91D.

In another embodiment shown in FIG. 92, the clip member 501 can include one or more prongs 513 that have a default closed state which allows passage of the procedure sheath, such that a retaining ring is not required to maintain the prongs 513 in an open state. The clip member 501 can also include tines that attach to the blood vessel. The tines are not visible from the view of FIG. 92. The sealing member 517 can be applied to the clip by lifting the prongs upward to provide a seat for the sealing member 517 over the clip. The sealing member 517 can then be placed onto the clip member 501 and the prongs 513 are released so that they return to the closed state and retain the sealing member 517 in place.

Figure 93C:
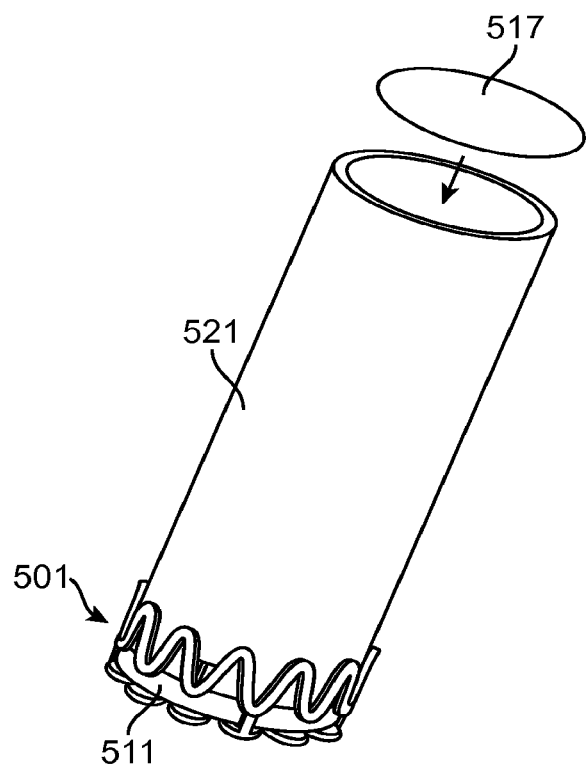

FIGS. 93A-93C show an example of a device for removing the retaining ring from any of the clip embodiments with retaining rings. In this embodiment, a removal member can include an elongate tube 521 having a lower end that attaches to the retaining ring 511. As shown in the enlarged view of FIG. 93B, the lower end of the tube 521 can have one or more features, such as notches 527, that attach to one or more features, such as protrusions 531, on the retaining ring 511. As the tube 521 can be lowered toward the retaining ring 511, the protrusions 531 insert into the notches 527 in a manner that couples the tube 521 to the retaining ring 511. In embodiments with a separate seal material as in FIGS. 90, 91, and 92, the tube 521 can also be used to guide the seal member 517 in place, as shown in FIG. 93C. In this case, the seal member 517 can be pushed down with a push rod. While the rod is holding the seal material in place, the tube 521 can then be lifted off the clip to remove the attached retaining ring 511. Alternately, the tube itself can serve as the retaining ring. The tube 521 then can remain in place during the entire procedure. As before, the tube can then be used to guide the seal material in place before being removed.

The tube 521 can also be pre-loaded onto the procedural sheath so it can slide down over the procedural sheath before the procedural sheath is removed. In this way, the tube 521 can act as a counter traction against the clip 501 while the procedural sheath is being removed.

Figure 94C:
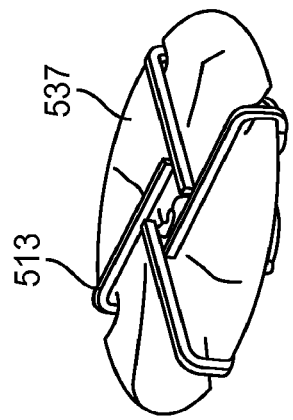
FIGS. 94A-94C show another embodiment of a closure device.
Figure 94B:
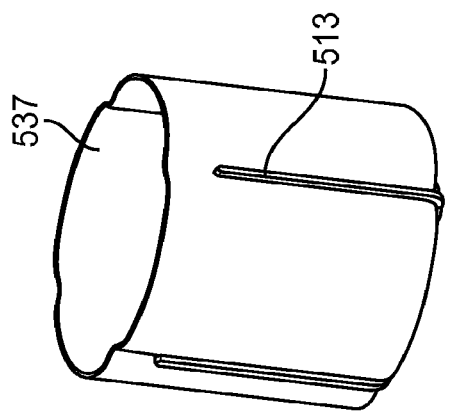
Figure 94A:
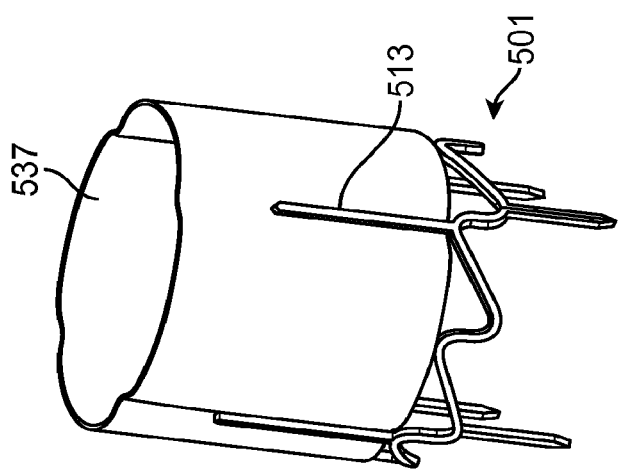

In another embodiment shown in FIGS. 94A-94C, the sealing member can be a cylindrical sealing sleeve 537 that is preattached to the clip 501. The sleeve 537 can have a height such that a set of prongs 513 can be positioned over the sleeve 537 to retain it in place during deployment of the clip 501, as shown in FIG. 94A. After the clip 501 is deployed in the blood vessel, the prongs 513 and sealing sleeve 537 can be initially maintained in an open state as shown in FIG. 94B. The prongs 513 can then be permitted to collapse inward and retain the sealing sleeve 537 in place as shown in FIG. 94C.

Clip Delivery Embodiments

Various features and modalities can be employed to deliver the clip onto the blood vessel and arteriotomy. A delivery system can be coupled to the clip and used to deliver the clip onto the blood vessel. The delivery system can include a delivery device including a central delivery shaft such as a cylindrical member over which the clip is mounted. A retaining sleeve can be positioned coaxially over the central delivery shaft and clip and prevent the clip from expanding outward and/or slipping from the central delivery shaft during delivery. A vessel locator can be included to assist in locating the distal tip of the delivery system securely against the vessel wall. A proximal actuator can push the clip from the central delivery shaft and retract the retaining sleeve to deploy the clip into the vessel wall. The delivery system can also include a central guidewire lumen (such as through the central delivery shaft) and be delivered to the outer surface of the vessel over a guidewire pre-positioned in the vessel. The guidewire can then remain in place while the delivery system is removed and then be used to delivery the procedural sheath through the deployed clip. Alternately, the delivery system can incorporate the procedural sheath as the central delivery shaft of the delivery system. In another embodiment, the central delivery shaft and procedural sheath are two separate components that are integrated into a single delivery system. In these embodiments, the clip delivery shaft and procedural sheath combination systems can also be delivered over a guidewire.

In one embodiment, suction can be used in combination with the delivery system during delivery of the clip. Various configurations can be used to apply suction, such as a syringe, suction cartridge, suction pump, wall suction, etc. The suction functions to secure at least a portion of the delivery system to the exterior surface of the vessel wall for reliable clip delivery to the vessel wall. FIG. 95A shows a suction delivery system 609 that is used to deliver the clip 611 (which can be any of the clip embodiments described herein or any type of closure clip not limited to the clips described herein) to a blood vessel V. The clip 611 can be mounted on a central delivery shaft 606 that is positioned coaxially within a retaining sleeve 608. As shown in FIG. 95B, a suction force can be applied to the vessel wall via the delivery system 609. The delivery system 609 can apply suction via an internal lumen in a component of the delivery system 609 such that the suction force gathers a region 607 of tissue into a portion of the delivery system 609, such as the retaining sleeve 608. With the region 607 gathered into the retaining sleeve 608, the clip 611 can more easily latch onto the tissue. The gathered tissue also can create the ability to create a bigger "bite" for closure, in other words, a greater distance between attachment points, thus potentially improving the security and closure force of the clip device.

The delivery system can include a clip carrier assembly having an elongated member that retains the vessel closure clip in a delivereable configuration during clip delivery. The carrier assembly can be adapted to deploy the vessel closure clip onto the artery. The carrier assembly can include an actuation element that actuates a pusher member with respect to an elongated member to push the clip off the elongated member and deploy the clip. The carrier assembly can further include a cover member for retaining the vessel closure clip on the elongated member during delivery.

Figure 96B:
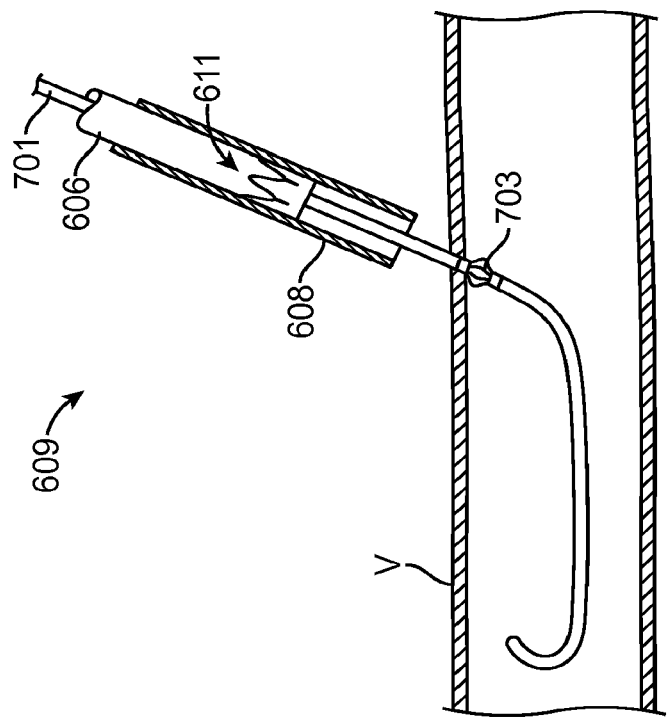
FIGS. 96A-96B show a locating device that can be used in conjunction with delivery of a closure device.
Figure 96A:
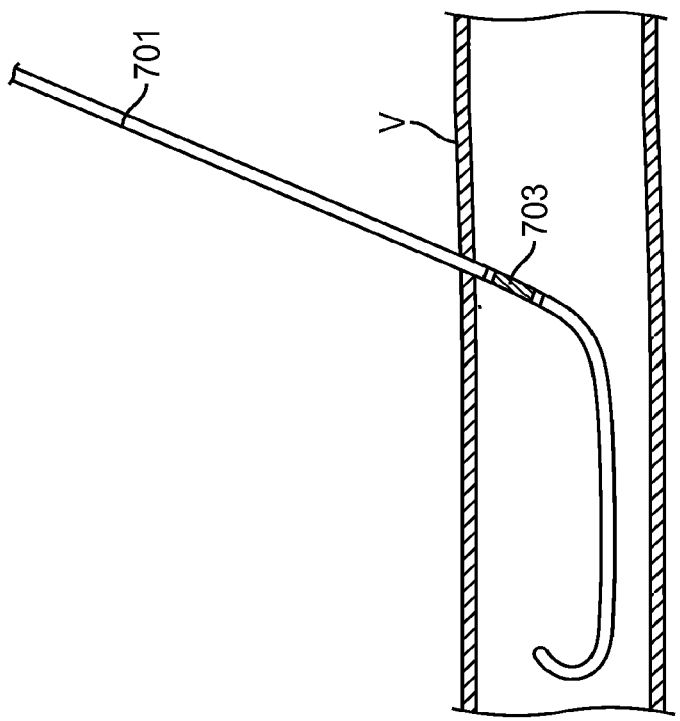

In another embodiment, a locating member in the form of a guidewire or small mandrel can be employed to position the delivery system with respect to the vessel wall during clip delivery. FIG. 96A shows a locating device 701 in the form of a guidewire having an expandable vessel wall locator 703 positioned thereon. The locating device 701 can be first inserted into the vessel with the vessel wall locator 703 in a collapsed, generally mandrel state, as shown in FIG. 96A. As shown in FIG. 96B, the vessel wall locator 703 can then be expanded, for example by an actuator (not shown) on the proximal end of the locating device 701. The vessel wall locator 703 can then be positioned against the vessel wall from inside the vessel. The clip delivery system 609 (including the central delivery shaft 606 and the retaining sleeve 608) can be guided to the vessel wall over the locating device 701 and the clip 611 is deployed. If a guidewire form is used, it can remain in place after the clip 611 is deployed and the delivery device is removed, and then be used to deliver the procedural sheath. Suction can be applied in combination with the vessel locating device 701.

Figure 97A:
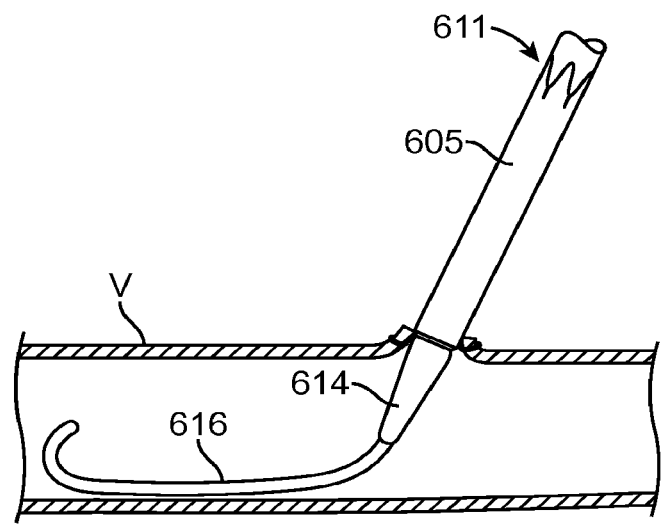
FIGS. 97A-97C show an example of a closure device pre-mounted on a procedural sheath such that the procedural sheath serves as a central delivery shaft of the delivery system.
Figure 97B:
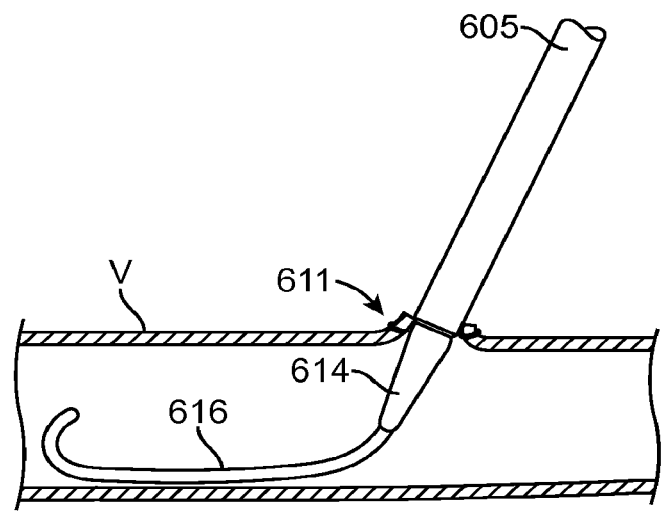
Figure 97C:
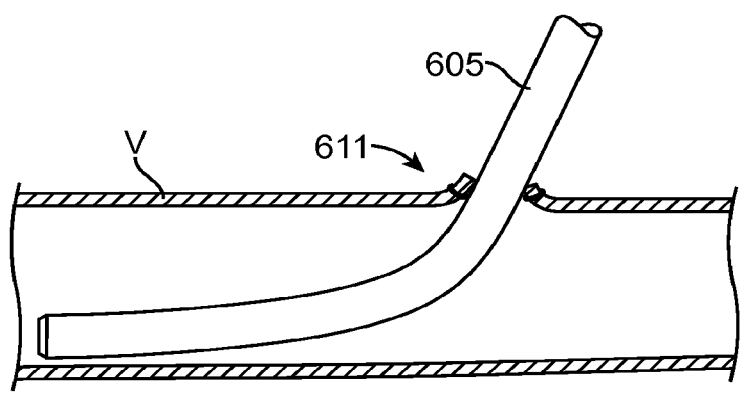

In yet another embodiment, shown in FIGS. 97A-97C, the clip 611 can be pre-mounted on the procedural sheath 605 such that the procedural sheath 605 serves as the central delivery shaft of the delivery system. In this case, as shown in FIG. 97A, the procedural sheath 605 can be inserted through the penetration in the vessel and into the vessel V via conventional means such as a micropuncture technique or modified Seldinger technique. The procedural sheath 605 can be coupled to a dilator 614 and a guidewire 616. The pre-mounted clip 611 is then pushed over the procedural sheath 605 toward the blood vessel V. The clip 611 can be deployed around the vessel at the site of procedural sheath insertion, as shown in FIG. 97B. After the clip 611 can be deployed, the guidewire 616 and dilator 614 can be removed, as shown in FIG. 97C, while the procedural sheath 605 stays in place to provide access for a procedural device that can be inserted through the procedural sheath 605 into the blood vessel V for performing a procedure. As with previous embodiments, after procedural sheath removal the clip then closes the arteriotomy.

Figure 98A:
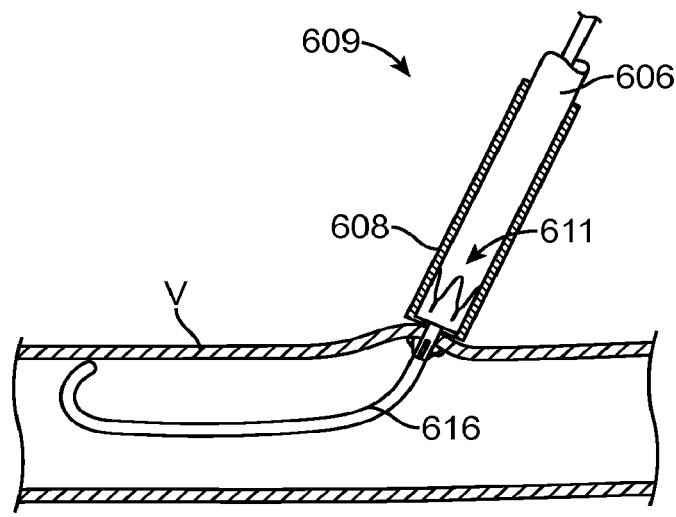
FIGS. 98A-98C show an example of the procedural sheath mounted on the central delivery shaft of the delivery system.
Figure 98B:
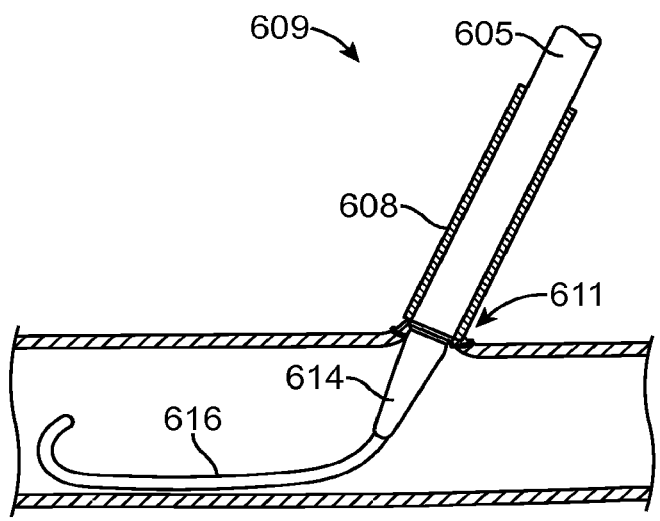
Figure 98C:
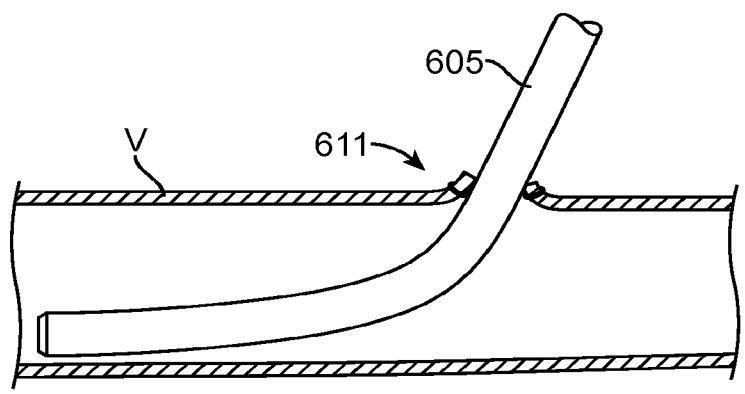

In yet another embodiment, shown in FIGS. 98A-98C, the procedural sheath 605 can be mounted on the central delivery shaft 606 of the delivery system 609. The procedural sheath 605 can be pre-mounted on a proximal region of the central delivery shaft 606 such that the procedural sheath 605 can slide distally over the delivery shaft 606 and through the central opening of the clip 611. The procedural sheath 605 can have a hemostasis valve, such as on the proximal end of the procedural sheath. Thus, when the delivery system 609 is removed, hemostasis can be maintained. If a procedural sheath 605 is used which requires a proximal extended section (as described below), an attachable extension can be added to the proximal end of the procedural sheath 605 after removal of the clip delivery system 609. Alternately, the delivery shaft 606 can have an extended length that permits pre-mounting of both the procedural sheath and proximal extension. In another embodiment, the procedural sheath 605 is not pre-mounted on the central delivery shaft 606 but is exchanged with the central delivery shaft 605 in conjunction with or after removal of the delivery shaft 606 from the blood vessel V. After the clip 611 is delivered, the procedural sheath 605 can be advanced through the retaining sleeve 608 of the delivery system 609 and through the clip 611 into the blood vessel V, as shown in FIG. 98B. The procedural sheath 605 can be coupled to a dilator 614 during this process. The delivery shaft 606, retaining sheath 608, dilator 614, and guidewire 616 (if present) can then be removed, leaving the procedural sheath 605 and clip 611 in place, as shown in FIG. 98C. The procedural sheath 605 can stay in place to provide access for a procedural device that can be inserted through the procedural sheath 605 into the blood vessel V for performing a procedure. At the end of the procedure, the procedural sheath 605 can be removed, and the clip 611 can seal the vessel opening.

The procedural sheath 605 can include an intravascular occlusion element for procedures requiring arterial occlusion. The intravascular occlusion element can be, for example, an inflatable balloon, an expandable member such as a braid, cage, or slotted tube around which is a sealing membrane, or the like. The procedural sheath can also include a sheath retention element such as an inflatable structure or an expandable wire, cage, or articulating structure which prevents inadvertent sheath removal from the blood vessel when the sheath is deployed.

Figure 99:
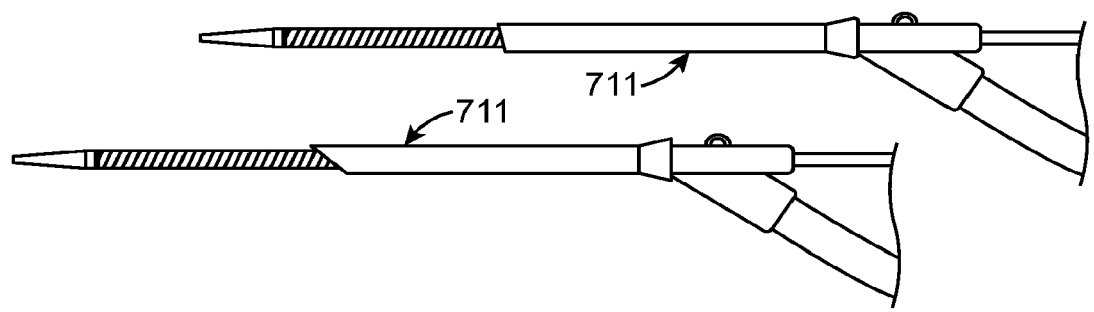
FIG. 99 shows a tube located on the outside of a delivery sheath.

The delivery device can include a countertraction feature that prevents the clip from being detached from the blood vessel during removal of the delivery device. Similarly, the procedural sheath can include a counter traction feature that prevents the clip from being detached during removal of the sheath. For example, as shown in FIG. 99, a tube 711 can be located on the outside of the sheath. The tube 711 can act as a countertraction feature and can be pushed forward along the outer surface of the procedural during sheath removal. The distal tip of the countertraction tube 711 can abut the clip and be held against the vessel wall to hold the preclose clip in place and prevent inadvertent removal of the clip during sheath removal. The distal tip of the tube 711 can be shaped in various manners depending on which pre-close clip embodiment is being used. For example, the tip can be blunt or beveled, to act as "sheath stop" to prevent the sheath from entering vessel too far. The tube 711 can have an extended tip that goes through clip so that clip does not interfere with sheath removal.

Embodiments of Interventional Catheters

Figure 100:
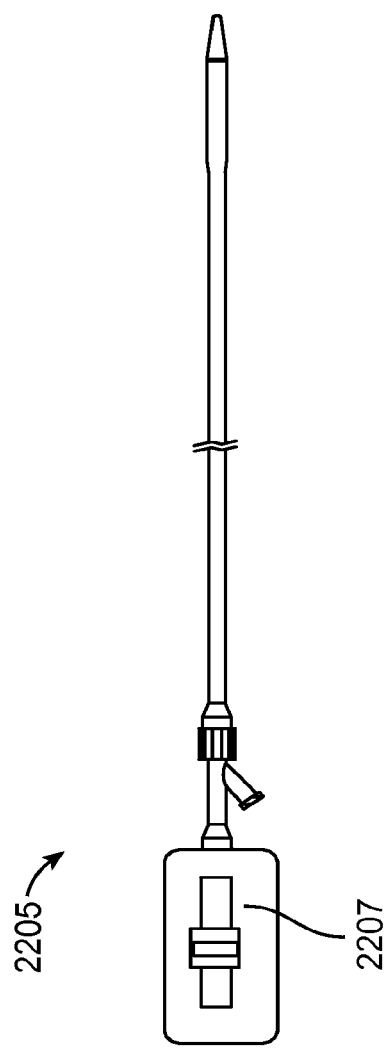
FIG. 100 shows a schematic view of an embodiment of an interventional catheter.

FIG. 100 shows a schematic view of an example of an interventional catheter 2205. The catheter 2205 can have an external dimension that is sized and shaped for insertion into a blood vessel. In an embodiment, the catheter 2205 is sized and shaped for insertion into an access sheath of a carotid artery access system. The proximal region of the catheter 2205 can have one or more mechanical or electro-mechanical control mechanisms 2207 for controlling different components on or near a distal end of the catheter 2205. For example, the control mechanism(s) can be used to control inflation of a balloon or balloons, advancement/deployment of a system component (such as a stent), flushing or aspirating a fluid through the catheter, and combinations thereof. As used herein, the term "proximal" means closer to the user and the term "distal" means further from the user.

The interventional catheters described herein provide several advantages over prior systems. For example, the disclosed catheters can be used to reduce the number of device exchanges required to perform a carotid artery stenting (CAS) procedure. The catheters also permit flush, aspiration, and clearing of embolic debris to a higher degree than prior systems. Moreover, the disclosed catheters provide augmented embolic protection through the use of intermittent internal carotid artery occlusion during specific, critical points in a carotid artery treatment procedure. When the catheter is used in a retrograde flow embolic protection system as described above, flow restrictions in the retrograde flow circuit can be decreased through use of the disclosed interventional catheters. The retrograde flow regimen can be optimized by communicating the timing of balloon deflation (which is a period of heightened risk for embolic debris release) to a retrograde flow controller. Furthermore, the interventional catheters used here can be optimally sized for insertion through a transcervical access into the carotid artery. The length of these catheters can be up to half, or even shorter, than currently available catheters which are designed for a transfemoral access route. This shorter length makes the catheters much easier to manipulate, and makes catheter exchanges simpler and more rapid. In an embodiment, the working length of the catheter is within the range of approximately 40-60 cm. In another embodiment, the working length is within the range of approximately 40-75 cm.

Although the devices and methods described hereinafter are sometimes described in the context of treatment of the carotid artery (such as carotid artery stenting), it should be appreciated that the devices and methods described herein would also be useful for angioplasty, artherectomy, and any other interventional procedures which might be carried out in the carotid arterial system, particularly at a location near the bifurcation between the internal and external carotid arteries. In addition, it will be appreciated that some of the disclosed devices and methods can be used in other vascular interventional procedures.

Stent Delivery Device and Dilatation Balloon on Single System

Figure 101:
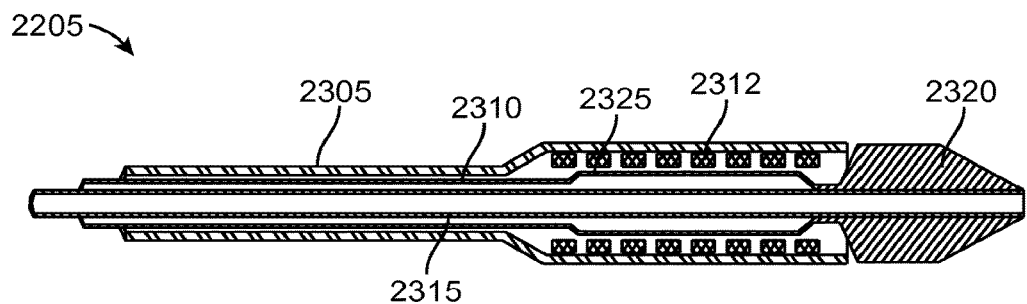
FIG. 101 shows a cross-sectional view of the distal region of the catheter.

FIG. 101 shows a cross-sectional view of the distal region of the catheter 2205, which includes an outer, stent constraint or containment member including an outer sheath 2305 having an internal lumen. A stent delivery shaft 2310 can be coaxially positioned in the internal lumen with a stent 2312 mounted on the stent delivery shaft 2310. A tubing 2315 with an internal lumen can be coaxially positioned inside the stent delivery shaft 2310. The lumen of the tubing 2315 can allow passage of a guide wire through the stent delivery shaft 2310, as is typical in cardiovascular and vascular interventional procedures. A tip 2320 can be positioned at the distal end of the stent delivery shaft 2310 such that the tip 2320 protrudes distally outside of the outer sheath 2305. The tubing 2315 can extend through the tip 2320 to form an opening at the tip's distal edge. The tip 2320 can have any of a variety of shapes and can be atraumatic, tapered, etc.

The stent 2312 can be a self-expanding stent that is compressed on the distal end of the stent delivery shaft 2310 over a length of the stent delivery shaft 2310. The outer sheath 2305 can cover the stent 2312 to maintain the stent 2312 in a low profile during access and delivery. The outer sheath 2305 can be retractable relative to the stent delivery shaft 2310. During deployment of the stent 2312, the outer sheath 2305 can be retracted to a position such that it no longer covers the stent 2312. The self-expanding stent 2312 can then spring open to position itself into the target treatment area. A control mechanism on the proximal end of the catheter 2205 can be used to retract the outer sheath 2305.

With reference still to FIG. 101, a dilatation balloon 2325 can be positioned under the compressed stent 2312. The balloon 2325 can be continuous with the stent delivery shaft 2310. The balloon 2325 can communicate with an inflation lumen that includes the annular space between stent delivery shaft 2310 and the tubing 2315. The inflation lumen can be used to inflate the balloon 2325 at a desired time during the procedure. After the stent 2312 is deployed, the position of the balloon 2325 can be adjusted relative to the stent 2312. Once the balloon is properly positioned, such as at the area of maximum stent "waist", the balloon can be inflated to perform a post-dilatation procedure on the stent. In an embodiment, the stent delivery shaft 2310 can contain two separate lumens in a single tubing. The two separate lumens can include a balloon inflation lumen and a guidewire lumen. In this embodiment, the balloon inflation lumen exits the side of the shaft at a location between the proximal and distal bonding locations between the balloon ands shaft. The guidewire lumen exits at the distal end of the catheter as shown in FIG. 101.

Figure 102:
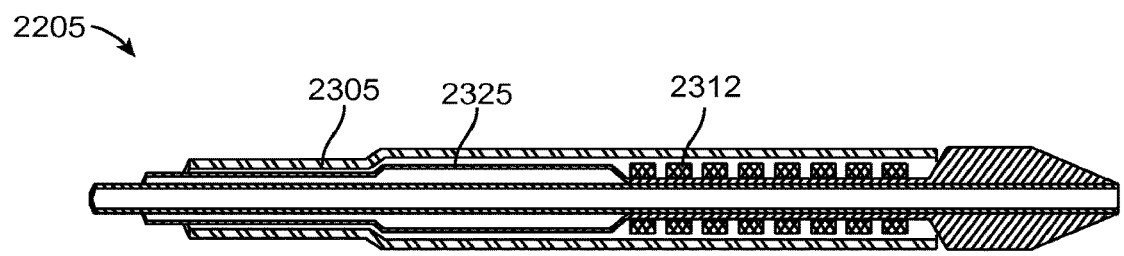
FIG. 102 shows a cross-sectional view of another embodiment of the catheter.

FIG. 102 shows a cross-sectional view of another embodiment of the catheter 2205. In an initial state, the balloon 2325 can be positioned proximal to the stent 2312 and under the retractable outer sheath 2305. The embodiment of FIG. 102 can have lower profile than the embodiment of FIG. 101, as the balloon thickness is not layered under the stent 2312 and the outer sheath 2305. Thus, the outer dimension of the outer sheath 2305 does not have to compensate for the stent 2312 being layered directly over the balloon 2325. In this embodiment, the balloon is positioned proximal to the stent while the stent is being deployed. After the stent is deployed, the balloon can be repositioned forward (i.e., distal) to place the balloon at the location of maximum stent "waist". Neither of the embodiments of FIGS. 101 and 102 are used for dilating the stent 2312 prior to stent deployment, as these embodiments would require deployment of the stent before the balloon can be inflated.

Figure 103A:
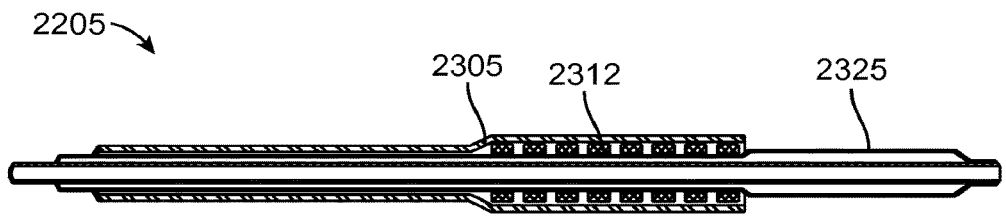
FIGS. 103A and 103B show additional embodiments of the catheter.

FIG. 103A shows another embodiment where the balloon 2325 is positioned distal to the stent 2312. The balloon 2325 can also be positioned distal of the distal end of the outer stent constraint sheath 2305. This embodiment can have the smallest outer dimension of the embodiments of FIGS.

101-103, as a balloon crossing profile is typically smaller than that of a stent delivery catheter. This embodiment can also be used for pre-dilatation of the stent. As with the embodiment of FIG. 102, the balloon 2325 can be repositioned after stent deployment to perform the post-dilatation step if desired. The foregoing devices do not preclude the exchange of further dilatation balloon catheters should the procedure require different balloon sizes to provide the desired end result.

The catheters shown in FIGS. 101-103A can have the guidewire lumen extend either through the entire length of the catheter, in an over-the-wire configuration, or have the guidewire lumen exit the catheter shaft at a position from 10 to 30 cm from the distal tip, in a rapid-exchange configuration. These configurations are well-known in the art for interventional catheters.

Figure 103B:
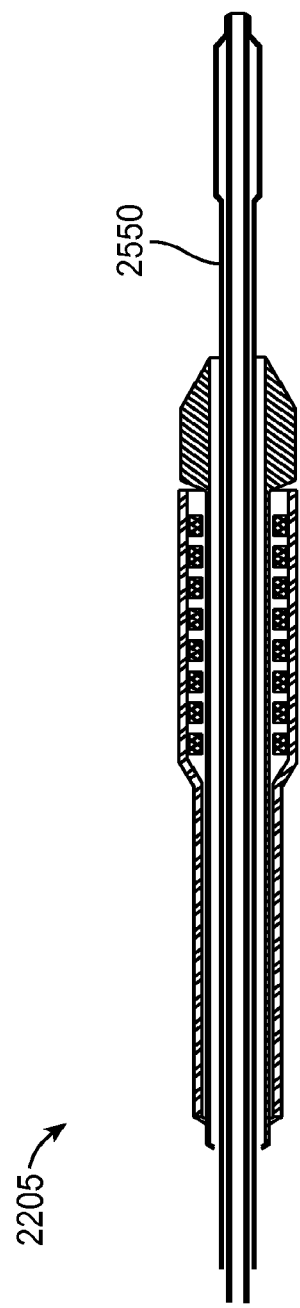

In another embodiment, shown in FIG. 103B, the stent delivery catheter 2205 contains an independently positionable balloon catheter shaft in its central lumen. The balloon catheter shaft can extend about 10-15 cm past the distal end of the stent delivery catheter, enabling the balloon to be advanced first to cross a lesion, and dilate the lesion if desired. The stent deployment portion of the catheter can then be advanced across the lesion to deploy the stent. As above, the balloon can be repositioned after stent deployment to perform the post-dilatation step if desired. In this embodiment, the balloon catheter shaft can be either a "fixed-wire" type with a built in guidewire tip, negating the need for a separate guide wire, or an over the wire or rapid exchange version wherein the central lumen of the balloon catheter shaft accepts a guidewire.

FIGS. 104A-104D show an example method of use of any of the stent delivery catheters having a dilation balloon 2325 and stent delivery capabilities on a single system. FIGS. 104A-104D are shown in the context of the catheter being used for carotid artery stenting although the catheter can be used in other anatomic locations. Initially, as shown in FIG. 104A, an arterial access sheath 605 can be introduced into the common carotid artery CCA via an access site in the CCA. Retrograde flow can then be established using a retrograde flow system, such as the type described above, and a catheter 2205 can be introduced through the sheath 605 and positioned across the target lesion.

The stent 2312 can be deployed at the bifurcation by retracting the outer sheath 2305, which permits the stent to expand and deploy, as shown in FIG. 104B. The rate of retrograde flow can be increased while the catheter 2205 is being introduced and optionally while the stent 2312 is being deployed.

With the stent 2312 deployed, as shown in FIG. 104C, the balloon 2325 can be expanded to perform a post dilation procedure on the stent 2312. The term "post dilation" refers to a procedure where a balloon is used to dilate the stent after the stent has been deployed, to achieve an optimal stent expansion. The rate of retrograde flow can be increased while the stent delivery catheter 2205 is performing the post-dilation procedure. After the dilatation is completed, the stent delivery catheter 2205 can be removed and antegrade flow reestablished, as shown in FIG. 104D. The sheath 605 can then be removed.

It should be appreciated these scenarios and figures are examples, and that access to the carotid artery can also be accessed transcervically through a percutaneous puncture with an intravascular occlusion means, or that the carotid artery can be accessed either percutaneously or using a surgical cut-down via a transfemoral arterial approach. It should also be appreciated the stent delivery system can be used in a variety of procedures that are not limited to retrograde flow. The described method is an example and the stent delivery catheter need not be used with a retrograde flow system or with retrograde flow.

Dilatation Balloon Catheter with Flushing Capabilities

In another embodiment, the catheter 2205 can be configured for dilation of the stent and can also be configured to flush or aspirate the blood vessel at a location proximal to the location of the balloon 2325. In the case of internal carotid artery stenting, this enables the user to flush or aspirate the internal carotid artery ICA just proximal to the balloon dilatation area, while the balloon occludes the ICA during post-dilatation. During flushing, the CCA can be un-occluded to allow forward flow of arterial blood into the ECA. Any embolic debris flowing towards the ICA can be removed by this flushing action. Alternately, the CCA can be un-occluded while the balloon occludes the ICA during post-dilatation and any embolic debris can be aspirated from the carotid arteries via this lumen.

Figure 105:
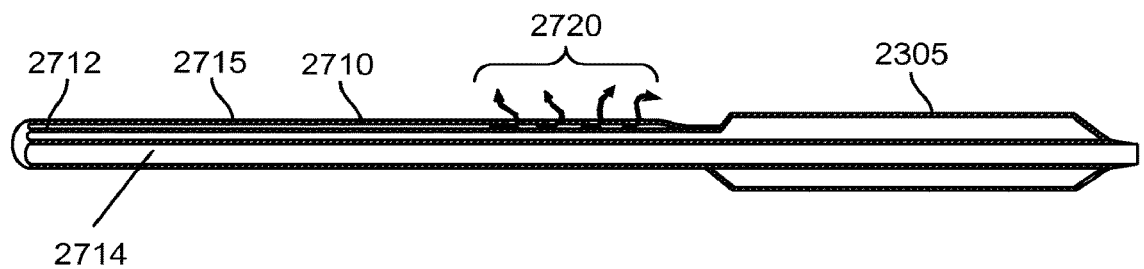
FIG. 105 shows a cross-sectional view of a distal region of a tri-lumen dilatation balloon catheter that has flushing capabilities.

FIG. 105 shows a cross-sectional view of a distal region of a tri-lumen dilatation balloon catheter that has flushing capabilities. A flush lumen 2710 can be located inside the shaft 2715 that carries the balloon 2325. The flush lumen 2710 can terminate proximal to the balloon 2325. The lumen 2710 can communicate with one or more exit ports that include side holes 2720 in the outer shaft 2715. A flush solution can be flowed through the lumen 2710 and out of the catheter 605 via the side hole(s) 2720. A proximal end of the flush lumen 2710 can be connected to a proximal adaptor, which enables the flush lumen to be connected to a syringe, pressurized bag, or other source for flushing. The catheter also can have a second lumen 2712 for inflation of the balloon 2325 and a third lumen 2714 for entry of a guide wire.

Figure 106:
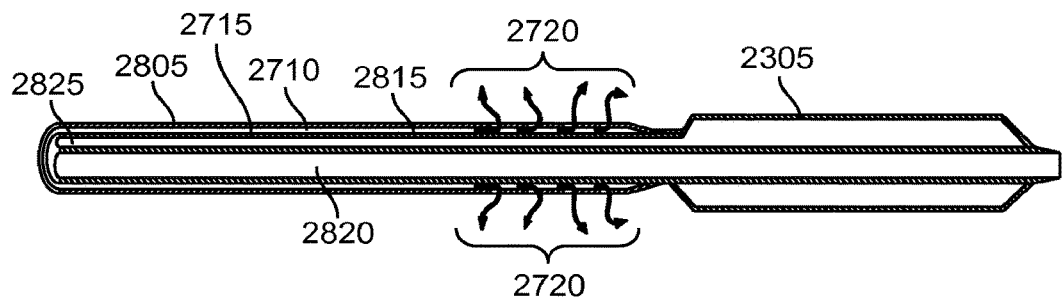
FIG. 106 shows another embodiment with an outer tubing positioned coaxial with a dual lumen shaft that carries the balloon.

In another embodiment, shown in FIG. 106, an outer tubing 2805 can be positioned coaxial with a dual lumen shaft 2815 that carries the balloon 2325. The two lumens of the shaft include a guide wire lumen 2820 and a balloon inflation lumen 2825. The outer tubing 2805 can terminate proximal to the balloon 2325 and in this manner forms an annular flush lumen 2710 positioned between the internal surface of the outer tubing 2805 and the external surface of the shaft 2815. The outer tubing 2805 and the flush lumen 2710 can be connected on the proximal end to a flush connector as discussed above. In an embodiment, the flush lumen 2710 can have an annular opening at the distal end of the outer tubing between the outer tubing 2805 and the shaft 2815. The flush solution can flow through the flush lumen 2710 and exit out the annular opening. Alternately, the distal tip of the outer tubing 2805 can be tapered down to the diameter of the shaft 2715 and can be bonded to the shaft to create a smooth transition between the outer tubing 2805 and the shaft 2715.

The outer tubing 2805 can have one or more side holes 2720 that permit the flush solution to exit the flush shaft 2710. Unlike the previous embodiment of FIG. 105, the exit ports can be placed around the entire circumference of the shaft to provide optimal flushing. If the outer tubing 2805 is not bonded to the shaft 2715, outer tubing can be slideable with respect to the shaft. Thus, the outer tubing 2805 can be retracted from the shaft 2715 if desired. In this manner, the outer tubing 2805 can remain retracted if flushing the ICA is deemed not necessary. The shaft 2715 can have a lower profile if the outer tubing 2805 is retracted. When flushing is desired, the outer tubing 2805 and flush shaft 2710 can be advanced for flushing purposes.

Figure 107:
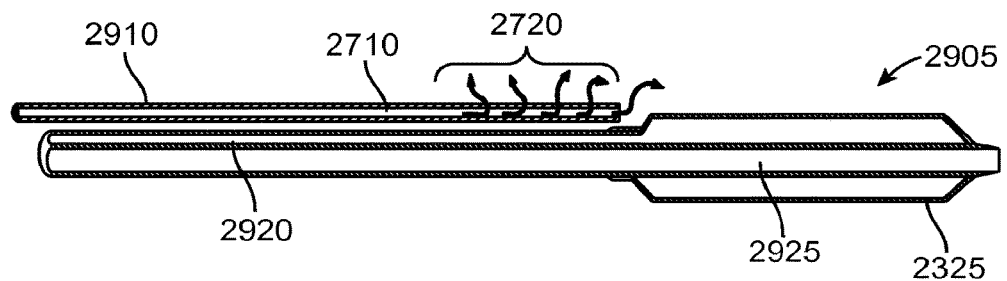
FIG. 107 shows another embodiment that includes a dilation balloon catheter with an external, single-lumen tubing for flushing.

FIG. 107 shows another embodiment that includes a dilation balloon catheter 2905 with an external, single-lumen tubing 2910 for flushing. The dilation balloon catheter 2905 is shown as a dual-lumen construction with a dilation balloon 2325 and an inflation lumen 2920 as well as a guidewire lumen 2925. Alternately, the dilatation balloon can be a co-axial construction, with an inner and an outer tubing, where the inner lumen of the inner tubing forms the guidewire lumen and the annular space between the inner and outer tubing form the balloon inflation lumen. Next to the dilatation balloon catheter 2905 can be the flushing tubing 2910 having a flush lumen 2710 with one or more distal side holes 2720 for the flush solution to exit. The distal tip of the flushing tubing 2910 can terminate proximal to the balloon 2325. This tubing can be fixed or slideably attached to all or a portion of the dilatation balloon catheter 2905, or be a completely separate flushing catheter. If completely separate, this infusion catheter can be inserted, if needed, during the flushing step, and be removed when not in use. This catheter can be placed over a separate guide wire.

The dilatation balloon catheter with the proximal flushing capabilities can be also positioned, or repositioned, as desired, at a location distal to the stented area. In the case of carotid artery stenting, the dilatation balloon can then be inflated at a low pressure simply to occlude the ICA. With the balloon thus positioned, the ICA (including the stented area) can be flushed while the common carotid artery occlusion is opened to forward flush arterial flow to the ECA. This procedural maneuver corresponds to the post-debridement flushing step performed during a CEA procedure. The side holes 2720 can further be designed to flush in a variety of directions, to improve the efficiency of the flush solution to clear embolic debris which can be trapped, or loosely attached, in the stented region.

The flush lumen in these embodiments can alternately be used to aspirate, rather than flush, during balloon deflation, to augment the reverse flow capture of embolic debris during this critical period of the procedure.

Figures 108A, 108B:
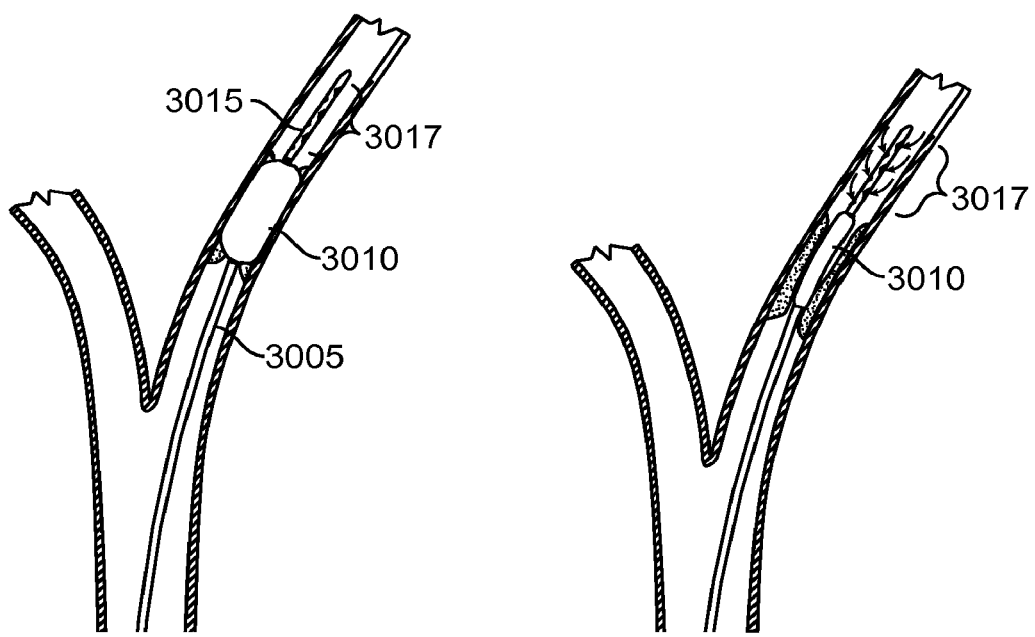
FIGS. 108A and 108B show a dilatation balloon catheter that has an internal flush lumen through which a flush solution can be passed.

In another embodiment shown in FIGS. 108A and 108B, a dilatation balloon catheter 3005 can have an occlusion balloon 3010 and an internal flush lumen through which a flush solution can be passed. A distal region 3015 of the catheter can extend distally beyond the balloon 3010. The flush lumen communicates with side holes 3017 positioned distal in this distal region 3015. The catheter 3005 can include a guide wire lumen and a separate flush lumen or the guide wire lumen can also serve as a flush lumen. In the latter case, the cross sectional area for flushing is limited by the annular space between the guide wire and the diameter of the lumen. The size of the annular space can be increased by increasing the guide wire lumen diameter. The diameter of the guide wire lumen can taper down at the distal tip to create a smooth transition where the guide wire exits the catheter.

A variation of the embodiments of FIG. 108A-108B is a dilatation balloon catheter 3005 with ports or side holes for flushing and/or aspiration in locations both distal and proximal to the balloon 3010. During balloon deflation, solution can be flushed from side holes distal to the balloon 3010 and aspirated into side holes proximal to the balloon 3010.

One method of use of the catheter 3005 is to flush the stented segment of the carotid artery under reverse flow during balloon deflation. The flush solution can flow retrograde along with the blood flow in the internal carotid artery ICA into a reverse or retrograde flow shunt line as described above. The reverse flow can be either passive or actively aspirated, or can be modulated between different states. The flush side holes in the distal region 3015 of the catheter 3005 can be configured to point in a variety of directions, in order to improve efficiency of embolic debris capture. This method can also increase the velocity of flow past the stented region, again potentially improving the efficiency of embolic debris capture. Another method of use is to aspirate from the flush lumen, which can augment the debris capture from the reverse flow. Alternately, some of the lumens can be used to flush while others are used to aspirate.

Interventional Catheter with Combined Dilation and Occlusion Capabilities

In another embodiment, a dual-balloon catheter includes a dilatation balloon for pre-dilating the target lesion or post-dilating a stented segment, and also includes an occlusion balloon distal of the dilation balloon. The occlusion balloon can be a lower pressure balloon relative to the dilation balloon. This catheter is advantageous during the period of the procedure when the dilation balloon is deflated after pre or post-dilation. The period of balloon deflation after dilation is typically a period when a heightened level of emboli is observed during a CAS procedure, as documented in studies utilizing transcranial Doppler measurements. The dual balloon catheter can be used to flush or aspirate the stented area during post-dilatation. After the dilation balloon is inflated in the stented segment, the potential emboli can be cleared from the stented area by first occluding the internal carotid artery distal to the stented zone by inflating the occlusion balloon positioned distal of the dilation balloon and then deflating the dilation balloon. The common carotid artery occlusion can then be opened to allow antegrade arterial flow to flush the common carotid artery and proximal internal carotid artery into the external carotid artery. In an alternate method, after dilation of the stent the distal occlusion balloon can be inflated to occlude the internal carotid artery while the stented segment is exposed to retrograde blood flow, either passively or with active aspiration, such as a syringe or other suction source.

Figures 109A, 109B:
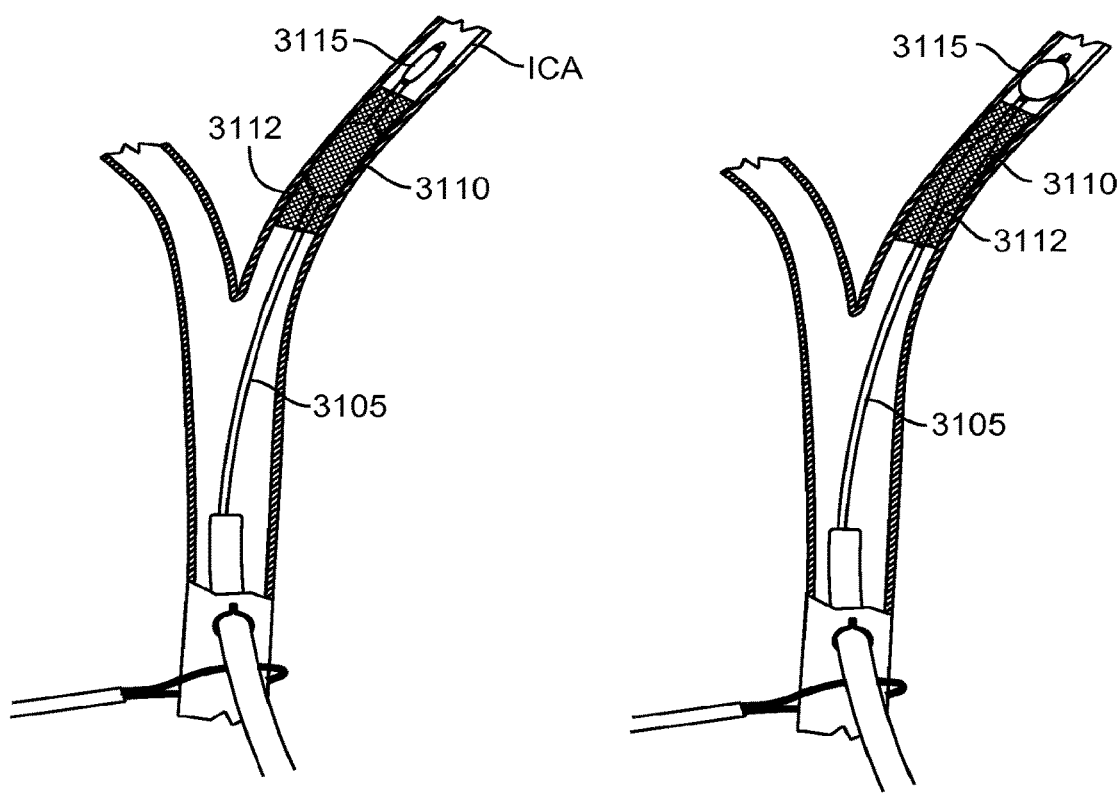
FIGS. 109A and 109B show a dual dilatation balloon and occlusion balloon catheter.

FIGS. 109A and 109B show the foregoing procedure. As shown in FIG. 109A, the dual balloon catheter 3105 can have a dilation balloon 3110 and an occlusion balloon 3115 located distal of the dilation balloon. In the stent post-dilation step shown in FIG. 109A, the dilation balloon 3110 can be inflated to dilate the stent 3112. As shown in FIG. 109B, during deflation of the dilation balloon 3110 the occlusion balloon 3115 can be inflated to occlude the ICA distal to the location of the stent 3112. In an embodiment, the dual balloon catheter 3105 can have two balloons combined onto a single shaft. The single shaft can have a pair of inflation lumens, one for each balloon. The separate inflation lumens can be used to inflate both balloons independently and at different pressures.

In another embodiment, the balloon catheter 3105 can have only a dilation balloon with the catheter having a central lumen. A low profile balloon catheter or guide wire with an inflatable balloon (also known as an inflatable guide wire) can be positioned into the central lumen and is movably positionable to a desired location relative to the dilatation balloon. This embodiment allows the occlusion balloon 3115 to be independently positionable with respect to the dilatation balloon 3110, and eliminates the need for an additional inflation lumen in the balloon catheter shaft.

Figure 110A:
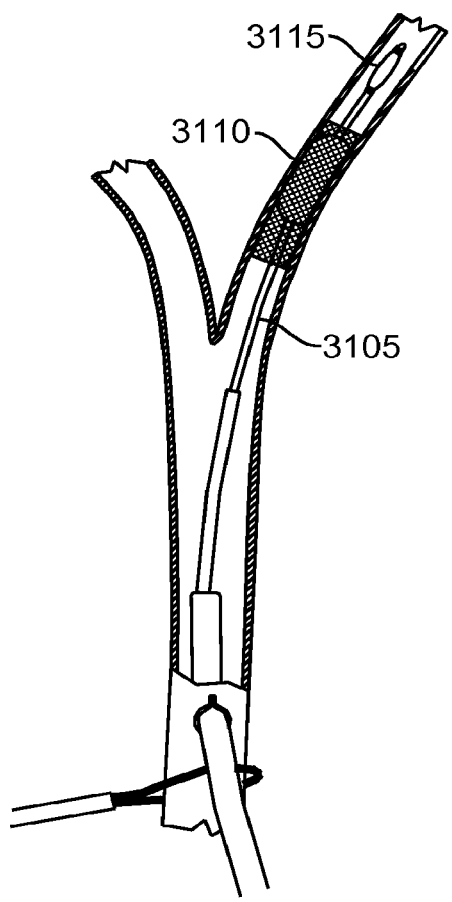
FIGS. 110A and 110B show a variation of the dual balloon catheter with flushing capabilities.
Figure 110B:
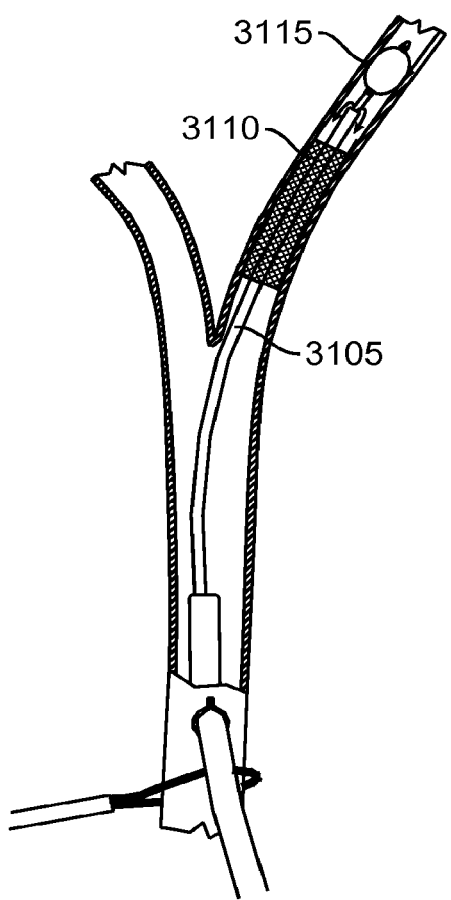

FIGS. 110A and 110B show a variation of the dual balloon catheter 3105 wherein the catheter includes a flush lumen that communicates with one or more flush holes positioned between the dilation balloon 3110 and the occlusion balloon 3115. This permits flushing of the stented area while the occlusion balloon 3115 occludes the distal ICA but the proximal dilatation balloon 3110 is deflated. The flush lumen can be a separate lumen in the catheter shaft, which terminates proximal to the distal occlusion balloon. The catheter shaft can have side holes to allow flush solution to exit the catheter. In the embodiment where the occlusion balloon is on separate shaft or guide wire in the central lumen, this flush lumen is the annular space between the occlusion balloon shaft or wire and the central lumen. Alternately, a separate micro-catheter can be positioned proximal to the distal occlusion balloon 3115 and can be used to flush the stented area. If a separate inflatable guide wire with inflatable balloon is used, the annular space between the two balloons can be used for flushing.

In a variation of the dual balloon catheter, a catheter 3305 has a single balloon 3310 with a dual diameter, as shown in FIGS. 111A-111C. The single balloon 3310 can be configured to inflate to two different diameters based on the inflation pressure of the balloon. A distal portion 3315 of the balloon 3310 can inflate to a larger diameter than a proximal portion 3320 of the balloon 3310, as shown in FIG. 111A. At a low inflation pressure, the distal portion 3315 can be inflated to a larger diameter and occlude the artery, as shown in FIG. 111B. At higher inflation pressures, the proximal portion 3320 can inflate to a diameter the same as or greater than the distal portion 3315, as shown in FIG. 111C. In this manner, the proximal portion 3320 can dilate the "waist" of the stented segment. The balloon 3310 can be designed of layered low and high durometer material, or reinforced material in which the reinforcement provides a limit to the expansion dimensions, such that the distal occlusive segment will not over inflate during the higher pressure inflation.

Interventional Catheter with Occlusion Balloon and Flush Capabilities

Figure 112:
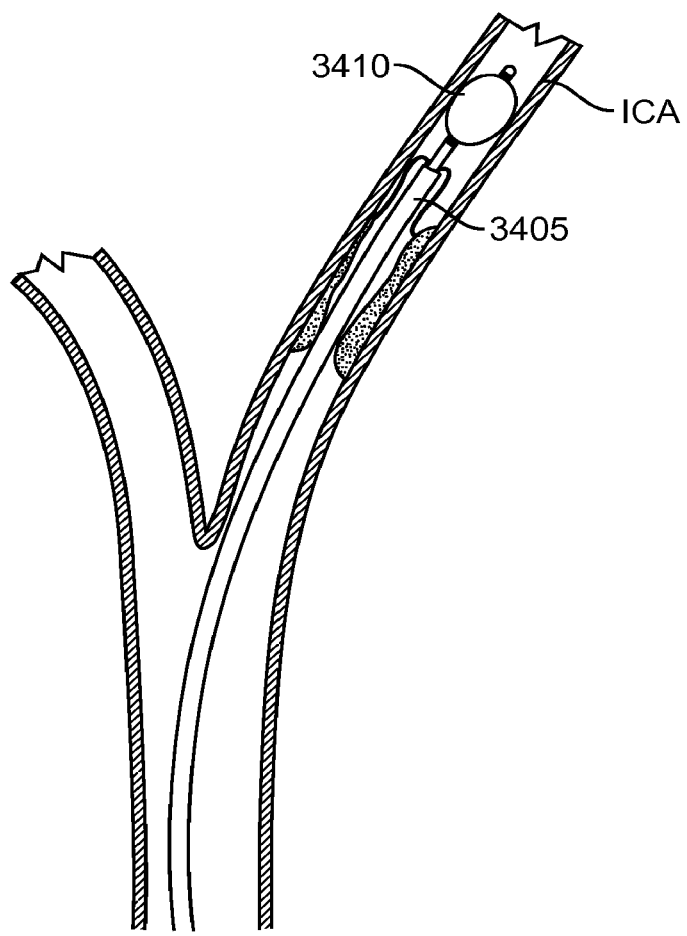
FIG. 112 shows an occlusion balloon catheter that has a distal occlusion balloon and flushing capabilities.

In another embodiment shown in FIG. 112, an occlusion balloon catheter 3405 can have a distal occlusion balloon 3410 and an internal flush lumen through which a flush solution can be passed. The flush lumen can communicate with side holes 3415 be positioned proximal of the occlusion balloon 3410. In use in a carotid artery setting, the balloon catheter 3405 can be positioned in the internal carotid artery such that the occlusion balloon 3410 can be inflated to block the internal carotid artery. The flush lumen can be used to flush or aspirate the internal carotid artery proximal to the occlusion balloon 3410.

In an embodiment, the catheter 3405 can be exchanged over a guide wire under retrograde flow so that the balloon 3410 can be at a position distal to the stented segment. This allows the catheter 3405 to flush the internal carotid artery stented segment during a period when the common carotid artery occlusion is opened to forward flush arterial flow from the internal carotid artery and common carotid artery into the external carotid artery. The flush lumen can be either integral to the occlusion balloon catheter 3410, via a separate elongate member having a lumen, coaxial to the catheter 3410 via a separate tubing over the outside of the catheter shaft, or via a separate single lumen infusion catheter. In the case of a separate lumen or a coaxial outer member, the flush solution can exit from side holes in the shaft of the catheter.

As described in previous embodiments, the side holes used for flushing can be configured to flush in a variety of directions, to improve the efficiency of the flush solution to clear embolic debris which can be trapped, or loosely attached, in the stented region. In this regard, the side holes can point in a desired direction or can have a shape or size that facilitates directional flow of the flushing solution.

Stent Delivery Catheter with Occlusion Balloon

There are now described stent delivery catheters that are combined with an occlusion balloon. Such systems can be used in a carotid artery retrograde flow system where the retrograde flow rate is insufficient to reverse the flow in the internal carotid artery when the stent delivery catheter is in a delivery sheath. The combined stent delivery catheter and occlusion balloon can provide protection against embolic release distal of the stent delivery location. The combined stent delivery catheter and occlusion balloon can also be used with an embolic protection system which uses occlusion distal of the stenosis.

In an embodiment, the occlusion balloon can be an inflatable guide wire with a removable inflation device. The stent delivery catheter can be backloaded onto the inflatable guide wire once the balloon is inflated. That is, the distal end of the stent delivery catheter can be loaded over the proximal end of the guidewire. The inflated balloon occludes the internal carotid artery during positioning of the stent delivery catheter and deployment of the stent. The inflatable guide wire can also be pre-loaded onto the stent delivery catheter such that the stent delivery catheter cannot be removed from the stent delivery catheter. The inflatable guide wire can be longer than the stent delivery catheter by a fixed amount (such as around 5-10 cm). Once inflatable guide wire is positioned in the artery and inflated, the stent delivery catheter can be moved into place and the stent deployed. The occlusion balloon can remain inflated during any number of steps which are perceived as higher risk for embolic generation, for example the removal of the stent delivery catheter, flushing, and opening the CCA to arterial flow into the ECA.

In another embodiment, the stent delivery catheter can have an internal lumen that receives a low profile balloon catheter. In a first variation of this embodiment, the low profile balloon can be a fixed or movable wire catheter. In another embodiment, the low profile balloon can be an over the wire or rapid exchange catheter that is placed over a standard PTCA catheter.

In yet another embodiment, an occlusion balloon can be built into a central lumen of a stent delivery catheter. The balloon can be used for vessel occlusion and positioned a predetermined distance from the stent. This embodiment can have a low profile but does not permit independent movement between the stent delivery catheter and the occlusion balloon.

Stent Delivery Catheter with Flush or Aspiration Lumen

There are now described stent delivery catheters that are combined with a capability for aspiration at the distal end. Such systems can be used to replace or augment reverse flow embolic protection systems by providing a port for aspiration at the target lesion site. The combined stent delivery and aspiration catheter can provide improved protection against embolic release at the site of the stent delivery location. The catheter can include an aspiration lumen that can be connected at a proximal end with a lower pressure receptacle or the venous side of a flow reversal circuit. Alternately, because the aspiration lumen is a relatively high flow resistance lumen, the lumen can be connected to an active aspiration source such as a syringe, suction pump, or the like.

Figures 113, 114:
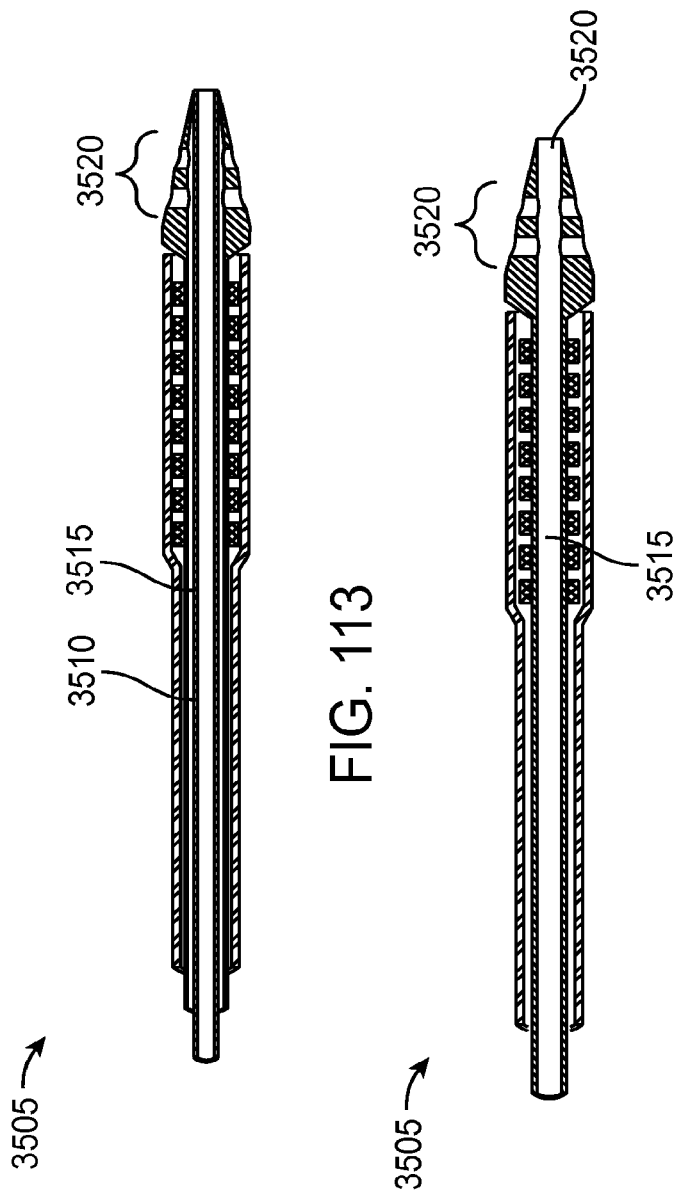
FIG. 113 shows a stent delivery catheter that has an internal coaxial tubing member that terminates at a distal tapered tip, creating an annular flush lumen.
FIG. 114 shows a catheter with a guidewire lumen that doubles as a flush or aspiration lumen.

In one embodiment, shown in FIG. 113, the stent delivery catheter 3505 can have an internal coaxial tubing member 3510 that terminates at the distal tapered tip. The annular space between the tubing 3510 and the central guidewire lumen can include an aspiration lumen 3515. Side holes 3520 at the distal tip can create entry ports for aspiration of blood and potential capture of embolic debris. The proximal end of the aspiration lumen 3515 can be a connection to a passive or active aspiration source.

In another embodiment as shown in FIG. 114, the guidewire lumen 3515 can double as the aspiration lumen. The distal end of the guidewire lumen 3515 can be an entry port 3525 into the aspiration lumen. Side holes 3520 in the tapered tip can create additional entry ports for augmented aspiration. The guidewire lumen 3515 can be connected to an aspiration port at the proximal end. Typically, the guidewire can enter the stent delivery catheter through a hemostasis valve; the aspiration source can be connected to a Y-arm in fluid communication with this hemostasis valve.

In an alternate method of use, the aspiration lumen can be used for flushing solution. In this method of use, the flow solution can increase flow past the lesion in procedures where the stent is being deployed in conjunction with reverse flow embolic protection, to improve the efficiency of the reverse flow hemodynamics to clear embolic debris which can be trapped, or loosely attached, in the stented region.

Low Profile Stent Delivery Catheter

In cases where the arterial access sheath is used as part of a reverse flow embolic protection system, it can be desirable to minimize the level of flow resistance caused by the presence of the stent delivery catheter in the arterial access sheath. In reverse flow protocols, where the stent delivery catheter adds resistance to reverse flow by taking up cross sectional area in the arterial access sheath, one way of minimizing the flow resistance is to reduce the diameter of the stent delivery catheter. This can be achieved by employing a retractable or removable stent constraint sleeve (or outer sheath) on the stent delivery catheter. In an embodiment, the stent constraint sleeve can be retracted sufficient to be removed entirely from the remainder of the catheter. Removal of the outer stent constraint sleeve during stent delivery from the arterial access sheath can reduce the flow restriction and thus increase the level of reverse flow, which in turn can improve the capture of embolic debris. In the case of a transfemoral approach in the reverse flow procedure, the outer sleeve can be nearly or completely removed from the catheter in a peel-away manner. To facilitate this, the outer stent constraint sleeve can have a slit along its length or is split along its length. Alternately, the outer stent constraint sleeve can also be a tear-away sleeve which is pre-weakened along the length and is split on removal, or a sleeve which is slit with a blade on removal.

In the case of a transcervical access for a reverse flow procedure in which only the distal-most portion of the stent delivery catheter is in the arterial access sheath 605, the outer sleeve retraction length does not need to be as great as in the transfemoral approach. In this case, the outer sleeve can retract from this distal portion of the stent delivery catheter, for example about 25 cm, in order to be removed from the reverse flow path. Current stent delivery systems retract the outer sleeve enough to release the stent, a little more than the length of the stent (typically less than 5 cm). In an embodiment, the disclosed stent delivery system is modified to allow a longer retraction length, for example 25 cm, to ensure that the sleeve can be removed from the reverse flow path. In an embodiment, this is facilitated by a slit or split sheath on the proximal portion of the sheath.

Figure 115:
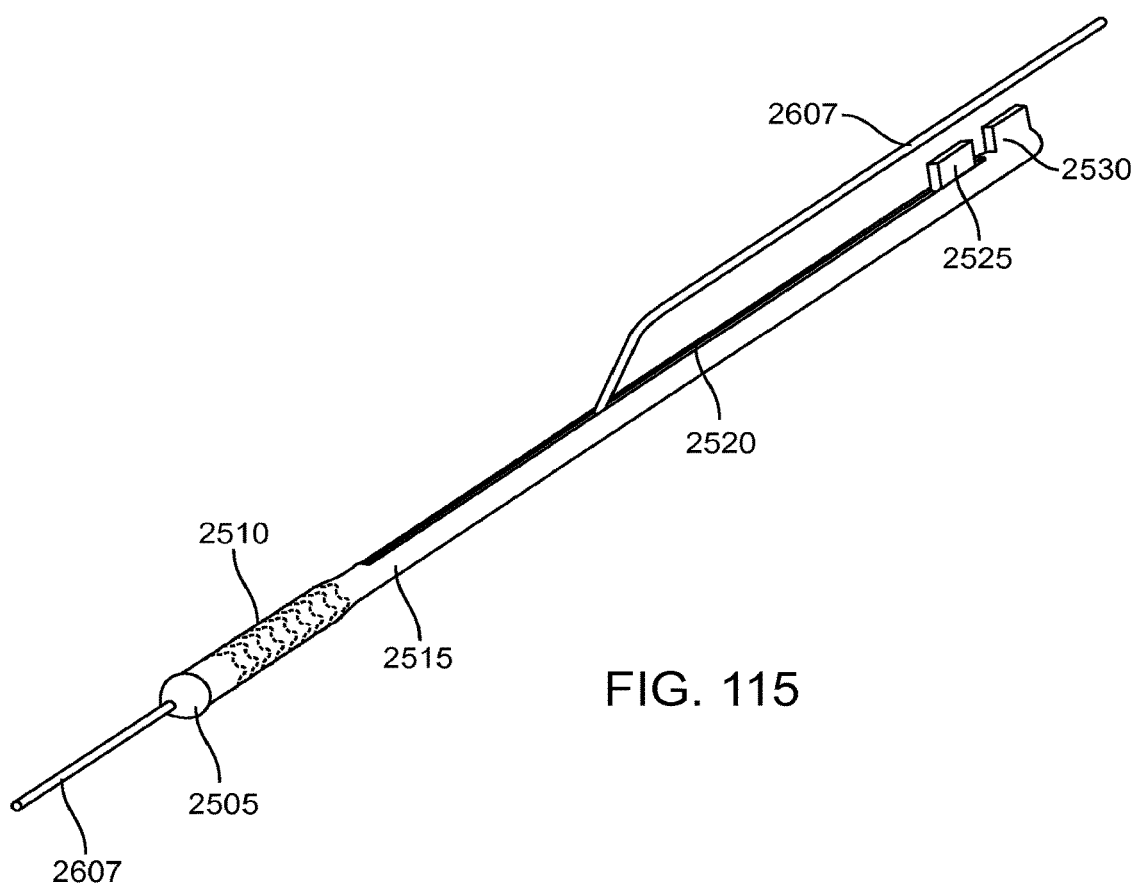
Figure 116:
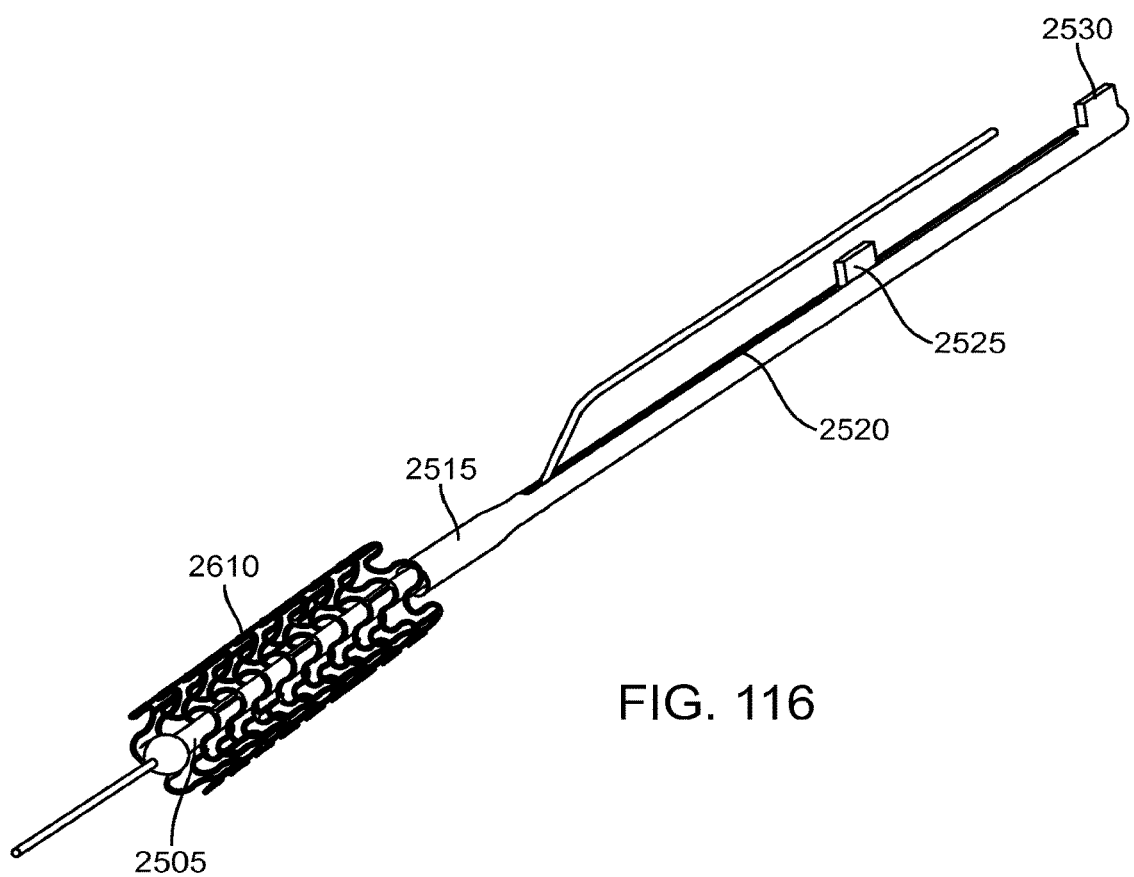
Figure 117:
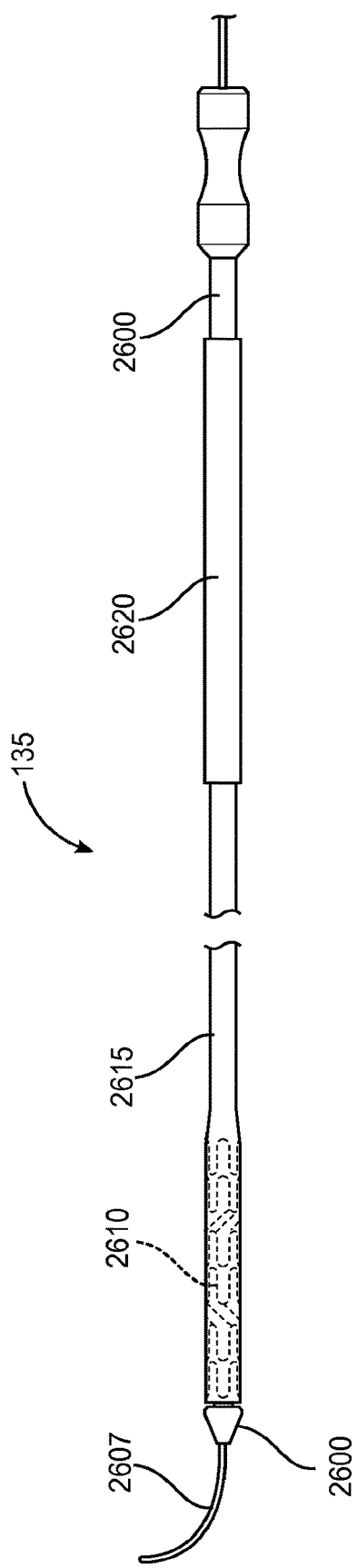

In an embodiment, as shown in FIGS. 115-116, the stent delivery system includes a shaft configuration that allows a much simpler long pull-back of the outer stent constraint sleeve. In typical stent delivery systems, the proximal ends of the inner catheter member and the outer stent constraint sleeve can be secured to two proximal terminating elements, with the outer stent constraint sleeve terminating element spaced forward of (distal to) the inner member terminating element such that a gap is located between the two proximal terminating elements. To deploy the stent, the two terminating elements can be moved toward one another to movably retract the outer stent constraint sleeve in a proximal direction. This configuration can limit the length which the outer sleeve can be pulled back to the length of the initial gap between the two terminating elements. In embodiments described below, the outer stent constraint sleeve can be configured such that the inner catheter member can be grasped at a location distal to the outer stent constraint sleeve.

As shown in FIGS. 115 and 116, the stent delivery system 135 can include an elongated inner member 2505 on which the stent 2610 is mounted. An outer stent constraint sleeve 2515 is slidably positioned over the inner member 2505 and can be positioned over the stent 2610 to retain the stent 2610 in an unexpanded state. The stent 2610 is shown in phantom lines in FIG. 115 to indicate that the stent is positioned beneath the outer stent constraint sleeve 2515. The outer stent constraint sleeve 2515 can include a slit 2520 that extends at least partially along the length of the outer constraint sleeve 2515. The inner member 2505 can include a protrusion or coupling member, such as a tab 2525 that extends outward through the slit 2520. The tab 2525 can be grasped to fix the position of the inner member 2505 while sliding the outer stent constraint sleeve 2515 relative to the inner member 2505. In a variation, the outer stent constraint sleeve 2515 can include a protrusion such as a tab 2530 positioned proximal to the proximal end of the end of the inner member 2505. The tab 2530 of the stent constraint sleeve 2515 can be located behind (proximal to) the tab 2525 of the inner member. In another variation, the two tabs 2525 and 2530 can be positioned side-by-side rather than in series along the length of the catheter. To deploy the stent, the tabs 2525 and 2530 can be moved apart from one another such that the stent constraint sleeve 2515 slides relative to the inner member 2505 to expose the stent 2610 and allow the stent 2610 to expand, as shown in FIG. 116. Movement of the stent constraint sleeve 2515 relative to the inner member 2505 is not limited by the initial distance between the tabs 2525 and 2530 as in prior systems. Pull-back of the stent constraint sleeve 2515 can thus be longer and faster than that in prior stent delivery systems.

In another embodiment shown in FIGS. 117-121, the stent delivery system 135 can include an inner member 2600 on which the stent 2610 is mounted on a distal region of the inner member 2600. A guidewire 2607 can extend through the inner member 2600. The outer stent constraint sleeve 2615 can be initially positioned over the inner member 2600 such that the outer stent constraint sleeve 2615 covers the stent 2610 and restrains the stent 2610 in an unexpanded state. The inner member 2600 can include a tube member 2620 that is positioned outside of the outer stent constraint sleeve 2615. The tube member 2620 can connect to the inner member 2600 via one or more connecting web elements 2625 that extend between the inner member 2600 and the tube member 2620, as shown in the partial cross-section view of FIGS. 118A-118B. The cross-sectional view of FIG. 118C shows that the web element 2625 is positioned through a slot or slots 2621 in the outer stent constraint sleeve 2615. The web element 2625 extends through the slot 2621 from the inner member 2600 to the tube member 2620.

Figure 119:
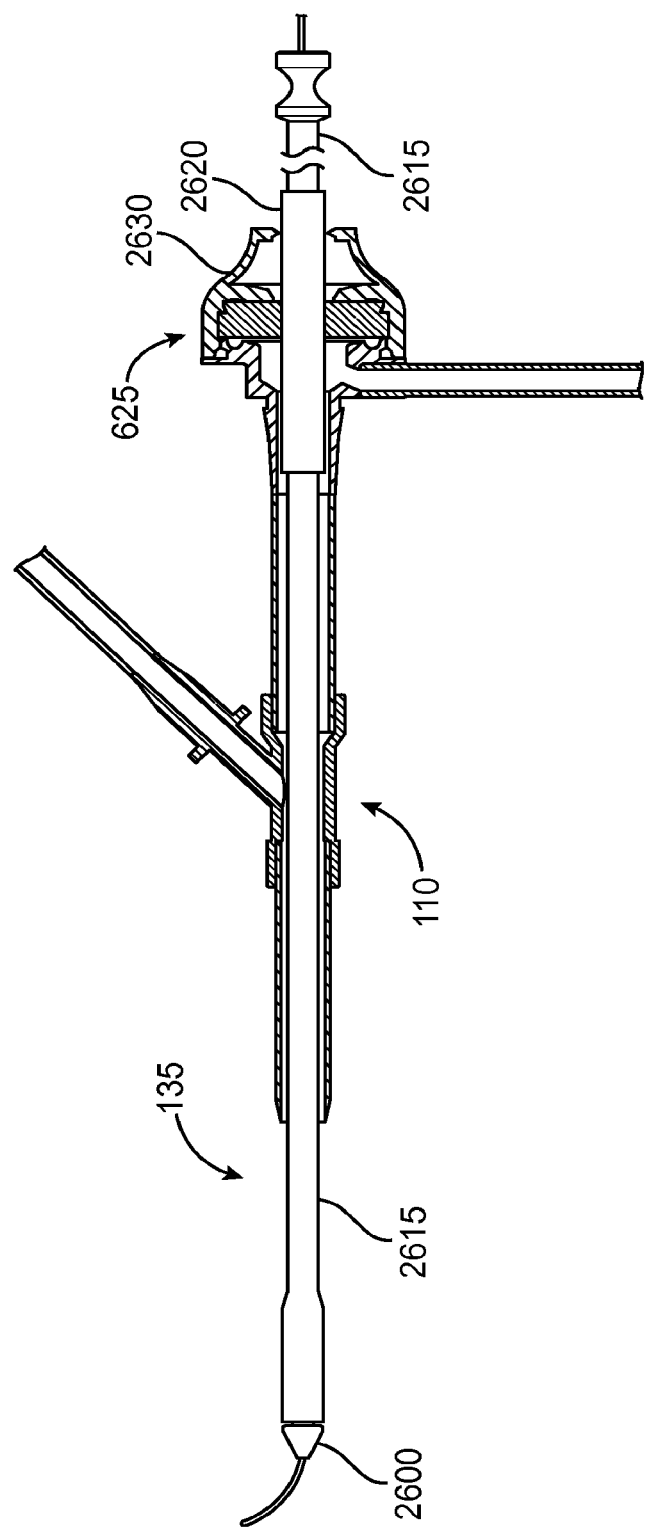

FIG. 119 shows the stent delivery system 135 being delivered through an arterial access device 110. The arterial access device 110 is shown in cross-section to provide a view of the stent delivery system. The tube member 2620 can be positioned in a hemostasis valve 625 at a proximal region of the arterial access device 110 during positioning of the stent delivery system 135. A securement member 2630 attached to the hemostasis valve 625 can be actuated to secure the tube member 2620 to the hemostasis valve 625 when the tube member portion of the stent delivery system is traversing the hemostasis valve 625 In this manner, the securement member 2630 also grasps and secures the inner member 2600 (which is attached to the tube member 2620) to the hemostasis valve 625. The securement members 2630 can grasp the tube member 2620 in a pinching configuration such that the user can quickly manually secure the stent delivery system 135 to the hemostasis valve 625, or a snap down or other locking configuration which would not require manual holding to keep the stent delivery system 135 secured to the hemostasis valve 625.

Figure 120:
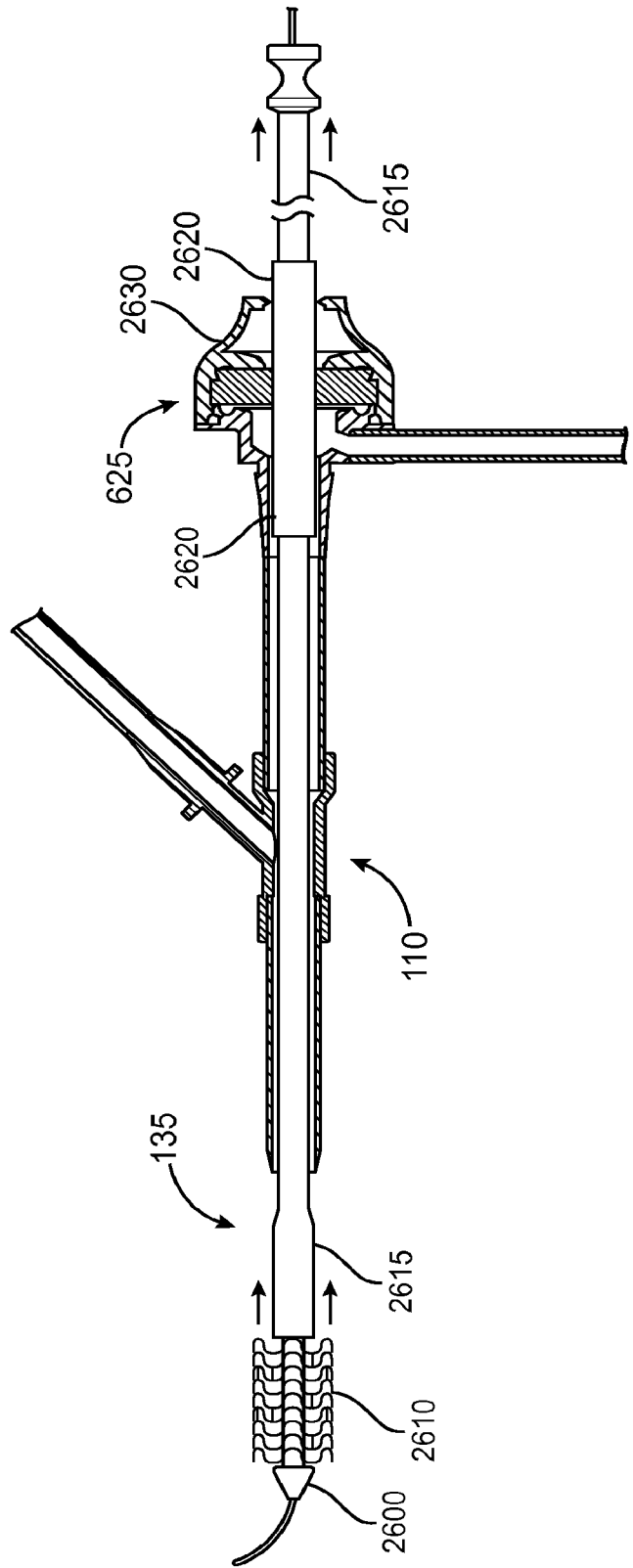
Figure 121:
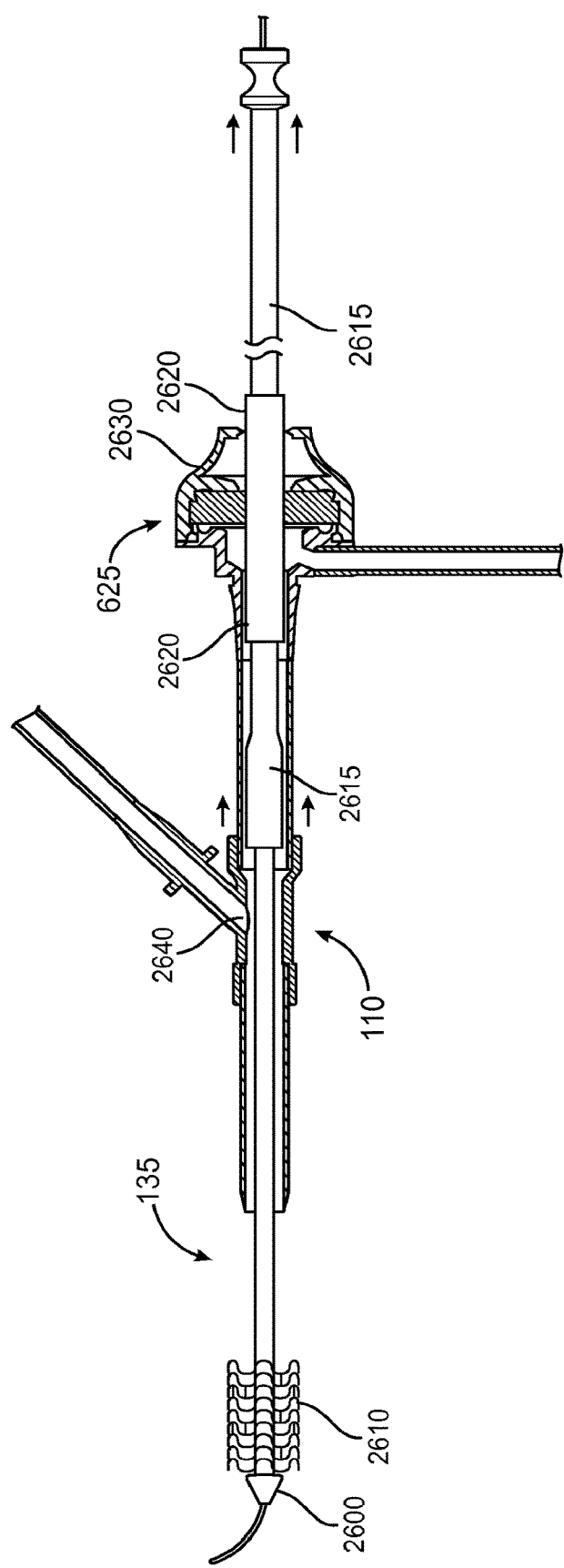

When the stent is located at its target position in the vasculature, the securement member 2630 can be preferably used to secure the inner member 2600 to the hemostasis valve 625. The proximal end of the outer stent constraint sleeve 2615 can then be pulled back in a proximal direction (with the inner member 2600 fixed relative to the hemostasis valve 625) such that the outer stent constraint sleeve 2615 no longer covers the stent 2610, as shown in FIG. 120, such that the stent is free to expand and deploy in the blood vessel. If repositioning of the stent delivery system is desired during stent deployment, the securement member 2630 can release the tube member 2620 so the user may move the stent delivery system, and then re-secure as needed to complete stent deployment. As shown in FIG. 121, the outer stent constraint sleeve 2615 can be desirably pulled back a distance sufficient so that the outer stent constraint sleeve 2615 does not block the entryway 2640 to the reverse flow path. The catheter shaft construction for the configuration of FIGS. 117-121 can be desirably configured to maintain its function and performance throughout all stages of stent positioning and deployment. Thus, the proximal region of the outer stent constraint sleeve 2615, which can contain one or more slots 2621 for the web elements 2625, can be constructed of relatively stiff material, for example stainless steel or nitinol hypotube or stiff plastic extrusion such as PEEK or PET. It can be also beneficial to construct the proximal region of the outer stent constraint sleeve 2615 such that it is stiff in the radial direction but can maintain flexibility. This can be done through catheter shaft constructions such as a hypotube with a laser-cut pattern. The inner member 2600 and tube member 2620 can also be flexible enough to be easily positioned in the vasculature, but maintain structural integrity. The inner member 2600 can be configured to slide easily with respect to the outer stent constraint sleeve 2615. Thus, it can be constructed from low friction material such as PTFE, FEP, or PE. Alternately, it can be constructed using multiple materials, for example nylon, Pebax or PE for the inner member, with a low friction material such as PTFE, FEP, or PE or a thin-walled stiffer material such as stainless steel, nitinol, polyimide, PET or PEEK for the outer tube, or alternately incorporate lubricating coatings such as Teflon, Parylene, or the like For procedures where the arterial access sheath is stepped in size, for example the distal end which enters the artery is a smaller diameter than the remaining proximal portion of the sheath, the sleeve retraction only needs to be long enough to pull the sleeve back into the proximal section of the arterial access sheath with the larger diameter.

It can be important during initial retraction of the sleeve to preserve precise and/or reversible distal sheath retraction during the actual stent delivery portion of the procedure. After the stent is deployed, however, the retraction of the sleeve can be optimized for rapid removal. For example, a distal portion (such as a 4 cm distal portion) of the sleeve can be adapted to be manually retracted by the operator. This permits precise placement of the stent as the sleeve can be moved back and forth during the stent placement process. The remainder of the sheath retraction can be implemented automatically, such as using a spring-loaded retraction system with a trigger or other control mechanism on the proximal end of the stent delivery catheter. Actuation of the control mechanism causes automatic and rapid retraction of the sleeve.

In another embodiment, the stent constraint sleeve is adapted to be able to shrink in size. For example, after the sleeve is pulled back from stent, the sleeve can shrink down from a larger size that fits over the stent to a smaller size that fits over the stent delivery shaft. This can be accomplished by constructing the stent constraint sleeve out of a compressible spring construction such as a braid, or an elastomeric material.

In yet another embodiment, the stent constraint is not a fully circumferential sleeve, but is something of lower profile, such as a rip cord tightly wound around a stent, a partial sleeve with at least one lace-up thread that pulls out to open up sleeve, wire(s) intertwined with a stent that are pulled for release, or wire(s) engaged with shaft under a stent which is pulled to release the stent. The stent can also be constrained using wires which can be released with an electric current or magnetic constraint which can be released by intravascular or external magnet. In another variation, the distal portion of constraint sleeve is a tube but proximal the portion is a rod or rods which can pull back the distal portion of the sleeve.

Balloon Deflation Sensor

In any of the embodiments with an inflation balloon, a sensor device can be coupled to the balloon inflation device wherein the sensor device can sense the moment of balloon deflation and output a signal to the controller 1112 of the reverse flow system 100. The sensor can be located on the balloon inflation device of at some location between the balloon inflation device and the balloon. The signal can automatically instruct the reverse flow system to switch to a higher level of reverse flow, either by reducing the flow restriction, switching to an active flow system, or switching to an aspiration source such as a pre-set VACULOK syringe, VACUTAINER, suction system, or the like. This signal can be electronic, such as an electromechanical vacuum sensor, or hydraulic, using the pressure drop to activate a pressure valve or similar hydraulically-controlled flow control component.

DETAILED DESCRIPTION OF SHEATH HEMOSTASIS VALVES AND ASSOCIATED DEVICES

Various embodiments of hemostasis valves are now described. The hemostasis valves are suited for use with arterial access devices or sheaths that are subject to negative pressure conditions, for example under a period of active aspiration. In conventional sheath hemostasis valves, a valve seal prevents a liquid such as blood from exiting the arterial access sheath, either when there are no interventional devices inserted into the sheath or when there are devices such as guide wires and catheters inserted through the valve seal into the sheath. In addition, the hemostasis valve limits or prevents air from entering the sheath if the outside, ambient pressure is higher than the pressure inside the sheath, for example during aspiration through a sheath flush or shunt connection. A conventional introducer sheath hemostasis valve includes a sealing member with a central opening for passage of one or more devices into the sheath. The sealing member is usually in compression such that, with or without devices in the central opening, the sealing member exerts a compressive force that closes the central opening against fluid (such as blood) leaking out, or fluid (such as air) entering into the valve. However, such sealing members are often not perfect seals, especially when there are one or more devices in the central opening. Thus, with these types of valves there is a risk of air ingress into the sheath through the central opening during aspiration of the sheath. This air is then at risk for being introduced into the arteries and downstream tissue beds during forward flushing or flow through the arterial sheath, leading to embolic complications such as tissue ischemia.

In an embodiment shown in FIGS. 122A-122C, a sheath hemostasis valve assembly is configured with two or more valve sealing members. The valve sealing members are positioned inside the valve assembly so as to maintain a fluid or gel layer (collectively referred to as a "fluid layer") on one side, such as the proximal side, of a distal-most valve sealing member. The fluid or gel layer prevents or substantially inhibits a fluid (such as air) from being aspirated into the sheath when the sheath is subject to negative pressure. In an embodiment, the valve sealing members are configured to prevent any fluid (gas or liquid) from being aspirated into the sheath when the sheath is subject to negative pressure. In an embodiment, the valve sealing members are particularly configured to prevent any a gaseous fluid from being aspirated into the sheath when the sheath is subject to negative pressure.

A liquid or gel by nature is simpler to seal against than a gaseous fluid such as air; thus the fluid layer creates a "lock" against air ingress into the sheath. Even if there were a small amount of the fluid sucked into the valve, the fluid layer would prevent air ingress into the sheath. FIG. 122A shows an arterial access device 4000. The arterial access device 4000 may be configured to include any of the features described in connection with any of the embodiments of arterial access devices described herein. In the embodiment of FIG. 122A, the arterial access device 4000 includes a distal sheath 4005, a distal sheath connector 4010, a proximal extension tube 4015, and a hemostasis valve assembly 4020. Aspiration may be performed through the arterial access device 4000 via a side port 4025 that communicates with an internal lumen of the arterial access device 4000.

FIG. 122B shows an enlarged, detailed view of the valve assembly 4020, which includes of a valve seat 4030, a valve housing 4035, at least two valve sealing member members 4040 and 4045, and a valve cap 4050. The valve assembly 4020 is configured such that there is a space 4055 between the two sealing members 4040 and 4045. The space 4055 may be filled with fluid during sheath preparation prior to use in the interventional procedure. During the interventional procedure, devices are introduced through both valve sealing members 4040 and 4045, across the space 4055, and into the internal lumen of the arterial access device 4000. During periods of aspiration using the arterial access device 4000, little or no liquid and no air may enter the sheath as long as the space 4055 contains fluid as the space 4055 acts as a seal or barrier to the entry of liquid or air.

As mentioned, the space 4055 may be filled with fluid during sheath preparation prior to use of the arterial access device in the interventional procedure. To fill the space 4055, a flush port may be provided between the two sealing members, such as shown in the exemplary embodiment of FIG. 122C. The flush port 4060 has a lumen that communicates with the space 4055 and provides a means of inserting fluid into the space 4055. In an alternate embodiment, the user may use a blunt end needle or a sheath dilator (such as the dilator 645 described above) attached to a syringe, with the tip of the needle or dilator positioned between the two sealing members 4040 and 4045, to fill the space 4055 with fluid. Alternately, the sheath dilator may include one or more side holes positioned at the location of the space 4055 when the dilator is assembled with the sheath. During preparation, the user covers the dilator tip with a finger and injects fluid through the dilator hub. The fluid passes through the dilator and into the space 4055 via the side hole to fill the space 4055. In another embodiment, the space 4055 may be pre-filled with fluid during manufacture with a self-sealing substance such as a gel or low durometer elastomer such as silicone rubber, eliminating the need to prep the space 4055 with fluid. Alternately, the space is filled with a hydrophilic material which swells to fill the space when it encounters a water based fluid. The material would desirably be configured to allow devices to be pushed through but would seal against negative pressure.

Figure 123:
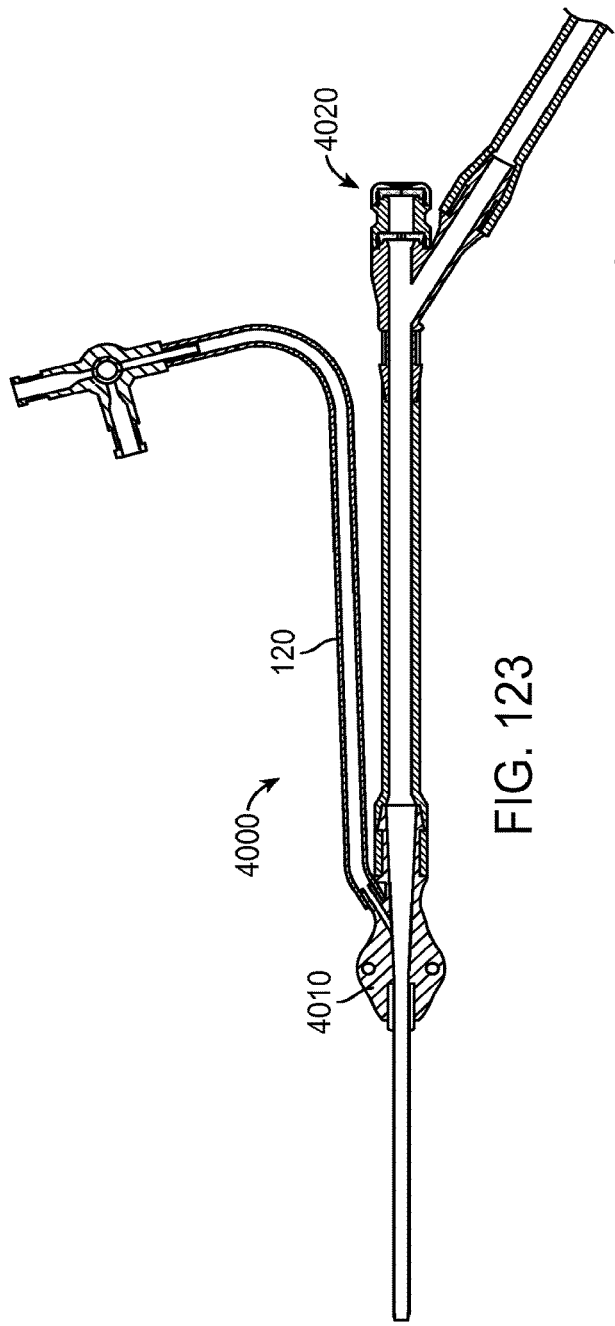
Figure 124:
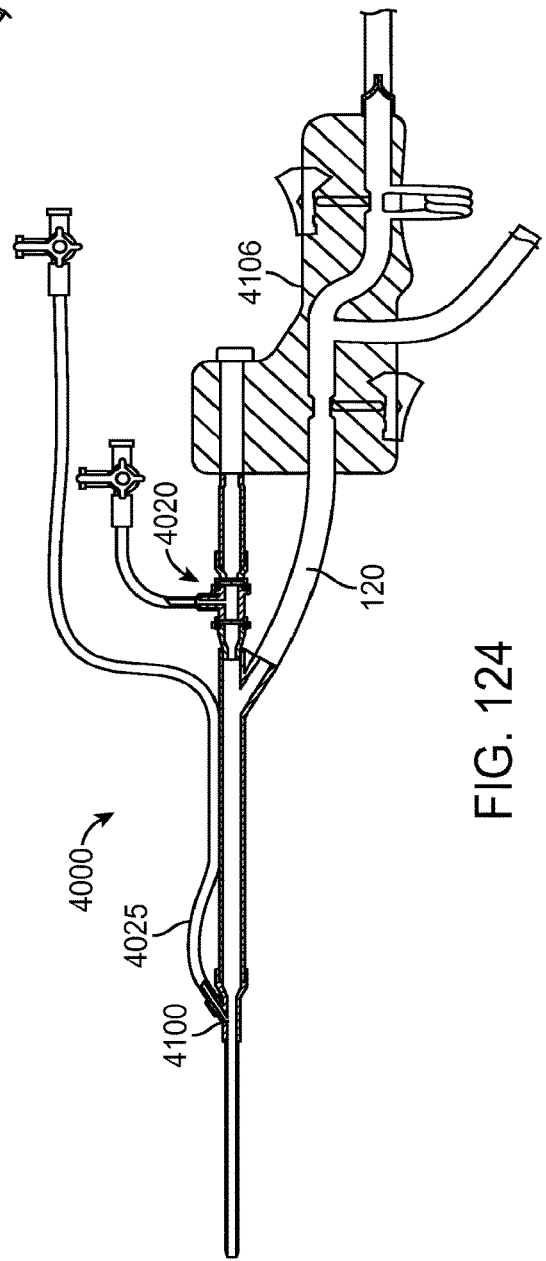

In an embodiment, the arterial access device 4000 may be used in a reverse flow circuit, such as the type described above. FIG. 123 shows an embodiment wherein the arterial access device 4000 couples to a shunt 120 via a Y-connection to the distal sheath connector 4010. Alternately, as shown in FIG. 124, the shunt 120 attaches to the proximal valve assembly 4020 of the arterial access device 4000. Aspiration of the arterial access device 4000 may be applied through the shunt 120, or through a side port 4100 to a flush line 4025. In the embodiment of FIG. 124, the side port 4100 is located on the sheath connector 4010. The side port 4100 may be located at various locations, such as at the proximal end of the arterial access device 4000 near the shunt 120. In FIG. 124, a flow controller housing 4106 is configured to contain or at least partially contain or incorporate a region of the valve assembly 4020 that includes the proximal-most seal member 4045. In the layout of FIG. 124, the flow controls for the reverse flow circuit are positioned near where devices are introduced into the arterial access device 4000 and may enable or facilitate a single person introducing catheters while maintaining control of a reverse flow circuit. The shunt 120 may also include a port for connection to and aspiration device. It may also include a one-way valve, to prevent fluid flowing from the venous side during aspiration.

Figure 125:
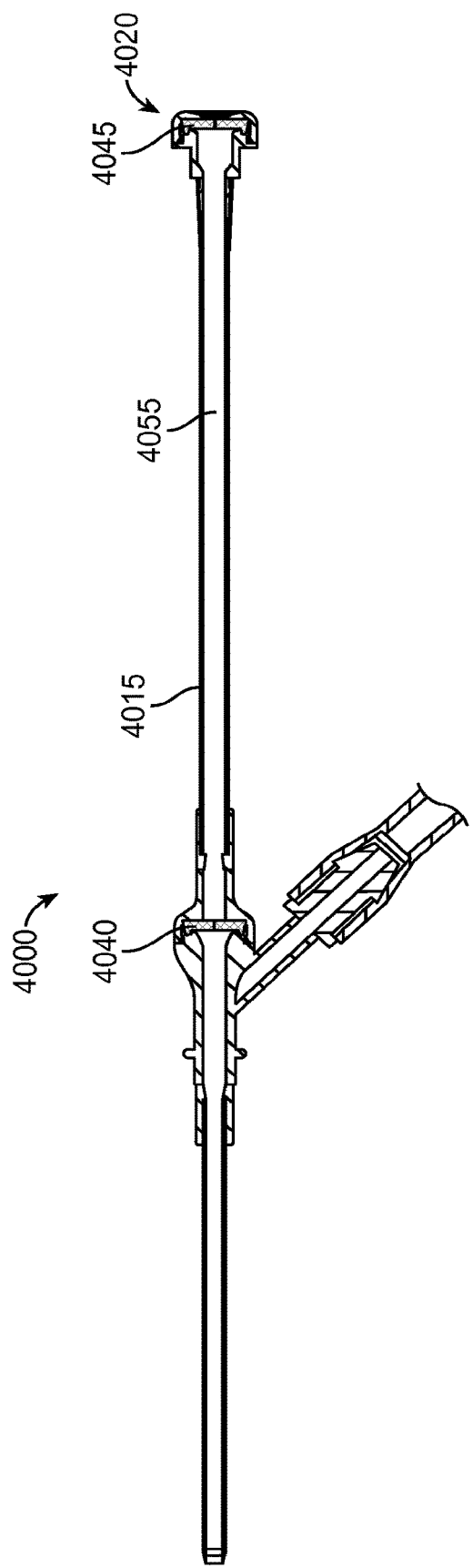

The sealing members 4040 and 4045 may be spaced close together (such as on the order of 0.25 to 1.0 inches apart), as shown in FIG. 122-124, or spaced further apart (such as on the order of 2-5 inches apart) to increase the volume of space 4055. Additional sealing members may be included along the length of the arterial access device 4000 as required or desired to provide the desired level of protection against air ingress into the arterial access device. For example one sealing member 4040 may be placed at the level of the sheath connector 4010, and the other sealing member 4045 at the proximal end of the proximal extension tube 4015, as shown in FIG. 125. In this manner, the volume of space 4055 may be relatively large, and enable a prolonged period for aspiration without risk of air ingress into the sheath.

In the embodiment of FIG. 125, in which one of the sealing members is distant from the proximal end of the arterial access device 4000, a stiff introducer may be required or helpful to provide sufficient stiffness and column strength to pass guidewires and devices through both valve sealing members. In conventional practice, blunt needles are often used to introduce guide wires into sheaths and catheters, especially if the wires need to pass through proximal connectors and/or hemostasis valves. These blunt needles are used to direct the floppy and often curved tip of the guidewire quickly and easily into the sheath and to protect the tip from damage. In the embodiment of FIG. 125, the stiff introducer is desirably longer than conventional introducers so as to be sufficiently long to pass through both of the spaced-apart valve sealing members 4040 and 4045. If the distal sealing member 4040 requires additional columnar support to pass a larger profile catheter, a support member may also be used to act as an introducer to pass the catheter through the sealing member, especially if the catheter has a larger distal profile such as many self-expanding stent delivery systems.

Figure 126A:
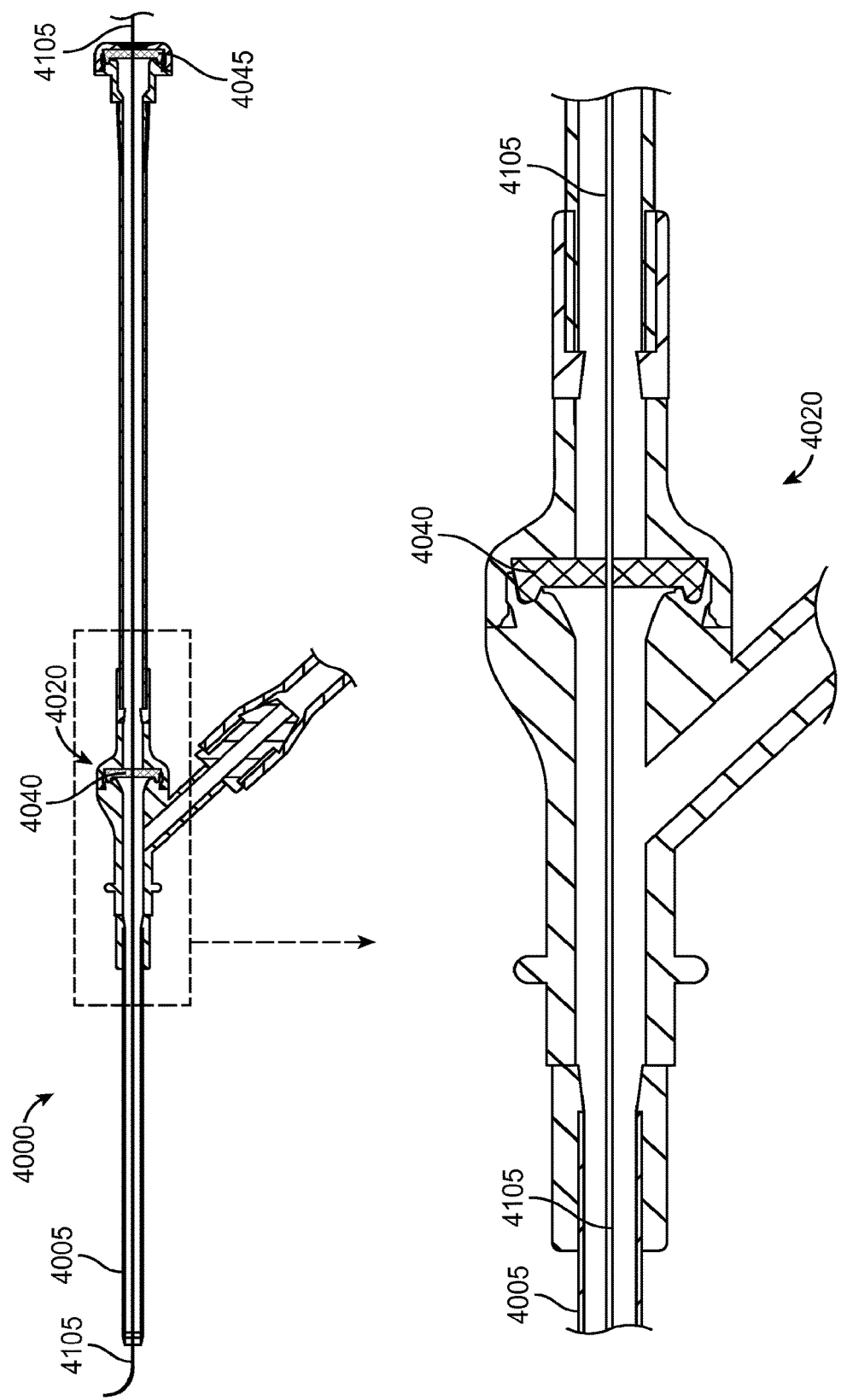
Figure 126B:
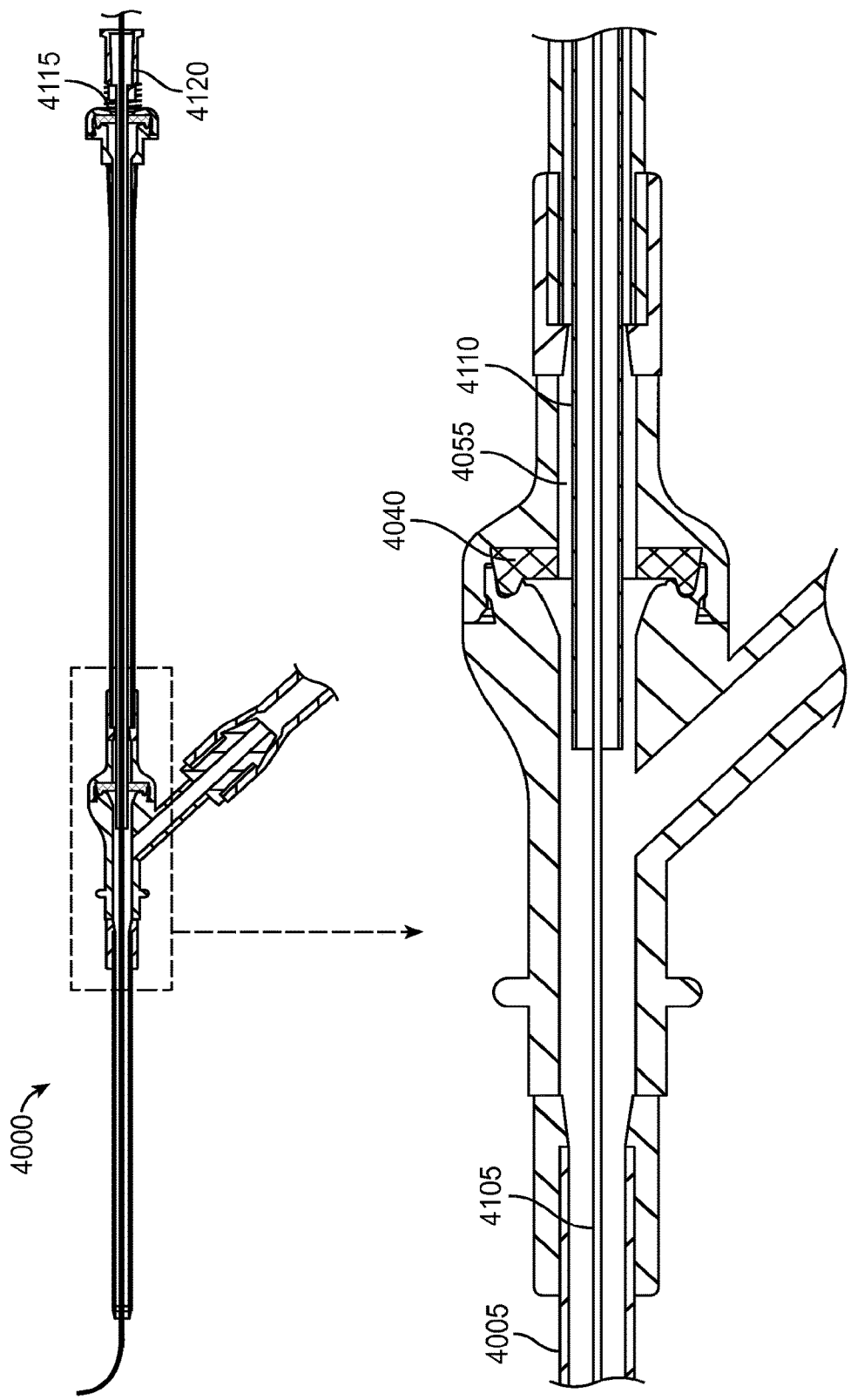
Figure 126C:
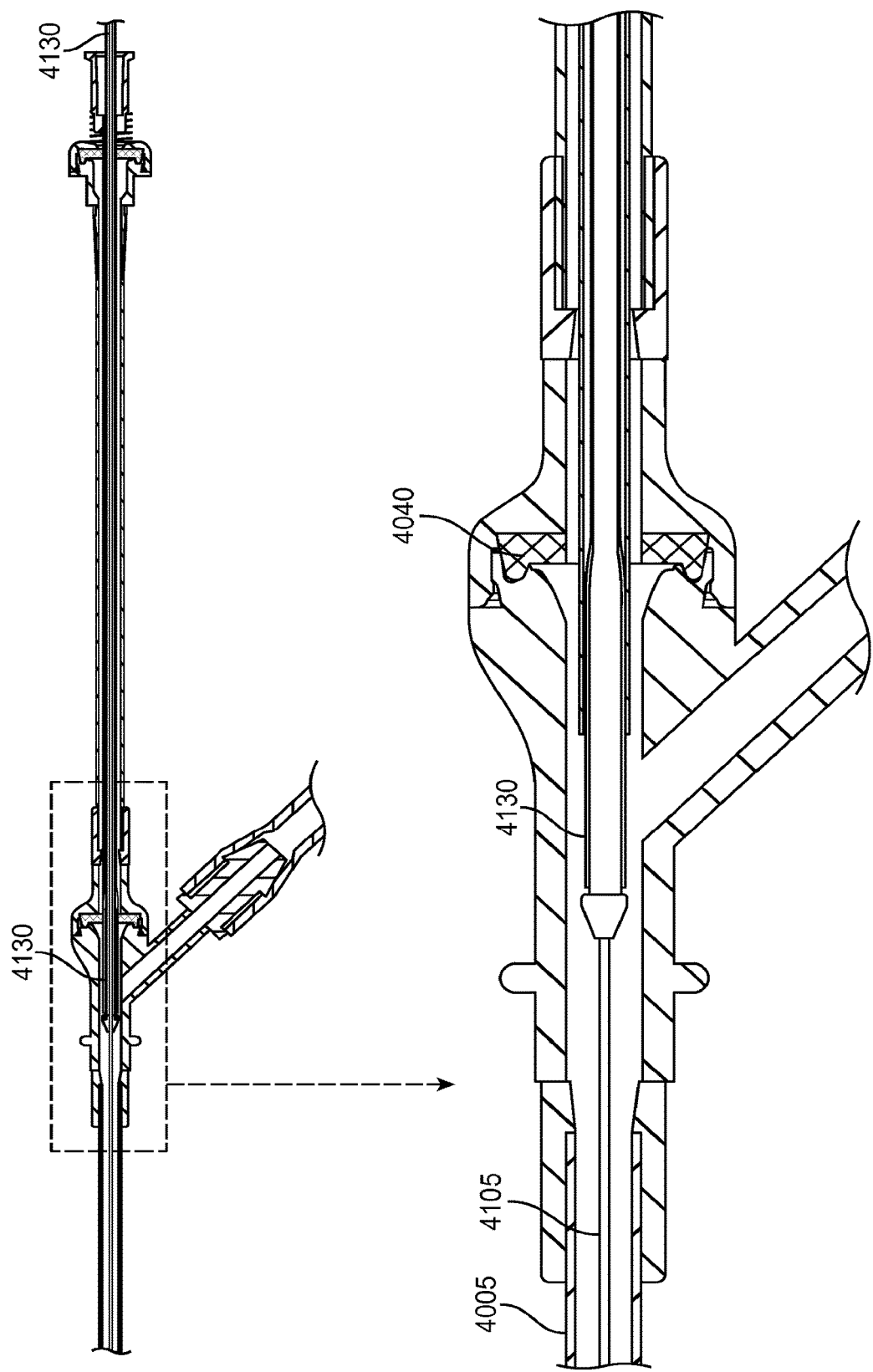

FIGS. 126A-126C show an embodiment wherein a catheter is introduced over a guidewire into arterial access device 4000 using a catheter introducer. As shown in FIG. 126A (which shows the arterial access device 4000 as well as an enlarged view of the valve assembly 4020), a guidewire 4105 is first placed though both valves 4040 and 4045 of an arterial access device 4000 using a guidewire introducer (not shown). In FIG. 126B, a catheter introducer 4110 is inserted over the guidewire 4105 through both valve members of the arterial access device 4000. The introducer 4110 optionally has a spring 4115 and a hub 4120. The length of the introducer 4110 is such that the distal-most tip of the introducer can cross both valves 4040 and 4045 when the spring 4115 is compressed, but the distal tip sits proximal to the distal sealing member 4040 when the spring 4115 is in the resting state. That is, the tip of the introducer 4110 is positioned in the space 4055. This configuration minimizes the possibility of leakage through the introducer 4110 if the introducer 4110 is inadvertently left positioned across both valves. In FIG. 126C, the catheter 4130 is introduced over the guidewire 4105 and through the introducer 4110 into the distal sheath 4005 of the arterial access device 4000. Once the catheter 4130 has passed both sealing members 4040 and 4045, the introducer 4110 may be pulled back and partially or completely removed from the arterial access device.

Alternately, the support element may be a component of the catheter system, and may comprise, for example, a slideable tube located over some or the entire distal portion of the catheter. As shown in FIG. 127, a portion of a stent delivery catheter 4130 is shown with a stiffening tube 4135 on the distal portion of the catheter shaft, terminating proximal to the larger diameter stent-mounted portion 4130a of the catheter 4130. Once the catheter with the tube crosses both sealing members 4040 and 4045 of an arterial access device 4000, the tube 4135 can be pulled back, partially or completely out of the arterial access device 4000. In this embodiment, a push rod 4137 is attached to the proximal portion of the tube 4135, to minimize the length of the tube and therefore to facilitate removal of the tube 4135 from the arterial access device 4000 once the catheter 4130 has been introduced through the sheath into the vasculature. In another embodiment, the tube 4135 extends long enough to facilitate passage of the catheter 4130 across both sealing members 4040 and 4045. In yet another embodiment, the tube 4135 is configured as a peel away tube, so that it can easily and rapidly be removed from the catheter shaft.

FIG. 128 shows an alternate embodiment of a hemostasis valve assembly 4020 on an arterial access device 4000. This embodiment does not include a proximal-most sealing member 4045 such that the proximal end of the space 4055 is open to atmosphere. The fluid is maintained in the space 4055 through surface tension rather than through the sealing member 4045. The space 4055 is defined by a chamber located proximal to the sealing member 4040. The chamber 4055 may have an elongate geometry, reduced diameter, reduced size proximal opening, and/or a complex inner surface geometry or texture to create or facilitate a sufficient surface tension to maintain fluid in the space 4055. The valve sealing member 4040 may be positioned within the sheath connector 4010, as shown in FIG. 128. A proximal extension tube 4015 defines an elongated, internal space 4055 that can be filled with fluid prior to use of the arterial access device 4000 in the procedure. The fluid in the space 4055 prevents air from being aspirated into the arterial access device 4000 if aspiration is to occur through the flush line 4025 or flow shunt 120.

Alternately, as shown in FIG. 129A, the valve member 4040 may be located on the proximal end of the extension tube 4015 and an elongate space 4055 may be incorporated into a valve cap 4200 that couples to the valve assembly. As shown in the enlarged view of FIG. 129B (which shows the portion of the device contained in the dashed box of FIG. 129A), fluid F can be positioned proximal to the valve sealing member 4040 so as to prevent air aspiration into the distal sheath 4005 through the valve assembly 4020. The inner walls of the space 4055 formed by the valve cap 4200 may have a convoluted geometry to increase the surface tension force of fluid in the space 4055. FIG. 130A shows an exemplary cross-section of the valve cap 4200 and space 4055 with a convoluted geometry.

In another embodiment of a hemostasis valve assembly, a portion of the assembly has an adjustably-sized central passage or opening. The valve assembly is configured such that smaller diameter devices such as guide wires or dilatation balloons may pass through with little or no interference, but relatively large diameter devices such as stent delivery catheters require that the size of the central opening be increased in order to pass though the valve assembly. This configuration optimizes the sealing ability of the proximal valve sealing member for use with a range of catheter profiles. In this configuration, the larger diameter catheter may include an additional component which couples with the adjustable-sized central opening to increase the size of the central opening during introduction of the catheter through the adjustable valve assembly.

FIGS. 130B and 131 show an exemplary embodiment of an adjustable sized valve assembly 4300. FIG. 130B shows an exploded, perspective view of the proximal valve portion of valve assembly 4300 while FIG. 131 shows an assembled cross section view of the valve assembly 4300. The valve assembly 4300 includes a conical or substantially conical sealing member 4305 which is constructed from stretchable material such as silicone rubber, and a valve cap 4310. The valve cap 4310 has a slotted conical or substantially conical central portion that is sized and shaped to fit within the conical sealing member 4305. When assembled, the valve cap 4310 captures the valve sealing member 4305 against an inner surface of the valve housing 4315. The slotted configuration of the valve cap 4310 and the stretchable nature of the conical sealing member 4305 enable the valve cap 4310 and valve sealing member 4305 to be expanded, which in turn opens the central passage of the valve assembly 4300. That is, the valve cap 4310 and valve sealing member 4305 can be expanded to form an opening that communicates with the central passage of the valve assembly. The valve assembly 4300 may also includes a distal seal 4040 and space 4055 as with previous embodiments to prevent air ingress during sheath aspiration.

Figure 132:
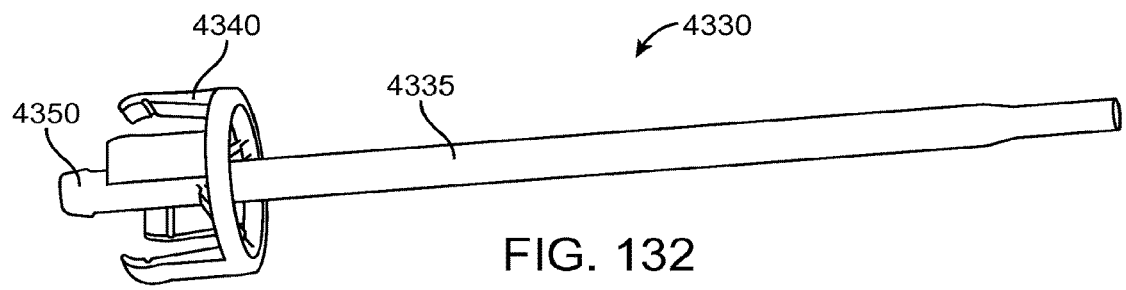
FIGS. 132-135 show a connector between a catheter and a sheath hemostasis valve
Figure 133A:
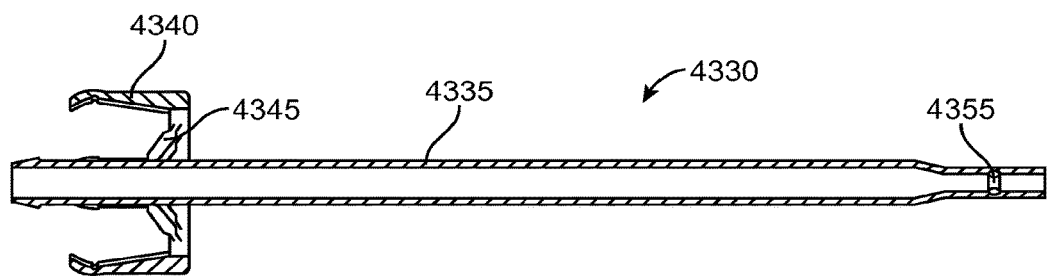
Figure 133B:
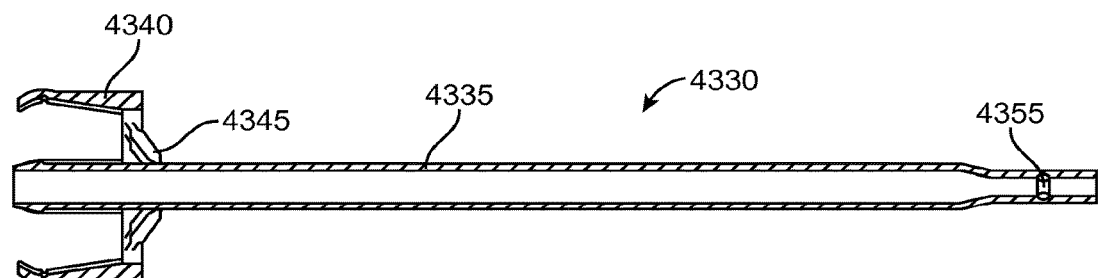

With reference to FIGS. 132, 133A, and 133B, a catheter connector 4330 is configured to couple to the valve assembly 4300 and also to a catheter. The catheter connector 4330 can be used to couple the catheter to the adjustable valve assembly 4300. The connector 4330 includes an elongated connector body 4335 and a plurality of attachment arms 4340 that extend outward from an annular base attached to the body 4335 via hinged link members 4345. The attachment arms 4340 are configured to mate with the valve assembly 4300 to couple the catheter to the adjustable valve assembly 4300. The connector body 4335 has a tapered tip 4350 configured such that when the tip 4350 is pushed into the adjustable valve assembly 4300, the valve sealing member 4305 and adjustable valve cap 4310 (FIG. 131) are pushed radially outward by the tip 4350 to open the central opening of the valve assembly.

The link members 4345 couple the connector body 4335 to the attachment arms 4340 such that the attachment arms 4340 move back and forth and thereby vary the position of the connector body 4335 relative to the attachment arms 4340 along the axis of the connector body 4335. When the catheter connector 4330 is attached to the adjustable valve assembly 4300, the connector body 4335 and tapered tip 4350 may be moved into one of two stable positions while the attachment arms 4340 remain fixedly attached to the valve assembly 4300. The two stable positions include: a forward position and a back position. When in the forward position, the connector body 4335 opens the central opening of the adjustable valve assembly 4300. When in the back position, the connector body 4335 is positioned such that valve sealing member 4305 and adjustable valve cap 4310 are in a default state when the central opening is closed, substantially closed, or sufficiently small to impede or prevent flow therethrough. The connector body 4335 may also be connected to the attachment arms 4340 via other distensible or spring mechanisms that allow the body to move forward and back with respect to the attachment arms 4340. For example, the connection may be a leaf spring design wherein the default position of the connector body is in the "back" position. The connector 4330 may also contain a proximal sealing member 4355 which seals against the catheter shaft when the catheter is coupled to the connector 4330. Thus, when the catheter is connected via the catheter connector 4330 to the adjustable valve assembly 4300 and the connector 4330 is pushed into the forward position to increase the valve opening, hemostasis is maintained.

Figure 134E:
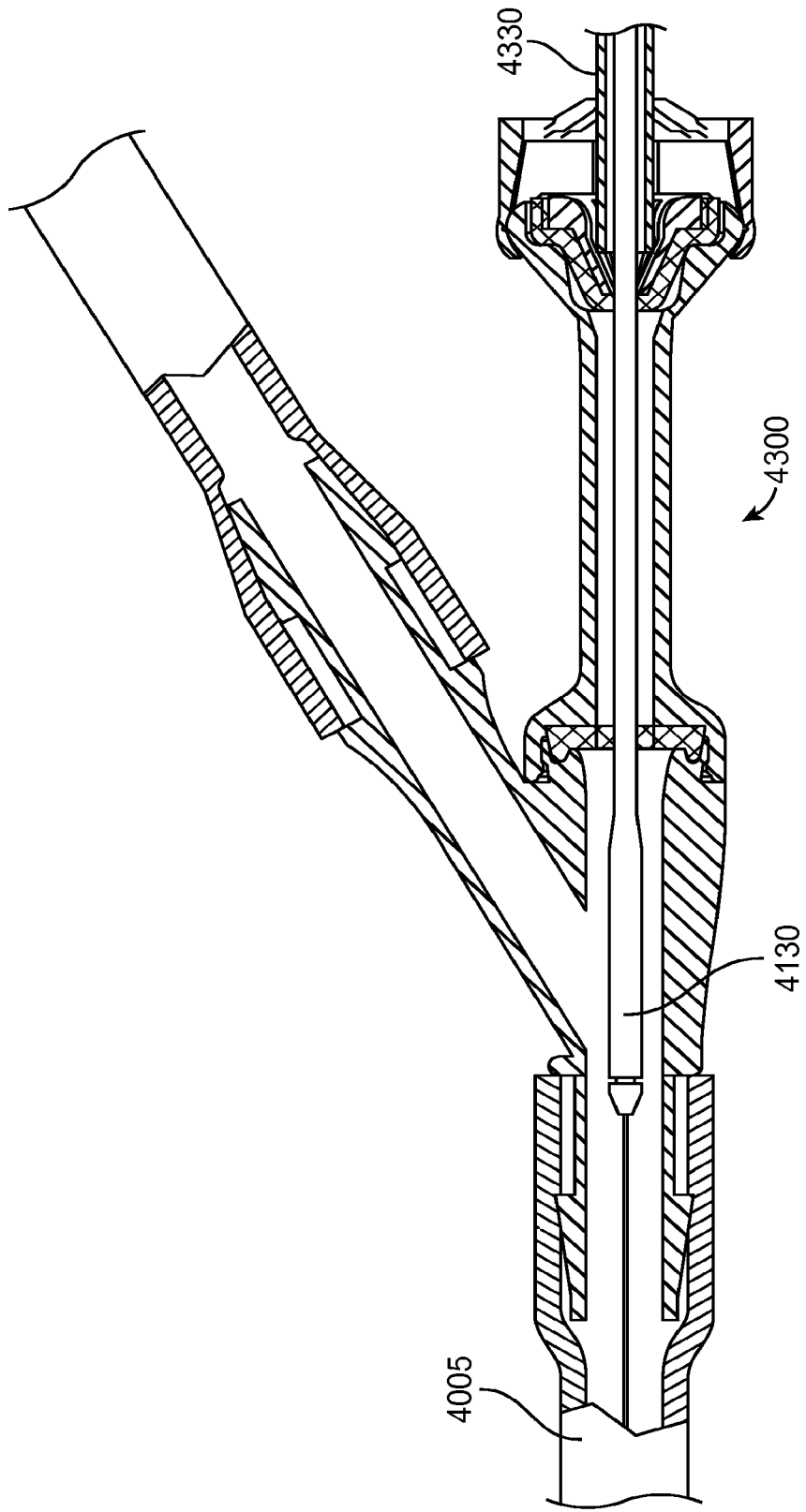

FIGS. 134A-134E show steps of an exemplary method of using the valve assembly 4300. FIG. 134A shows an overall layout of an arterial access device 4000 with a valve assembly 4300, where the proximal seal is configured in the manner described above with reference to FIGS. 130-133. A guidewire 4105 is first placed across the hemostasis valve members and through the distal sheath 4005 into the artery. FIG. 134B shows an enlarged view of the valve assembly 4300 with the guidewire 4105 inserted into the access device 4000. Fluid F is shown in this view in both the sheath and the space 4055 between the two valve members 4040 and 4305. In FIG. 134C, a catheter 4130 and catheter connector 4330 are connected to the adjustable valve assembly 4300 by attaching the arms 4340 to the valve housing 4315. The connector 4330 is in the "back" position in FIG. 134C, such that the adjustable valve assembly is unexpanded with the central opening closed, substantially closed or sufficiently small to prevent or inhibit fluid flow therethrough. The distal end of the connector body 4335 is positioned so that it does not open the valve seal 4305. As the catheter 4130 is pushed in a distal direction and inserted through the valve, as shown in FIG. 134D, the connector body 4335 on the catheter connector 4330 is pushed forward to enlarge the central opening of valve assembly 4300. Once the catheter 4130 has passed through the valve assembly 4300 into the sheath 4005, the connector 4330 may be pulled back proximally to seal tightly around the catheter shaft, as shown in FIG. 134E. Alternately, if the adjustable valve proximal sealing member 4305 seals against the catheter shaft in the expanded position, the connector 4330 may remain in the forward position until the catheter 4130 is removed from the sheath.

Figure 135:
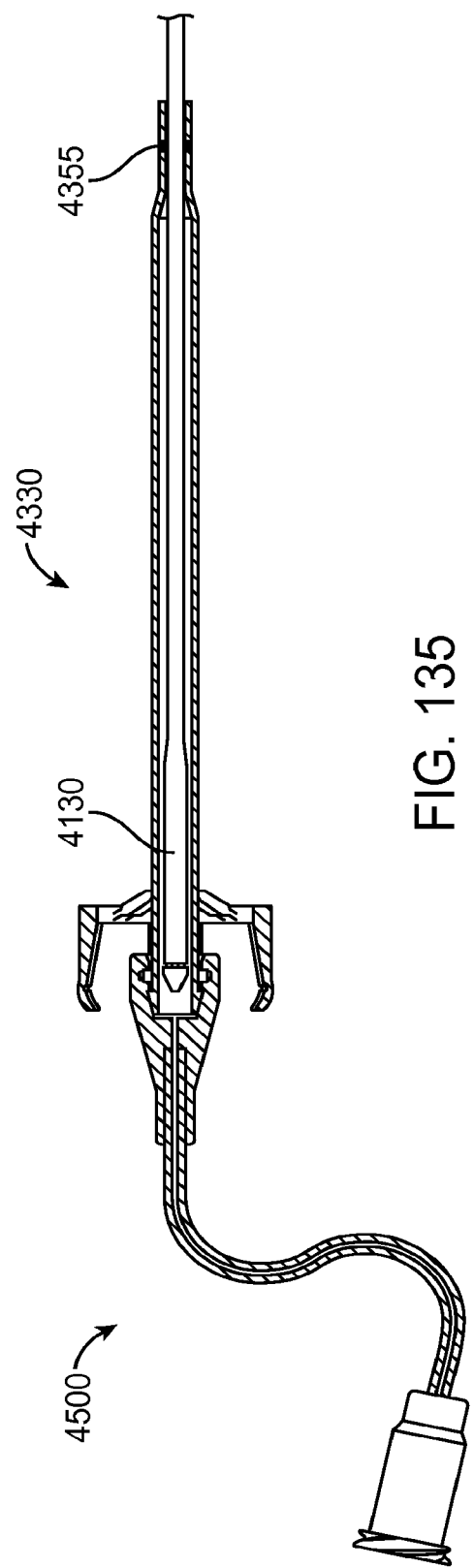

The catheter connector 4330 may also be configured to enable catheter distal flushing prior to use in the procedure. Typically, catheter inner lumens are flushed with fluid prior to a procedure. In an embodiment as shown in FIG. 135, a flush port assembly 4500 may be attached to the tip of the catheter connector 4330. A syringe (not shown) may be attached to a luer connector on the flush port assembly 4500 to prep the catheter. The proximal seal 4355 seals the shaft of the catheter 4130 against the connector 4330 to maintain hemostasis during flushing. The flush port assembly 4500 is then removed prior to coupling the catheter 4130 and connector 4330 to the adjustable valve assembly 4300.

Figure 136A:
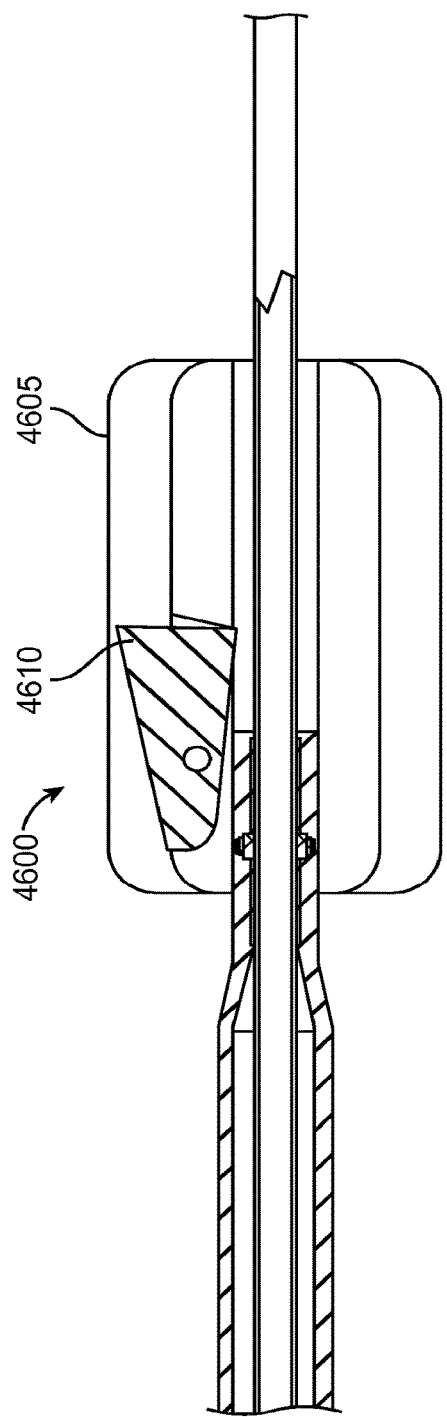
FIGS. 136A and 136B show a catheter connector with a slitting feature.
Figure 136B:
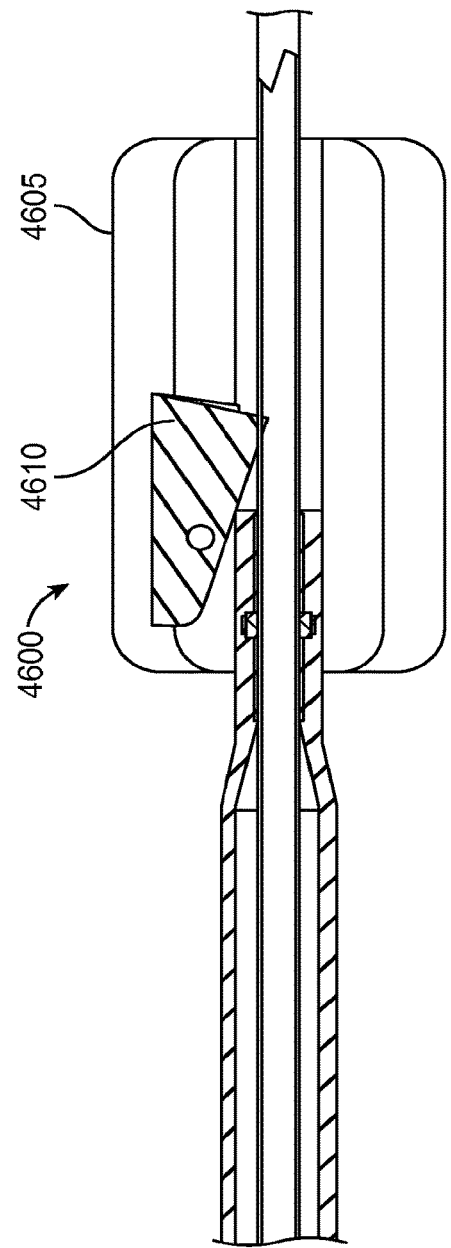

The catheter connector 4330 may also include a feature to assist in retraction of a stent retention sleeve during stent deployment, especially in the situation where a long retraction length is desired. In an embodiment as shown in FIGS. 136A and 136B, a sheath slitting assembly 4600 couples to the proximal end of the catheter connector 4330. The slitting assembly 4600 may be removably attached to the connector 4330, or may be an integral part of the connector. The slitting assembly 4600 includes a slitter housing 4605 and a slitter blade 4610. The housing 4605 has a central passage 4615 through which the catheter is inserted. The blade 4610 can be moved from a retracted position to a slitting position extending into the central passage 4615. During stent deployment when the outer stent retention sleeve is being pulled back, the blade 4610 is moved into the slitting position where the blade 4610 interacts with the retention sleeve to slit the outer retention sleeve of the catheter. The blade 4610 may be a cutting blade, or it may be a non-cutting blade which separates the outer retention sleeve along a pre-weakened section of wall.

In another embodiment of an adjustable valve, the valve is connected to a solenoid mechanism which enlarges and shrinks the opening of the valve. The solenoid is connected to a sensor, which in turn senses the presence of a stent delivery catheter, for example if the distal tip of the stent delivery catheter contains an active signal, a magnet, or other detectable feature. During insertion of the stent delivery catheter into the arterial access device 4000, as the tip of the catheter nears the valve, the solenoid opens up the valve. Once the tip has passed the valve, the solenoid returns the valve to its smaller opening. This embodiment may be particularly useful if the adjustable valve were remote from the proximal end of the arterial access device 4000 and could not easily be opened on the proximal end as in the previous embodiment. For example, the adjustable valve could be located at the position of sealing member 4040 in FIG. 126.

Example Methods of Use

Referring now to FIG. 1, example methods of use are described. In a first method, transcervical access to the common carotid artery is gained about 4 to 7 cm proximal to the carotid artery bifurcation. This access can be obtained either via a percutaneous puncture or a surgical cut-down to the carotid artery. The arterial access device 10 can be inserted into the common carotid artery and secured to the patient. A limitation of the amount of insertion of the arterial access device into the artery can be controlled by the external tube 24. A guidewire 19 can be introduced via the arterial access device 10 into the carotid artery and across the target treatment site.

An embolic protection system can now be positioned. In an embodiment, the common carotid artery is occluded, either surgically using a vessel loop or umbilical tape, or intravascularly with an occlusion balloon on the arterial access device 10 such as shown in FIG. 12. If desired, an aspiration device can be connected to a side port of the arterial access device 10, and aspiration applied to the sheath at specific moments during the procedure. In a variation of this embodiment, the ECA can also be occluded, either via a separate balloon or through use of an arterial access device with two occlusion members, as shown in FIG. 13. In another embodiment, the embolic protection system includes restricting flow through the common carotid artery using a flow restriction element on the sheath, as shown in FIG. 14. In another embodiment, a distal protection device such as a distal filter or distal occlusion device is positioned distal to the target treatment site.

Once the embolic protection system is positioned, an interventional procedure can be performed. The target lesion site can be imaged using angiography. Contrast agent can be injected into the target lesion site via a flush port connected to the arterial sheath. In an embodiment, a reverse flow system with automatic contrast control features can be used so that the reverse flow line is automatically closed during injection of the contrast agent. In a method embodiment, the target lesion site can also be imaged using intravascular ultrasound (IVUS). An IVUS catheter can be positioned at the target lesion site and the lesion viewed on a monitor. External ultrasound devices can also be used during any point in the procedure to image the access site and/or treatment site. Therapeutic interventional devices can then be introduced through the arterial access device into the CCA and from there to the target treatment site. In a method, a balloon dilatation device can be used to pre-dilate the target treatment site. A stent delivery catheter which has been configured for transcervical access can be inserted into the arterial access device, and a stent can be deployed at the target treatment site. If desired, additional dilatation of the stent can be performed after removal of the stent delivery catheter using a balloon dilatation catheter.

In a method embodiment, a preclose device can be used to apply vessel closure means prior to insertion of the access sheath, as described previously. Alternately, a vessel closure device can be used at the time of removal of the arterial access device. If desired, an arterial access device with a removable proximal extension can be used for the procedure, and the proximal extension removed at the conclusion of the procedure so that the vessel closure device can be inserted as required through the arterial access device, or exchanged for a sheath suitable for vessel closure device used.

In a method embodiment, the embolic protection system includes a reverse flow system wherein the common carotid artery is occluded and arterial access device is connected to a reverse flow shunt, as shown in FIG. 2A, and the CCA is occluded and reverse flow is initiated to provide embolic protection. Reverse flow can be achieved in various manners, including via either a passive shunt or active aspiration, or a combination of the two, during the course of the procedure. In a variation, the ECA can also be occluded, either via a separate balloon or through use of an arterial access device with two occlusion members, similar to the device shown in FIG. 13. In such an embodiment, a stent delivery catheter with features to optimize flow reversal can be used. For example, the outer retention sleeve of the stent delivery catheter can have a reduced outer diameter to minimize flow restriction through the arterial sheath when the stent delivery catheter is in the arterial sheath. During stent deployment, once the retention sleeve of the stent is partially pulled back to accurately position the stent at the target treatment site, the retention sleeve can be pulled back until it is completely removed from the reverse flow path portion of the arterial access device.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of accessing and treating a carotid artery, the method comprising:
  inserting an arterial access device into an artery, wherein the arterial access device comprises a distal sheath adapted to enter the common carotid artery, an aspiration port communicating with an internal lumen of the distal sheath, and a proximal hemostasis valve assembly providing access to the internal lumen of the distal sheath for an interventional device;
  the hemostasis valve assembly comprising:
  (a) a housing defining an internal chamber that communicates with the internal lumen of the distal sheath, wherein the internal chamber is adapted to contain a liquid or gel;
  (b) a first seal member that seals the internal chamber from the internal lumen of the distal sheath, the first seal member having a central passageway that opens for passage of an interventional device into the internal lumen of the distal sheath from the internal chamber, wherein the central passageway is closed in a default state to prevent passage of fluid across the first seal member;
  (c) wherein, when the internal chamber is filled with liquid or gel, the liquid or gel prevents air from entering the internal lumen of the distal sheath via the hemostasis valve assembly when the internal lumen of the distal sheath is aspirated, via the aspiration port;

a second seal member, wherein the second seal member is positioned on a proximal end of the internal chamber and the first seal member is positioned on a distal end of the internal chamber so that the first seal member and second seal member define the internal chamber therebetween and can enclose liquid or gel within the internal chamber, and wherein the first seal member and second seal member are aligned along a common, straight axis;

and wherein the internal chamber is pre-filled with liquid or gel prior to a first use of the arterial access device.

2. A method as in claim 1, wherein a proximal end of the internal chamber is open to atmosphere, and wherein the internal chamber has a size such that surface tension of liquid or gel in the internal chamber maintains the liquid or gel within the internal chamber.

3. A method as in claim 1, further comprising:

inserting an interventional device through the internal chamber of the hemostasis valve assembly, across the first seal member, and into the internal lumen of the distal sheath; and coupling an introducer to the interventional device so as to provide the interventional device with sufficient columnar stiffness to pass entirely through the internal chamber and into the hemostasis valve assembly.

4. A method as in claim 3, wherein the introducer is removably coupled to the interventional device.

5. A method as in claim 1, wherein the arterial access device further comprises a flush port having a lumen in communication with the internal chamber of the hemostasis valve assembly, the flush port adapted to inject liquid or gel into the internal chamber of the hemostasis valve assembly.

6. A method as in claim 1, wherein the arterial access device further comprise a shunt fluidly connected to the arterial access device, wherein the shunt provides a pathway for blood to flow in a retrograde direction from the arterial access device to a return site.

7. A method as in claim 6, wherein a flow control assembly is coupled to the shunt and adapted to regulate blood flow through the shunt between at least a first blood flow state and at least a second blood flow state, wherein the flow control assembly includes one or more components that interact with the blood flow through the shunt.

8. A method as in claim 6, wherein the flow control assembly includes a flow resistance element adapted to adjust a resistance of blood flow through the shunt.

9. A method as in claim 6, wherein the shunt is adapted to be connected to an external receptacle such that the blood flows from the common carotid artery through the shunt to the external receptacle.

10. A method as in claim 1, further comprising inserting a venous return device into a vein, and wherein a shunt fluidly connects the arterial access device to the venous return device such that the blood flows through the shunt from the common carotid artery to the vein.

\* \* \* \* \*